(12) United States Patent
Gonzalez Lopez de Turiso et al.

(10) Patent No.: US 11,999,715 B2
(45) Date of Patent: Jun. 4, 2024

(54) ASK1 INHIBITING AGENTS

(71) Applicant: BIOGEN MA INC., Cambridge, MA (US)

(72) Inventors: Felix Gonzalez Lopez de Turiso, Cambridge, MA (US); Zhili Xin, Lexington, MA (US); Martin Himmelbauer, Cambridge, MA (US); John H. Jones, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 759 days.

(21) Appl. No.: 17/267,631

(22) PCT Filed: Aug. 13, 2019

(86) PCT No.: PCT/US2019/046334
§ 371 (c)(1),
(2) Date: Feb. 10, 2021

(87) PCT Pub. No.: WO2020/036949
PCT Pub. Date: Feb. 20, 2020

(65) Prior Publication Data
US 2021/0317103 A1    Oct. 14, 2021

Related U.S. Application Data

(60) Provisional application No. 62/718,622, filed on Aug. 14, 2018.

(51) Int. Cl.
*C07D 401/14* (2006.01)
*C07D 405/14* (2006.01)

(52) U.S. Cl.
CPC ......... *C07D 401/14* (2013.01); *C07D 405/14* (2013.01)

(58) Field of Classification Search
None
See application file for complete search history.

(56) References Cited

U.S. PATENT DOCUMENTS

2017/0196844 A1    7/2017  Graupe et al.

FOREIGN PATENT DOCUMENTS

WO    WO 2005/040152 A1 *    5/2005    ........... C07D 401/12

OTHER PUBLICATIONS

Lovering et al., Rational approach to highly potent and selective apoptosis signal-regulating kinase 1 (ASK1) inhibitors. Eur J Med Chem. Dec. 15, 2017;145:606-621.
International Search Report and Written Opinion for Application No. PCT/US2019/046334, dated Nov. 21, 2019, 9 pages.

* cited by examiner

*Primary Examiner* — Joseph R Kosack
*Assistant Examiner* — David M Shim
(74) *Attorney, Agent, or Firm* — McCarter & English, LLP

(57) ABSTRACT

Provided are compounds of Formula (I): Formula (I), including compounds of Formulas (II), (III), (IV), (V) and (VI), wherein X, $R^1$, $R^2$, $R^3$, $R^4$ and n are as defined herein, and pharmaceutically acceptable salts thereof, and methods for their use and production. These compounds can be useful, e.g., in the treatment of disorders responsive to the inhibition of apoptosis signal-regulating kinase 1 (ASK1).

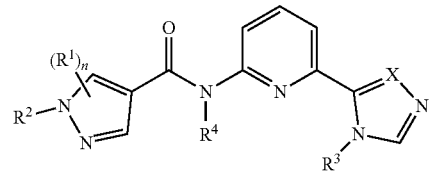

20 Claims, No Drawings

ASK1 INHIBITING AGENTS

This application is a 35 U.S.C. § 371 national stage filing of International Application No. PCT/US2019/046334, filed on Aug. 13, 2019, which in turn claims the benefit of the filing date, under 35 U.S.C. § 119(e), of U.S. Provisional Application No. 62/718,622, filed on Aug. 14, 2018, the entire contents of each of which are incorporated herein by reference.

TECHNICAL FIELD

Provided are certain agents that inhibit apoptosis signal-regulating kinase 1 (ASK1), and methods of making and using such agents.

BACKGROUND

Apoptosis Signal-regulating Kinase 1 (ASK1), also known as MAP3K5, is a member of the mitogen-activated protein kinase kinase kinase ("MAP3K") family that activates the c-Jun N-terminal protein kinase ("JNK") and p38 MAP kinase (Ichijo, H. et al., Science 1997, 275, 90-94). ASK1 is an evolutionary conserved and stress-responsive mitogen-activated protein kinase (MAPK). In mouse, ASK1 has been found to be expressed in heart, brain, lung, liver and kidney, as well as in developing skin, cartilage and bone (Tobiume et al., Biochem Biophys Res Commun. 1997, 239(3), 905-10). ASK1 is a central regulator of cell death and participates in several stress-induced and receptor-mediated cell death pathways triggered by various forms of cellular stress, including oxidative stress, reactive oxygen species (ROS), endoplasmic reticulum (ER) stress and unfolded protein response (UPR), mitochondrial stress, bacterial infection, increased calcium influx, DNA damage, UV radiation, viral infection, heat shock, osmotic shock, endotoxic lipopolysaccharide (LPS), FasL, and activation by pro-inflammatory cytokines such as tumor necrosis factor (TNF) and interleukin-1 (Nishitoh et al., Genes Dev. 2002, 16, 1345-1355; Matsukawa et al., Nat. Immunol., 2005, 6, 587-592; Tobiume et al., EMBO Rep. 2001, 2, 222-228; Hayakawa R. et al., Proc. Jpn. Acad. Ser B Phys. Biol. Sci. 2012, 88(8), 434-53; Takeda et al. Cell Struct. Funct. 2003, 28(1), 23-29; Tibbles et al., Cell Mol Life Sci. 1999, 55(10), 1230-1254; Hattori et al., Cell Comm. Signal. 2009, 7, 1-10; Takeda et al., Annu. Rev. Pharmacol. Toxicol. 2007, 48, 1-8.27; Nagai et al. J. Biochem. Mol. Biol. 2007, 40, 1-6).

ASK1 undergoes activation via autophosphorylation at Thr838 in response to these signals and in turn phosphorylates MAP2Ks, such as MKK3/6 and MKK4/7, which then phosphorylate and activate p38 and JNK MAPKs, respectively. Activation of the JNK and p38 pathways induces stress responses related to cell death, differentiation and the production of inflammatory cytokines. In non-stressed conditions, ASK1 is kept in an inactive state through binding to its repressor Thioredoxin (Trx) (Saitoh, M. et al., Embo J. 1998, 17, 2596-2606), and through association with AKT (Zhang, L., et al. Proc. Natl. Acad. Sci. U.S.A 1999, 96, 8511-8515).

ASK1 plays an essential role not only in cell death pathways, but also in inflammatory and innate immune responses including cytokine responses, and cell differentiation. Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmunity, and metabolic disorders. In addition, ASK1 has been implicated in mediating organ damage following ischemia and reperfusion of the heart, brain, and kidney (Watanabe et al. BBRC 2005, 333, 562-567; Zhang et al., Life Sci 2003, 74-37-43; Terada et al. BBRC 2007, 364: 1043-49).

Therefore, there is a need for new compounds that can function as ASK1 inhibitors.

SUMMARY

In one aspect, the present invention provides a compound of Formula (I):

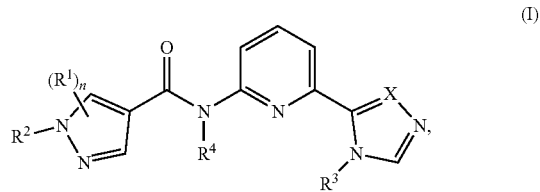

(I)

or a pharmaceutically acceptable salt thereof, wherein:

X is CH or N;

n is 1 or 2;

$R^1$ in each occurrence is independently selected from H, $C_{1-6}$alkyl, $C_{2-6}$alkenyl, $C_{2-6}$alkynyl, carbocyclyl, heterocyclyl, halo, —CN, —C(O)$R^{1a}$, —C(O)O$R^{1a}$, —C(O)N($R^{1a}$)$_2$, —N($R^{1a}$)$_2$, —N($R^{1a}$)C(O)$R^{1a}$, —N($R^{1a}$)C(O)O$R^{1a}$, —N($R^{1a}$)C(O)N($R^{1a}$)$_2$, —N($R^{1a}$)S(O)$_2$$R^{1a}$, —O$R^{1a}$, —OC(O)$R^{1a}$, —OC(O)N($R^{1a}$)$_2$, —S$R^{1a}$, —S(O)$R^{1a}$, —S(O)$_2$$R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, carbocyclyl, and heterocyclyl are optionally substituted with one or more $R^{10}$;

$R^{1a}$ in each occurrence is independently selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2$$R^{10a}$, —O$R^{10a}$, —OC(O)$R^{10a}$, —OC(O)N($R^{10a}$)$_2$, —S$R^{10a}$, —S(O)$R^{10a}$, —S(O)$_2$$R^{10a}$, —S(O)N($R^{10a}$)$_2$, and —S(O)$_2$N($R^{10a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2$$R^{10a}$, —O$R^{10a}$, —OC(O)$R^{10a}$, —OC(O)N($R^{10a}$)$_2$, —S$R^{10a}$, —S(O)$R^{10a}$, —S(O)$_2$$R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, carbocyclyl, and heterocyclyl;

$R^2$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally and independently substituted with one or more $R^{20}$.

$R^{20}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{20a}$, —C(O)O$R^{20a}$, —C(O)N($R^{20a}$)$_2$, —N($R^{20a}$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2$$R^{20a}$, —O$R^{20a}$, —OC(O)$R^{20a}$, —OC(O)N($R^{20a}$)$_2$, —S$R^{20a}$, —S(O)$R^{20a}$, —S(O)$_2$$R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{20a}$, —C(O)O$R^{20a}$, —C(O)N($R^{20a}$)$_2$, —N($R^2$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2$$R^{20a}$, —O$R^{20a}$, —OC(O)$R^{20a}$, —OC(O)N($R^{20a}$)$_2$, —S$R^{20a}$, —S(O)$R^{20a}$, —S(O)$_2$$R^{20a}$, —S(O)N($R^{20a}$)$_2$, and —S(O)$_2$N($R^{20a}$)$_2$;

$R^{20a}$ in each occurrence is independently selected from H, $C_{1-6}$alkyl, $C_{2-6}$alkenyl, $C_{2-6}$alkynyl, carbocyclyl, and heterocyclyl;

$R^3$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally substituted with one or more $R^{30}$;

$R^{30}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, carbocyclyl, and heterocyclyl, wherein said carbocyclyl, and heterocyclyl are each optionally substituted with $C_{1-4}$alkyl or halo; and $R^4$ is H or $C_{1-6}$alkyl.

The compounds or pharmaceutically acceptable salts thereof as described herein can have activity as ASK1 modulators. In particular, compounds or pharmaceutically acceptable salts thereof as described herein can be ASK1 inhibitors.

The present invention also provides a pharmaceutical composition comprising at least one compound described herein, or a pharmaceutically acceptable salt thereof, and at least one pharmaceutically acceptable excipient.

In one aspect, the invention provides a method of treating a disorder responsive to inhibition of ASK1 in a subject comprising administering to said subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of ASK1. Also provided is a compound described herein, or a pharmaceutically acceptable salt thereof, for use in a method of treating a disorder responsive to inhibition of ASK1.

Other features or advantages will be apparent from the following detailed description of several embodiments, and also from the appended claims.

DETAILED DESCRIPTION

Definitions

As used herein, unless expressly stated to the contrary or otherwise clear from context, the term "include" and its variations ("includes", "including", etc.) are intended to be non-limiting. That is, unless expressly stated to the contrary or otherwise clear from context, "include" means "include but are not limited to", and so on.

As used herein, the term "alkyl" refers to a saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Examples of alkyl include methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, propynyl, but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to (1) a saturated or unsaturated, monocyclic or bicyclic (e.g., bridged or spiro ring systems) ring system which has from 3 to 10 ring members, or in particular 3 to 8 ring members, 3 to 7 ring members, 3 to 6 ring members or 5 to 7 ring members or 4 to 7 ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and/or sulfone; or (2) a heteroaryl group. As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring or a 4- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or-7-membered bicyclic ring. In yet another embodiment, a heterocyclyl is a 4- to 7-membered monocyclic non-aromatic ring. In another embodiment, a heterocyclyl is 6- to 8-membered spiro or bridged bicyclic ring. The heterocyclyl group can be attached at a heteroatom or a carbon atom. Examples of heterocyclyls include aziridinyl, oxiranyl, thiiranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like.

In one embodiment, a heterocyclyl is a 4- to 7-membered monocyclic heterocyclyl. Examples of 4- to 7-membered monocyclic heterocyclic ring systems include azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl.

As used herein, a "4- to 7-membered monocyclic saturated heterocyclyl" is a monocyclic heterocyclyl having 4- to 7-ring members and is saturated. Examples of 4- to 7-membered monocyclic saturated heterocyclyls include azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, azepanyl, oxepanyl, and thiepanyl. In one embodiment, the 4- to 7-membered monocyclic saturated heterocyclyl is azetidinyl, piperidinyl, oxetanyl, piperazinyl or morpholinyl.

As used herein, "5- or 6-membered heteroaryl" refers to a monocyclic aromatic heterocyclyl having 5 or 6-ring members. Examples of 5 or 6-membered heteroaryl include pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl. In one embodiment, the 5 or 6-membered heteroaryl is pyrrolyl, furanyl, imidazolyl, pyrazolyl, oxazolyl, isoxazolyl, thiazolyl, isothiazolyl, oxadiazolyl, thiadiazolyl, dithiazolyl, triazolyl, tetrazolyl, pyridinyl, pyrazinyl, pyrimidinyl, pyridazinyl, triazinyl, and tetrazinyl. In another embodiment, the 5 or 6-membered heteroaryl is pyridinyl, pyrimidinyl, pyrazinyl, and pyridazinyl.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6 to 8 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 8 ring members.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to saturated monocyclic or bicyclic or spiro hydrocarbon groups of 3-7 carbon atoms, 3-6 carbon atoms, or 5-7 carbon atoms. Exemplary monocyclic carbocyclyl groups include cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

As used herein, "$C_{3-6}$cycloalkyl" refers to monocyclic saturated cycloalkyl having 3-6 carbon atoms.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include sodium, potassium, lithium, ammonium, calcium or magnesium salts. Salts derived from organic bases can include salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. Other carboxylic acid derivatives can be useful, for example, carboxylic acid amides, including carboxamides, lower alkyl carboxamides, dialkyl carboxamides, and the like.

The compounds or pharmaceutically acceptable salts thereof as described herein, can contain one or more asymmetric centers in the molecule. In accordance with the present disclosure, any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). When a particular stereoisomer of a compound used in the disclosed methods is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers. When a particular stereoisomer of a compound used in the disclosed methods is depicted by name or structure as indicating a single enantiomer, the enantiomeric purity of the compound is at least 60%, 70%, 80%, 90%, 95%, 97%, 99%, 99.5% or 99.9%. "Enantiomeric purity" means the weight percent of the desired stereoisomer relative to the combined weight of the desired stereoisomer and its enantiomer.

The disclosed compounds may exist in tautomeric forms and mixtures and separate individual tautomers are contemplated. In addition, some compounds may exhibit polymorphism.

By way of clarity, compounds of the invention include all isotopes of the atoms present in formula (I) and any of the examples or embodiments disclosed herein. For example, H (or hydrogen) represents any isotopic form of hydrogen including $^1H$, $^2H$ (D), and $^3H$ (T); C represents any isotopic form of carbon including $^{12}C$, $^{3}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formula (I) comprises isotopes of the atoms therein in their naturally occurring abundance. However, in certain instances, it is desirable to enrich one or more atom in a particular isotope which would normally be present in less abundance. For example, $^1H$ would normally be present in greater than 99.98% abundance; however, a compound of the invention can be enriched in $^2H$ or $^3H$ at one or more positions where H is present. In particular embodiments of the compounds of formula (I), when, for example, hydrogen is enriched in the deuterium isotope, the symbol "D" may be used to represent the enrichment in deuterium. In one embodiment, when a compound of the invention is enriched in a radioactive isotope, for example $^3H$ and $^{14}C$, they may be useful in drug and/or substrate tissue distribution assays. It is to be understood that the invention encompasses all such isotopic forms which inhibit ASK1 activity.

Compounds of the Invention

In a first embodiment, a compound of the present invention is represented by Formula (I):

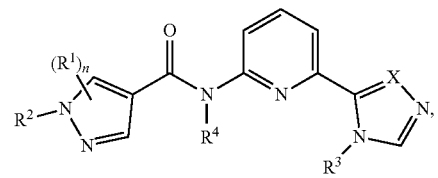

or a pharmaceutically acceptable salt thereof, wherein the definitions for the variable are as defined above.

In a second embodiment, a compound of the present invention is represented by Formula (II):

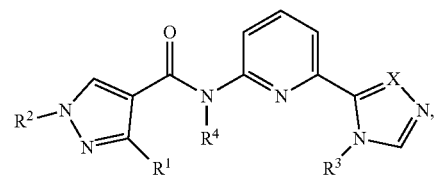

or a pharmaceutically acceptable salt thereof, wherein the variables are as defined above for Formula (I).

In a third embodiment, a compound of the present invention is represented by Formula (III):

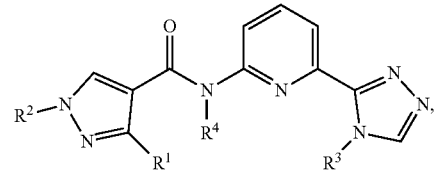

or a pharmaceutically acceptable salt thereof, wherein the variables are as defined above for Formula (I).

In a fourth embodiment, a compound of the present invention is represented by Formula (IV):

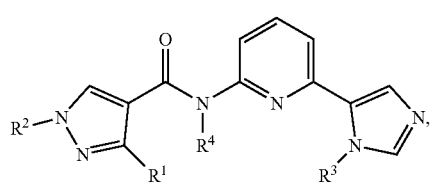

(IV)

or a pharmaceutically acceptable salt thereof, wherein the variables are as defined above for Formula (I).

In a fifth embodiment, a compound of the present invention is represented by Formula (I), (II), (III) or (IV), or a pharmaceutically acceptable salt thereof, wherein:
$R^1$ is H, $C_{1-6}$alkyl or —$OR^{1a}$, wherein said $C_{1-6}$alkyl is optionally substituted with one to three $R^{10}$;
$R^{1a}$ in each occurrence is independently selected from H and $C_{1-6}$alkyl;
$R^{10}$ in each occurrence is independently selected from halo and —$OR^{1a}$; and the remaining variables are as defined in the first, second, third or fourth embodiment.

In a sixth embodiment, a compound of the present invention is represented by Formula (I), (II), (III) or (IV), or a pharmaceutically acceptable salt thereof, wherein $R^1$ is H, —$OCH_3$, —$OCH_2CH_3$, —$CH_2OCH_3$, —$CF_3$, or —$CHF_2$; and the remaining variables are as defined in the first, second, third, fourth or fifth embodiment.

In a seventh embodiment, a compound of the present invention is represented by Formula (I), (II), (III) or (IV), or a pharmaceutically acceptable salt thereof, wherein:
$R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$;
$R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —$C(O)R^{20a}$, —$C(O)OR^{20a}$, —$C(O)N(R^{20a})_2$, —$N(R^{20a})_2$, —$N(R^{20a})C(O)R^{20a}$, —$N(R^{20a})C(O)OR^{20a}$, —$N(R^{20a})C(O)N(R^{20a})_2$, —$N(R^{20a})S(O)_2R^{20a}$, —$OR^{20a}$, —$OC(O)R^{20a}$, —$OC(O)N(R^{20a})_2$, —$SR^{20a}$, —$S(O)R^{20a}$, —$S(O)_2R^{20a}$, —$S(O)N(R^{20a})_2$, and —$S(O)_2N(R^{20a})_2$, wherein said $C_{1-4}$alkyl, $C_{2-4}$alkenyl, $C_{3-6}$cycloalkyl, phenyl, 4- to 7-membered monocyclic saturated heterocyclyl, and 5- or 6-membered heteroaryl in each occurrence are optionally and independently substituted with one or more substituents independently selected from halo, —CN, —$C(O)R^{20a}$, —$C(O)OR^{20a}$, —$C(O)N(R^{20a})_2$, —$N(R^{20a})_2$, —$N(R^{20a})C(O)R^{20a}$, —$N(R^{20a})C(O)OR^{20a}$, —$N(R^{20a})C(O)N(R^{20a})_2$, —$N(R^{20a})S(O)_2R^{20a}$, —$OR^{20a}$, —$OC(O)R^{20a}$, —$OC(O)N(R^{20a})_2$, —$SR^{20a}$, —$S(O)R^{20a}$, —$S(O)_2R^{20a}$, —$S(O)N(R^{20a})_2$, and —$S(O)_2N(R^{20a})_2$;
$R^{20a}$ in each occurrence is independently H or $C_{1-4}$alkyl; and the remaining variables are as defined in the first, second, third, fourth, fifth or sixth embodiment.

In an eighth embodiment, a compound of the present invention is represented by Formula (I), (II), (III) or (IV), or a pharmaceutically acceptable salt thereof, wherein:

$R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$.
$R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —$N(R^{20a})_2$, and —$OR^{20a}$;
$R^{20a}$ in each occurrence is independently H or $C_{1-4}$alkyl; and the remaining variables are as defined in the first, second, third, fourth, fifth, sixth or seventh embodiment.

In a ninth embodiment, the 5- or 6-membered heteroaryl described in the seventh or eighth embodiment is selected from pyridinyl, pyrimidinyl, pyrazinyl, and pyridazinyl.

In a tenth embodiment, the 4- to 7-membered monocyclic saturated heterocyclyl described in the eighth or ninth embodiment is selected from azetidinyl, piperidinyl, oxetanyl, piperazinyl and morpholinyl.

In an eleventh embodiment, a compound of the present invention is represented by Formula (I), (II), (III) or (IV), or a pharmaceutically acceptable salt thereof, wherein:
$R^2$ is —$CH_3$, —$CH_2CH_3$, —$CH_2CF_3$, —$C(CH_3)_3$, —$CH_2CH_2OCH_3$, —$CH_2CH(CH_3)_2$, —$CH_2CH_2N(CH_3)_2$, —$CH_2CH=CH_2$, —$CH_2CH_2CH_3$,

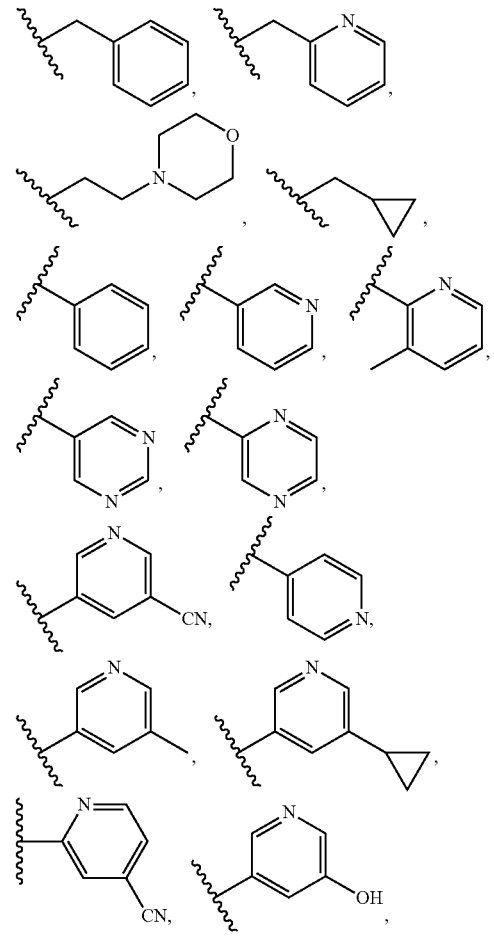

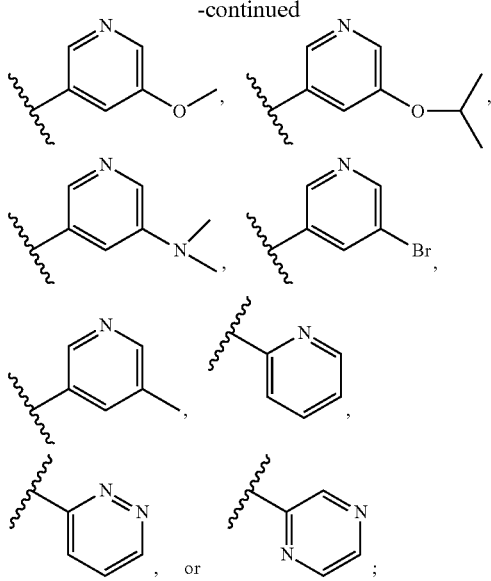

and the remaining variables are as defined in the first, second, third, fourth, fifth or sixth embodiment.

In a twelfth embodiment, a compound of the present invention is represented by Formula (I), (II), (III) or (IV), or a pharmaceutically acceptable salt thereof, wherein:

$R^3$ is selected from H, $C_{1-6}$alkyl, $C_{3-6}$cycloalkyl, and 4 to 7-membered monocyclic saturated heterocyclyl, wherein said $C_{1-6}$alkyl, $C_{3-6}$cycloalkyl, and 4 to 7-membered monocyclic saturated heterocyclyl are optionally substituted with one to three $R^{30}$;

$R^{30}$ in each occurrence is independently selected from $C_{1-6}$alkyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$, wherein said $C_{1-6}$alkyl in each occurrence is optionally and independently substituted with one to three substituents independently selected from $C_{1-4}$alkyl and halo;

$R^{30a}$ in each occurrence is independently H or $C_{1-6}$alkyl, wherein $C_{1-6}$alkyl is optionally substituted with one to three substituents independently selected from $C_{1-4}$alkyl and halo;

and the remaining variables are as defined in the first, second, third, fourth, fifth, sixth, seventh, eighth, ninth, tenth or eleventh embodiment.

In a thirteenth embodiment, a compound of the present invention is represented by Formula (I), (II), (III) or (IV), or a pharmaceutically acceptable salt thereof, wherein:

$R^3$ is $C_{1-6}$alkyl, $C_{3-6}$cycloalkyl, or 4 to 7-membered monocyclic saturated heterocyclyl, wherein said $C_{1-6}$alkyl, $C_{3-6}$cycloalkyl, and 4 to 7-membered monocyclic saturated heterocyclyl are each optionally substituted with one to three $R^{30}$;

$R^{30}$ in each occurrence is independently $C_{1-3}$alkyl, halo, —C(O)O$R^{30a}$, or —O$R^{30a}$, wherein said $C_{1-3}$alkyl is optionally substituted with one to three halo;

$R^{30a}$ in each occurrence is independently selected from H and $C_{1-4}$alkyl;

and the remaining variables are as defined in the twelfth embodiment.

In a fourteenth embodiment, a compound of the present invention is represented by Formula (I), (II), (III) or (IV), or a pharmaceutically acceptable salt thereof, wherein:

$R^3$ is —CH(CH$_3$)$_2$, —CH(CH$_3$)CF$_3$, —C(CH$_3$)$_3$, —CH(CH$_3$)CHF$_2$, —CH(CH$_3$)CH(CH$_3$)$_2$, —CH(CH$_3$)CH$_2$OCH$_3$, —CH(CH$_3$)CH$_2$OH,

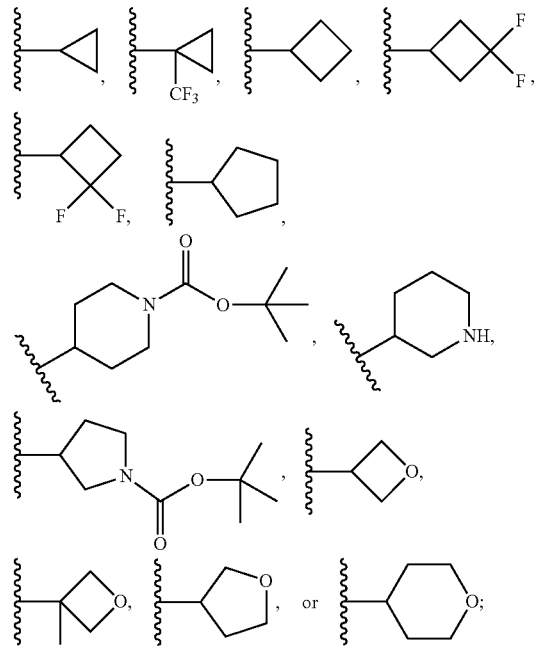

and the remaining variables are as defined in the twelfth embodiment.

In a fifteenth embodiment, a compound of the present invention is represented by Formula (I), (II), (III) or (IV), or a pharmaceutically acceptable salt thereof, wherein $R^4$ is H or —CH$_3$; and the remaining variables are as defined in the first, second, third, fourth, fifth, sixth, seventh, eighth, ninth, tenth, eleventh, twelfth, thirteenth or fourteenth embodiment. In a specific embodiment, $R^4$ is H.

In certain embodiments, a compound of the present invention is represented by Formula (I), (II), (III) or (IV), or a pharmaceutically acceptable salt thereof, wherein:

$R^1$ is H, $C_{1-6}$alkyl or —O$R^{1a}$, wherein said $C_{1-6}$alkyl is optionally substituted with one to three $R^{10}$;

$R^{1a}$ in each occurrence is independently selected from H and $C_{1-6}$alkyl;

$R^{10}$ in each occurrence is independently selected from halo and —O$R^{1a}$;

$R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$;

$R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —C(O)$R^{20a}$, —C(O)O$R^{20a}$, —C(O)N($R^{20a}$)$_2$, —N($R^{20a}$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl in each occurrence are optionally and independently substituted with one or more substituents independently selected from halo, —CN, —C(O)$R^{20a}$, —C(O)O$R^{20a}$, —C(O)N($R^{20a}$)$_2$, —N($R^{20a}$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$;

$R^{20a}$ in each occurrence is independently H or $C_{1-4}$alkyl;

$R^3$ is selected from H, $C_{1-6}$alkyl, $C_{3-6}$cycloalkyl, and 4 to 7-membered monocyclic saturated heterocyclyl, wherein said $C_{1-6}$alkyl, $C_{3-6}$cycloalkyl, and 4 to 7-membered monocyclic saturated heterocyclyl are optionally substituted with one to three $R^{30}$.

$R^{30}$ in each occurrence is independently selected from $C_{1-6}$alkyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$, wherein said $C_{1-6}$alkyl in each occurrence are optionally and independently substituted with one to three substituents independently selected from $C_{1-4}$alkyl and halo;

$R^{30a}$ in each occurrence is independently H or $C_{1-4}$alkyl, wherein $C_{1-6}$alkyl is optionally substituted with one to three substituents independently selected from $C_{1-4}$alkyl and halo; and $R^4$ is H or $C_{1-6}$alkyl.

In certain embodiments, a compound of the present invention is represented by Formula (I), (II), (III) or (IV), or a pharmaceutically acceptable salt thereof, wherein:

$R^1$ is selected from H, $C_{1-6}$alkyl or —O$R^{1a}$, wherein said $C_{1-6}$alkyl is optionally substituted with one to three $R^{10}$;

$R^{1a}$ in each occurrence is independently selected from H and $C_{1-6}$alkyl;

$R^{10}$ in each occurrence is independently selected from halo and —O$R^{1a}$;

$R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$;

$R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —N($R^{20a}$)$_2$, and —O$R^{20a}$;

$R^{20a}$ in each occurrence is independently H or $C_{1-4}$alkyl;

$R^3$ is $C_{1-6}$alkyl, $C_{3-6}$cycloalkyl, or 4 to 7-membered monocyclic saturated heterocyclyl, wherein said $C_{1-6}$alkyl, $C_{3-6}$cycloalkyl, and 4 to 7-membered monocyclic saturated heterocyclyl are each optionally substituted with one to three $R^{30}$;

$R^{30}$ in each occurrence is independently $C_{1-3}$alkyl, halo, —C(O)O$R^{30a}$, or —O$R^{30a}$, wherein said $C_{1-3}$alkyl is optionally substituted with one to three halo;

$R^{30a}$ in each occurrence is independently selected from H and $C_{1-4}$alkyl; and $R^4$ is H or $C_{1-6}$alkyl.

In a sixteenth embodiment, a compound of the present invention is represented by Formula (V) or (VI):

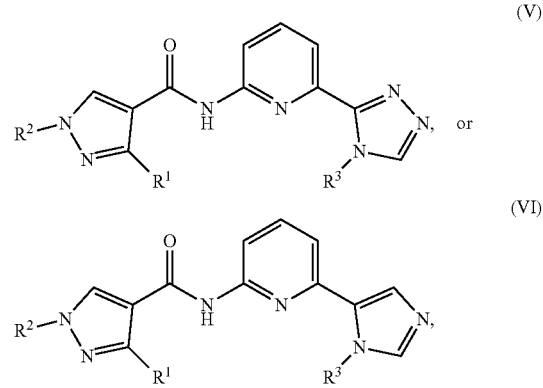

or a pharmaceutically acceptable salt thereof, wherein:

$R^1$ is $C_{1-4}$alkyl or —O$R^{1a}$, wherein said $C_{1-4}$alkyl is optionally substituted with one to three halo;

$R^{1a}$ in each occurrence is independently H or $C_{1-4}$alkyl;

$R^2$ is $C_{1-4}$alkyl, $C_{2-4}$alkenyl or 5- or 6-membered heteroaryl, wherein said $C_{1-4}$alkyl, $C_{2-4}$alkenyl and 5- or 6-membered heteroaryl are optionally and independently substituted with one to three $R^{20}$;

$R^{20}$ in each occurrence is independently selected from $C_{3-6}$cycloalkyl, halo and —O$R^{20a}$;

$R^{20a}$ in each occurrence is independently H or $C_{1-4}$alkyl;

$R^3$ is $C_{1-4}$alkyl or $C_{3-6}$cycloalkyl, wherein said $C_{1-4}$alkyl and $C_{3-6}$cycloalkyl are each optionally substituted with one to three $R^{30}$; and $R^{30}$ in each occurrence is independently $C_{1-3}$alkyl or halo, wherein said $C_{1-3}$alkyl is optionally substituted with one to three halo.

In a seventeenth embodiment, a compound of the present invention is represented by Formula (V) or (VI), or a pharmaceutically acceptable salt thereof, wherein:

$R^1$ is —OCH$_3$, —OCH$_2$CH$_3$, or —CHF$_2$;

$R^2$ is —CH$_3$, —CH$_2$CH$_3$, —CH$_2$CH$_2$OCH$_3$, —CH$_2$CF$_3$, —CH$_2$CH=CH$_2$,

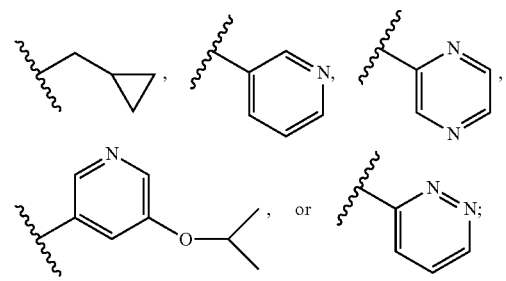

$R^3$ is —CH(CH$_3$)$_2$, —CH(CH$_3$)CF$_3$, —CH(CH$_3$)CHF$_2$,

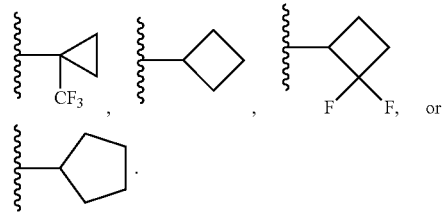

In an eighteenth embodiment, the compound of the present invention is selected from:

N-(6-(4-isopropyl-4H-1,2,4-triazol-3-yl)pyridin-2-yl)-3-methoxy-1-methyl-1H-pyrazole-4-carboxamide;
N-(6-(4-isopropyl-4H-1,2,4-triazol-3-yl)pyridin-2-yl)-1-methyl-1H-pyrazole-4-carboxamide;
3-ethoxy-N-(6-(4-isopropyl-4H-1,2,4-triazol-3-yl)pyridin-2-yl)-1-methyl-1H-pyrazole-4-carboxamide;
N-(6-(4-isopropyl-4H-1,2,4-triazol-3-yl)pyridin-2-yl)-3-(methoxymethyl)-1-methyl-1H-pyrazole-4-carboxamide;
N-(6-(4-isopropyl-4H-1,2,4-triazol-3-yl)pyridin-2-yl)-1-methyl-3-(trifluoromethyl)-1H-pyrazole-4-carboxamide;
3-(difluoromethyl)-N-(6-(4-isopropyl-4H-1,2,4-triazol-3-yl)pyridin-2-yl)-1-methyl-1H-pyrazole-4-carboxamide;
1-ethyl-N-(6-(4-isopropyl-4H-1,2,4-triazol-3-yl)pyridin-2-yl)-3-methoxy-1H-pyrazole-4-carboxamide;
1-benzyl-N-(6-(4-isopropyl-4H-1,2,4-triazol-3-yl)pyridin-2-yl)-3-methoxy-1H-pyrazole-4-carboxamide;
1-(tert-butyl)-N-(6-(4-isopropyl-4H-1,2,4-triazol-3-yl)pyridin-2-yl)-1H-pyrazole-4-carboxamide;
3-methoxy-1-methyl-N-(6-(4-(1,1,1-trifluoropropan-2-yl)-4H-1,2,4-triazol-3-yl)pyridin-2-yl)-1H-pyrazole-4-carboxamide;
(R)-3-methoxy-1-methyl-N-(6-(4-(1,1,1-trifluoropropan-2-yl)-4H-1,2,4-triazol-3-yl)pyridin-2-yl)-1H-pyrazole-4-carboxamide;
(S)-3-methoxy-1-methyl-N-(6-(4-(1,1,1-trifluoropropan-2-yl)-4H-1,2,4-triazol-3-yl)pyridin-2-yl)-1H-pyrazole-4-carboxamide;
1-ethyl-3-methoxy-N-(6-(4-(1,1,1-trifluoropropan-2-yl)-4H-1,2,4-triazol-3-yl)pyridin-2-yl)-1H-pyrazole-4-carboxamide;
3-(methoxymethyl)-1-methyl-N-(6-(4-(1,1,1-trifluoropropan-2-yl)-4H-1,2,4-triazol-3-yl)pyridin-2-yl)-1H-pyrazole-4-carboxamide
(S)-3-(methoxymethyl)-1-methyl-N-(6-(4-(1,1,1-trifluoropropan-2-yl)-4H-1,2,4-triazol-3-yl)pyridin-2-yl)-1H-pyrazole-4-carboxamide;
(R)-3-(methoxymethyl)-1-methyl-N-(6-(4-(1,1,1-trifluoropropan-2-yl)-4H-1,2,4-triazol-3-yl)pyridin-2-yl)-1H-pyrazole-4-carboxamide;
(S)-1-ethyl-3-methoxy-N-(6-(4-(1,1,1-trifluoropropan-2-yl)-4H-1,2,4-triazol-3-yl)pyridin-2-yl)-1H-pyrazole-4-carboxamide;
(R)-1-ethyl-3-methoxy-N-(6-(4-(1,1,1-trifluoropropan-2-yl)-4H-1,2,4-triazol-3-yl)pyridin-2-yl)-1H-pyrazole-4-carboxamide;
3-ethoxy-1-methyl-N-(6-(4-(1,1,1-trifluoropropan-2-yl)-4H-1,2,4-triazol-3-yl)pyridin-2-yl)-1H-pyrazole-4-carboxamide;
(S)-3-ethoxy-1-methyl-N-(6-(4-(1,1,1-trifluoropropan-2-yl)-4H-1,2,4-triazol-3-yl)pyridin-2-yl)-1H-pyrazole-4-carboxamide;
(R)-3-ethoxy-1-methyl-N-(6-(4-(1,1,1-trifluoropropan-2-yl)-4H-1,2,4-triazol-3-yl)pyridin-2-yl)-1H-pyrazole-4-carboxamide;
N-(6-(4-cyclobutyl-4H-1,2,4-triazol-3-yl)pyridin-2-yl)-3-methoxy-1-methyl-1H-pyrazole-4-carboxamide;
N-(6-(4-cyclopropyl-4H-1,2,4-triazol-3-yl)pyridin-2-yl)-3-methoxy-1-methyl-1H-pyrazole-4-carboxamide;
N-(6-(4-(3,3-difluorocyclobutyl)-4H-1,2,4-triazol-3-yl)pyridin-2-yl)-3-methoxy-1-methyl-1H-pyrazole-4-carboxamide;
N-(6-(4-cyclopentyl-4H-1,2,4-triazol-3-yl)pyridin-2-yl)-3-methoxy-1-methyl-1H-pyrazole-4-carboxamide;
N-(6-(4-(tert-butyl)-4H-1,2,4-triazol-3-yl)pyridin-2-yl)-3-methoxy-1-methyl-1H-pyrazole-4-carboxamide;
3-(difluoromethyl)-1-methyl-N-(6-(4-(1,1,1-trifluoropropan-2-yl)-4H-1,2,4-triazol-3-yl)pyridin-2-yl)-1H-pyrazole-4-carboxamide
(S)-3-(difluoromethyl)-1-methyl-N-(6-(4-(1,1,1-trifluoropropan-2-yl)-4H-1,2,4-triazol-3-yl)pyridin-2-yl)-1H-pyrazole-4-carboxamide;
(R)-3-(difluoromethyl)-1-methyl-N-(6-(4-(1,1,1-trifluoropropan-2-yl)-4H-1,2,4-triazol-3-yl)pyridin-2-yl)-1H-pyrazole-4-carboxamide;
3-(difluoromethyl)-1-methyl-N-(6-(4-(1-(trifluoromethyl)cyclopropyl)-4H-1,2,4-triazol-3-yl)pyridin-2-yl)-1H-pyrazole-4-carboxamide;
3-methoxy-1-methyl-N-(6-(4-(1-(trifluoromethyl)cyclopropyl)-4H-1,2,4-triazol-3-yl)pyridin-2-yl)-1H-pyrazole-4-carboxamide;
N-(6-(4-(1,1-difluoropropan-2-yl)-4H-1,2,4-triazol-3-yl)pyridin-2-yl)-3-methoxy-1-methyl-1H-pyrazole-4-carboxamide;
(S)—N-(6-(4-(1,1-difluoropropan-2-yl)-4H-1,2,4-triazol-3-yl)pyridin-2-yl)-3-methoxy-1-methyl-1H-pyrazole-4-carboxamide;
(R)—N-(6-(4-(1,1-difluoropropan-2-yl)-4H-1,2,4-triazol-3-yl)pyridin-2-yl)-3-methoxy-1-methyl-1H-pyrazole-4-carboxamide;
3-methoxy-1-methyl-N-(6-(4-(3-methylbutan-2-yl)-4H-1,2,4-triazol-3-yl)pyridin-2-yl)-1H-pyrazole-4-carboxamide;
(S)-3-methoxy-1-methyl-N-(6-(4-(3-methylbutan-2-yl)-4H-1,2,4-triazol-3-yl)pyridin-2-yl)-1H-pyrazole-4-carboxamide;
(R)-3-methoxy-1-methyl-N-(6-(4-(3-methylbutan-2-yl)-4H-1,2,4-triazol-3-yl)pyridin-2-yl)-1H-pyrazole-4-carboxamide;
N-(6-(4-(2,2-difluorocyclobutyl)-4H-1,2,4-triazol-3-yl)pyridin-2-yl)-3-methoxy-1-methyl-1H-pyrazole-4-carboxamide;
(S)—N-(6-(4-(2,2-difluorocyclobutyl)-4H-1,2,4-triazol-3-yl)pyridin-2-yl)-3-methoxy-1-methyl-1H-pyrazole-4-carboxamide;
(R)—N-(6-(4-(2,2-difluorocyclobutyl)-4H-1,2,4-triazol-3-yl)pyridin-2-yl)-3-methoxy-1-methyl-1H-pyrazole-4-carboxamide;
3-methoxy-N-(6-(4-(1-methoxypropan-2-yl)-4H-1,2,4-triazol-3-yl)pyridin-2-yl)-1-methyl-1H-pyrazole-4-carboxamide;
(S)-3-methoxy-N-(6-(4-(1-methoxypropan-2-yl)-4H-1,2,4-triazol-3-yl)pyridin-2-yl)-1-methyl-1H-pyrazole-4-carboxamide;
(R)-3-methoxy-N-(6-(4-(1-methoxypropan-2-yl)-4H-1,2,4-triazol-3-yl)pyridin-2-yl)-1-methyl-1H-pyrazole-4-carboxamide;
rac-N-(6-(4-(1-hydroxypropan-2-yl)-4H-1,2,4-triazol-3-yl)pyridin-2-yl)-3-methoxy-1-methyl-1H-pyrazole-4-carboxamide;
(R)—N-(6-(4-(1-hydroxypropan-2-yl)-4H-1,2,4-triazol-3-yl)pyridin-2-yl)-3-methoxy-1-methyl-1H-pyrazole-4-carboxamide;
(S)—N-(6-(4-(1-hydroxypropan-2-yl)-4H-1,2,4-triazol-3-yl)pyridin-2-yl)-3-methoxy-1-methyl-1H-pyrazole-4-carboxamide;
tert-butyl 4-(3-(6-(3-methoxy-1-methyl-1H-pyrazole-4-carboxamido)pyridin-2-yl)-4H-1,2,4-triazol-4-yl)piperidine-1-carboxylate;
3-methoxy-1-methyl-N-(6-(4-(piperidin-3-yl)-4H-1,2,4-triazol-3-yl)pyridin-2-yl)-1H-pyrazole-4-carboxamide;
(R)-3-methoxy-1-methyl-N-(6-(4-(piperidin-3-yl)-4H-1,2,4-triazol-3-yl)pyridin-2-yl)-1H-pyrazole-4-carboxamide;

(S)-3-methoxy-1-methyl-N-(6-(4-(piperidin-3-yl)-4H-1,2,4-triazol-3-yl)pyridin-2-yl)-1H-pyrazole-4-carboxamide;

tert-butyl 3-(3-(6-(3-methoxy-1-methyl-1H-pyrazole-4-carboxamido)pyridin-2-yl)-4H-1,2,4-triazol-4-yl)pyrrolidine-1-carboxylate;

(S)-tert-butyl 3-(3-(6-(3-methoxy-1-methyl-1H-pyrazole-4-carboxamido)pyridin-2-yl)-4H-1,2,4-triazol-4-yl)pyrrolidine-1-carboxylate;

(R)-tert-butyl 3-(3-(6-(3-methoxy-1-methyl-1H-pyrazole-4-carboxamido)pyridin-2-yl)-4H-1,2,4-triazol-4-yl)pyrrolidine-1-carboxylate;

N-(6-(4-isopropyl-4H-1,2,4-triazol-3-yl)pyridin-2-yl)-3-methoxy-1-(2-methoxyethyl)-1H-pyrazole-4-carboxamide;

1-isobutyl-N-(6-(4-isopropyl-4H-1,2,4-triazol-3-yl)pyridin-2-yl)-3-methoxy-1H-pyrazole-4-carboxamide;

1-isobutyl-3-methoxy-N-(6-(4-(1,1,1-trifluoropropan-2-yl)-4H-1,2,4-triazol-3-yl)pyridin-2-yl)-1H-pyrazole-4-carboxamide;

N-(6-(4-isopropyl-4H-1,2,4-triazol-3-yl)pyridin-2-yl)-3-methoxy-1-(pyridin-2-ylmethyl)-1H-pyrazole-4-carboxamide;

1-(2-(dimethylamino)ethyl)-N-(6-(4-isopropyl-4H-1,2,4-triazol-3-yl)pyridin-2-yl)-3-methoxy-1H-pyrazole-4-carboxamide;

N-(6-(4-isopropyl-4H-1,2,4-triazol-3-yl)pyridin-2-yl)-3-methoxy-1-(2-morpholinoethyl)-1H-pyrazole-4-carboxamide;

1-(cyclopropylmethyl)-N-(6-(4-isopropyl-4H-1,2,4-triazol-3-yl)pyridin-2-yl)-3-methoxy-1H-pyrazole-4-carboxamide;

1-(cyclopropylmethyl)-3-methoxy-N-(6-(4-(1,1,1-trifluoropropan-2-yl)-4H-1,2,4-triazol-3-yl)pyridin-2-yl)-1H-pyrazole-4-carboxamide;

(S)-1-(cyclopropylmethyl)-3-methoxy-N-(6-(4-(1,1,1-trifluoropropan-2-yl)-4H-1,2,4-triazol-3-yl)pyridin-2-yl)-1H-pyrazole-4-carboxamide;

(R)-1-(cyclopropylmethyl)-3-methoxy-N-(6-(4-(1,1,1-trifluoropropan-2-yl)-4H-1,2,4-triazol-3-yl)pyridin-2-yl)-1H-pyrazole-4-carboxamide;

3-methoxy-1-methyl-N-(6-(4-(3-methyloxetan-3-yl)-4H-1,2,4-triazol-3-yl)pyridin-2-yl)-1H-pyrazole-4-carboxamide;

1-(cyclopropylmethyl)-3-(difluoromethyl)-N-(6-(4-isopropyl-4H-1,2,4-triazol-3-yl)pyridin-2-yl)-1H-pyrazole-4-carboxamide;

3-(difluoromethyl)-1-(2-methoxyethyl)-N-(6-(4-(1,1,1-trifluoropropan-2-yl)-4H-1,2,4-triazol-3-yl)pyridin-2-yl)-1H-pyrazole-4-carboxamide;

(S)-3-(difluoromethyl)-1-(2-methoxyethyl)-N-(6-(4-(1,1,1-trifluoropropan-2-yl)-4H-1,2,4-triazol-3-yl)pyridin-2-yl)-1H-pyrazole-4-carboxamide;

(R)-3-(difluoromethyl)-1-(2-methoxyethyl)-N-(6-(4-(1,1,1-trifluoropropan-2-yl)-4H-1,2,4-triazol-3-yl)pyridin-2-yl)-1H-pyrazole-4-carboxamide;

3-methoxy-1-(2-methoxyethyl)-N-(6-(4-(1,1,1-trifluoropropan-2-yl)-4H-1,2,4-triazol-3-yl)pyridin-2-yl)-1H-pyrazole-4-carboxamide;

(S)-3-methoxy-1-(2-methoxyethyl)-N-(6-(4-(1,1,1-trifluoropropan-2-yl)-4H-1,2,4-triazol-3-yl)pyridin-2-yl)-1H-pyrazole-4-carboxamide;

(R)-3-methoxy-1-(2-methoxyethyl)-N-(6-(4-(1,1,1-trifluoropropan-2-yl)-4H-1,2,4-triazol-3-yl)pyridin-2-yl)-1H-pyrazole-4-carboxamide;

N-(6-(4-cyclopropyl-4H-1,2,4-triazol-3-yl)pyridin-2-yl)-3-methoxy-1-(2-methoxyethyl)-1H-pyrazole-4-carboxamide;

1-allyl-N-(6-(4-isopropyl-4H-1,2,4-triazol-3-yl)pyridin-2-yl)-3-methoxy-1H-pyrazole-4-carboxamide;

1-allyl-3-methoxy-N-(6-(4-(1,1,1-trifluoropropan-2-yl)-4H-1,2,4-triazol-3-yl)pyridin-2-yl)-1H-pyrazole-4-carboxamide;

(S)-1-allyl-3-methoxy-N-(6-(4-(1,1,1-trifluoropropan-2-yl)-4H-1,2,4-triazol-3-yl)pyridin-2-yl)-1H-pyrazole-4-carboxamide;

(R)-1-allyl-3-methoxy-N-(6-(4-(1,1,1-trifluoropropan-2-yl)-4H-1,2,4-triazol-3-yl)pyridin-2-yl)-1H-pyrazole-4-carboxamide;

N-(6-(4-isopropyl-4H-1,2,4-triazol-3-yl)pyridin-2-yl)-3-methoxy-1-propyl-1H-pyrazole-4-carboxamide;

3-methoxy-1-propyl-N-(6-(4-(1,1,1-trifluoropropan-2-yl)-4H-1,2,4-triazol-3-yl)pyridin-2-yl)-1H-pyrazole-4-carboxamide;

N-(6-(4-isopropyl-4H-1,2,4-triazol-3-yl)pyridin-2-yl)-3-methoxy-1-phenyl-1H-pyrazole-4-carboxamide;

N-(6-(4-isopropyl-4H-1,2,4-triazol-3-yl)pyridin-2-yl)-3-methoxy-1-(pyridin-3-yl)-1H-pyrazole-4-carboxamide;

N-(6-(4-isopropyl-4H-1,2,4-triazol-3-yl)pyridin-2-yl)-3-methoxy-1-(3-methylpyridin-2-yl)-1H-pyrazole-4-carboxamide;

N-(6-(4-isopropyl-4H-1,2,4-triazol-3-yl)pyridin-2-yl)-3-methoxy-1-(pyrimidin-5-yl)-1H-pyrazole-4-carboxamide;

N-(6-(4-isopropyl-4H-1,2,4-triazol-3-yl)pyridin-2-yl)-3-methoxy-1-(pyrazin-2-yl)-1H-pyrazole-4-carboxamide;

1-(4-cyanopyridin-2-yl)-N-(6-(4-isopropyl-4H-1,2,4-triazol-3-yl)pyridin-2-yl)-3-methoxy-1H-pyrazole-4-carboxamide;

N-(6-(4-isopropyl-4H-1,2,4-triazol-3-yl)pyridin-2-yl)-3-methoxy-1-(pyridin-4-yl)-1H-pyrazole-4-carboxamide;

N-(6-(4-isopropyl-4H-1,2,4-triazol-3-yl)pyridin-2-yl)-3-methoxy-1-(5-methylpyridin-3-yl)-1H-pyrazole-4-carboxamide;

N-(6-(4-isopropyl-4H-1,2,4-triazol-3-yl)pyridin-2-yl)-3-methoxy-1-(pyridin-4-yl)-1H-pyrazole-4-carboxamide;

1-(5-cyanopyridin-3-yl)-N-(6-(4-isopropyl-4H-1,2,4-triazol-3-yl)pyridin-2-yl)-3-methoxy-1H-pyrazole-4-carboxamide;

1-(5-hydroxypyridin-3-yl)-N-(6-(4-isopropyl-4H-1,2,4-triazol-3-yl)pyridin-2-yl)-3-methoxy-1H-pyrazole-4-carboxamide;

N-(6-(4-isopropyl-4H-1,2,4-triazol-3-yl)pyridin-2-yl)-3-methoxy-1-(5-methoxypyridin-3-yl)-1H-pyrazole-4-carboxamide;

1-(5-isopropoxypyridin-3-yl)-N-(6-(4-isopropyl-4H-1,2,4-triazol-3-yl)pyridin-2-yl)-3-methoxy-1H-pyrazole-4-carboxamide;

1-(5-(dimethylamino)pyridin-3-yl)-N-(6-(4-isopropyl-4H-1,2,4-triazol-3-yl)pyridin-2-yl)-3-methoxy-1H-pyrazole-4-carboxamide;

1-(5-bromopyridin-3-yl)-3-(difluoromethyl)-N-(6-(4-isopropyl-4H-1,2,4-triazol-3-yl)pyridin-2-yl)-1H-pyrazole-4-carboxamide;

3-(difluoromethyl)-N-(6-(4-isopropyl-4H-1,2,4-triazol-3-yl)pyridin-2-yl)-1-(5-methylpyridin-3-yl)-1H-pyrazole-4-carboxamide;

1-(5-cyanopyridin-3-yl)-3-(difluoromethyl)-N-(6-(4-isopropyl-4H-1,2,4-triazol-3-yl)pyridin-2-yl)-1H-pyrazole-4-carboxamide;

1-(5-cyclopropylpyridin-3-yl)-3-(difluoromethyl)-N-(6-(4-isopropyl-4H-1,2,4-triazol-3-yl)pyridin-2-yl)-1H-pyrazole-4-carboxamide;

3-(difluoromethyl)-N-(6-(4-isopropyl-4H-1,2,4-triazol-3-yl)pyridin-2-yl)-1-(5-methoxypyridin-3-yl)-1H-pyrazole-4-carboxamide;

3-(difluoromethyl)-1-(5-(dimethylamino)pyridin-3-yl)-N-(6-(4-isopropyl-4H-1,2,4-triazol-3-yl)pyridin-2-yl)-1H-pyrazole-4-carboxamide;

3-(difluoromethyl)-1-(5-hydroxypyridin-3-yl)-N-(6-(4-isopropyl-4H-1,2,4-triazol-3-yl)pyridin-2-yl)-1H-pyrazole-4-carboxamide;

3-(difluoromethyl)-1-(5-isopropoxypyridin-3-yl)-N-(6-(4-isopropyl-4H-1,2,4-triazol-3-yl)pyridin-2-yl)-1H-pyrazole-4-carboxamide;

3-(difluoromethyl)-N-(6-(4-isopropyl-4H-1,2,4-triazol-3-yl)pyridin-2-yl)-1-(pyridin-3-yl)-1H-pyrazole-4-carboxamide;

N-(6-(4-isopropyl-4H-1,2,4-triazol-3-yl)pyridin-2-yl)-3-methoxy-1-(pyridin-2-yl)-1H-pyrazole-4-carboxamide;

N-(6-(4-isopropyl-4H-1,2,4-triazol-3-yl)pyridin-2-yl)-3-methoxy-1-(pyridazin-3-yl)-1H-pyrazole-4-carboxamide;

3-methoxy-1-(pyridazin-3-yl)-N-(6-(4-(1,1,1-trifluoropropan-2-yl)-4H-1,2,4-triazol-3-yl)pyridin-2-yl)-1H-pyrazole-4-carboxamide;

(S)-3-methoxy-1-(pyridazin-3-yl)-N-(6-(4-(1,1,1-trifluoropropan-2-yl)-4H-1,2,4-triazol-3-yl)pyridin-2-yl)-1H-pyrazole-4-carboxamide;

(R)-3-methoxy-1-(pyridazin-3-yl)-N-(6-(4-(1,1,1-trifluoropropan-2-yl)-4H-1,2,4-triazol-3-yl)pyridin-2-yl)-1H-pyrazole-4-carboxamide;

3-methoxy-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide;

(S)-3-methoxy-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide;

(R)-3-methoxy-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide;

3-(difluoromethyl)-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide;

(S)-3-(difluoromethyl)-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide;

(R)-3-(difluoromethyl)-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide;

N-(6-(1-isopropyl-1H-imidazol-5-yl)pyridin-2-yl)-3-methoxy-1-methyl-1H-pyrazole-4-carboxamide;

1-(cyclopropylmethyl)-N-(6-(1-isopropyl-1H-imidazol-5-yl)pyridin-2-yl)-3-methoxy-1H-pyrazole-4-carboxamide;

N-(6-(1-isopropyl-1H-imidazol-5-yl)pyridin-2-yl)-3-methoxy-1-(2-methoxyethyl)-1H-pyrazole-4-carboxamide;

N-(6-(1-isopropyl-1H-imidazol-5-yl)pyridin-2-yl)-3-methoxy-1-(5-methylpyridin-3-yl)-1H-pyrazole-4-carboxamide;

3-(difluoromethyl)-N-(6-(1-isopropyl-1H-imidazol-5-yl)pyridin-2-yl)-1-(pyridin-3-yl)-1H-pyrazole-4-carboxamide;

1-(5-cyanopyridin-3-yl)-3-(difluoromethyl)-N-(6-(1-isopropyl-1H-imidazol-5-yl)pyridin-2-yl)-1H-pyrazole-4-carboxamide;

1-(5-cyclopropylpyridin-3-yl)-3-(difluoromethyl)-N-(6-(1-isopropyl-1H-imidazol-5-yl)pyridin-2-yl)-1H-pyrazole-4-carboxamide;

3-(difluoromethyl)-N-(6-(1-isopropyl-1H-imidazol-5-yl)pyridin-2-yl)-1-(5-methoxypyridin-3-yl)-1H-pyrazole-4-carboxamide;

3-(difluoromethyl)-1-(5-(dimethylamino)pyridin-3-yl)-N-(6-(1-isopropyl-1H-imidazol-5-yl)pyridin-2-yl)-1H-pyrazole-4-carboxamide;

3-(difluoromethyl)-1-(5-hydroxypyridin-3-yl)-N-(6-(1-isopropyl-1H-imidazol-5-yl)pyridin-2-yl)-1H-pyrazole-4-carboxamide;

3-(difluoromethyl)-1-(5-isopropoxypyridin-3-yl)-N-(6-(1-isopropyl-1H-imidazol-5-yl)pyridin-2-yl)-1H-pyrazole-4-carboxamide;

N-(3-(1-cyclopropyl-1H-imidazol-5-yl)phenyl)-3-methoxy-1-methyl-1H-pyrazole-4-carboxamide;

N-(6-(4-isopropyl-4H-1,2,4-triazol-3-yl)pyridin-2-yl)-3-methoxy-1-(2,2,2-trifluoroethyl)-1H-pyrazole-4-carboxamide;

3-methoxy-1-(2,2,2-trifluoroethyl)-N-(6-(4-(1,1,1-trifluoropropan-2-yl)-4H-1,2,4-triazol-3-yl)pyridin-2-yl)-1H-pyrazole-4-carboxamide;

(S)-3-methoxy-1-(2,2,2-trifluoroethyl)-N-(6-(4-(1,1,1-trifluoropropan-2-yl)-4H-1,2,4-triazol-3-yl)pyridin-2-yl)-1H-pyrazole-4-carboxamide;

(R)-3-methoxy-1-(2,2,2-trifluoroethyl)-N-(6-(4-(1,1,1-trifluoropropan-2-yl)-4H-1,2,4-triazol-3-yl)pyridin-2-yl)-1H-pyrazole-4-carboxamide;

3-methoxy-N-(6-(4-(3-methylbutan-2-yl)-4H-1,2,4-triazol-3-yl)pyridin-2-yl)-1-(2,2,2-trifluoroethyl)-1H-pyrazole-4-carboxamide;

(S)-3-methoxy-N-(6-(4-(3-methylbutan-2-yl)-4H-1,2,4-triazol-3-yl)pyridin-2-yl)-1-(2,2,2-trifluoroethyl)-1H-pyrazole-4-carboxamide;

(R)-3-methoxy-N-(6-(4-(3-methylbutan-2-yl)-4H-1,2,4-triazol-3-yl)pyridin-2-yl)-1-(2,2,2-trifluoroethyl)-1H-pyrazole-4-carboxamide;

N-(6-(4-cyclopropyl-4H-1,2,4-triazol-3-yl)pyridin-2-yl)-3-methoxy-1-(2,2,2-trifluoroethyl)-1H-pyrazole-4-carboxamide;

N-(6-(1-isopropyl-1H-imidazol-5-yl)pyridin-2-yl)-3-methoxy-1-(2,2,2-trifluoroethyl)-1H-pyrazole-4-carboxamide;

3-methoxy-1-methyl-N-(6-(4-(oxetan-3-yl)-4H-1,2,4-triazol-3-yl)pyridin-2-yl)-1H-pyrazole-4-carboxamide;

3-methoxy-1-methyl-N-(6-(4-(tetrahydro-2H-pyran-4-yl)-4H-1,2,4-triazol-3-yl)pyridin-2-yl)-1H-pyrazole-4-carboxamide;

3-methoxy-1-methyl-N-(6-(4-(tetrahydrofuran-3-yl)-4H-1,2,4-triazol-3-yl)pyridin-2-yl)-1H-pyrazole-4-carboxamide;

(R)-3-methoxy-1-methyl-N-(6-(4-(tetrahydrofuran-3-yl)-4H-1,2,4-triazol-3-yl)pyridin-2-yl)-1H-pyrazole-4-carboxamide; and (S)-3-methoxy-1-methyl-N-(6-(4-(tetrahydrofuran-3-yl)-4H-1,2,4-triazol-3-yl)pyridin-2-yl)-1H-pyrazole-4-carboxamide;

or a pharmaceutically acceptable salt thereof.

In a nineteenth embodiment, the compound of the present invention is any one of the compounds disclosed in the Exemplification section as a free compound or a pharmaceutically acceptable salt thereof.

In some embodiments, the compounds of the invention or a pharmaceutically acceptable salt thereof include deuterium.

Compositions and Methods of the Invention

In another aspect, the present invention provides a pharmaceutical composition comprising at least one compound described herein, or a pharmaceutically acceptable salt thereof, and at least one pharmaceutically acceptable carrier.

The compounds or pharmaceutically acceptable salts thereof described herein may be used to decrease the activity of ASK1, or to otherwise affect the properties and/or behavior of ASK1, e.g., stability, phosphorylation, kinase activity, interactions with other proteins, etc.

One aspect of the invention includes a method of treating a disorder responsive to inhibition of ASK1 in a subject comprising administering to said subject an effective amount of at least one compound described herein, or a pharmaceutically acceptable salt thereof.

Studies have demonstrated that ASK1 is involved in ROS- or ER stress-related disease mechanisms, suggesting that ASK1 inhibitors could have a therapeutic role in various human diseases. The accumulation of misfolded proteins in the endoplasmic reticulum (ER) induces ER stress, leading to the disturbance of ER function. Unfolded-protein response (UPR) is the ER quality control system to restore function. Apoptosis signaling is induced with prolonged ER stress or malfunction of the UPR. The role for ASK1 activation in neurodegenerative disease involves both ER and oxidative stress mechanisms.

In some embodiments, the disorders responsive to inhibition of ASK1 include neurodegenerative disorders, cardiovascular diseases, metabolic (e.g. diabetes) disorders, inflammatory diseases, damage following ischemia, autoimmune disorders, destructive bone disorders, polyglutamine diseases, glutamate neurotoxicity, pain, traumatic brain injury, hemorrhagic stroke, ischemia, acute hypoxia, kidney fibrosis (renal fibrosis), kidney injury (Terada et al., Biochem Biophys Res Commun. 2007, 364(4), 1043-92007), diabetic kidney disease/diabetic nephropathy, non-alcoholic steatohepatitis (NASH), pulmonary arterial hypertension (PAH), optic neuritis, liver diseases, respiratory diseases (chronic obstructive pulmonary disease (COPD), lung injury), heart reperfusion injury (Gerczuk P Z et al., J Cardiovasc Pharmacol. 2012, 60(3), 276-82), cardiac hypertrophy, cardiac fibrosis (Yamaguchi et al., J Clin Invest. 2004, 114(7), 937-43), energy metabolic disorders, cancers (such as liver cancer, gastric cancer (Hayakawa et al., Proc Natl Acad Sci USA. 2011, 108(2), 780-5), and infection (e.g. sepsis).

In some embodiments, the invention provides a method for treating a neurodegenerative disease. In some embodiments, the neurodegenerative diseases include Alzheimer disease, hippocampal sclerosis, frontotemporal dementia (FTD), frontotemporal lobar degeneration (FTLD), Huntington's disease, corticobasal degeneration, amyotrophic lateral sclerosis, spinal muscular atrophy, motor neuron disease, inclusion body myositis, Parkinson's disease, dementia with Lewy bodies, Lewy body disease, multiple system atrophy, progressive supranuclear palsy, Pick's disease, prion diseases, traumatic brain injury, ischemic and hemorrhagic stroke, cerebral ischemia, hypoxia, and glutamate neurotoxicity. In some embodiments, the neurodegenerative disease is selected from Alzheimer's disease (AD), Parkinson's disease, Huntington's disease, and amyotrophic lateral sclerosis (ALS).

ALS is a progressive neurodegenerative disease that affects nerve cells in the brain and spinal cord. The progressive degeneration of motor neurons in ALS eventually leads to their death. When motor neurons die, the ability of the brain to initiate and control muscle movement is lost. With voluntary muscle action progressively affected, people may lose the ability to speak, eat, move, and breathe. Patients in the later stages of the disease may become totally paralyzed.

In vitro studies show that ASK1 is required for Fas receptor induced death of mouse primary motor neurons, and mutSOD1 motor neurons demonstrate increased susceptibility to death via this mechanism (Raoul et al., Neuron. 2002, 35(6), 1067-83). Mutant SOD1 protein causes motor neuron death through activation of ASK1. Activation of the ASK1 pathway is increased in mutSOD1 motor neurons, and is active early in SOD1 mouse disease progression (Wengenack et al., Brain Res. 2004, 1027(1-2), 73-86; Holsek et al., Brain Res. 2005, 1045(1-2), 185-98). In cells, ASK1 mediates cytotoxic signaling in mutSOD1 expressing cells, and the protective effect of pro-survival pathways in mutSOD1 motor neurons involves inhibition of ASK1 (Pevani et al., Mol Neurobiol. 2014, 49(1):136-48).

In transgenic mouse studies, both genetic deletion (Nishitoh et al., Genes and Dev 2008, 22(11), 1451-64) and pharmacological inhibition of ASK1 (Fujisawa et al., Hum. Mol. Genet. 2016, 25(2), 245-53) has demonstrated reduced motor neuron loss and increased/extended lifespan, as well as reduced neuroinflammation in the SOD1_G93A transgenic mouse model of ALS.

Parkinson's disease is a disorder of the nervous system that results from the loss of cells in various parts of the brain, including a region called the substantia nigra. The substantia nigra cells produce dopamine, a chemical messenger responsible for transmitting signals within the brain that allow for coordination of movement. Loss of dopamine causes neurons to fire without normal control, leaving patients less able to direct or control their movement. Parkinson's disease is one of several diseases categorized by clinicians as movement disorders.

In the mitochondrial complex 1 inhibitor MPTP (1-methyl-4-phenyl-1,2,3,6-tetrahydropyridine) model of dopaminergic cell loss, ASK1 deficient mice are shown to be relatively resistant to MPTP lesions. MPTP-induced dopamine neuron toxicity and motor impairment is also attenuated in ASK1 knock-out mice, as is neuroinflammation, suggesting protective effects of ASK1 inhibition (Lee et al., PlosOne 2012; 7(1), e29935). Abolishing ASK1 activity in another MPTP model also attenuated dopaminergic cell loss (Karunakaran et al., FASEB J. 2007, 21(9), 2226-36).

Accumulation of pathogenic proteins such as alpha-synuclein, in alpha-synucleopathies including Parkinson's disease, and its overexpression and aggregation in model systems is associated with neuroinflammation and increased oxidative stress. Alpha-synuclein transgenic mice deficient in ASK1 demonstrate improved motor function (Lee et al., NeuroBiolAging 2015, 36(1), 519-26).

Further, in 6-hydroxydopamine (6-OHDA, a toxin that causes dopaminergic cell loss) models, attenuating the ASK1 signaling cascade provides protection against dopaminergic neuron loss (Hu et al., J Neurosci. 2011, 31(1), 247-61).

AD is a type of dementia that causes problems with memory, thinking and behavior. In AD the brain cells degenerate and die, causing a steady decline in memory and mental function. AD is characterized by increased levels of amyloid-beta (ABeta) peptides and hyper-phosphorylated Tau which lead to the hallmark pathologies ABeta plaques and Tau tangles.

ASK1 activation may be associated with AD. Neurons treated with toxic ABeta peptides demonstrate increased toxicity due to oxidative stress (ROS). Exposure to ABeta peptides leads to ASK1 activation (Wang et al., J Mol Neurosci. 2015, 55(1), 227-32). ABeta-induced neuronal death via ROS-mediated ASK1 activation is a key mechanism for ABeta-induced neurotoxicity (Kadowaki et al., Cell Death Differ. 2005, 12(1), 19-24). ASK1 is also required for ROS-induced JNK activation and apoptosis.

Huntington's disease is an inherited disease that causes the progressive breakdown (degeneration) of nerve cells in the brain. Huntington's disease has a broad impact on a person's functional abilities and usually results in movement, thinking (cognitive) and psychiatric disorders. Mutations in the HTT gene cause Huntington's disease. The HTT gene provides instructions for making a protein called huntingtin. Although the function of this protein is unknown, it appears to play an important role in nerve cells (neurons) in the brain.

The HTT mutation that causes Huntington's disease involves a DNA segment known as a CAG trinucleotide repeat. This segment is made up of a series of three DNA building blocks (cytosine, adenine, and guanine) that appear multiple times in a row. Normally, the CAG segment is repeated 10 to 35 times within the gene. In people with Huntington's disease, the CAG segment is repeated 36 to more than 120 times. People with 36 to 39 CAG repeats may or may not develop the signs and symptoms of Huntington's disease, while people with 40 or more repeats almost always develop the disorder. During protein synthesis, the expanded CAG repeats are translated into a series of uninterrupted glutamine residues forming what is known as a polyglutamine tract ("polyQ"). Such polyglutamine tracts may be subject to increased aggregation.

Studies have shown that ASK1 is essential for endoplasmic reticulum stress-induced neuronal cell death triggered by expanded polyglutamine repeats. (Nishitoh et al., Genes Dev. 2002, 16(11), 1345-55).

Another embodiment of the invention includes a method for treating an autoimmune disease in a subject comprising administering to the subject a therapeutically effective amount of a compound disclosed herein, or a pharmaceutically acceptable salt thereof.

In some embodiments, the autoimmune disease is selected from rheumatoid arthritis, systemic lupus erythematosus, multiple sclerosis, diabetes, systemic sclerosis, Grave's disease, Guillain-Barre syndrome, myasthenia gravis, psoriasis, Crohn's disease, ulcerative colitis, optic neuritis, and Sjogren's syndrome.

In some embodiments, the autoimmune disease is multiple sclerosis (MS).

Multiple sclerosis (MS) involves an immune-mediated process in which an abnormal response of the body's immune system is directed against the central nervous system (CNS), which is made up of the brain, spinal cord and optic nerves. The immune system attacks, myelin, which surrounds and insulates nerve fibers. When myelin is damaged, scar tissue is formed (sclerosis) which gives the disease its name. Twenty percent of MS patients initially present with optic neuritis, and 30-70% of MS patients develop optic neuritis during the course of disease (loss of visual acuity, which can lead to neuromyelitis optica severe and irreversible visual loss). Optic neuritis is inflammation of the optic nerve, which is the most common form of optic neuropathy.

In experimental autoimmune encephalomyelitis (EAE) models of inflammation, demyelination, and axonal degeneration, the severity of EAE is reduced in ASK1 deficient mice, as well as mice treated with ASK1 inhibitors. Inhibitors of ASK1 suppressed EAE-induced inflammation in both the spinal cord and optic nerves, suggesting the TLR-ASK1-p38 pathway may serve as a therapeutic target for immune-related demyelinating disorders (Guo et al., EMBOMol. Med. 2 (2010) 504-515; Azuchi et al., Neurosci Lett. 2017, 639, 82-87).

In some embodiments, the invention provides a method of treating a cardiovascular disease in a subject comprising administering to the subject a therapeutically effective amount of a compound disclosed herein, or a pharmaceutically acceptable salt thereof.

Cardiovascular diseases refer to diseases of the cardio-vasculature (heart and blood vessels) arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, atherosclerosis, and intermittent claudication. Cardiovascular diseases also include diseases associated with malfunction of heart valves which do not allow sufficient amount of blood to flow through (such as valvular stenosis, valvular insufficiency or regurgitation, congenital valve disease, bicuspid aortic valve disease, or acquired valve disease).

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

In another embodiment, the invention provides a method for treating ischemia in a subject comprising administering to the subject a therapeutically effective amount of a compound disclosed herein, or a pharmaceutically acceptable salt thereof.

Activation of ASK1 by reactive oxygen species (ROS) has been linked to vascular injury and neuronal death following cerebral ischemia. Studies show that induction of ASK1 expression promotes apoptotic cell death following ischemia and silencing ASK1 expression reduces cerebral infarction in the brain (Kim et al BrainRes. 2011, 1412, 73-78). The inhibition of ASK1 has been shown to exert protective effects in ischemia induced brain edema (Song et al., BrainRes. 2015, 1595, 143-155). Preventing ASK1 activation in a cerebral ischemia-reperfusion model is also shown to exert neuroprotection (Liu et al., Neuroscience. 2013, 229, 36-48).

In a middle cerebral artery (MCA) occlusion model, ASK1 inhibition showed decreased neuronal death as well as in hypoxia/reperfusion injury models (Cheon et al., Front Cell Neurosci. 2016, 10, 213).

Stroke occurs when blood flow to an area of the brain is cut off. When this happens, brain cells are deprived of oxygen and begin to die. A hemorrhagic stroke is either a brain aneurysm burst or a weakened blood vessel leak. Intracerebral hemorrhage, a more common hemorrhagic stroke, happens when a blood vessel inside the brain bursts and leaks blood into surrounding brain tissue. Subarachnoid hemorrhage involves bleeding in the area between the brain and the tissue covering the brain, known as the subarachnoid space. This type of stroke is most often caused by a burst aneurysm. Cerebral (or brain) ischemia is a condition that occurs when there is not enough blood flow to the brain to meet metabolic demand, and can be considered a subtype of stroke. This results in limited oxygen supply or cerebral hypoxia and leads to the death of brain tissue, cerebral infarction, or ischemic stroke. Ischemic stroke occurs when a blood vessel carrying blood to the brain is blocked by a blood clot. Embolic and thrombotic stroke are ways in which an ischemic stroke can occur. In an embolic stroke, a blood clot or plaque fragment forms somewhere in the body (usually the heart) and travels to the brain. Once in the brain, the clot travels to a blood vessel small enough to block its passage. A thrombotic stroke is caused by a blood clot that forms inside one of the arteries supplying blood to the brain.

In some embodiments, the invention provides a method of treating stroke in a subject comprising administering to the subject a therapeutically effective amount of a compound disclosed herein, or a pharmaceutically acceptable salt thereof.

Traumatic brain injury (TBI), a form of acquired brain injury, occurs when a sudden trauma causes damage to the brain. Because little can be done to reverse the initial brain damage caused by trauma, medical personnel try to stabilize an individual with TBI and focus on preventing further injury. Primary concerns include insuring proper oxygen supply to the brain and the rest of the body, maintaining adequate blood flow, and controlling blood pressure.

In some embodiments, the invention provides a method of treating traumatic brain injury in a subject comprising administering to the subject a therapeutically effective amount of a compound disclosed herein, or a pharmaceutically acceptable salt thereof.

In one embodiment, the invention provides a method for treating liver injury in a subject comprising administering to the subject a therapeutically effective amount of a compound disclosed herein, or a pharmaceutically acceptable salt thereof.

Acetaminophen (APAP) overdose is the most common form of drug-induced liver injury. JNK activation is a consequence of oxidative stress produced during APAP metabolism, resulting in hepatocyte damage with necrotic and apoptotic cell death. (Nakagawa et al., Gastroenterology. 2008, 135(4), 1311-21). It has been shown that ASK1 inhibitors protect against APAP induced liver injury (Xie et al., Toxicol Appl Pharmacol. 2015, 286(1), 1-9; He et al., Asian Pac J Trop Med. 2016, 9(3), 283-7).

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment. "A subject in need of treatment" refers to a subject that already has a disease specified herein or a subject who is at risk of developing a disease specified herein.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; and/or delaying the onset of the disease, disorder or syndrome.

The dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound or a pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATION

Example 1: N-(6-(4-Isopropyl-4H-1,2,4-triazol-3-yl)pyridin-2-yl)-3-methoxy-1-methyl-1H-pyrazole-4-carboxamide

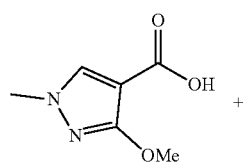

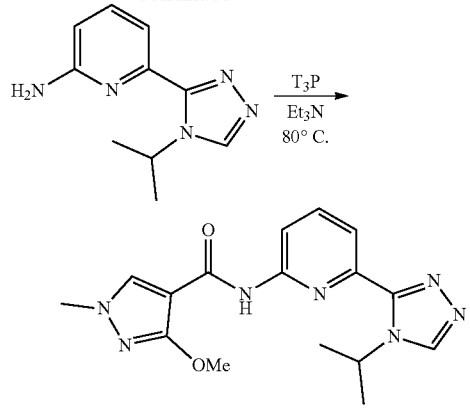

To a mixture of 6-(4-isopropyl-1,2,4-triazol-3-yl)pyridin-2-amine (72 mg, 0.35 mmol) and 3-methoxy-1-methyl-pyrazole-4-carboxylic acid (55 mg, 0.35 mmol) was added Et$_3$N (0.73 mL, 5.3 mmol) and propylphosphonic anhydride (≥50 wt % in EtOAc, 0.63 mL) and the reaction was heated at 80° C. for 4 h. After this time the mixture was quenched with a small amount of MeOH (~2 mL) and then it was partitioned between EtOAc and water. The separated aqueous layer was extracted with EtOAc and the combined organic extracts were dried over MgSO$_4$, filtered and concentrated in vacuo. The crude product was triturated with MeCN (~2 mL) and dried under vacuum to give the title compound (22 mg, 18%) as a yellow solid. $^1$H NMR (500 MHz, MeOD) δ ppm 8.85 (s, 1H), 8.34 (d, J=7.94 Hz, 1H), 7.93-8.10 (m, 2H), 7.81 (d, J=7.94 Hz, 1H), 5.29-5.62 (m, 1H), 4.10 (s, 3H), 3.81 (s, 3H), 1.64 (d, J=6.71 Hz, 6H). MS (ESI): 342.2 [M+H]$^+$.

Example 2: N-(6-(4-Isopropyl-4H-1,2,4-triazol-3-yl)pyridin-2-yl)-1-methyl-1H-pyrazole-4-carboxamide

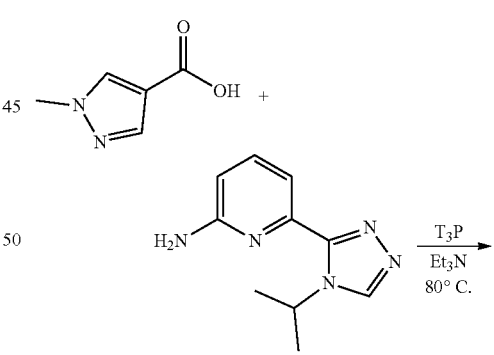

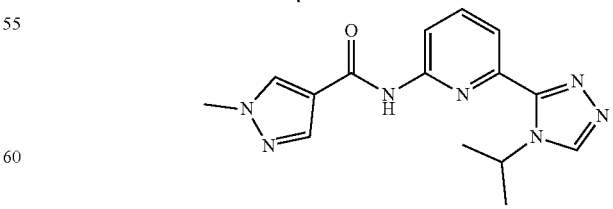

To a mixture of 6-(4-isopropyl-1,2,4-triazol-3-yl)pyridin-2-amine (61 mg, 0.30 mmol) and 1-methyl-1H-pyrazole-4-carboxylic acid (45 mg, 0.36 mmol) was added Et$_3$N (0.5 mL, 3.6 mmol) and propylphosphonic anhydride (≥50 wt % in EtOAc, 0.5 mL) and the mixture was heated at 80° C. for 4 h. After this time the reaction was quenched with a small amount of MeOH (~2 mL) and then it was partitioned between EtOAc and water. The separated aqueous layer was extracted with EtOAc and the combined organic extracts were dried over MgSO₄, filtered and concentrated in vacuo. The product was purified by normal phase column eluting with EtOAc/EtOH (3/1) to give the title compound (34 mg, 36%). ¹H NMR (400 MHz, MeOD) δ ppm 8.82 (s, 1H), 8.20-8.32 (m, 2H), 8.08 (s, 1H), 7.98 (t, J=8.03 Hz, 1H), 7.81 (d, J=7.53 Hz, 1H), 5.75 (quin, J=6.71 Hz, 1H), 3.97 (s, 3H), 1.54 (d, J=6.78 Hz, 6H). MS (ESI): 312.2 [M+H]⁺.

Example 3: 3-Ethoxy-N-(6-(4-isopropyl-4H-1,2,4-triazol-3-yl)pyridin-2-yl)-1-methyl-1H-pyrazole-4-carboxamide

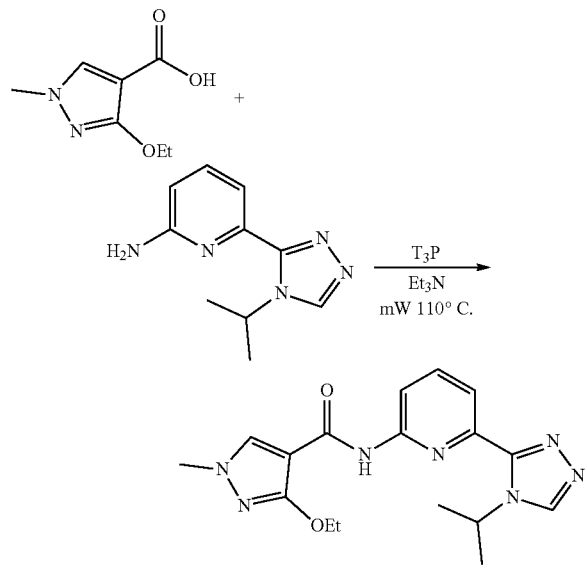

To a mixture of 6-(4-isopropyl-1,2,4-triazol-3-yl)pyridin-2-amine (39 mg, 0.19 mmol and 3-ethoxy-1-methyl-1H-pyrazole-4-carboxylic acid (34 mg, 0.20 mmol) was added Et₃N (0.3 mL, 2.16 mmol) and propylphosphonic anhydride (≥50 wt % in EtOAc, 0.3 mL) and the mixture was heated with microwave irritation at 110° C. for 1 h. After this time the reaction was quenched with a small amount of MeOH (~2 mL) and then it was partitioned between EtOAc and water. The separated aqueous layer was extracted with EtOAc and the combined organic extracts were dried over MgSO₄, filtered and concentrated in vacuo. The crude product was triturated with MeCN (~2 mL) and dried under vacuum to give the title compound as an off-white solid (20 mg, 29%). ¹H NMR (400 MHz, MeOD) δ ppm 8.84 (s, 1H), 8.38 (d, J=8.03 Hz, 1H), 7.93-8.04 (m, 2H), 7.82 (d, J=7.28 Hz, 1H), 5.54 (quin, J=6.78 Hz, 1H), 4.45 (q, J=7.03 Hz, 2H), 3.80 (s, 3H), 1.60 (d, J=6.78 Hz, 6H), 1.51 (t, J=7.03 Hz, 3H). MS (ESI): 356.2 [M+H]⁺.

Example 4: N-(6-(4-Isopropyl-4H-1,2,4-triazol-3-yl)pyridin-2-yl)-3-(methoxymethyl)-1-methyl-1H-pyrazole-4-carboxamide

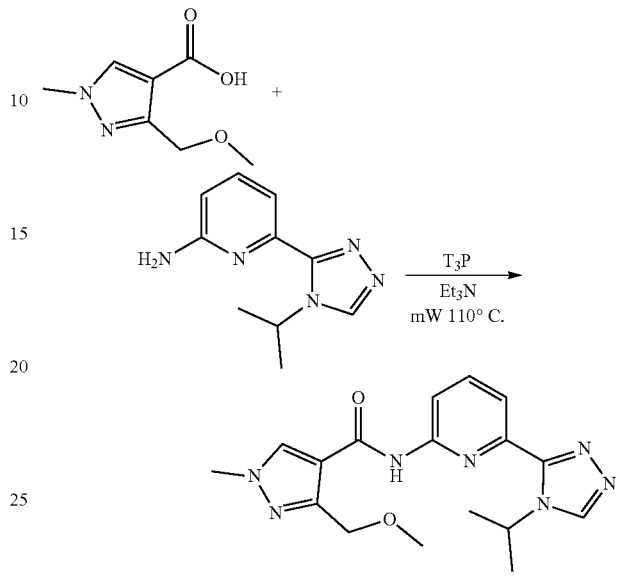

To a mixture of 6-(4-isopropyl-1,2,4-triazol-3-yl)pyridin-2-amine (30 mg, 0.15 mmol) and 3-(methoxymethyl)-1-methyl-pyrazole-4-carboxylic acid (27 mg, 0.16 mmol) was added Et₃N (328 μL, 2.37 mmol) and propylphosphonic anhydride (≥50 wt % in EtOAc, 0.25 mL) and the reaction was heated with microwave irritation at 110° C. for 1.5 h. After this time the mixture was quenched with a small amount of MeOH (~1 mL) and then it was partitioned between EtOAc and water. The separated aqueous layer was extracted with EtOAc and the combined organic extracts were dried over MgSO₄, filtered and concentrated in vacuo. The product was purified by normal phase column eluting with EtOAc/EtOH (3/1) to give the title compound as an off-white solid (34 mg, 64%). ¹H NMR (400 MHz, MeOD) δ ppm 8.84 (s, 1H), 8.31 (d, J=8.28 Hz, 1H), 8.07 (s, 1H), 8.00 (t, J=8.03 Hz, 1H), 7.84 (d, J=7.53 Hz, 1H), 5.74 (dt, J=13.36, 6.75 Hz, 1H), 4.94 (s, 2H), 3.89-4.06 (m, 3H), 3.45 (s, 3H), 1.42-1.68 (m, 6H). MS (ESI): 356.0 [M+H]⁺.

Example 5: N-(6-(4-Isopropyl-4H-1,2,4-triazol-3-yl)pyridin-2-yl)-1-methyl-3-(trifluoromethyl)-1H-pyrazole-4-carboxamide

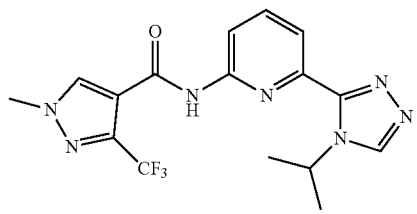 [SMILES: CC(C)n1cnnc1-c1cccc(NC(=O)c2cn(C)nc2C(F)(F)F)n1]

The product was synthesized according to the general procedure described in Example 2 but using 1-methyl-3-(trifluoromethyl)-1H-pyrazole-4-carboxylic acid in place of 1-methyl-1H-pyrazole-4-carboxylic acid to give the title compound (48 mg, 51%) as an off-white powder after lyophilization. $^1$H NMR (400 MHz, MeOD) δ ppm 8.82 (s, 1H), 8.34 (s, 1H), 8.25 (d, J=8.03 Hz, 1H), 8.00 (t, J=8.03 Hz, 1H), 7.84 (d, J=7.03 Hz, 1H), 5.71 (quin, J=6.71 Hz, 1H), 4.01 (s, 3H), 1.53 (d, J=6.78 Hz, 6H). MS (ESI): 380.1 [M+H]$^+$.

Example 6: 3-(Difluoromethyl)-N-(6-(4-isopropyl-4H-1,2,4-triazol-3-yl)pyridin-2-yl)-1-methyl-1H-pyrazole-4-carboxamide

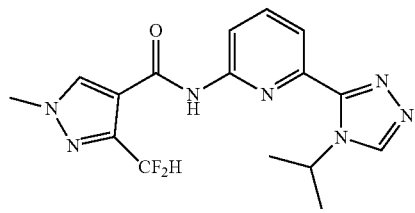 [SMILES: CC(C)n1cnnc1-c1cccc(NC(=O)c2cn(C)nc2C(F)F)n1]

The product was synthesized according to the general procedure described in Example 2 but using 3-(difluoromethyl)-1-methyl-1H-pyrazole-4-carboxylic acid in place of 1-methyl-1H-pyrazole-4-carboxylic acid to give the title compound (48 mg, 53%) as an off-white powder after lyophilization. $^1$H NMR (400 MHz, MeOD) δ ppm 8.82 (s, 1H), 8.36 (s, 1H), 8.28 (d, J=8.03 Hz, 1H), 7.99 (t, J=8.03 Hz, 1H), 7.83 (d, J=7.28 Hz, 1H), 6.97-7.43 (m, 1H), 5.69 (dt, J=13.49, 6.68 Hz, 1H), 4.00 (s, 3H), 1.55 (d, J=6.53 Hz, 6H). MS (ESI): 362.1 [M+H]$^+$.

Example 7: 1-Ethyl-N-(6-(4-isopropyl-4H-1,2,4-triazol-3-yl)pyridin-2-yl)-3-methoxy-1H-pyrazole-4-carboxamide

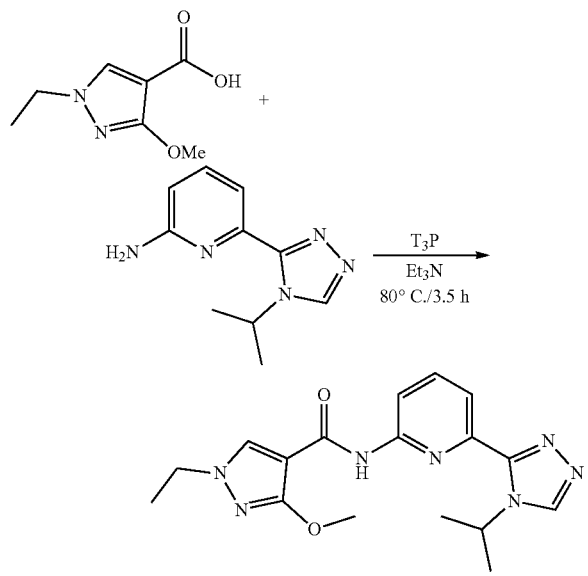

To a mixture of 6-(4-isopropyl-1,2,4-triazol-3-yl)pyridin-2-amine (102 mg, 0.5 mmol) and 1-ethyl-3-methoxy-pyrazole-4-carboxylic acid (85 mg, 0.5 mmol) was added Et$_3$N (1 mL, 7.21 mmol) and propylphosphonic anhydride (≥50 wt % in EtOAc, 1 mL) and the reaction was heated at 80° C. for 3.5 h. After this time the mixture was quenched with a small amount of MeOH (~2 mL) and then it was partitioned between EtOAc and water. The separated aqueous layer was extracted with EtOAc and the combined organic extracts were dried over MgSO$_4$, filtered and concentrated in vacuo. The crude product was triturated with MeCN (~2 mL) and dried under vacuum to give the title compound (13 mg, 7%) as a pale brown solid. $^1$H NMR (400 MHz, MeOD) δ ppm 8.85 (s, 1H), 8.34 (d, J=8.28 Hz, 1H), 8.06 (s, 1H), 7.98 (t, J=8.03 Hz, 1H), 7.81 (d, J=7.28 Hz, 1H), 5.44 (quin, J=6.78 Hz, 1H), 3.95-4.17 (m, 5H), 1.64 (d, J=6.78 Hz, 6H), 1.46 (t, J=7.28 Hz, 3H). MS (ESI): 356.2 [M+H]$^+$.

Example 8: 1-Benzyl-N-(6-(4-isopropyl-4H-1,2,4-triazol-3-yl)pyridin-2-yl)-3-methoxy-1H-pyrazole-4-carboxamide

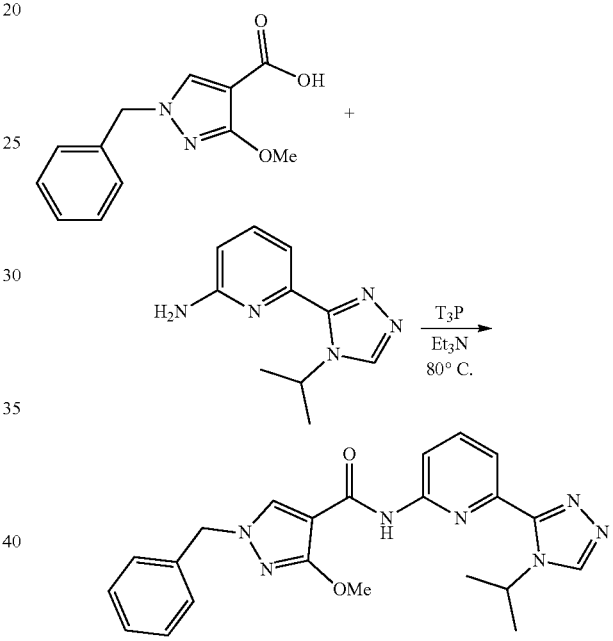

To a mixture of 6-(4-isopropyl-1,2,4-triazol-3-yl)pyridin-2-amine (203 mg, 1.00 mmol) and 1-benzyl-3-methoxy-1H-pyrazole-4-carboxylic acid (232 mg, 1.00 mmol) was added Et$_3$N (2 mL 14.4 mmol) and propylphosphonic anhydride (≥50 wt % in EtOAc, 2 mL) and the mixture was heated at 80° C. for 4 h. After this time the reaction was quenched with a small amount of MeOH (~2 mL) and then it was partitioned between EtOAc and satd. NaHCO$_3$. The separated aqueous layer was extracted with EtOAc and the combined organic extracts were dried over MgSO$_4$, filtered and concentrated in vacuo. The crude product was triturated with MeCN (~5 mL) and dried under vto give the title compound (142 mg, 34%) as a pale brown solid. $^1$H NMR (400 MHz, MeOD) δ ppm 8.87 (s, 1H), 8.36 (d, J=8.03 Hz, 1H), 8.13 (s, 1H), 8.00 (t, J=8.03 Hz, 1H), 7.83 (d, J=7.03 Hz, 1H), 7.29-7.45 (m, 5H), 5.46 (quin, J=6.78 Hz, 1H), 5.26 (s, 2H), 4.12 (s, 3H), 1.65 (d, J=6.78 Hz, 6H). MS (ESI): 418.0 [M+H]$^+$.

Example 9: 1-(tert-Butyl)-N-(6-(4-isopropyl-4H-1,2,4-triazol-3-yl)pyridin-2-yl)-1H-pyrazole-4-carboxamide

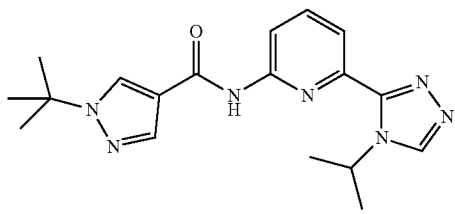 [SMILES: CC(C)n1cnnc1-c1cccc(NC(=O)c2cnn(C(C)(C)C)c2)n1]

The product was synthesized according to the general procedure described in Example 2 but using 1-(tert-butyl)-1H-pyrazole-4-carboxylic acid in place of 1-methyl-1H-pyrazole-4-carboxylic acid to give the title compound (63 mg, 75%) as an off-white solid. $^1$H NMR (400 MHz, MeOD) δ ppm 8.82 (s, 1H), 8.47 (s, 1H), 8.26 (d, J=8.03 Hz, 1H), 8.11 (s, 1H), 7.98 (t, J=8.03 Hz, 1H), 7.80 (d, J=7.28 Hz, 1H), 5.75 (dt, J=13.49, 6.68 Hz, 1H), 1.64 (s, 9H), 1.54 (d, J=6.78 Hz, 6H). MS (ESI): 354.2 [M+H]$^+$.

Example 10: 3-Methoxy-1-methyl-N-(6-(4-(1,1,1-trifluoropropan-2-yl)-4H-1,2,4-triazol-3-yl)pyridin-2-yl)-1H-pyrazole-4-carboxamide

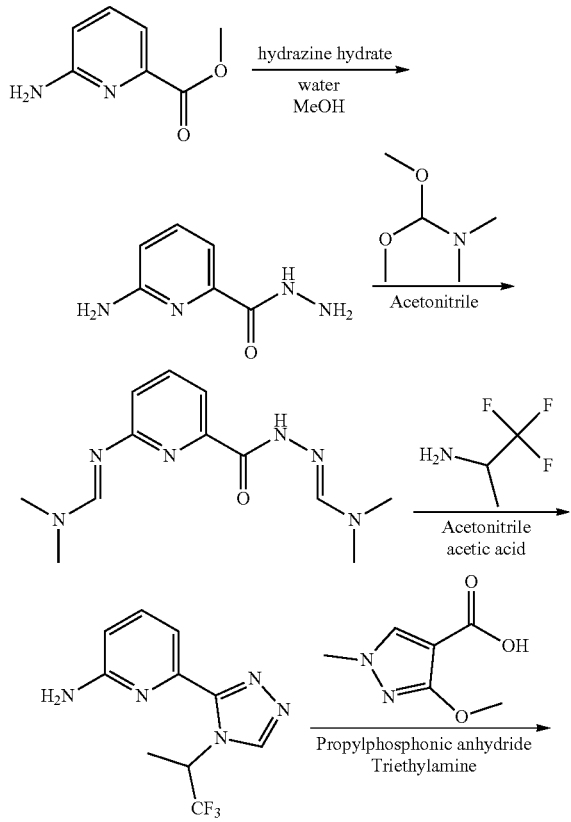

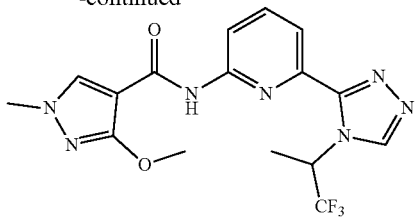

Step A: 6-Aminopicolinohydrazide

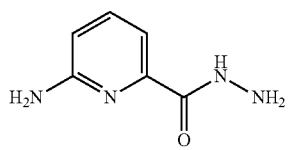 [SMILES: NNC(=O)c1cccc(N)n1]

A solution of methyl 6-aminopicolinate (1.0 g, 6.6 mmol), hydrazine hydrate (2.3 g, 23 mmol, 2.2 mL, 50% purity) in water (3 mL) and MeOH (3 mL) was heated at 100° C. for 2 h. After this time, the volatiles were removed under reduced pressure to afford a white product which was co-evaporated with toluene (40 mL) to give the title compound (980 mg, 98%).

Step B: (E)-N'-(6-(2-((E)-(Dimethylamino)methylene)hydrazine-1-carbonyl)pyridin-2-yl)-N,N-dimethylformimidamide

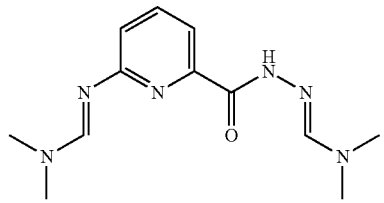

1,1-Dimethoxy-N,N-dimethyl-methanamine (2.6 mL, 19.7 mmol) was added to 6-aminopicolinohydrazide (1.0 g, 6.6 mmol) and MeCN (10 mL) at rt and the reaction was heated at 75° C. and stirred for 4 h. The reaction was cooled to rt and filtered to give the title compound (1.5 g, 87%). MS (ESI): 263.0 [M+H]$^+$.

Step C: 6-(4-(1,1,1-Trifluoropropan-2-yl)-4H-1,2,4-triazol-3-yl)pyridin-2-amine

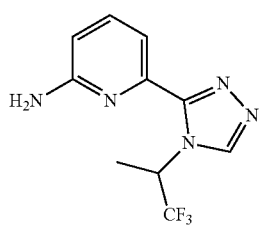 [SMILES: CC(n1cnnc1-c1cccc(N)n1)C(F)(F)F]

(E)-N'-(6-(2-((E)-(dimethylamino)methylene)hydrazine-1-carbonyl)pyridin-2-yl)-N,N-dimethylformimidamide (1.5 g, 5.7 mmol) and 1,1,1-trifluoropropan-2-amine (1.4 g, 12.8 mmol) were dissolved in MeCN (9 mL). Acetic acid (3 mL) was then added and the resulting mixture was heated in a sealed tube at 120° C. overnight. After this time the reaction was concentrated, dissolved in EtOAc and washed with NaHCO₃ (saturated aqueous solution). The separated organic phase was dried over MgSO₄, filtered and concentrated to give the crude product as a colorless oil. Purification by silica gel chromatography (EtOAc) gave the title compound (1.40 g, 95%) as a white solid. ¹H NMR (400 MHz, MeOD) δ ppm 8.91 (s, 1H), 7.57 (dd, J=8.4, 7.4 Hz, 1H), 7.34 (dd, J=7.3, 0.8 Hz, 1H), 6.99 (quin, J=7.3 Hz, 1H), 6.65 (dd, J=8.4, 0.9 Hz, 1H), 1.84 (d, J=7.3 Hz, 3H), MS (ESI): 258.2 [M+H]⁺.

Step D: 3-Methoxy-1-methyl-N-(6-(4-(1,1,1-trifluoropropan-2-yl)-4H-1,2,4-triazol-3-yl)pyridin-2-yl)-1H-pyrazole-4-carboxamide

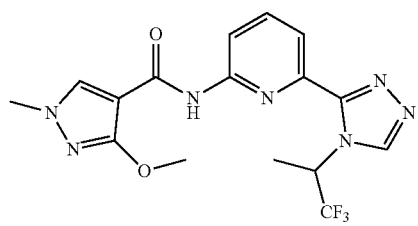 [SMILES: COc1nn(C)cc1C(=O)Nc1cccc(-c2nncn2C(C)C(F)(F)F)n1]

3-Methoxy-1-methyl-pyrazole-4-carboxylic acid (704 mg, 4.5 mmol) and 6-(4-(1,1,1-trifluoropropan-2-yl)-4H-1,2,4-triazol-3-yl)pyridin-2-amine (1.1 g, 4.5 mmol) were dissolved in Et₃N (6.2 mL, 45 mmol). Propylphosphonic anhydride (≥50 wt % in EtOAc, 4.6 mL) was then added and the reaction heated at 80° C. for 3 h. After this time, the reaction was cooled to rt and quenched by addition of MeOH (5 mL). The resulting solid was dried under vacuum to give the title compound (110 mg, 62%). ¹H NMR (400 MHz, CDCl₃) δ ppm 9.17 (s, 1H), 8.44 (s, 1H), 8.39 (dd, J=8.5, 0.8 Hz, 1H), 8.07 (dd, J=7.5, 0.8 Hz, 1H), 7.80-7.94 (m, 2H), 6.74 (quin, J=7.2 Hz, 1H), 4.09 (s, 3H), 3.81 (s, 3H), 1.81 (d, J=7.0 Hz, 3H). MS (ESI): 396.1 [M+H]⁺.

Example 11: (R)-3-Methoxy-1-methyl-N-(6-(4-(1,1,1-trifluoropropan-2-yl)-4H-1,2,4-triazol-3-yl)pyridin-2-yl)-1H-pyrazole-4-carboxamide

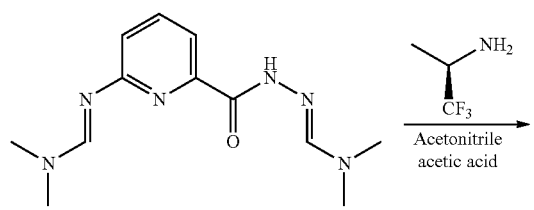

Step A: (R)-6-(4-(1,1,1-Trifluoropropan-2-yl)-4H-1,2,4-triazol-3-yl)pyridin-2-amine

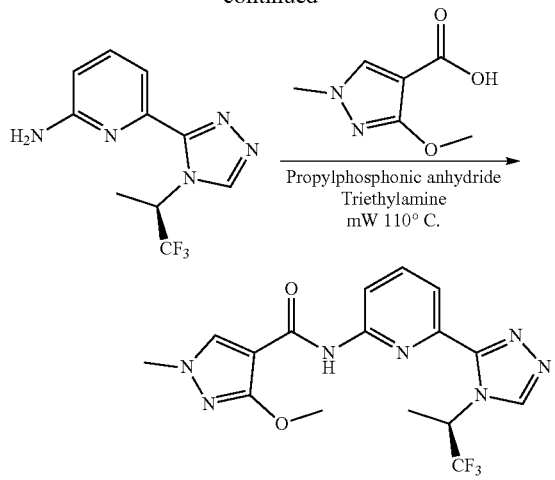

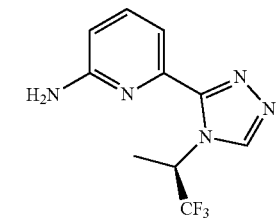 [SMILES: C[C@@H](n1cnnc1-c1cccc(N)n1)C(F)(F)F]

N,6-bis[(E)-dimethylaminomethyleneamino]pyridine-2-carboxamide (1.0 g, 3.8 mmol) and (2R)-1,1,1-trifluoropropan-2-amine (966 mg, 8.5 mmol) were dissolved in MeCN (9 mL). Acetic acid (3 mL) was then added, and the resulting mixture was heated in a sealed tube at 120° C. overnight. After this time, the reaction was concentrated, dissolved in EtOAc and washed with NaHCO₃ (saturated aqueous solution). The separated organic phase was dried over MgSO₄, filtered and concentrated in vacuo to give the crude title product as a colorless oil. It was purified by silica gel chromatography (EtOAc 100%) to give the title compound as a white solid (860 mg, 88%).

Step B: (R)-3-Methoxy-1-methyl-N-(6-(4-(1,1,1-trifluoropropan-2-yl)-4H-1,2,4-triazol-3-yl)pyridin-2-yl)-1H-pyrazole-4-carboxamide

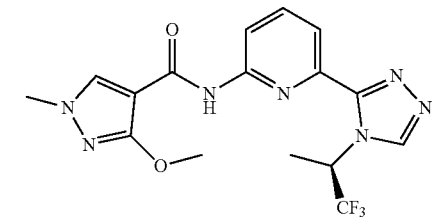 [SMILES: COc1nn(C)cc1C(=O)Nc1cccc(-c2nncn2[C@H](C)C(F)(F)F)n1]

To a mixture of 6-[(4R)-4-(2,2,2-trifluoro-1-methylethyl)-1,2,4-triazol-3-yl]pyridin-2-amine (48 mg, 0.19 mmol) and 3-methoxy-1-methyl-pyrazole-4-carboxylic acid (32 mg, 0.21 mmol) in Et₃N (0.3 mL, 2.2 mmol) was added propylphosphonic anhydride (≥50 wt % in EtOAc, 0.3 mL). The mixture was heated with microwave irritation at 110° C. for 1 h. After this time, the mixture was quenched with a small amount of MeOH (~0.5 mL) and then it was partitioned between EtOAc and water. The aqueous layer was extracted with EtOAc and the combined organic extracts were dried over MgSO₄, filtered and concentrated in vacuo. The crude product was triturated with MeCN (~1 mL) and dried under vacuum to give the title compound as an off-white solid (26 mg, 35%). ¹H NMR (400 MHz, MeOD) δ ppm 9.01 (s, 1H), 8.33 (dd, J=8.16, 0.88 Hz, 1H), 7.81-8.08 (m, 3H), 6.79 (quin, J=7.22 Hz, 1H), 4.10 (s, 3H), 3.81 (s, 3H), 1.87 (d, J=7.28 Hz, 3H). MS (ESI): 396.1 [M+H]⁺.

Example 12: (S)-3-Methoxy-1-methyl-N-(6-(4-(1,1,1-trifluoropropan-2-yl)-4H-1,2,4-triazol-3-yl)pyridin-2-yl)-1H-pyrazole-4-carboxamide

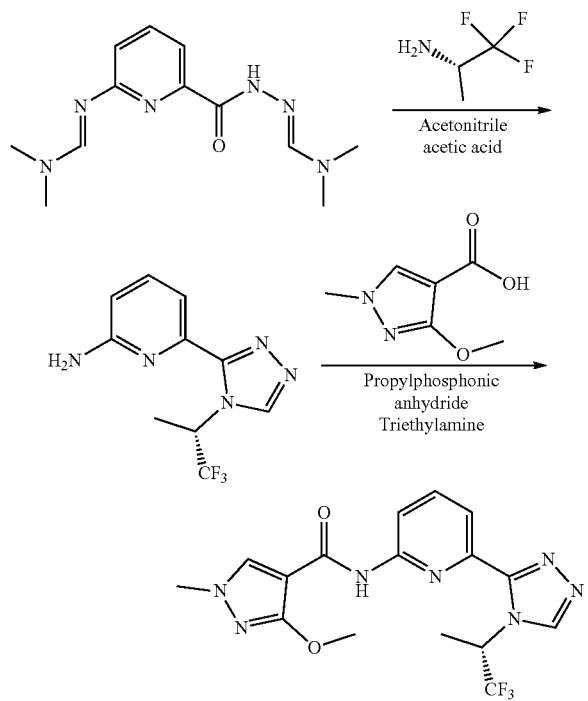

Step A: (S)-6-(4-(1,1,1-Trifluoropropan-2-yl)-4H-1,2,4-triazol-3-yl)pyridin-2-amine

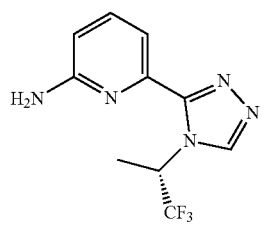 [SMILES: C[C@H](n1cnnc1-c1cccc(N)n1)C(F)(F)F]

N,6-bis[(E)-dimethylaminomethyleneamino]pyridine-2-carboxamide (650 mg, 2.5 mmol) and (2S)-1,1,1-trifluoropropan-2-amine (628 mg, 5.5 mmol) were dissolved in MeCN (9.0 mL). Acetic acid (3.0 mL) was then added and the resulting mixture was heated in a sealed tube at 120° C. overnight. After this time, the reaction was concentrated, dissolved in EtOAc and washed with NaHCO₃ (saturated aqueous solution). The separated organic phase was dried over MgSO₄, filtered and concentrated in vacuo to give the crude product as a colorless oil. Purification by silica gel chromatography (EtOAc, 100%) gave the title compound (580 mg, 91%) as a white solid. ¹H NMR (400 MHz, MeOD) δ ppm 8.91 (s, 1H), 7.57 (dd, J=8.4, 7.4 Hz, 1H), 7.34 (dd, J=7.3, 0.8 Hz, 1H), 6.99 (quin, J=7.3 Hz, 1H), 6.65 (dd, J=8.4, 0.9 Hz, 1H), 1.84 (d, J=7.3 Hz, 3H), MS (ESI): 258.2 [M+H]⁺.

Step B: (S)-3-Methoxy-1-methyl-N-(6-(4-(1,1,1-trifluoropropan-2-yl)-4H-1,2,4-triazol-3-yl)pyridin-2-yl)-1H-pyrazole-4-carboxamide

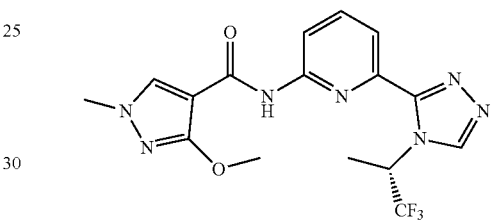

3-Methoxy-1-methyl-pyrazole-4-carboxylic acid (515 mg, 3.3 mmol) and (S)-6-(4-(1,1,1-trifluoropropan-2-yl)-4H-1,2,4-triazol-3-yl)pyridin-2-amine (850 mg, 3.3 mmol) were dissolved in Et₃N (4.6 mL, 33.0 mmol). Propylphosphonic anhydride (≥50 wt % in EtOAc, 3.4 mL) was then added and the reaction was heated at 80° C. for 3 h. After this time, the reaction was cooled to rt and quenched by addition of MeOH (2 mL). The resulting solid was filtered and dried under vacuum to give the title compound (950 mg, 73%) as a white solid. ¹H NMR (400 MHz, MeOD) δ ppm 9.01 (s, 1H), 8.33 (dd, J=8.16, 0.88 Hz, 1H), 7.81-8.08 (m, 3H), 6.79 (quin, J=7.22 Hz, 1H), 4.10 (s, 3H), 3.81 (s, 3H), 1.87 (d, J=7.28 Hz, 3H). MS (ESI): 396.1 [M+H]⁺.

Example 13: 1-Ethyl-3-methoxy-N-(6-(4-(1,1,1-trifluoropropan-2-yl)-4H-1,2,4-triazol-3-yl)pyridin-2-yl)-1H-pyrazole-4-carboxamide

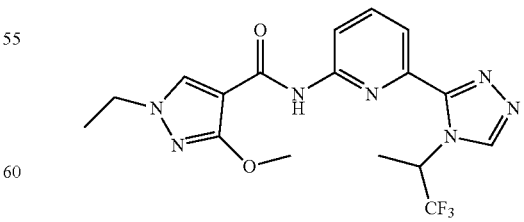

The product was synthesized according to the general procedure described in Example 2 but using 1-ethyl-3-methoxy-1H-pyrazole-4-carboxylic acid in place of 1-methyl-1H-pyrazole-4-carboxylic acid and 6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine to give the title compound (17 mg, 22%) as an off-white solid. ¹H NMR (400 MHz, MeOD) δ ppm 9.01 (s, 1H), 8.34 (d, J=7.28 Hz, 1H), 8.06 (s, 1H), 7.81-8.04 (m, 2H), 6.79 (quin, J=7.15 Hz, 1H), 3.99-4.21 (m, 5H), 1.87 (d, J=7.28 Hz, 3H), 1.46 (t, J=7.28 Hz, 3H). MS (ESI): 410.0 [M+H]⁺.

Example 14: ((S)-3-(Methoxymethyl)-1-methyl-N-(6-(4-(1,1,1-trifluoropropan-2-yl)-4H-1,2,4-triazol-3-yl)pyridin-2-yl)-1H-pyrazole-4-carboxamide

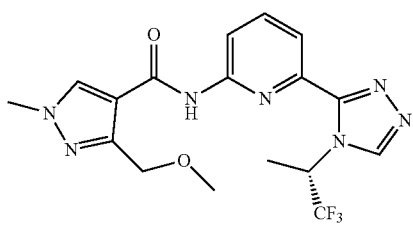 [SMILES: COCc1nn(C)cc1C(=O)Nc1cccc(-c2nncn2[C@@H](C)C(F)(F)F)n1]

The product was synthesized according to the general procedure described in Example 3 but using 3-(methoxymethyl)-1-methyl-1H-pyrazole-4-carboxylic acid in place of 3-ethoxy-1-methyl-pyrazole-4-carboxylic acid and (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine to give the title compound (27 mg, 66%) as an off-white solid. ¹H NMR (400 MHz, MeOD) δ ppm 9.00 (s, 1H), 8.22 (dd, J=8.16, 0.88 Hz, 1H), 7.81-8.13 (m, 3H), 7.16 (dt, J=14.56, 7.28 Hz, 1H), 4.94 (s, 2H), 3.96 (s, 3H), 3.42 (s, 3H), 1.89 (d, J=7.28 Hz, 3H). MS (ESI): 410.0 [M+H]⁺.

Example 15: (S)-1-Ethyl-3-methoxy-N-(6-(4-(1,1,1-trifluoropropan-2-yl)-4H-1,2,4-triazol-3-yl)pyridin-2-yl)-1H-pyrazole-4-carboxamide

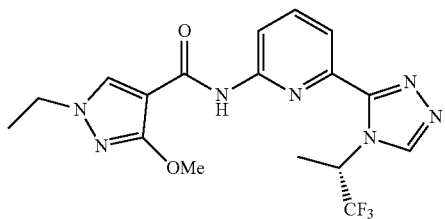 [SMILES: CCn1cc(C(=O)Nc2cccc(-c3nncn3[C@@H](C)C(F)(F)F)n2)c(OC)n1]

The product was synthesized according to the general procedure described in Example 4 but using 1-ethyl-3-methoxy-1H-pyrazole-4-carboxylic acid in place of 3-(methoxymethyl)-1-methyl-pyrazole-4-carboxylic acid and (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine to give the title compound (11 mg, 18%) as an off-white solid. ¹H NMR (400 MHz, MeOD) δ ppm 9.01 (s, 1H), 8.33 (dd, J=8.16, 0.88 Hz, 1H), 8.06 (s, 1H), 7.84-8.03 (m, 2H), 6.79 (quin, J=7.22 Hz, 1H), 4.00-4.15 (m, 5H), 1.87 (d, J=7.28 Hz, 3H), 1.46 (t, J=7.28 Hz, 3H). MS (ESI): 410.2 [M+H]⁺.

Example 16: (S)-3-Ethoxy-1-methyl-N-(6-(4-(1,1,1-trifluoropropan-2-yl)-4H-1,2,4-triazol-3-yl)pyridin-2-yl)-1H-pyrazole-4-carboxamide

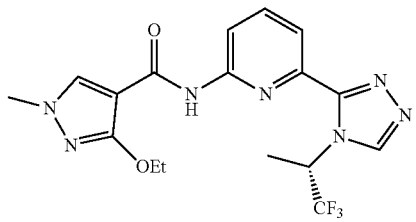 [SMILES: CCOc1nn(C)cc1C(=O)Nc1cccc(-c2nncn2[C@@H](C)C(F)(F)F)n1]

The product was synthesized according to the general procedure described in Example 3 but using (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine to give the title compound (26 mg, 49%) as an off-white solid. ¹H NMR (400 MHz, MeOD) δ ppm 9.02 (s, 1H), 8.37 (dd, J=8.16, 0.88 Hz, 1H), 7.88-8.10 (m, 3H), 6.75 (quin, J=7.22 Hz, 1H), 4.46 (dtt, J=10.54, 7.03, 7.03, 3.39, 3.39 Hz, 2H), 3.80 (s, 3H), 1.88 (d, J=7.03 Hz, 3H), 1.51 (t, J=7.03 Hz, 3H). MS (ESI): 410.2 [M+H]⁺.

Example 17: N-(6-(4-Cyclobutyl-4H-1,2,4-triazol-3-yl)pyridin-2-yl)-3-methoxy-1-methyl-1H-pyrazole-4-carboxamide

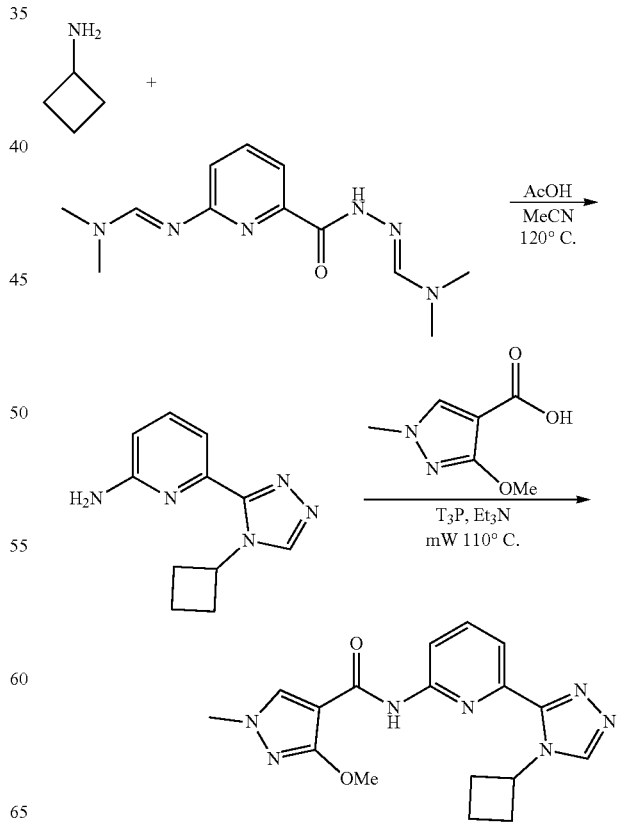

Step A: 6-(4-Cyclobutyl-4H-1,2,4-triazol-3-yl)pyridin-2-amine

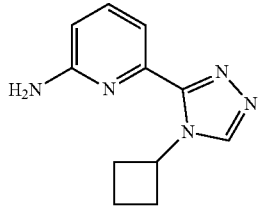 [SMILES: Nc1cccc(-c2nncn2C2CCC2)n1]

To a mixture of (E)-N'-(6-(2-((E)-(dimethylamino)methylene)hydrazine-1-carbonyl)pyridin-2-yl)-N,N-dimethylformimidamide (263 mg, 1.00 mmol) and cyclobutanamine (171 µL, 2.00 mmol) in a microwave tube was added MeCN (3 mL), followed by acetic acid (1 mL). The mixture was heated in a hot plate at 120° C. for 24 h. After this time, the reaction was partitioned between EtOAc and satd. NaHCO₃. The aqueous layer was extracted by EtOAc and the combined organic extracts were dried over MgSO₄, filtered and concentrated in vacuo. The product was purified by normal phase column chromatography eluting with 100% EtOAc to give the title compound (188 mg, 87%). $^1$H NMR (400 MHz, MeOD) δ ppm 8.79 (s, 1H), 7.55 (dd, J=8.28, 7.53 Hz, 1H), 7.17 (d, J=7.28 Hz, 1H), 6.64 (d, J=8.28 Hz, 1H), 5.38-5.59 (m, 1H), 2.48-2.67 (m, 2H), 2.39 (quind, J=9.57, 9.57, 9.57, 9.57, 2.64 Hz, 2H), 1.79-1.99 (m, 2H). MS (ESI): 216.0 [M+H]⁺.

Step B: N-(6-(4-Cyclobutyl-4H-1,2,4-triazol-3-yl)pyridin-2-yl)-3-methoxy-1-methyl-1H-pyrazole-4-carboxamide

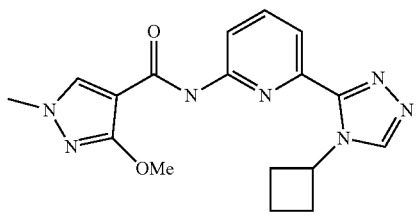 [SMILES: COc1nn(C)cc1C(=O)Nc1cccc(-c2nncn2C2CCC2)n1]

The product was synthesized according to the general procedure described in Example 3 but using 3-methoxy-1-methyl-1H-pyrazole-4-carboxylic acid in place of 3-ethoxy-1-methyl-1H-pyrazole-4-carboxylic acid and 6-(4-cyclobutyl-4H-1,2,4-triazol-3-yl)pyridin-2-amine in place of 6-(4-isopropyl-1,2,4-triazol-3-yl)pyridin-2-amine to give the title compound (18 mg, 27%) as an off-white solid (18 mg, 27%). $^1$H NMR (400 MHz, MeOD) δ ppm 8.88 (s, 1H), 8.34 (d, J=8.28 Hz, 1H), 8.02 (s, 1H), 7.96 (t, J=8.03 Hz, 1H), 7.82 (d, J=7.53 Hz, 1H), 5.44 (quin, J=8.53 Hz, 1H), 4.12 (s, 3H), 3.81 (s, 3H), 2.59-2.73 (m, 2H), 2.42-2.59 (m, 2H), 1.86-2.15 (m, 2H). MS (ESI): 354.1 [M+H]⁺.

Example 18: N-(6-(4-Cyclopropyl-4H-1,2,4-triazol-3-yl)pyridin-2-yl)-3-methoxy-1-methyl-1H-pyrazole-4-carboxamide

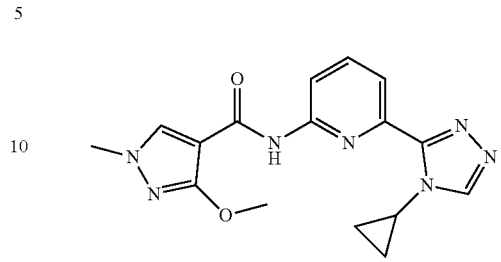

The product was synthesized according to the general procedure described in Example 17 but using cyclopropamine in place of cyclobutanamine in Step A to give the title compound (10 mg, 17%) as an off-white solid. $^1$H NMR (500 MHz, MeOD) δ ppm 8.63 (s, 1H), 8.34 (d, J=8.55 Hz, 1H), 7.89-8.17 (m, 2H), 7.81 (d, J=7.32 Hz, 1H), 4.08 (s, 3H), 3.86-3.94 (m, 1H), 3.81 (s, 3H), 1.12-1.24 (m, 2H), 0.92-1.12 (m, 2H). MS (ESI): 340.1 [M+H]⁺.

Example 19: N-(6-(4-(3,3-Difluorocyclobutyl)-4H-1,2,4-triazol-3-yl)pyridin-2-yl)-3-methoxy-1-methyl-1H-pyrazole-4-carboxamide

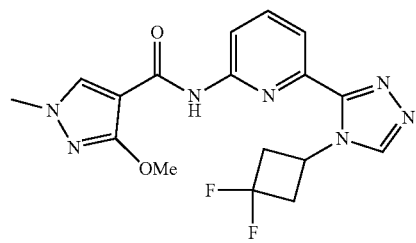 [SMILES: COc1nn(C)cc1C(=O)Nc1cccc(-c2nncn2C2CC(F)(F)C2)n1]

The product was synthesized according to the general procedure described in Example 17 but using 3,3-difluorocyclobutan-1-amine in place of cyclobutanamine in Step A to give the title compound (14 mg, 24% for the last step) as an off-white solid. $^1$H NMR (400 MHz, MeOD) δ ppm 8.93 (s, 1H), 8.36 (dd, J=8.16, 0.88 Hz, 1H), 7.76-8.08 (m, 3H), 5.32-5.70 (m, 1H), 4.12 (s, 3H), 3.81 (s, 3H), 3.00-3.40 (m, 4H). MS (ESI): 390.0 [M+H]⁺.

Example 20: N-(6-(4-Cyclopentyl-4H-1,2,4-triazol-3-yl)pyridin-2-yl)-3-methoxy-1-methyl-1H-pyrazole-4-carboxamide

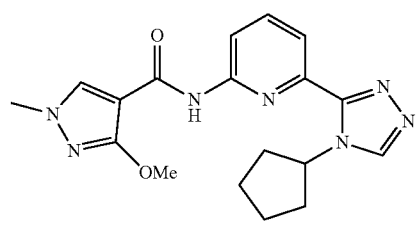 [SMILES: COc1nn(C)cc1C(=O)Nc1cccc(-c2nncn2C2CCCC2)n1]

The product was synthesized according to the general procedure described in Example 17 but using cyclopentanamine in place of cyclobutanamine in Step A to give the title compound (22 mg, 40% for the last step) as an off-white solid. ¹H NMR (400 MHz, MeOD) δ ppm 8.80 (s, 1H), 8.34 (d, J=8.28 Hz, 1H), 7.90-8.13 (m, 2H), 7.81 (d, J=7.53 Hz, 1H), 5.47 (quin, J=7.09 Hz, 1H), 4.10 (s, 3H), 3.81 (s, 3H), 2.28-2.47 (m, 2H), 1.54-2.12 (m, 6H). MS (ESI): 368.0 [M+H]⁺.

Example 21: N-(6-(4-(tert-Butyl)-4H-1,2,4-triazol-3-yl)pyridin-2-yl)-3-methoxy-1-methyl-1H-pyrazole-4-carboxamide

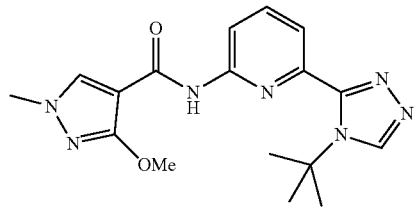 [SMILES: COc1nn(C)cc1C(=O)Nc1cccc(-c2nncn2C(C)(C)C)n1]

The product was synthesized according to the general procedure described in Example 17 but using 2-methylpropan-2-amine in place of cyclobutanamine in Step A to give the title compound (17 mg, 48% for the last step) as a pale yellow solid. ¹H NMR (400 MHz, MeOD) δ ppm 8.76 (s, 1H), 8.39 (d, J=8.28 Hz, 1H), 8.02 (s, 1H), 7.98 (t, J=8.03 Hz, 1H), 7.50 (d, J=7.53 Hz, 1H), 4.06 (s, 3H), 3.80 (s, 3H), 1.68 (s, 9H). MS (ESI): 356.2 [M+H]⁺.

Example 22: (S)-3-(Difluoromethyl)-1-methyl-N-(6-(4-(1,1,1-trifluoropropan-2-yl)-4H-1,2,4-triazol-3-yl)pyridin-2-yl)-1H-pyrazole-4-carboxamide

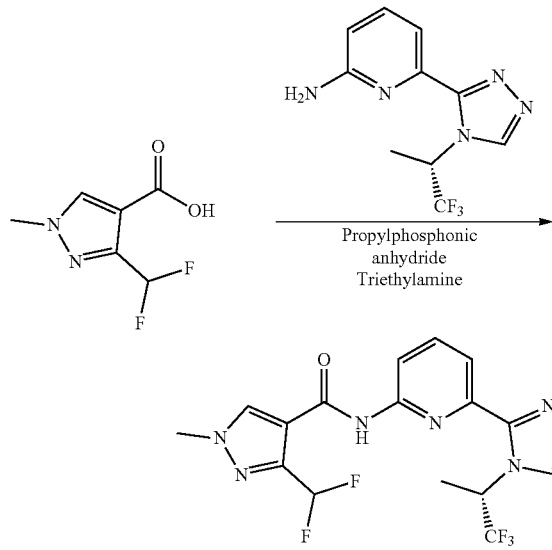

3-(Difluoromethyl)-1-methyl-pyrazole-4-carboxylic acid (75 mg, 0.43 mmol) and (S)-6-(4-(1,1,1-trifluoropropan-2-yl)-4H-1,2,4-triazol-3-yl)pyridin-2-amine (110 mg, 0.43 mmol) were dissolved in Et₃N (0.60 mL, 4.3 mmol). Propylphosphonic anhydride (≥50 wt % in EtOAc, 0.44 mL) was then added and the reaction was heated at 80° C. for 3 h. After this time, the reaction was cooled to rt and quenched by addition of MeOH (2 mL). The resulting solid was filtered and dried under vacuum to give the title compound (150 mg, 85%) as a white solid. ¹H NMR (400 MHz, MeOD) δ ppm 9.01 (s, 1H), 8.30-8.38 (m, 1H), 8.18-8.26 (m, 1H), 7.92-8.05 (m, 2H), 7.05-7.41 (m, 2H), 4.02 (s, 3H), 1.85-1.94 (m, 3H). MS (ESI): 416.0 [M+H]⁺.

Example 23: (R)-3-(Difluoromethyl)-1-methyl-N-(6-(4-(1,1,1-trifluoropropan-2-yl)-4H-1,2,4-triazol-3-yl)pyridin-2-yl)-1H-pyrazole-4-carboxamide

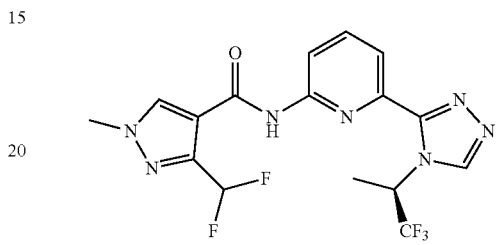

3-(Difluoromethyl)-1-methyl-pyrazole-4-carboxylic acid (68 mg, 0.39 mmol) and 6-[4-[(1R)-2,2,2-trifluoro-1-methyl-ethyl]-1,2,4-triazol-3-yl]pyridin-2-amine (100 mg, 0.39 mmol) were dissolved in Et₃N (0.54 mL, 3.9 mmol). Propylphosphonic anhydride (≥50 wt % in EtOAc, 0.4 mL) was then added and the reaction was heated at 80° C. for 3 h. After this time, the reaction was cooled to rt and quenched by addition of MeOH (2 mL). The resulting solid was filtered and dried under vacuum to give the title compound (92 mg, 57%). ¹H NMR (400 MHz, MeOD) δ ppm 9.01 (s, 1H), 8.30-8.38 (m, 1H), 8.18-8.26 (m, 1H), 7.92-8.05 (m, 2H), 7.05-7.41 (m, 2H), 4.02 (s, 3H), 1.85-1.94 (m, 3H). MS (ESI): 416.0 [M+H]⁺.

Example 24: 3-(Difluoromethyl)-1-methyl-N-(6-(4-(1-(trifluoromethyl)cyclopropyl)-4H-1,2,4-triazol-3-yl)pyridin-2-yl)-1H-pyrazole-4-carboxamide

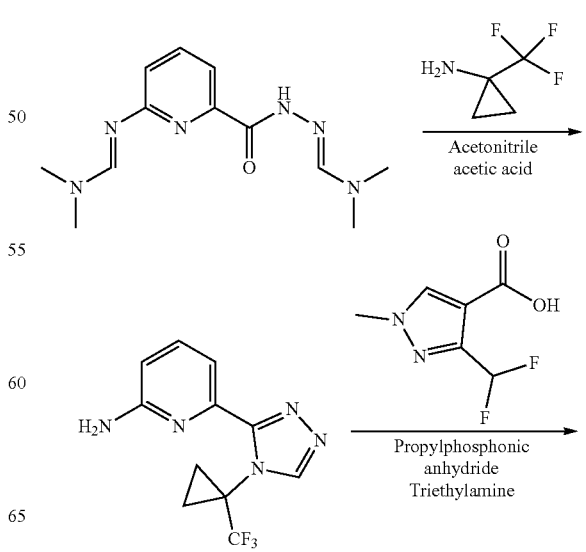

-continued

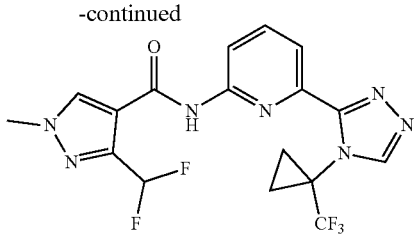

Step A: 6-(4-(1-(Trifluoromethyl)cyclopropyl)-4H-1,2,4-triazol-3-yl)pyridin-2-amine

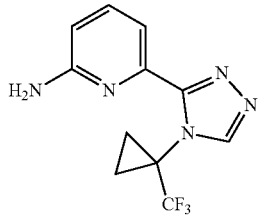 [SMILES: Nc1cccc(-c2nncn2C2(C(F)(F)F)CC2)n1]

N,6-bis[(E)-dimethylaminomethyleneamino]pyridine-2-carboxamide (1.0 g, 3.8 mmol) and 1-(trifluoromethyl)cyclopropanamine (954 mg, 0.20 mL, 7.6 mmol) were dissolved in MeCN (6 mL). Acetic acid (2 mL) was then added and the resulting mixture was heated in a sealed tube at 120° C. overnight. After this time, the reaction was concentrated, dissolved in EtOAc and washed with NaHCO₃ (saturated aqueous solution). The separated organic phase was dried over MgSO₄, filtered and concentrated in vacuum to give the crude product as a colorless oil. Purification by silica gel chromatography (EtOAc) gave the title compound as a white solid (223 mg, 22%). MS (ESI): 270.1[M+H]⁺.

Step B: 3-(Difluoromethyl)-1-methyl-N-(6-(4-(1-(trifluoromethyl)cyclopropyl)-4H-1,2,4-triazol-3-yl)pyridin-2-yl)-1H-pyrazole-4-carboxamide

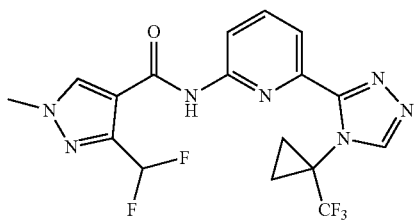 [SMILES: Cn1cc(C(=O)Nc2cccc(-c3nncn3C3(C(F)(F)F)CC3)n2)c(C(F)F)n1]

3-(Difluoromethyl)-1-methyl-pyrazole-4-carboxylic acid (65 mg, 0.37 mmol) and 6-[4-[1-(trifluoromethyl)cyclopropyl]-1,2,4-triazol-3-yl]pyridin-2-amine (100 mg, 0.37 mmol) were dissolved in Et₃N (0.50 mL, 3.7 mmol). Propylphosphonic anhydride (≥50 wt % in EtOAc, 0.4 mL) was then added and the reaction was heated at 80° C. for 3 h. After this time, the reaction was cooled to rt and quenched by addition of MeOH (2 mL). The resulting solid was filtered and dried under vacuum to give the title compound (100 mg, 63%). ¹H NMR (400 MHz, CDCl₃) δ ppm 8.85 (br s, 1H), 8.44 (dd, J=8.4, 0.9 Hz, 1H), 8.37 (s, 1H), 8.13 (s, 1H), 8.09 (dd, J=7.7, 0.9 Hz, 1H), 7.88 (t, J=8.0 Hz, 1H), 6.70-7.03 (m, 1H), 3.98 (s, 3H), 1.77-1.90 (m, 2H), 1.47-1.59 (m, 2H). MS (ESI): 428.0 [M+H]⁺.

Example 25: 3-Methoxy-1-methyl-N-(6-(4-(1-(trifluoromethyl)cyclopropyl)-4H-1,2,4-triazol-3-yl)pyridin-2-yl)-1H-pyrazole-4-carboxamide

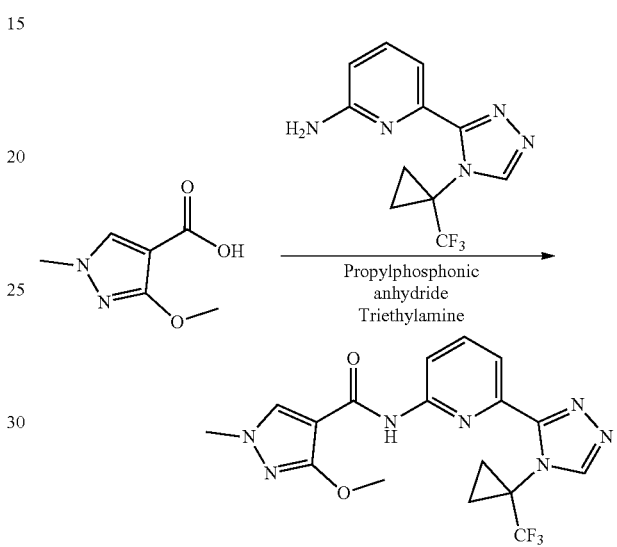

3-Methoxy-1-methyl-pyrazole-4-carboxylic acid (70 mg, 0.45 mmol) and 6-[4-[1-(trifluoromethyl)cyclopropyl]-1,2,4-triazol-3-yl]pyridin-2-amine (120 mg, 0.45 mmol) were dissolved in Et₃N (618 µL, 4.5 mmol). Propylphosphonic anhydride (≥50 wt % in EtOAc, 0.45 mL) was then added and the reaction was heated at 80° C. for 3 h. After this time, the reaction was cooled to rt and quenched by addition of MeOH (2 mL). The resulting solid was filtered and dried under vacuum to give the title compound (110 mg, 61%). ¹H NMR (400 MHz, CDCl₃) δ ppm 9.17 (s, 1H), 8.41 (dd, J=8.3, 0.8 Hz, 1H), 8.38 (s, 1H), 7.98-8.03 (m, 1H), 7.81-7.88 (m, 2H), 4.08 (s, 3H), 3.81 (s, 3H), 3.77-3.77 (m, 1H), 1.76-1.85 (m, 2H), 1.48-1.57 (m, 2H). MS (ESI): 408.0 [M+H]⁺.

Example 26: N-(6-(4-(1,1-Difluoropropan-2-yl)-4H-1,2,4-triazol-3-yl)pyridin-2-yl)-3-methoxy-1-methyl-1H-pyrazole-4-carboxamide

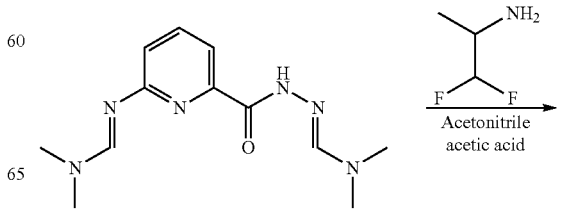

47
-continued

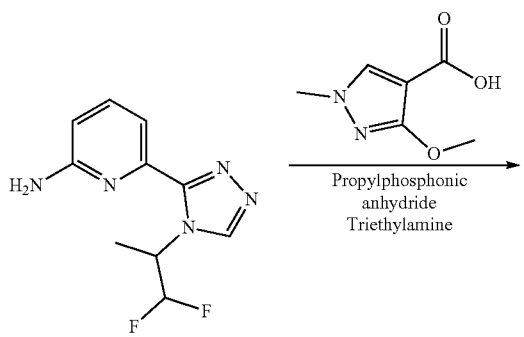

Step B: N-(6-(4-(1,1-Difluoropropan-2-yl)-4H-1,2,4-triazol-3-yl)pyridin-2-yl)-3-methoxy-1-methyl-1H-pyrazole-4-carboxamide

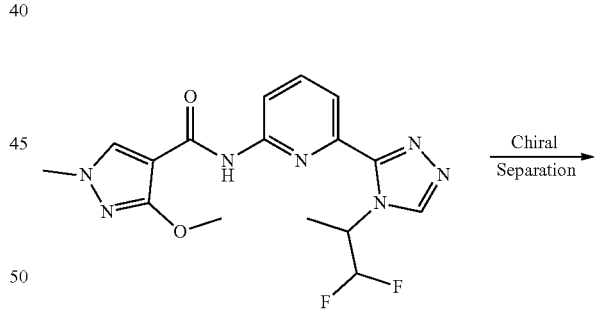

3-Methoxy-1-methyl-pyrazole-4-carboxylic acid (104 mg, 0.67 mmol) and 6-[4-(2,2-difluoro-1-methyl-ethyl)-1,2,4-triazol-3-yl]pyridin-2-amine (160 mg, 0.67 mmol) were dissolved in Et$_3$N (0.93 mL, 6.69 mmol). Propylphosphonic anhydride (≥50 wt % in EtOAc, 0.7 mL) was then added and the reaction was heated at 80° C. for 3 h. After this time, the reaction was cooled to rt and quenched by addition of MeOH (2 mL). The resulting solid was filtered and dried under vacuum to give the title compound (83 mg, 33%) as a white solid. $^1$H NMR (400 MHz, CDCl$_3$) δ ppm 9.11 (s, 1H), 8.41 (td, J=8.2, 1.0 Hz, 2H), 8.06 (dd, J=7.7, 0.9 Hz, 1H), 7.85-7.91 (m, 1H), 7.83 (s, 1H), 6.17-6.49 (m, 1H), 5.80-5.93 (m, 1H), 4.10 (s, 3H), 3.81 (s, 3H), 1.73 (d, J=7.3 Hz, 3H). MS (ESI): 378.0 [M+H]$^+$.

Examples 27 and Example 28: (S)—N-(6-(4-(1,1-Difluoropropan-2-yl)-4H-1,2,4-triazol-3-yl)pyridin-2-yl)-3-methoxy-1-methyl-1H-pyrazole-4-carboxamide and (R)—N-(6-(4-(1,1-Difluoropropan-2-yl)-4H-1,2,4-triazol-3-yl)pyridin-2-yl)-3-methoxy-1-methyl-1H-pyrazole-4-carboxamide

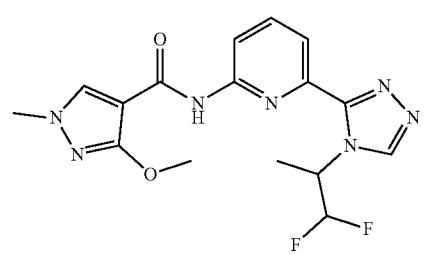

Step A: 6-(4-(1,1-Difluoropropan-2-yl)-4H-1,2,4-triazol-3-yl)pyridin-2-amine

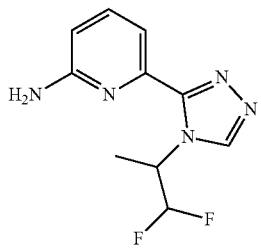 [SMILES: CC(C(F)F)n1cnnc1-c1cccc(N)n1]

N,6-bis[(E)-dimethylaminomethyleneamino]pyridine-2-carboxamide (600 mg, 2.3 mmol) and 1,1-difluoropropan-2-amine hydrochloride (435 mg, 3.3 mmol) were dissolved in a solution of MeCN (6 mL) and acetic acid (2 mL). The reaction was heated in a sealed tube at 120° C. overnight. After this time, the reaction was cooled to rt and concentrated in vacuo. The reaction was diluted with EtOAc and washed with satd. NaHCO$_3$ (×2). The combined organic phases were washed with brine, dried over MgSO$_4$ and concentrated. Purification by silica gel chromatography (EtOAc 100%) gave the title compound as a white solid (510 mg, 93%). $^1$H NMR (400 MHz, MeOD) δ ppm 8.77 (s, 1H), 7.48-7.63 (m, 1H), 7.29 (dd, J=7.4, 0.9 Hz, 1H), 6.56-6.72 (m, 1H), 5.95-6.41 (m, 2H), 1.68 (d, J=7.3 Hz, 3H). MS (ESI): 240.0 [M+H]$^+$.

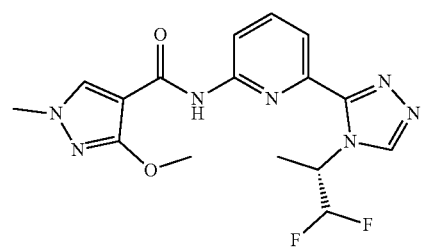

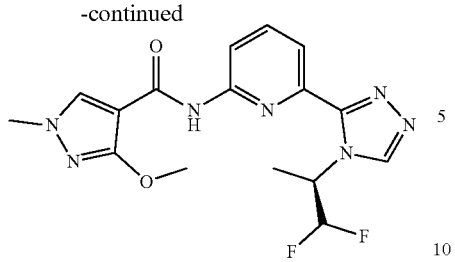

N-(6-(4-(1,1-Difluoropropan-2-yl)-4H-1,2,4-triazol-3-yl)pyridin-2-yl)-3-methoxy-1-methyl-1H-pyrazole-4-carboxamide was purified by chiral prep SFC (using a CHIRALPAK AS-H 5 μm, 30×250 mm column and using 30% MeOH (containing 0.1% Et$_2$NH) in CO$_2$ as the mobile phase at a flow rate of 100 mL/min, ABPR 120 bar, MBPR 40 psi) to give in order of elution:

Example 27 (absolute stereochemistry was arbitrarily assigned) (11 mg, 37%). $^1$H NMR (400 MHz, CDCl$_3$) δ ppm 9.11 (s, 1H), 8.41 (td, J=8.2, 1.0 Hz, 2H), 8.06 (dd, J=7.7, 0.9 Hz, 1H), 7.85-7.91 (m, 1H), 7.83 (s, 1H), 6.17-6.49 (m, 1H), 5.80-5.93 (m, 1H), 4.10 (s, 3H), 3.81 (s, 3H), 1.73 (d, J=7.3 Hz, 3H). MS (ESI): 378.0 [M+H]$^+$.

Example 28 (absolute stereochemistry was arbitrarily assigned) (12 mg, 40%). $^1$H NMR (400 MHz, CDCl$_3$) δ ppm 9.11 (s, 1H), 8.41 (td, J=8.2, 1.0 Hz, 2H), 8.06 (dd, J=7.7, 0.9 Hz, 1H), 7.85-7.91 (m, 1H), 7.83 (s, 1H), 6.17-6.49 (m, 1H), 5.80-5.93 (m, 1H), 4.10 (s, 3H), 3.81 (s, 3H), 1.73 (d, J=7.3 Hz, 3H). MS (ESI): 378.0 [M+H]$^+$.

Example 29: (S)-3-Methoxy-1-methyl-N-(6-(4-(3-methylbutan-2-yl)-4H-1,2,4-triazol-3-yl)pyridin-2-yl)-1H-pyrazole-4-carboxamide

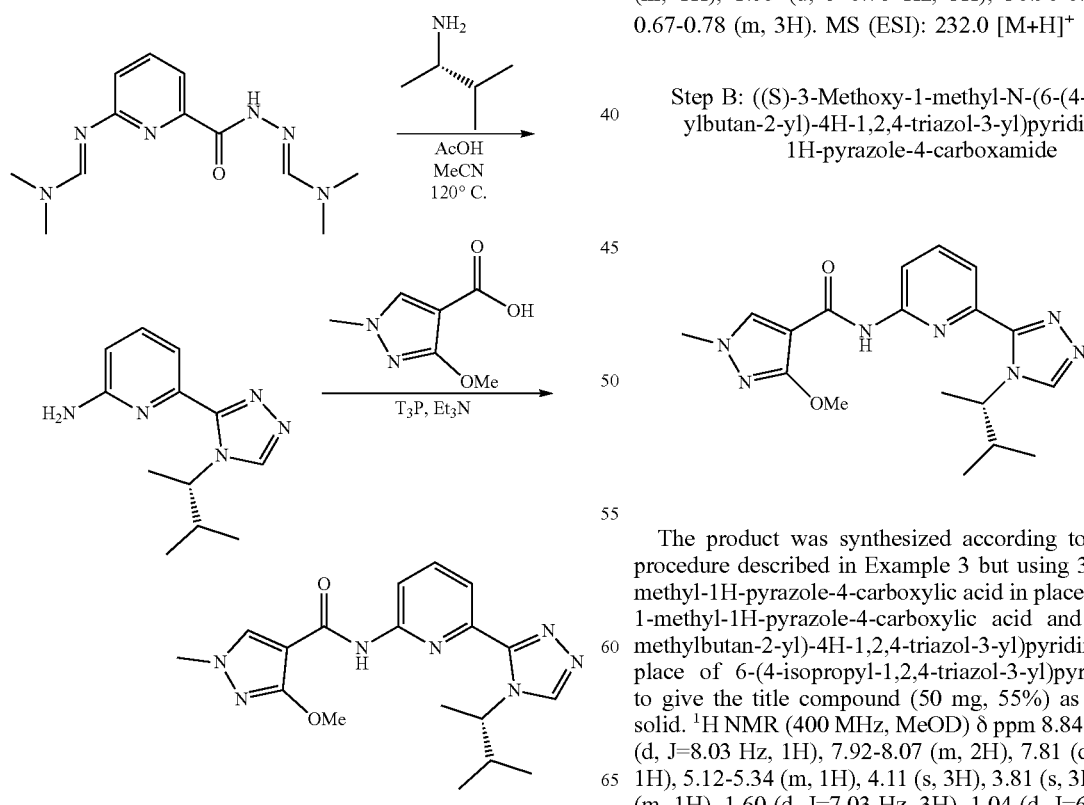

Step A: (S)-6-(4-(3-Methylbutan-2-yl)-4H-1,2,4-triazol-3-yl)pyridin-2-amine

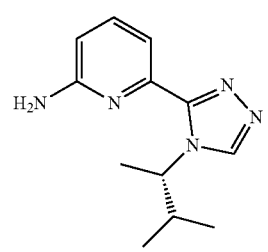 [SMILES: CC(C)[C@H](C)n1cnnc1-c1cccc(N)n1]

To a mixture of (E)-N'-(6-(2-((E)-(dimethylamino)methylene)hydrazine-1-carbonyl)pyridin-2-yl)-N,N-dimethylformimidamide (1.05 g, 4.00 mmol) and (S)-3-methylbutan-2-amine (1.05 mL, 9.06 mmol) in a microwave tube was added MeCN (6 mL), followed by acetic acid (2 mL). The mixture was heated in a hot plate at 120° C. for 24 h. After this time the reaction was partitioned between EtOAc and satd. NaHCO$_3$. The separated aqueous layer was extracted with EtOAc and the combined organic extracts were dried over MgSO$_4$, filtered and concentrated in vacuo. The product was purified by normal phase column chromatography eluting with EtOAc/EtOH (3/1) to give the title compound (802 mg, 87%). $^1$H NMR (400 MHz, MeOD) δ ppm 8.73 (s, 1H), 7.57 (dd, J=8.28, 7.53 Hz, 1H), 7.17 (d, J=7.03 Hz, 1H), 6.65 (d, J=8.03 Hz, 1H), 5.08-5.34 (m, 1H), 1.96-2.11 (m, 1H), 1.55 (d, J=6.78 Hz, 3H), 30.90-0.97 (m, 3H), 0.67-0.78 (m, 3H). MS (ESI): 232.0 [M+H]$^+$ Step B: ((S)-3-Methoxy-1-methyl-N-(6-(4-(3-methylbutan-2-yl)-4H-1,2,4-triazol-3-yl)pyridin-2-yl)-1H-pyrazole-4-carboxamide The product was synthesized according to the general procedure described in Example 3 but using 3-methoxy-1-methyl-1H-pyrazole-4-carboxylic acid in place of 3-ethoxy-1-methyl-1H-pyrazole-4-carboxylic acid and (S)-6-(4-(3-methylbutan-2-yl)-4H-1,2,4-triazol-3-yl)pyridin-2-amine in place of 6-(4-isopropyl-1,2,4-triazol-3-yl)pyridin-2-amine to give the title compound (50 mg, 55%) as an off-white solid. $^1$H NMR (400 MHz, MeOD) δ ppm 8.84 (s, 1H), 8.35 (d, J=8.03 Hz, 1H), 7.92-8.07 (m, 2H), 7.81 (d, J=7.28 Hz, 1H), 5.12-5.34 (m, 1H), 4.11 (s, 3H), 3.81 (s, 3H), 2.08-2.27 (m, 1H), 1.60 (d, J=7.03 Hz, 3H), 1.04 (d, J=6.78 Hz, 3H), 0.86 (d, J=6.78 Hz, 3H). MS (ESI): 370.0 [M+H]$^+$.

Example 30: N-(6-(4-(2,2-Difluorocyclobutyl)-4H-1,2,4-triazol-3-yl)pyridin-2-yl)-3-methoxy-1-methyl-1H-pyrazole-4-carboxamide

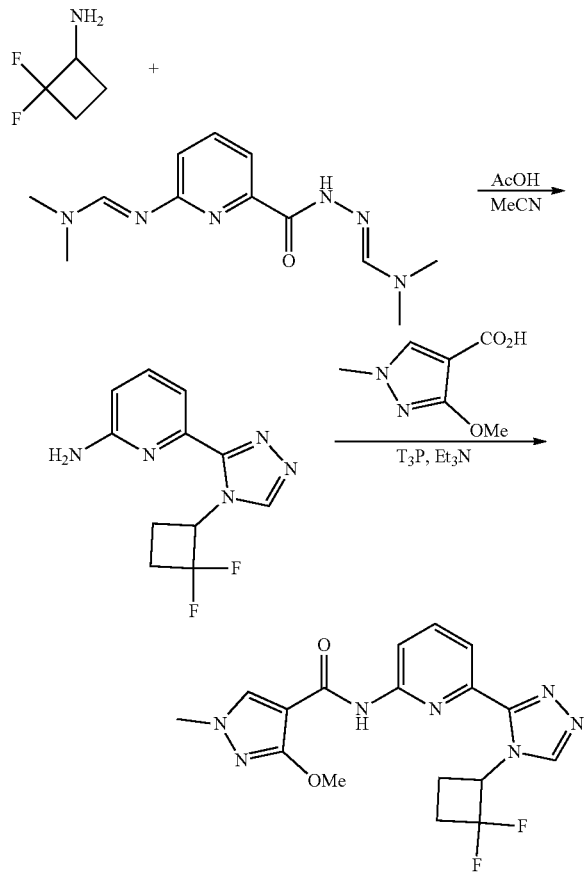

Step A: 6-(4-(2,2-Difluorocyclobutyl)-4H-1,2,4-triazol-3-yl)pyridin-2-amine

To a mixture of (E)-N'-(6-(2-((E)-(dimethylamino)methylene)hydrazine-1-carbonyl)pyridin-2-yl)-N,N-dimethylformimidamide (501 mg, 1.91 mmol) and 2,2-difluorocyclobutan-1-amine hydrochloride (558 mg, 3.89 mmol) was added MeCN (3 mL), and acetic acid (1 mL) and the reaction was heated in a hot plate at 120° C. for 24 h. After this time the reaction was cooled to rt and partitioned between EtOAc and NaHCO₃ (saturated aqueous solution). The aqueous layer was extracted with EtOAc and the combined organic extracts were dried over MgSO₄, filtered and evaporated in vacuo. The residue was purified by column chromatography using EtOAc as eluent to give the title compound (203 mg, 42%). MS (ESI): 252.0 [M+H]$^+$.

Step B: N-(6-(4-(2,2-Difluorocyclobutyl)-4H-1,2,4-triazol-3-yl)pyridin-2-yl)-3-methoxy-1-methyl-1H-pyrazole-4-carboxamide

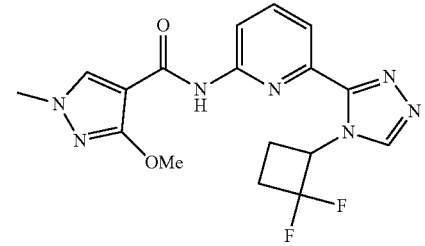 [SMILES: COc1nn(C)cc1C(=O)Nc1cccc(-c2nncn2C2CCC2(F)F)n1]

The product was synthesized according to the general procedure described in Example 3 but using 3-methoxy-1-methyl-1H-pyrazole-4-carboxylic acid in place of 3-ethoxy-1-methyl-1H-pyrazole-4-carboxylic acid and 6-(4-(2,2-difluorocyclobutyl)-4H-1,2,4-triazol-3-yl)pyridin-2-amine in place of 6-(4-isopropyl-1,2,4-triazol-3-yl)pyridin-2-amine to give the title compound (19 mg, 34%) as an off-white solid. $^1$H NMR (400 MHz, MeOD) δ ppm 8.95 (d, J=2.01 Hz, 1H), 8.38 (d, J=8.53 Hz, 1H), 7.91-8.09 (m, 2H), 7.86 (d, J=7.28 Hz, 1H), 6.07-6.39 (m, 1H), 4.10 (s, 3H), 3.81 (s, 3H), 2.42-2.80 (m, 4H). MS (ESI): 390.0 [M+H]$^+$.

Example 31 and Example 32: (S)—N-(6-(4-(2,2-Difluorocyclobutyl)-4H-1,2,4-triazol-3-yl)pyridin-2-yl)-3-methoxy-1-methyl-1H-pyrazole-4-carboxamide and (R)—N-(6-(4-(2,2-Difluorocyclobutyl)-4H-1,2,4-triazol-3-yl)pyridin-2-yl)-3-methoxy-1-methyl-1H-pyrazole-4-carboxamide

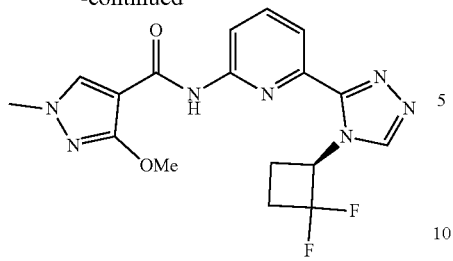

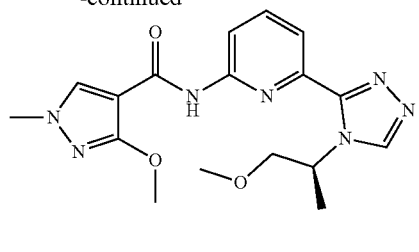

N-[6-[4-(2,2-difluorocyclobutyl)-1,2,4-triazol-3-yl]-2-pyridyl]-3-methoxy-1-methyl-pyrazole-4-carboxamide (34 mg, 0.087 mmol, from Example 30) was separated by chiral HPLC (using a CHIRALPAK AD-H 5 μm, 30×250 mm column and using 25% MeOH in 0.1% Et$_2$NH in CO$_2$ as the eluent at a flow rate of 100 m/min, ABPR 120 bar, MBPR 40 psi) to give:

Example 31 (absolute stereochemistry was arbitrarily assigned) (11 mg, 32%): $^1$H NMR (400 MHz, MeOD) δ ppm 8.97 (d, J=1.76 Hz, 1H), 8.39 (d, J=8.28 Hz, 1H), 7.91-8.08 (m, 2H), 7.87 (d, J=7.53 Hz, 1H), 6.10-6.47 (m, 1H), 4.11 (s, 3H), 3.82 (s, 3H), 2.42-2.84 (m, 4H). (ESI): 390.1 [M+H]$^+$.

Example 32 (absolute stereochemistry was arbitrarily assigned) (8 mg, 24%): $^1$H NMR (400 MHz, MeOD) δ ppm 8.96 (d, J=1.76 Hz, 1H), 8.38 (d, J=7.78 Hz, 1H), 7.93-8.08 (m, 2H), 7.86 (d, J=7.28 Hz, 1H), 6.14-6.44 (m, 1H), 4.10 (s, 3H), 3.82 (s, 3H), 2.41-2.81 (m, 4H). (ESI): 390.1 [M+H]$^+$.

Example 33 and Example 34: (S)-3-Methoxy-N-(6-(4-(1-methoxypropan-2-yl)-4H-1,2,4-triazol-3-yl)pyridin-2-yl)-1-methyl-1H-pyrazole-4-carboxamide and (R)-3-methoxy-N-(6-(4-(1-methoxypropan-2-yl)-4H-1,2,4-triazol-3-yl)pyridin-2-yl)-1-methyl-1H-pyrazole-4-carboxamide

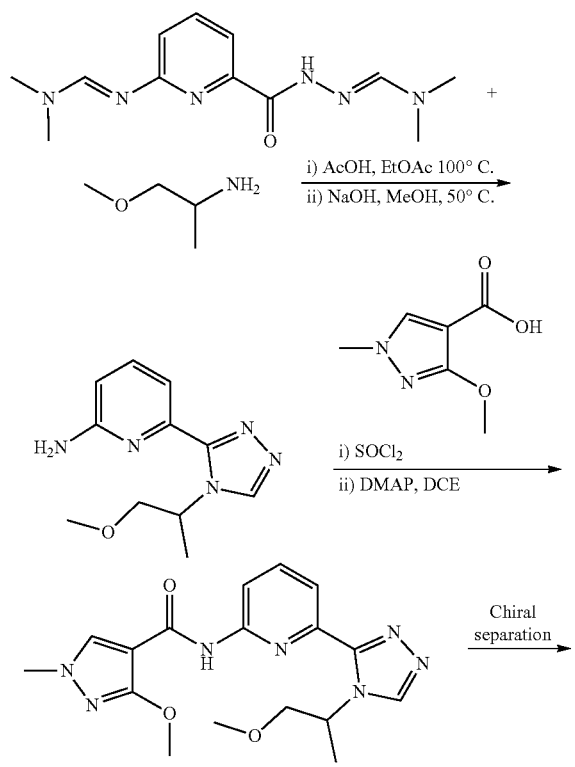

Step A: 6-(4-(1-Methoxypropan-2-yl)-4H-1,2,4-triazol-3-yl)pyridin-2-amine

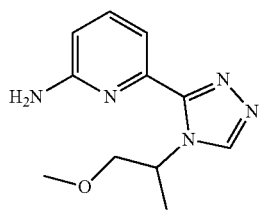 [SMILES: COCC(C)n1cnnc1-c1cccc(N)n1]

A solution of 1-methoxypropan-2-amine (0.12 mL, 1.14 mmol) and N-[(E)-dimethylaminomethyleneamino]-6-[(Z)-dimethylaminomethyleneamino]pyridine-2-carboxamide (300 mg, 1.14 mmol) in a mixture of MeCN (7.5 mL) and acetic acid (4.5 mL) was heated at 90° C. for 20 h. After this time the resulting pale yellow solution was concentrated under reduced pressure. The remaining yellow oil was dissolved in MeOH and sodium hydroxide (120 mg, 3.0 mmol) was added and the resulting orange reaction mixture was heated at 50° C. for 2 h. After this time, the volatiles were removed and the resulting residue was purified by prep-HPLC (using a Sunfire Prep C18 OBD, 5 μm 30×50 mm column and using 100% water (initial conditions) to 80% water/20% MeCN over 20 minutes in 0.1% TFA as the mobile phase at a flow rate of 50 mL/min) to give the title compound (156 mg, 68%). $^1$H NMR (400 MHz, MeOD) δ ppm 9.17 (s, 1H), 7.78 (dd, J=7.3, 8.8 Hz, 1H), 7.29 (dd, J=0.8, 7.3 Hz, 1H), 6.90 (dd, J=0.8, 8.8 Hz, 1H), 5.45 (dquin, J=4.1, 6.9 Hz, 1H), 3.76-3.63 (m, 2H), 3.30 (s, 3H), 1.60 (d, J=7.0 Hz, 3H). MS (ESI): 234.1 [M+H]$^+$.

Step B: rac-3-Methoxy-N-(6-(4-(1-methoxypropan-2-yl)-4H-1,2,4-triazol-3-yl)pyridin-2-yl)-1-methyl-1H-pyrazole-4-carboxamide

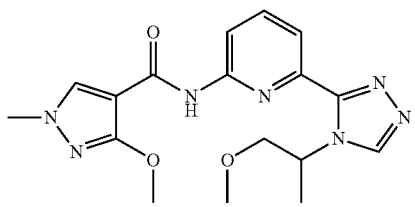 [SMILES: COCC(C)n1cnnc1-c1cccc(NC(=O)c2cn(C)nc2OC)n1]

To a solution of 6-[4-(2-methoxy-1-methyl-ethyl)-1,2,4-triazol-3-yl]pyridin-2-amine (80 mg, 0.35 mmol) and DMAP (4 mg, 0.03 mmol) in DCE (2 mL) and DIPEA (240 µL, 1.37 mmol) was added 3-methoxy-1-methyl-pyrazole-4-carbonyl chloride (180 mg, 1.0 mmol) (derived from heating the corresponding acid chloride in thionyl chloride for 15 min and removal of the volatiles) at rt. The reaction was stirred at rt for 30 min and after this time the mixture was concentrated under reduced pressure. The product was purified by prep-HPLC (using an XTerra Prep RP18 OBD, 10 µm 50×250 mm column and using water (containing 0.1% TFA)/MeCN from 90/10 to 10/90 as the mobile phase at a flow rate of 50 mL/min) to give the title compound (10 mg, 8%). $^1$H NMR (400 MHz, CD$_3$CN) δ ppm 9.20 (br s, 1H), 8.49 (s, 1H), 8.29 (dd, J=1.0, 8.0 Hz, 1H), 7.93-7.88 (m, 2H), 7.87-7.82 (m, 1H), 5.59 (dquin, J=4.5, 6.8 Hz, 1H), 4.05 (s, 3H), 3.75 (s, 3H), 3.74-3.70 (m, 1H), 3.70-3.65 (m, 1H), 3.28 (s, 3H), 1.56 (d, J=7.0 Hz, 3H). MS (ESI): 372.2 [M+H]$^+$.

Step C: (S)-3-Methoxy-N-(6-(4-(1-methoxypropan-2-yl)-4H-1,2,4-triazol-3-yl)pyridin-2-yl)-1-methyl-1H-pyrazole-4-carboxamide and (R)-3-methoxy-N-(6-(4-(1-methoxypropan-2-yl)-4H-1,2,4-triazol-3-yl)pyridin-2-yl)-1-methyl-1H-pyrazole-4-carboxamide

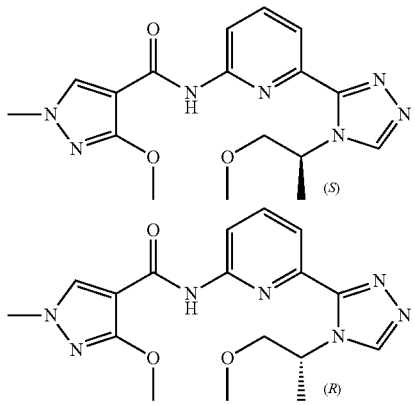

3-Methoxy-N-(6-(4-(1-methoxypropan-2-yl)-4H-1,2,4-triazol-3-yl)pyridin-2-yl)-1-methyl-1H-pyrazole-4-carboxamide (10 mg) was purified by SFC (using a Chiralpak IG 5 µm, 30×250 mm column and using: 40% MeOH in 0.1% Et$_2$NH in CO$_2$ as the mobile phase at a flow rate of 100 m/min, ABPR 120 bar, MBPR 40 psi) to give in order of elution: (S)-3-Methoxy-N-(6-(4-(1-methoxypropan-2-yl)-4H-1,2,4-triazol-3-yl)pyridin-2-yl)-1-methyl-1H-pyrazole-4-carboxamide (4 mg, 0.01 mmol, 3%; stereochemistry arbitrarily assigned) and (R)-3-methoxy-N-(6-(4-(1-methoxypropan-2-yl)-4H-1,2,4-triazol-3-yl)pyridin-2-yl)-1-methyl-1H-pyrazole-4-carboxamide (4 mg, 0.01 mmol, 3%; stereochemistry arbitrarily assigned). $^1$H NMR (400 MHz, CD$_3$CN) δ ppm 9.20 (br s, 1H), 8.49 (s, 1H), 8.29 (dd, J=1.0, 8.0 Hz, 1H), 7.93-7.88 (m, 2H), 7.87-7.82 (m, 1H), 5.59 (dquin, J=4.5, 6.8 Hz, 1H), 4.05 (s, 3H), 3.75 (s, 3H), 3.74-3.70 (m, 1H), 3.70-3.65 (m, 1H), 3.28 (s, 3H), 1.56 (d, J=7.0 Hz, 3H). MS (ESI): 372.2 [M+H]$^+$.

Example 35: rac-N-(6-(4-(1-Hydroxypropan-2-yl)-4H-1,2,4-triazol-3-yl)pyridin-2-yl)-3-methoxy-1-methyl-1H-pyrazole-4-carboxamide

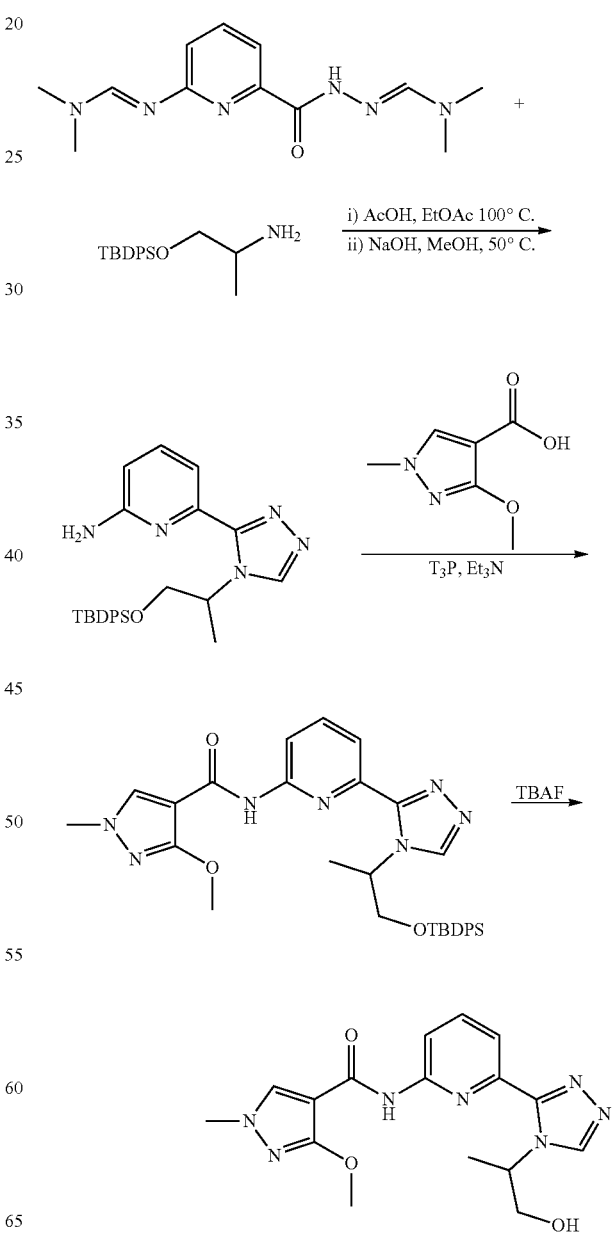

Step A: 6-(4-(1-((tert-Butyldiphenylsilyl)oxy)propan-2-yl)-4H-1,2,4-triazol-3-yl)pyridin-2-amine

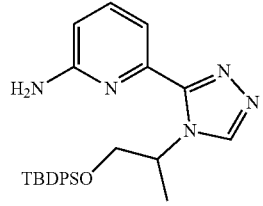

A solution of 1-((tert-butyldiphenylsilyl)oxy)propan-2-amine (2.5 g, 8.0 mmol) and N-[(E)-dimethylaminomethyleneamino]-6-[(Z)-dimethylaminomethyleneamino]pyridine-2-carboxamide (2.1 g mg, 1.14 mmol) in a mixture of MeCN (24 mL) and acetic acid (8 mL) was heated in two identical batches in a biotage microwave at 120° C. for 1 h. The resulting pale yellow solution was concentrated under reduced pressure and the remaining yellow oil was dissolved in EtOAc (100 mL) and washed with sat. NaHCO$_3$ (2×20 mL). The organic phase was dried over Na$_2$SO$_4$, filtered and concentrated under reduced pressure. The resulting crude oil was dissolved in MeOH (70 mL) and sodium hydroxide (840 mg, 21.0 mmol) was added and the resulting orange reaction mixture was heated at 70° C. for 6 h. The volatiles were removed and the resulting residue was used without further purification in the next step.

Step B: N-(6-(4-(1-((tert-Butyldiphenylsilyl)oxy)propan-2-yl)-4H-1,2,4-triazol-3-yl)pyridin-2-yl)-3-methoxy-1-methyl-1H-pyrazole-4-carboxamide

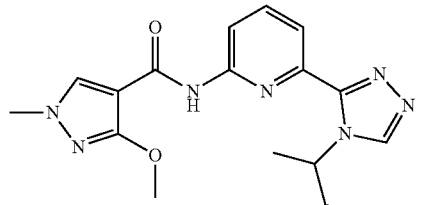

To a mixture of 6-[4-[2-[tert-butyl(diphenyl)silyl]oxy-1-methyl-ethyl]-1,2,4-triazol-3-yl]pyridin-2-amine (600 mg, 1.31 mmol) and 3-methoxy-1-methyl-pyrazole-4-carboxylic acid (410 mg, 2.6 mmol) in a reaction vial was added Et$_3$N (3.6 mL, 26 mmol) and propylphosphonic anhydride (≥50 wt % in EtOAc, 4 mL) and the mixture was heated at 80° C. for 4 h. After this time, the reaction was quenched with MeOH and co-evaporated several times with MeOH/MeCN. The crude residue was partitioned between satd. NaHCO$_3$ and EtOAc. The organic layer was separated, dried over Na$_2$SO$_4$, filtered and concentrated in vacuo to give the title compound which was used in the next step without further purification.

Step C: rac-N-(6-(4-(1-Hydroxypropan-2-yl)-4H-1,2,4-triazol-3-yl)pyridin-2-yl)-3-methoxy-1-methyl-1H-pyrazole-4-carboxamide

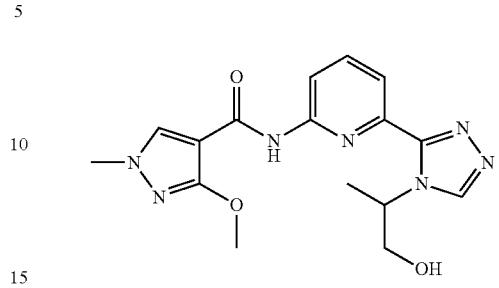

To a solution of N-[6-[4-[2-[tert-butyl(diphenyl)silyl]oxy-1-methyl-ethyl]-1,2,4-triazol-3-yl]-2-pyridyl]-3-methoxy-1-methyl-pyrazole-4-carboxamide (222 mg, 0.37 mmol) in THF (4 mL) was added a solution of TBAF (1 M, 0.41 mL) at 0° C. After 15 min the reaction was quenched by addition of a satd. NaHCO$_3$ solution. EtOAc was then added and the product crashed out in between the aqueous and organic layers. The title compound was isolated by filtration as a white solid (72 mg, 54%). $^1$H NMR (400 MHz, MeOD) δ ppm 8.82 (s, 1H), 8.32 (dd, J=0.9, 8.4 Hz, 1H), 8.01 (s, 1H), 7.98 (dd, J=7.5, 8.3 Hz, 1H), 7.82 (dd, J=0.9, 7.7 Hz, 1H), 5.48-5.39 (m, 1H), 4.11 (s, 3H), 3.97-3.86 (m, 2H), 3.81 (s, 3H), 1.64 (d, J=7.0 Hz, 3H). MS (ESI): 358.2 [M+H]$^+$.

Example 36 and Example 37: (R)—N-(6-(4-(1-Hydroxypropan-2-yl)-4H-1,2,4-triazol-3-yl)pyridin-2-yl)-3-methoxy-1-methyl-1H-pyrazole-4-carboxamide and (S)—N-(6-(4-(1-Hydroxypropan-2-yl)-4H-1,2,4-triazol-3-yl)pyridin-2-yl)-3-methoxy-1-methyl-1H-pyrazole-4-carboxamide

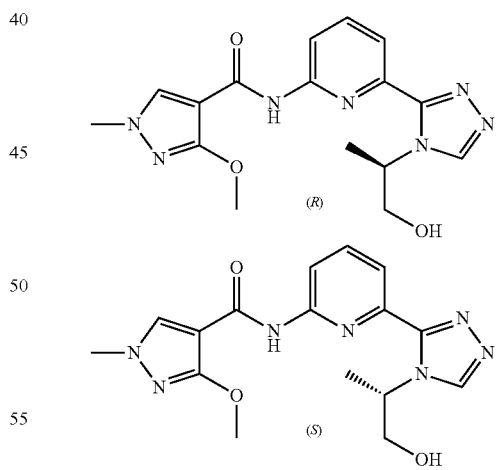

rac-N-(6-(4-(1-hydroxypropan-2-yl)-4H-1,2,4-triazol-3-yl)pyridin-2-yl)-3-methoxy-1-methyl-1H-pyrazole-4-carboxamide (16 mg) was purified by SFC (using a Chiralpak OX—H 5 µm, 30×250 mm column and using: 45% MeOH in 0.1% Et$_2$NH in CO$_2$ as the mobile phase at a flow rate of 100 m/min, ABPR 120 bar, MBPR 40 psi) to give in order of elution: (R)—N-(6-(4-(1-hydroxypropan-2-yl)-4H-1,2,4-triazol-3-yl)pyridin-2-yl)-3-methoxy-1-methyl-1H-pyrazole-4-carboxamide (8 mg, stereochemistry arbitrarily assigned) and (S)—N-(6-(4-(1-hydroxypropan-2-yl)-4H-1,2,4-triazol-3-yl)pyridin-2-yl)-3-methoxy-1-methyl-1H-pyrazole-4-carboxamide (8 mg, stereochemistry arbitrarily assigned). $^1$H NMR (400 MHz, MeOD) δ ppm 8.82 (s, 1H), 8.32 (dd, J=0.9, 8.4 Hz, 1H), 8.01 (s, 1H), 7.98 (dd, J=7.5, 8.3 Hz, 1H), 7.82 (dd, J=0.9, 7.7 Hz, 1H), 5.48-5.39 (m, 1H), 4.11 (s, 3H), 3.97-3.86 (m, 2H), 3.81 (s, 3H), 1.64 (d, J=7.0 Hz, 3H). MS (ESI): 358.2 [M+H]+.

Example 38: tert-Butyl 4-(3-(6-(3-methoxy-1-methyl-1H-pyrazole-4-carboxamido)pyridin-2-yl)-4H-1,2,4-triazol-4-yl)piperidine-1-carboxylate

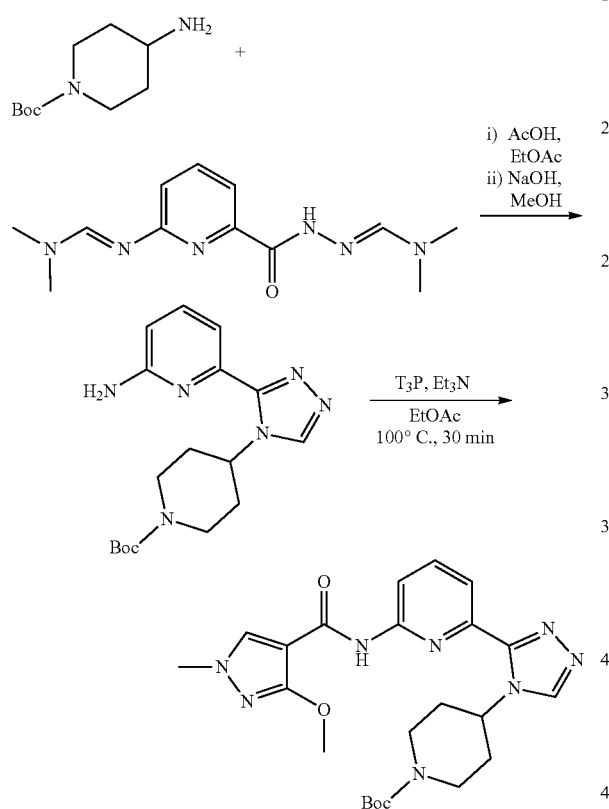

Step A: tert-Butyl 4-(3-(6-aminopyridin-2-yl)-4H-1,2,4-triazol-4-yl)piperidine-1-carboxylate

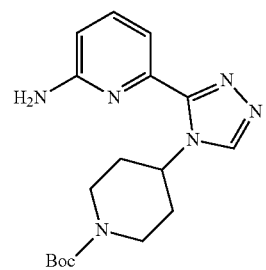 [SMILES: CC(C)(C)OC(=O)N1CCC(n2cnnc2-c2cccc(N)n2)CC1]

A solution of tert-butyl 4-aminopiperidine-1-carboxylate (916 mg, 4.6 mmol) and N-[(E)-dimethylaminomethyleneamino]-6-[(Z)-dimethylaminomethyleneamino]pyridine-2-carboxamide (1.0 g, 3.8 mmol) in a mixture of MeCN (24 mL) and acetic acid (8 mL) was heated in two identical batches in a biotage microwave at 100° C. for 1 h. The resulting pale yellow solution was concentrated under reduced pressure and the remaining yellow oil was dissolved in EtOAc (100 mL) and washed with satd. NaHCO3 (2×20 mL). The organic phase was dried over Na2SO4, filtered and concentrated in vacuo. The resulting crude oil was dissolved in MeOH (70 mL) and sodium hydroxide (470 mg, 12 mmol) was added and the resulting orange reaction mixture was heated at 70° C. for 1 h. The volatiles were removed and the resulting residue was used without further purification in the next step.

Step B: tert-Butyl 4-(3-(6-(3-methoxy-1-methyl-1H-pyrazole-4-carboxamido)pyridin-2-yl)-4H-1,2,4-triazol-4-yl)piperidine-1-carboxylate

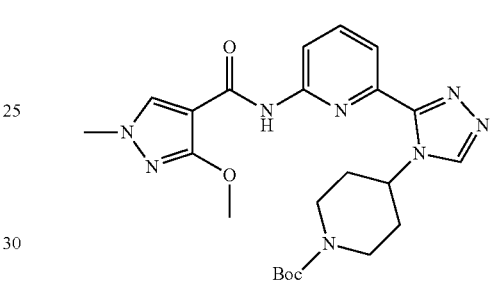

A solution of 3-methoxy-1-methyl-1H-pyrazole-4-carboxylic acid (136 mg, 0.9 mmol), tert-butyl 4-(3-(6-aminopyridin-2-yl)-4H-1,2,4-triazol-4-yl)piperidine-1-carboxylate (250 mg, 0.7 mmol), Et3N (0.80 mL, 5.8 mmol) and propylphosphonic anhydride (≥50 wt % in EtOAc, 0.5 mL) in EtOAc (0.5 mL) was heated in a biotage microwave at 100° C. for 1 h. After this time, the reaction was quenched by addition of MeOH (5 mL). Silica gel (2 g) was then added and the volatiles were removed. Column chromatography (12 g, SiO2, using 0-15% MeOH in DCM (containing 5% NH4OH) as eluent), followed by mass directed HPLC purification (using 5-65% MeCN in H2O (containing 4% NH4OH) as eluent) gave the title compound (28 mg, 8%). $^1$H NMR (500 MHz, CDCl3) δ ppm 8.93 (s, 1H), 8.37 (d, J=8.5 Hz, 1H), 8.33 (s, 1H), 8.03 (d, J=7.3 Hz, 1H), 7.89-7.83 (m, 2H), 5.35 (tt, J=3.7, 11.9 Hz, 1H), 4.39 (br s, 2H), 4.08 (s, 3H), 3.81 (s, 3H), 3.00-2.84 (m, 2H), 2.28 (br d, J=11.0 Hz, 2H), 2.01-1.78 (m, 2H), 1.48 (s, 9H). MS (ESI): 483.1 [M+H]+.

Example 39: (R)-3-Methoxy-1-methyl-N-(6-(4-(piperidin-3-yl)-4H-1,2,4-triazol-3-yl)pyridin-2-yl)-1H-pyrazole-4-carboxamide

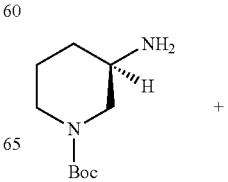

-continued

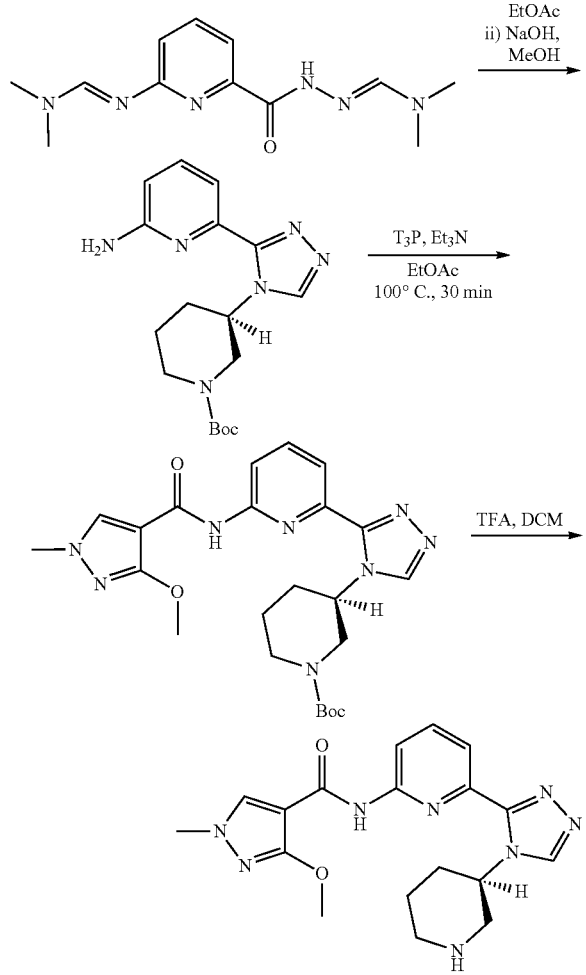

Steps A and B: tert-Butyl (R)-3-(3-(6-(3-methoxy-1-methyl-1H-pyrazole-4-carboxamido)pyridin-2-yl)-4H-1,2,4-triazol-4-yl)piperidine-1-carboxylate The product was synthesized according to the general procedure described in Steps A and B of Example 38 but using tert-butyl (3R)-3-aminopiperidine-1-carboxylate in place of tert-butyl 4-aminopiperidine-1-carboxylate (916 mg, 4.57 mmol) to give the title compound (90 mg, 25% for the last step). ¹H NMR (500 MHz, CD₃CN) δ ppm 9.11 (br s, 1H), 8.50 (s, 1H), 8.30 (d, J=9.2 Hz, 1H), 7.89 (m, J=7.9 Hz, 2H), 7.87 (s, 1H), 5.55-4.87 (m, 1H), 4.54-4.12 (m, 1H), 4.00 (s, 3H), 3.73 (s, 3H), 3.04-2.94 (m, 1H), 2.94-2.79 (m, 1H), 2.33 (br s, 1H), 2.05-1.79 (m, 3H), 1.69-1.58 (m, 1H), 1.24 (br s, 9H). MS (ESI): 483.2 [M+H]⁺.

Step C: (R)-3-Methoxy-1-methyl-N-(6-(4-(piperidin-3-yl)-4H-1,2,4-triazol-3-yl)pyridin-2-yl)-1H-pyrazole-4-carboxamide

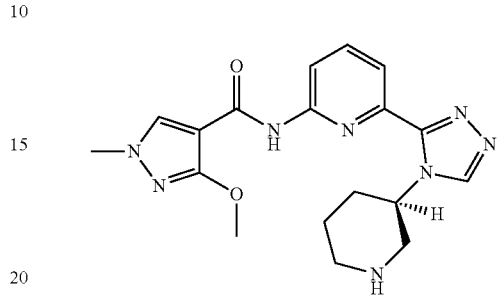

To a solution of tert-butyl (R)-3-(3-(6-(3-methoxy-1-methyl-1H-pyrazole-4-carboxamido)pyridin-2-yl)-4H-1,2,4-triazol-4-yl)piperidine-1-carboxylate (84 mg, 0.17 mmol) in DCM (1.2 mL) was added TFA (300 µL) at rt. The resulting mixture was stirred for 1 h. The volatiles were removed and the crude residue was purified by mass directed HPLC (using 5-65% MeCN in H₂O (containing 4% NH₄OH) as eluent) to give the title compound (35 mg, 52%) as a colorless film. ¹H NMR (500 MHz, MeOD) δ ppm 8.91 (s, 1H), 8.34 (d, J=8.5 Hz, 1H), 8.02 (s, 1H), 8.01-7.95 (m, 1H), 7.81 (d, J=7.3 Hz, 1H), 5.24-5.02 (m, 1H), 4.11 (s, 3H), 3.82 (s, 3H), 3.33 (br s, 1H), 3.06 (br d, J=12.2 Hz, 1H), 2.94 (t, J=11.3 Hz, 1H), 2.70 (br t, J=12.2 Hz, 1H), 2.39 (br d, J=12.2 Hz, 1H), 2.08-1.91 (m, 2H), 1.81-1.70 (m, 1H). MS (ESI): 383.3 [M+H]⁺.

Example 40: (S)-tert-Butyl 3-(3-(6-(3-methoxy-1-methyl-1H-pyrazole-4-carboxamido)pyridin-2-yl)-4H-1,2,4-triazol-4-yl)pyrrolidine-1-carboxylate

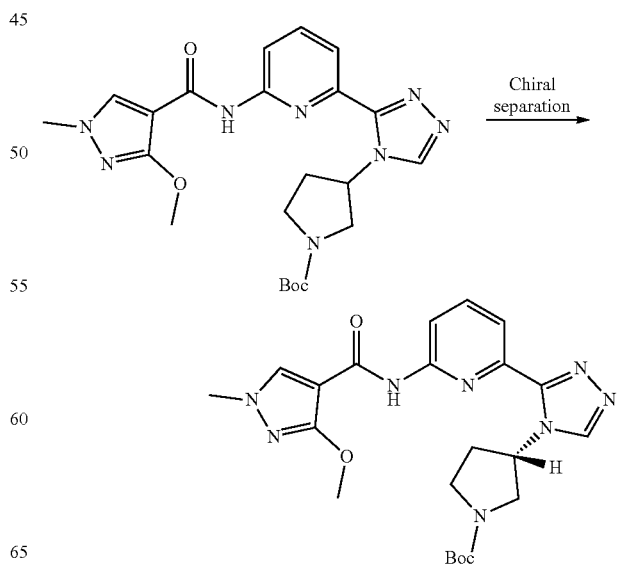

Step A: tert-Butyl 3-(3-(6-(3-methoxy-1-methyl-1H-pyrazole-4-carboxamido)pyridin-2-yl)-4H-1,2,4-triazol-4-yl)pyrrolidine-1-carboxylate

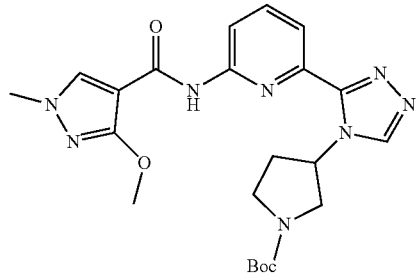 [SMILES: COc1nn(C)cc1C(=O)Nc1cccc(-c2nncn2C2CCN(C(=O)OC(C)(C)C)C2)n1]

A solution of 3-methoxy-1-methyl-1H-pyrazole-4-carboxylic acid (141 mg, 0.9 mmol), tert-butyl (S)-3-(3-(6-aminopyridin-2-yl)-4H-1,2,4-triazol-4-yl)pyrrolidine-1-carboxylate (250 mg, 0.7 mmol), Et₃N (840 µL, 6 mmol) and propylphosphonic anhydride (≥50 wt % in EtOAc, 0.5 mL) in EtOAc (0.5 mL) was heated in a biotage microwave at 100° C. for 1 h. The reaction was quenched by the addition of MeOH (5 mL) and then silica gel (2 g) was added and the volatiles were removed. Column chromatography (12 g, SiO₂, 0-15% MeOH (5% NH₄OH) in DCM) gave the racemic title compound (28 mg, 8%). ¹H NMR (500 MHz, CDCl₃) δ ppm 9.11 (s, 1H), 8.40-8.34 (m, 1H), 8.30 (s, 1H), 8.02 (d, J=7.3 Hz, 1H), 7.87 (t, J=7.9 Hz, 1H), 7.84 (s, 1H), 6.00-5.78 (m, 1H), 4.10 (s, 3H), 3.98-3.83 (m, 2H), 3.81 (s, 3H), 3.76-3.53 (m, 2H), 2.59-2.46 (m, 1H), 2.46-2.32 (m, 1H), 1.49 (br s, 9H). MS (ESI): 469.2 [M+H]⁺.

Step B: (S)-3-(3-(6-(3-Methoxy-1-methyl-1H-pyrazole-4-carboxamido)pyridin-2-yl)-4H-1,2,4-triazol-4-yl)pyrrolidine-1-carboxylate

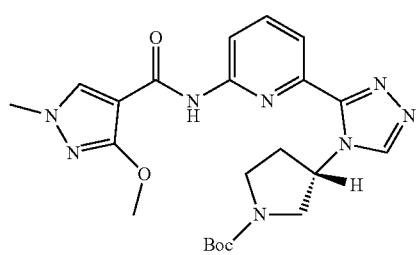 [SMILES: COc1nn(C)cc1C(=O)Nc1cccc(-c2nncn2[C@H]2CCN(C(=O)OC(C)(C)C)C2)n1]

tert-butyl rac-3-(3-(6-(3-methoxy-1-methyl-1H-pyrazole-4-carboxamido)pyridin-2-yl)-4H-1,2,4-triazol-4-yl)pyrrolidine-1-carboxylate (28 mg, 0.06 mmol) was purified by SFC (using a Chiralpak IA-H 5 µm, 30×250 mm column and using: 40% isopropanol in 0.1% Et₂NH in CO₂ as the mobile phase at a flow rate of 100 mL/min, ABPR 120 bar, MBPR 60 psi) to give in order of elution: tert-butyl (R)-3-(3-(6-(3-methoxy-1-methyl-1H-pyrazole-4-carboxamido)pyridin-2-yl)-4H-1,2,4-triazol-4-yl)pyrrolidine-1-carboxylate (13 mg, 0.02 mmol, stereochemistry arbitrarily assigned) and tert-butyl (S)-3-(3-(6-(3-methoxy-1-methyl-1H-pyrazole-4-carboxamido)pyridin-2-yl)-4H-1,2,4-triazol-4-yl)pyrrolidine-1-carboxylate (10 mg, stereochemistry arbitrarily assigned). ¹H NMR (500 MHz, CDCl₃) δ ppm 9.11 (s, 1H), 8.40-8.34 (m, 1H), 8.30 (s, 1H), 8.02 (d, J=7.3 Hz, 1H), 7.87 (t, J=7.9 Hz, 1H), 7.84 (s, 1H), 6.00-5.78 (m, 1H), 4.10 (s, 3H), 3.98-3.83 (m, 2H), 3.81 (s, 3H), 3.76-3.53 (m, 2H), 2.59-2.46 (m, 1H), 2.46-2.32 (m, 1H), 1.49 (br s, 9H). MS (ESI): 469.2 [M+H]⁺.

Example 41: N-(6-(4-Isopropyl-4H-1,2,4-triazol-3-yl)pyridin-2-yl)-3-methoxy-1-(2-methoxyethyl)-1H-pyrazole-4-carboxamide

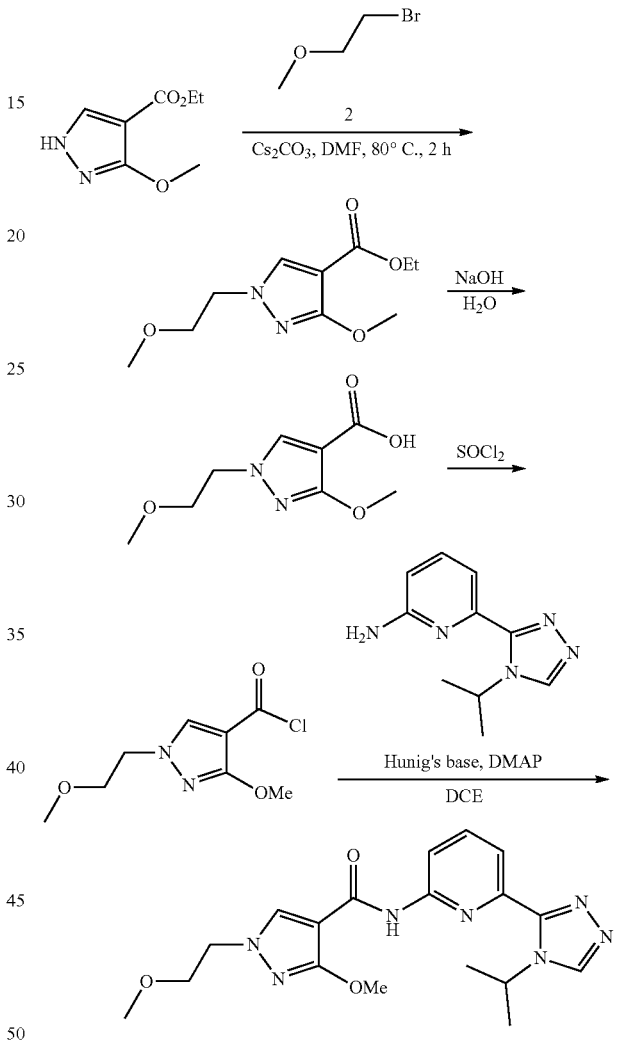

Step A: Ethyl 3-methoxy-1-(2-methoxyethyl)-1H-pyrazole-4-carboxylate

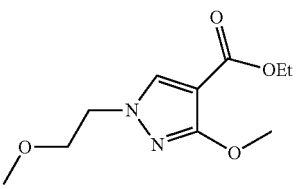

To a solution of ethyl 3-methoxy-1H-pyrazole-4-carboxylate (30 g, 176 mmol) in DMF (350 mL) was added 1-bromo-2-methoxyethane (31.8 g, 229 mmol) and Cs$_2$CO$_3$ (57.4 g, 176 mmol) and the mixture was stirred at 80° C. for 2 h. After this time, the mixture was concentrated in vacuo to give a gum which was poured into EtOAc (900 mL), and washed with sat. NaCl (500 mL×2). The separated organic phase was dried over Na$_2$SO$_4$, filtered and concentrated in vacuo and the product was purified by column chromatography on silica gel using Petroleum Ether/EtOAc (from 4/1 to 1/1) as eluent to give the title compound (28 g, 70%) as a yellow oil. $^1$H NMR (400 MHz, MeOD) δ ppm 7.90 (s, 1H), 4.21 (q, J=7.2 Hz, 2H), 4.11-4.15 (m, 2H), 3.91 (s, 3H), 3.70 (t, J=4.8 Hz, 2H), 3.31 (s, 3H), 1.29 (t, J=6.8 Hz, 3H).

Step B: 3-Methoxy-1-(2-methoxyethyl)-1H-pyrazole-4-carboxylic acid

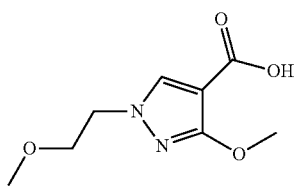

To a solution of NaOH (9.8 g, 245.3 mmol) in H$_2$O (300 mL) was added ethyl 3-methoxy-1-(2-methoxyethyl)-1H-pyrazole-4-carboxylate (28 g, 122.6 mmol) and stirred at 100° C. for 2 h. After this time the mixture was acidified with 2N HCl (30 mL) and extracted with DCM/MeOH (500 mL/50 mL×3). The combined organic extracts were dried over Na$_2$SO$_4$, filtered and concentrated in vacuo to give the title compound (15 g, 61%) as a white solid. $^1$H NMR (400 MHz, DMSO-d$_6$) δ ppm 11.94 (s, 1H), 8.00 (s, 1H), 4.12 (t, J=5.2 Hz, 2H), 3.82 (s, 3H), 3.65 (t, J=5.2 Hz, 2H), 3.24 (s, 3H). MS (ESI): 201.0 [M+H]$^+$.

Step C: 3-Methoxy-1-(2-methoxyethyl)-1H-pyrazole-4-carbonyl chloride

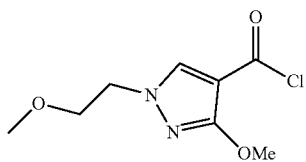

A mixture of 3-methoxy-1-(2-methoxyethyl)pyrazole-4-carboxylic acid (81 mg, 0.40 mmol) in thionyl chloride (0.5 mL, 6.85 mmol) was heated at 80° C. for 5 min. After this time the mixture was concentrated and co-evaporated with MeCN to give the title compound (85 mg, 98%).

Step D: N-(6-(4-Isopropyl-4H-1,2,4-triazol-3-yl)pyridin-2-yl)-3-methoxy-1-(2-methoxyethyl)-1H-pyrazole-4-carboxamide

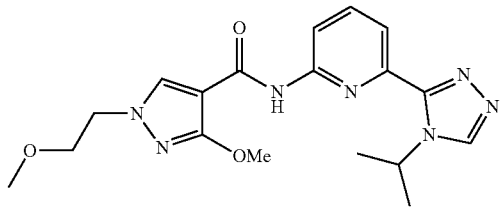 [SMILES: COCCn1cc(C(=O)Nc2cccc(-c3nncn3C(C)C)n2)c(OC)n1]

To a mixture of 3-methoxy-1-(2-methoxyethyl)-1H-pyrazole-4-carbonyl chloride (85 mg, 0.39 mmol), 6-(4-isopropyl-4H-1,2,4-triazol-3-yl)pyridin-2-amine (80 mg, 0.39 mmol) and DMAP (48 mg, 0.39 mmol) in DCE (1.00 mL) was added Hunig's base (340 μL, 1.94 mmol) and the mixture was stirred at rt overnight. After this time the reaction was partitioned between EtOAc and satd. NaHCO$_3$. The separated aqueous layer was re-extracted with EtOAc (×3) and the combined organic extracts were dried over MgSO$_4$, filtered and evaporated in vacuo. The product was purified by column chromatography using EtOAc/EtOH (3/1) as eluent to give the title compound (35 mg, 23%) as a white powder after lyophilization. $^1$H NMR (400 MHz, MeOD) δ ppm 8.85 (s, 1H), 8.28-8.42 (m, 1H), 8.06 (s, 1H), 7.92-8.04 (m, 1H), 7.81 (d, J=7.28 Hz, 1H), 5.25-5.64 (m, 1H), 4.20 (t, J=5.02 Hz, 2H), 4.11 (s, 3H), 3.74 (t, J=5.02 Hz, 2H), 3.34 (s, 3H), 1.64 (d, J=6.78 Hz, 6H). MS (ESI): 386.2 [M+H]$^+$ Example 42: 1-Isobutyl-N-(6-(4-isopropyl-4H-1,2,4-triazol-3-yl)pyridin-2-yl)-3-methoxy-1H-pyrazole-4-carboxamide

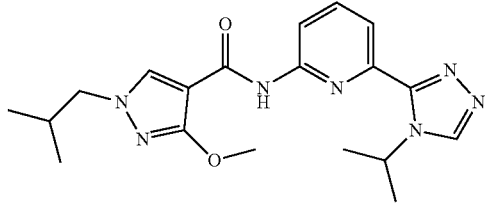 [SMILES: COc1nn(CC(C)C)cc1C(=O)Nc1cccc(-c2nncn2C(C)C)n1]

The title compound was synthesized according to the general procedure described in Example 41 but using 1-chloro-2-methylpropane in place of 1-bromo-2-methoxyethane in Step A to give the title compound (27 mg, 19% for the last step) as an off-white solid. $^1$H NMR (400 MHz, MeOD) δ ppm 8.85 (s, 1H), 8.34 (d, J=8.28 Hz, 1H), 8.04 (s, 1H), 7.98 (t, J=8.03 Hz, 1H), 7.81 (d, J=7.53 Hz, 1H), 5.45 (quin, J=6.78 Hz, 1H), 4.11 (s, 3H), 3.85 (d, J=7.03 Hz, 2H), 2.22 (dt, J=13.74, 6.81 Hz, 1H), 1.64 (d, J=6.78 Hz, 6H), 0.93 (d, J=6.78 Hz, 6H). MS (ESI): 384.0 [M+H]$^+$.

Example 43: 1-Isobutyl-3-methoxy-N-(6-(4-(1,1,1-trifluoropropan-2-yl)-4H-1,2,4-triazol-3-yl)pyridin-2-yl)-1H-pyrazole-4-carboxamide

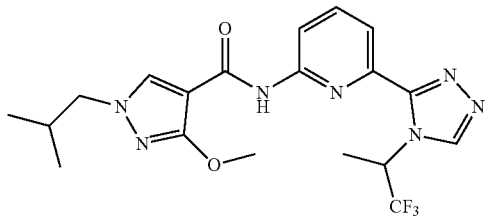 [SMILES: COc1nn(CC(C)C)cc1C(=O)Nc1cccc(-c2nncn2C(C)C(F)(F)F)n1]

The title compound was synthesized according to the general procedure described in Example 41 but using 1-chloro-2-methylpropane in place of 1-bromo-2-methoxyethane in Step A and 6-(4-(1,1,1-trifluoropropan-2-yl)-4H-1,2,4-triazol-3-yl)pyridin-2-amine in place of 6-(4-isopropyl-4H-1,2,4-triazol-3-yl)pyridin-2-amine in Step D to give the title compound (8 mg, 16% for the last step) as an off-white solid. $^1$H NMR (400 MHz, MeOD) δ ppm 9.01 (s, 1H), 8.34 (d, J=7.28 Hz, 1H), 7.84-8.13 (m, 3H), 6.79 (quin, J=7.22 Hz, 1H), 4.10 (s, 3H), 3.85 (d, J=7.28 Hz, 2H), 2.22 (dt, J=13.74, 6.81 Hz, 1H), 1.87 (d, J=7.03 Hz, 3H), 0.93 (d, J=6.78 Hz, 6H). MS (ESI): 438.0 [M+H]$^+$.

Example 44: N-(6-(4-Isopropyl-4H-1,2,4-triazol-3-yl)pyridin-2-yl)-3-methoxy-1-(pyridin-2-ylmethyl)-1H-pyrazole-4-carboxamide

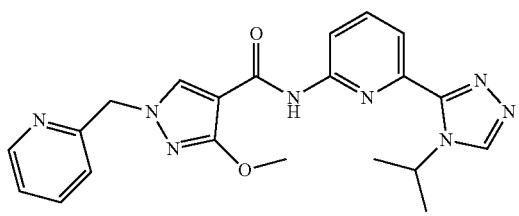 [SMILES: COc1nn(Cc2ccccn2)cc1C(=O)Nc1cccc(-c2nncn2C(C)C)n1]

The product was synthesized according to the general procedure described in Example 41 but using 2-(bromomethyl)pyridine in place of 1-bromo-2-methoxyethane in Step A to give the title compound (22 mg, 18% for the last step) as an off-white solid. MS (ESI): 419.2 [M+H]$^+$.

Example 45: 1-(2-(Dimethylamino)ethyl)-N-(6-(4-isopropyl-4H-1,2,4-triazol-3-yl)pyridin-2-yl)-3-methoxy-1H-pyrazole-4-carboxamide

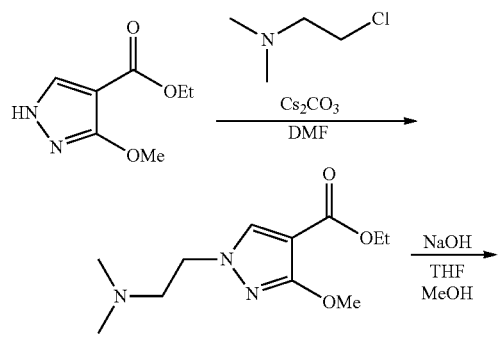

Step A: Ethyl 1-(2-(dimethylamino)ethyl)-3-methoxy-1H-pyrazole-4-carboxylate

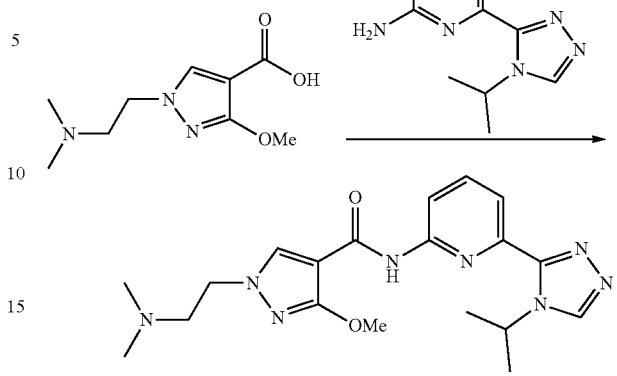

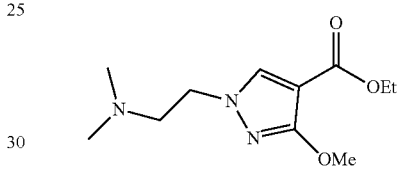

A mixture of ethyl 3-methoxy-1H-pyrazole-4-carboxylate (85 mg, 0.50 mmol), 2-chloro-N,N-dimethylethan-1-amine HCl (108 mg, 0.75 mmol) and Cs$_2$CO$_3$ (326 mg, 1.0 mmol) in DMF (1 mL) was heated in a reaction vial at 80° C. for 6 h. After this time, the reaction was partitioned between EtOAc and water. The separated aqueous layer was extracted with EtOAc and the combined organic extracts were dried over MgSO$_4$, filtered and concentrated in vacuo. The product was purified by normal phase column (eluting with EtOAc/EtOH (containing 1% Et$_3$N), 3/1) to give the title compound (70 mg, 58%) as a white solid. MS (ESI): 242.1 [M+H]$^+$.

Step B: 1-(2-(Dimethylamino)ethyl)-3-methoxy-1H-pyrazole-4-carboxylic acid

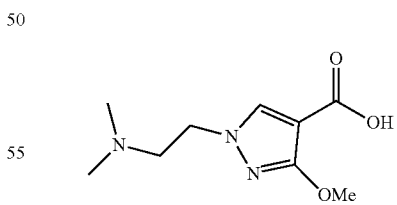

A mixture of ethyl 1-(2-(dimethylamino)ethyl)-3-methoxy-1H-pyrazole-4-carboxylate (99 mg, 0.41 mmol) in THF (1 mL) and MeOH (1 mL) was treated with 1N sodium hydroxide (0.5 mL) and the reaction mixture was heated at 60° C. for 1.5 h. After this time the reaction was neutralized by addition of 1N HCl (0.5 mL) and evaporated in vacuo to give the title compound as a solid, which was used without further purification in the next step. MS (ESI): 214.0 [M+H]$^+$.

Step C: 1-(2-(Dimethylamino)ethyl)-N-(6-(4-isopropyl-4H-1,2,4-triazol-3-yl)pyridin-2-yl)-3-methoxy-1H-pyrazole-4-carboxamide

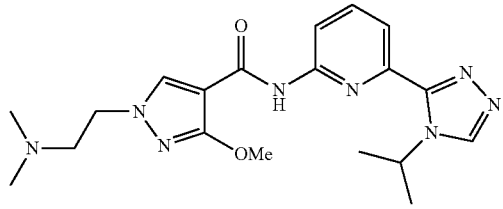 [SMILES: COc1nn(CCN(C)C)cc1C(=O)Nc1cccc(-c2nncn2C(C)C)n1]

The product was synthesized according to the general procedure described in Example 2 but using 1-(2-(dimethylamino)ethyl)-3-methoxy-1H-pyrazole-4-carboxylic acid in place of 1-methyl-1H-pyrazole-4-carboxylic acid. The product was purified by normal phase column (eluting with EtOAc/EtOH (containing 1% Et₃N), 3/1) to give the title compound (28 mg, 17%) as a pale brown oil. $^1$H NMR (400 MHz, MeOD) δ ppm 8.84 (s, 1H), 8.32 (d, J=7.78 Hz, 1H), 8.09 (s, 1H), 7.96 (t, J=7.91 Hz, 1H), 7.80 (d, J=7.28 Hz, 1H), 5.34-5.53 (m, 1H), 4.15-4.23 (m, 2H), 4.1 (s, 3H) 2.84 (t, J=6.53 Hz, 2H), 2.32 (s, 6H), 1.64 (d, J=6.78 Hz, 6H). MS (ESI): 399.2 [M+H]⁺.

Example 46: N-(6-(4-Isopropyl-4H-1,2,4-triazol-3-yl)pyridin-2-yl)-3-methoxy-1-(2-morpholinoethyl)-1H-pyrazole-4-carboxamide

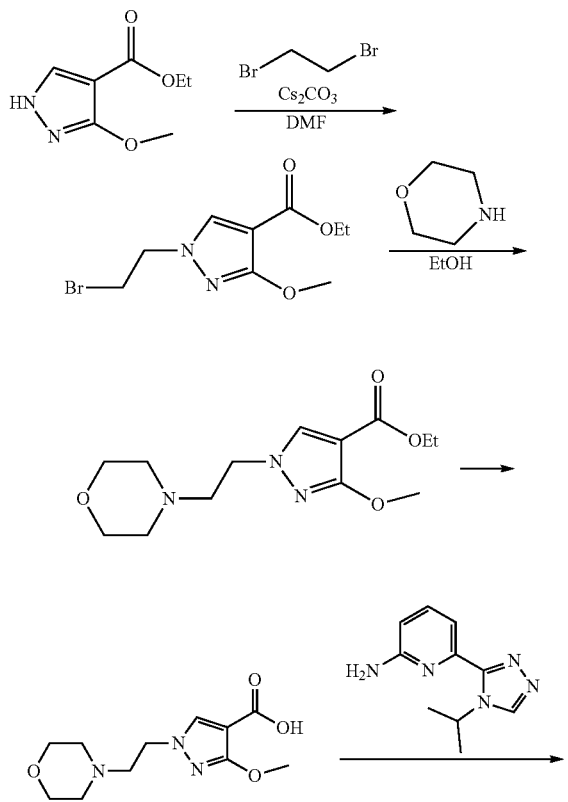

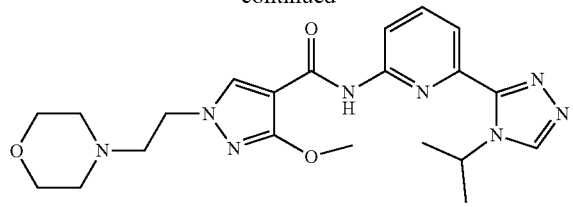

Step A: Ethyl 1-(2-bromoethyl)-3-methoxy-1H-pyrazole-4-carboxylate

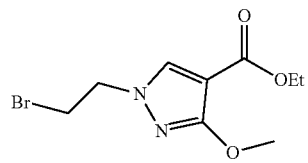

A mixture ethyl 3-methoxy-1H-pyrazole-4-carboxylate (85 mg, 0.5 mmol), 1,2-dibromoethane (86 mL, 1.0 mmol) and Cs₂CO₃ (163 mg, 0.5 mmol) in DMF (1 mL) was heated in a reaction vial at 80° C. for 3 h. The reaction was repeated under the same conditions and the combined crude mixtures were partitioned between EtOAc and water. The separated aqueous layer was extracted with EtOAc (×2) and the combined organic extracts were dried over MgSO₄, filtered and concentrated in vacuo. The product was purified by normal phase chromatography eluting with 50% EtOAc in heptane to give the title compound (78 mg, 28%). MS (ESI): 277.0 [M+H (⁷⁹Br)]+.

Step B: Ethyl 3-methoxy-1-(2-morpholinoethyl)-1H-pyrazole-4-carboxylate

A mixture of ethyl 1-(2-bromoethyl)-3-methoxy-1H-pyrazole-4-carboxylate (78 mg, 0.28 mmol) and morpholine (0.8 mL, 9.2 mmol) in EtOH (0.8 mL) was heated in a reaction vial at 60° C. for 1 h. After this time the reaction mixture was partitioned between EtOAc and water. The separated aqueous layer was extracted with EtOAc and the combined organic extracts were dried over MgSO₄, filtered and concentrated in vacuo to give the title compound (80 mg, 100%).

Step C: 3-Methoxy-1-(2-morpholinoethyl)-1H-pyrazole-4-carboxylic acid

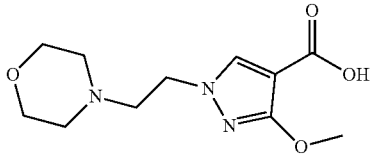 [SMILES: COc1nn(CCN2CCOCC2)cc1C(=O)O]

A mixture of ethyl 3-methoxy-1-(2-morpholinoethyl)-1H-pyrazole-4-carboxylate (80 mg, 0.28 mmol) in THF (0.5 mL) and MeOH (0.5 mL) was treated with 1N sodium hydroxide (0.5 mL) and the reaction mixture was heated at 60° C. for 1.5 h. After this time the mixture was neutralized by addition of 1N HCl (0.5 mL) and then it was concentrated in vacuo to give the title compound (71 mg, 100%) as a solid. MS (ESI): 256.0 [M+H]$^+$.

Step D: N-(6-(4-Isopropyl-4H-1,2,4-triazol-3-yl)pyridin-2-yl)-3-methoxy-1-(2-morpholinoethyl)-1H-pyrazole-4-carboxamide

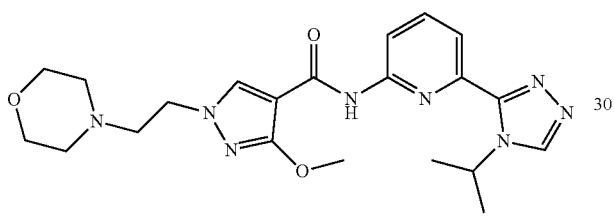

To a mixture of 3-methoxy-1-(2-morpholinoethyl)-1H-pyrazole-4-carboxylic acid (71 mg, 0.28 mmol) and 6-(4-isopropyl-4H-1,2,4-triazol-3-yl)pyridin-2-amine (57 mg, 0.28 mmol) was added Et$_3$N (38 µL, 0.28 mmol) and propylphosphonic anhydride (≥50 wt % in EtOAc, 0.8 mL) and the mixture was heated at 80° C. for 2.5 h. After this time the reaction was quenched with a small amount of MeOH (~2 mL) and then it was partitioned between EtOAc and water. The aqueous layer was extracted with EtOAc and the combined organic extracts were dried over MgSO$_4$, filtered and concentrated in vacuo. The product was purified by normal phase chromatography eluting with EtOAc/EtOH (3/1) to give the title compound (24 mg, 20%). $^1$H NMR (400 MHz, MeOD) δ ppm 8.85 (s, 1H), 8.34 (d, J=8.03 Hz, 1H), 8.11 (s, 1H), 7.98 (t, J=8.03 Hz, 1H), 7.81 (d, J=7.28 Hz, 1H), 5.44 (dt, J=13.49, 6.68 Hz, 1H), 4.15-4.25 (m, 2H), 4.12 (s, 3H), 3.59-3.76 (m, 4H), 3.46 (q, J=7.03 Hz, 2H), 2.36-2.62 (m, 4H), 1.64 (d, J=6.78 Hz, 6H), MS (ESI): 441.2 [M+H]$^+$.

Example 47: 1-(Cyclopropylmethyl)-N-(6-(4-isopropyl-4H-1,2,4-triazol-3-yl)pyridin-2-yl)-3-methoxy-1H-pyrazole-4-carboxamide

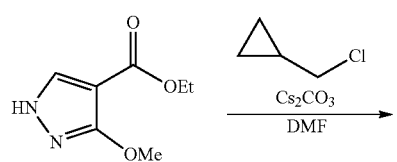

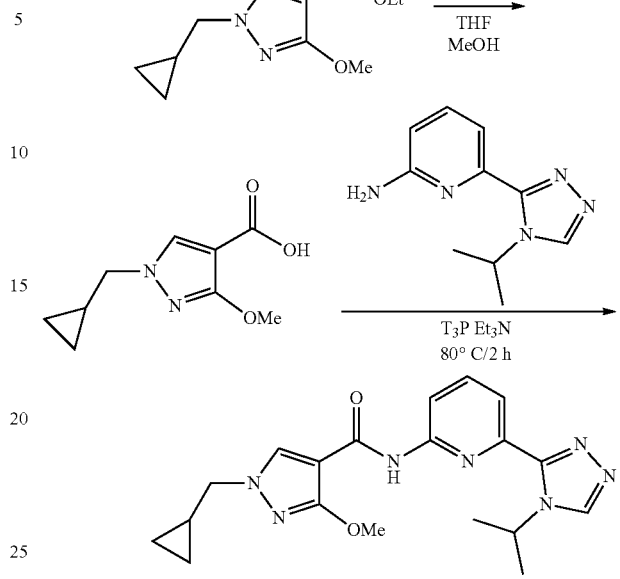

Step A: Ethyl 1-(cyclopropylmethyl)-3-methoxy-1H-pyrazole-4-carboxylate

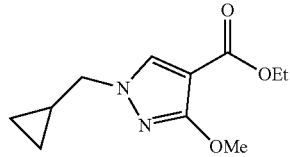 [SMILES: CCOC(=O)c1cn(CC2CC2)nc1OC]

A mixture of ethyl 3-methoxy-1H-pyrazole-4-carboxylate (85 mg, 0.50 mmol), (chloromethyl)cyclopropane (68 mg, 0.75 mmol) and Cs$_2$CO$_3$ (163 mg, 0.5 mmol) in DMF (1 mL) was heated in a reaction vial at 80° C. for 1 h. The reaction was repeated under the same conditions and the combined crude mixture was partitioned between EtOAc and water. The aqueous layer was then extracted with EtOAc and the combined organic extracts were dried over MgSO$_4$, filtered and concentrated in vacuo. The product was purified by normal phase chromatography eluting with 30-40% EtOAc in heptane to give the title compound (180 mg, 80%) as a white solid. MS (ESI): 225.1 [M+H]$^+$.

Step B: 1-(Cyclopropylmethyl)-3-methoxy-1H-pyrazole-4-carboxylic acid

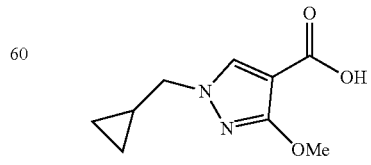

To a solution of ethyl 1-(cyclopropylmethyl)-3-methoxy-1H-pyrazole-4-carboxylate (178 mg, 0.79 mmol) in THF Step C: 1-(Cyclopropylmethyl)-N-(6-(4-isopropyl-4H-1,2,4-triazol-3-yl)pyridin-2-yl)-3-methoxy-1H-pyrazole-4-carboxamide

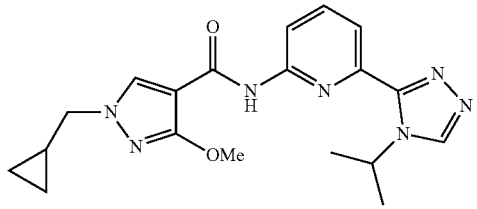 [SMILES: COc1nn(CC2CC2)cc1C(=O)Nc1cccc(-c2nncn2C(C)C)n1]

To a mixture of 6-(4-isopropyl-1,2,4-triazol-3-yl)pyridin-2-amine (61 mg, 0.3 mmol) and 1-(cyclopropylmethyl)-3-methoxy-pyrazole-4-carboxylic acid (59 mg, 0.3 mmol) was added Et$_3$N (1.1 mL, 7.91 mmol) and propylphosphonic anhydride (≥50 wt % in EtOAc, 0.8 mL) and the mixture was heated at 80° C. for 2 h. After this time the mixture was quenched with a small amount of MeOH (~0.5 mL) and then it was partitioned between EtOAc and water. The separated aqueous layer was extracted with EtOAc and the combined organic extracts were dried over MgSO$_4$, filtered and concentrated in vacuo. The product was purified by normal phase chromatography eluting with EtOAc/EtOH (from 1/0 to 3/1) to give title compound as a pale yellow solid (24 mg, 21%). $^1$H NMR (400 MHz, MeOD) δ ppm 8.85 (s, 1H), 8.34 (d, J=8.03 Hz, 1H), 8.11 (s, 1H), 7.97 (t, J=7.91 Hz, 1H), 7.81 (d, J=7.28 Hz, 1H), 5.44 (dt, J=13.36, 6.75 Hz, 1H), 4.11 (s, 3H), 3.86-3.98 (m, 2H), 1.60-1.69 (m, 6H), 1.19-1.41 (m, 1H), 0.51-0.81 (m, 2H), 0.19-0.50 (m, 2H). MS (ESI): 382.0 [M+H]$^+$.

Example 48: (S)-1-(Cyclopropylmethyl)-3-methoxy-N-(6-(4-(1,1,1-trifluoropropan-2-yl)-4H-1,2,4-triazol-3-yl)pyridin-2-yl)-1H-pyrazole-4-carboxamide

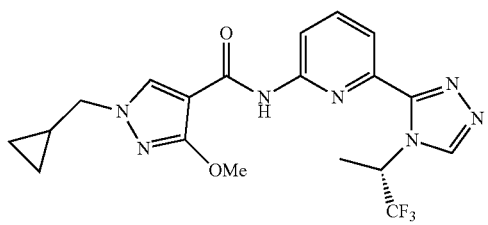 [SMILES: COc1nn(CC2CC2)cc1C(=O)Nc1cccc(-c2nncn2[C@@H](C)C(F)(F)F)n1]

The product was synthesized according to the general procedure described in Example 47 but using (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine in Step C to give the title compound (12 mg, 35%) as an off-white solid. $^1$H NMR (400 MHz, MeOD) δ ppm 8.92 (s, 1H), 8.24 (dd, J=8.03, 0.75 Hz, 1H), 8.03 (s, 1H), 7.75-7.98 (m, 3H), 6.70 (dt, J=14.37, 7.25 Hz, 1H), 4.02 (s, 3H), 3.81 (d, J=7.28 Hz, 2H), 1.78 (d, J=7.03 Hz, 3H), 1.05-1.36 (m, 1H), 0.42-0.71 (m, 2H), 0.13-0.42 (m, 2H). MS (ESI): 436.0 [M+H]$^+$.

Example 49: 3-Methoxy-1-methyl-N-(6-(4-(3-methyloxetan-3-yl)-4H-1,2,4-triazol-3-yl)pyridin-2-yl)-1H-pyrazole-4-carboxamide

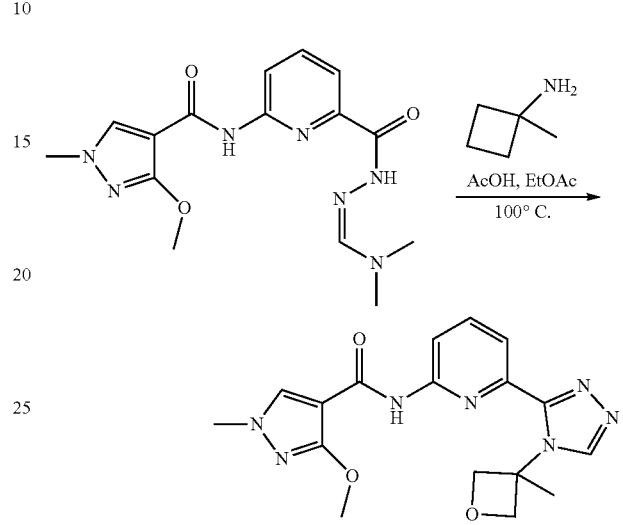

A reaction vial was charged with a mixture of N-(6-(2-((dimethylamino)methylene)hydrazine-1-carbonyl)pyridin-2-yl)-3-methoxy-1-methyl-1H-pyrazole-4-carboxamide (50 mg, 0.15 mmol), tetrahydro-2H-pyran-4-amine (30 mg, 0.29 mmol), MeCN (2 mL) and acetic acid (0.7 mL). The resulting mixture was heated at reflux for 1 h. Purification by mass-directed HPLC (using 5-65% MeCN in H$_2$O (containing 4% NH$_4$OH) as eluent) gave the title compound (7 mg, 13%). $^1$H NMR (500 MHz, MeOD) δ ppm 8.91 (br s, 1H), 8.07 (br d, J=9.2 Hz, 1H), 7.94 (s, 1H), 7.70 (br t, J=7.9 Hz, 1H), 7.47 (br d, J=6.7 Hz, 1H), 5.41 (d, J=15.3 Hz, 1H), 4.37 (br d, J=14.7 Hz, 1H), 3.93 (s, 3H), 3.76 (s, 3H), 3.74 (m, 2H), 1.73 (s, 3H). MS (ESI): 370.2 [M+H]$^+$.

Example 50: 1-(Cyclopropylmethyl)-3-(difluoromethyl)-N-(6-(4-isopropyl-4H-1,2,4-triazol-3-yl)pyridin-2-yl)-1H-pyrazole-4-carboxamide

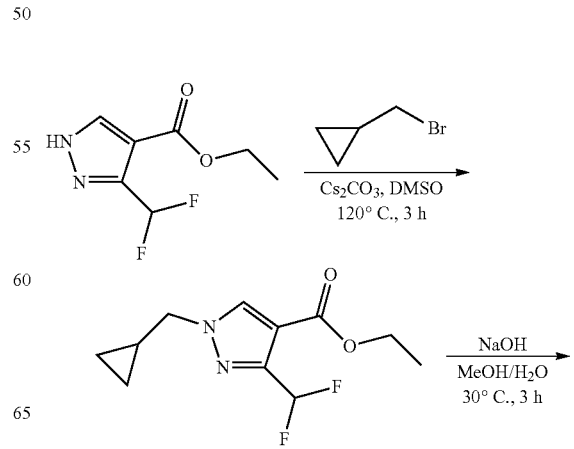

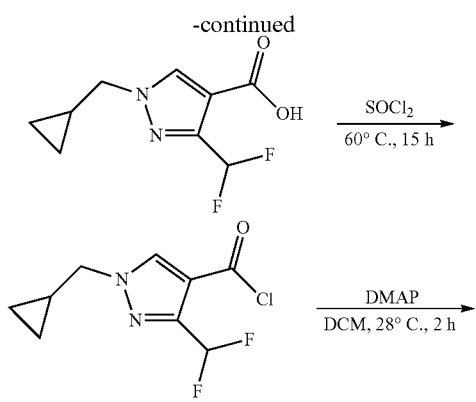

Step A: Ethyl 1-(cyclopropylmethyl)-3-(difluoromethyl)-1H-pyrazole-4-carboxylate

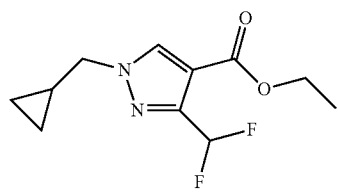 [SMILES: CCOC(=O)c1cn(CC2CC2)nc1C(F)F]

To a solution of ethyl 3-(difluoromethyl)-1H-pyrazole-4-carboxylate (2 g, 10.5 mmol) in DMSO (30 mL) was added (bromomethyl)cyclopropane (5.68 g, 42.0 mmol) and Cs$_2$CO$_3$ (6.85 g, 21.0 mmol) and the mixture was heated at 120° C. for 3 h. After this time the mixture was concentrated in vacuo and purified by HPLC (using a Phenomenex Synergi Max-RP 10 μm, 150×50 mm column and using water (containing 0.225% HCOOH) and MeCN from 25% to 55% as the mobile phase at a flow rate of 120 mL/min) to give the title compound as a white solid (1.1 g, 47%). $^1$H NMR (400 MHz, DMSO-d$_6$) δ ppm 8.48 (s, 1H), 7.35-7.03 (m, 1H), 4.32-4.19 (m, 2H), 4.05 (d, J=7.0 Hz, 2H), 1.34-1.24 (m, 4H), 0.57-0.50 (m, 2H), 0.43-0.36 (m, 2H). MS (ESI): 245.1 [M+H]$^+$.

Step B: 1-(Cyclopropylmethyl)-3-(difluoromethyl)-1H-pyrazole-4-carboxylic acid

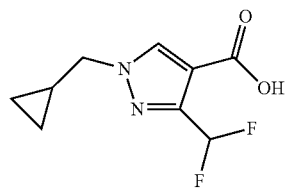 [SMILES: O=C(O)c1cn(CC2CC2)nc1C(F)F]

To a solution of ethyl 1-(cyclopropylmethyl)-3-(difluoromethyl)-1H-pyrazole-4-carboxylate (1 g, 4.09 mmol) in MeOH/H$_2$O (40 mL, 1/1) was added NaOH (819 mg, 20.5 mmol) and the mixture was stirred at 30° C. for 3 h. After this time the mixture was concentrated in vacuo and dissolved in H$_2$O (100 mL). The pH of the mixture was adjusted to 3-4 by addition of an aqueous solution of HCl (3N) and extracted with EtOAc (300 mL×3). The combined organic layers were washed with brine (300 mL), dried over Na$_2$SO$_4$, filtered and concentrated in vacuo to give the title compound as a brown solid (800 mg, 89%). MS (ESI): 217.1 [M+H]$^+$.

Step C: 1-(Cyclopropylmethyl)-3-(difluoromethyl)-1H-pyrazole-4-carbonyl chloride

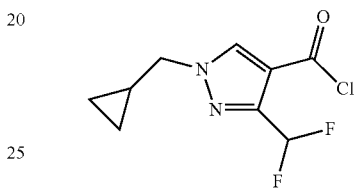

A solution of 1-(cyclopropylmethyl)-3-(difluoromethyl)-1H-pyrazole-4-carboxylic acid (200 mg, 0.93 mmol) in SOCl$_2$ (4 mL) was stirred at 60° C. for 15 h. After this time the mixture was concentrated in vacuo to give the title compound (200 mg, 91%).

Step D: 1-(Cyclopropylmethyl)-3-(difluoromethyl)-N-(6-(4-isopropyl-4H-1,2,4-triazol-3-yl)pyridin-2-yl)-1H-pyrazole-4-carboxamide

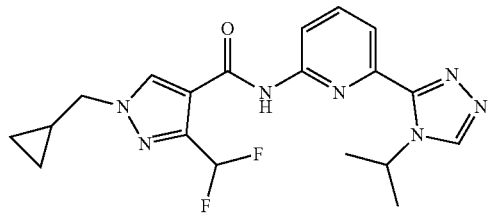 [SMILES: CC(C)n1cnnc1-c1cccc(NC(=O)c2cn(CC3CC3)nc2C(F)F)n1]

A solution of 1-(cyclopropylmethyl)-3-(difluoromethyl)-1H-pyrazole-4-carbonyl chloride (200 mg, 0.85 mmol) in DCM (10 mL) was stirred at 28° C. for 30 min. After this time the mixture was adjusted to pH 7-8 with pyridine and DMAP (260 mg, 2.13 mmol) was added and the mixture was stirred at 28° C. for 2 h. After this time the reaction was concentrated in vacuo and purified by prep-HPLC (using a Waters Xbridge Prep OBD C18 5 μm, 150×30 mm column and using water (containing 0.05% NH$_3$·H$_2$O) and MeCN from 24 to 54% as the mobile phase at a flow rate of 25 mL/min) to give the title compound (91 mg, 26%). $^1$H NMR (400 MHz, DMSO-d$_6$) δ ppm 10.56 (s, 1H), 8.88 (s, 1H), 8.72 (s, 1H), 8.16 (dd, J=0.8, 8.3 Hz, 1H), 8.05-7.98 (m, 1H), 7.80 (dd, J=0.8, 8.8 Hz, 1H), 7.49-7.19 (m, 1H), 5.51 (m, 1H), 4.11 (d, J=7.2 Hz, 2H), 1.44 (d, J=6.4 Hz, 6H), 1.36-1.24 (m, 1H), 0.64-0.58 (m, 2H), 0.47-0.42 (m, 2H). MS (ESI): 402.2 [M+H]$^+$.

Example 51: (S)-3-(Difluoromethyl)-1-(2-methoxy-ethyl)-N-(6-(4-(1,1,1-trifluoropropan-2-yl)-4H-1,2,4-triazol-3-yl)pyridin-2-yl)-1H-pyrazole-4-carboxamide

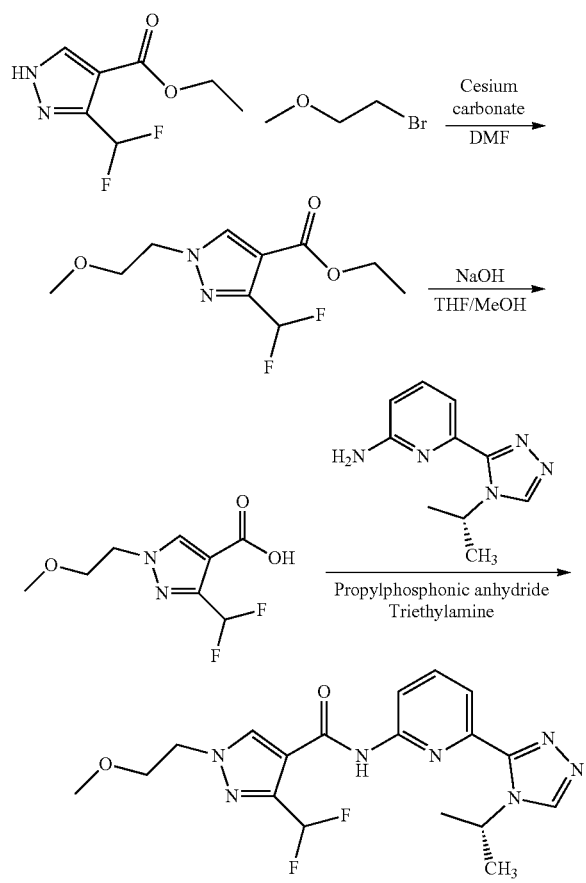

Step A: Ethyl 3-(difluoromethyl)-1-(2-methoxyethyl)-1H-pyrazole-4-carboxylate

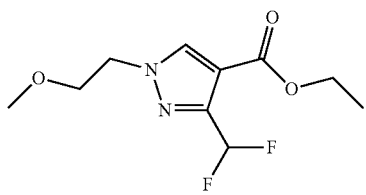 [SMILES: CCOC(=O)c1cn(CCOC)nc1C(F)F]

Ethyl 3-(difluoromethyl)-1H-pyrazole-4-carboxylate (250 mg, 1.3 mmol) and 1-bromo-2-methoxy-ethane (237 mg, 1.7 mmol, 160 µL) were dissolved in DMF (2.0 mL) and the mixture was heated at 80° C. for 3 h. After this time the reaction was cooled to rt, diluted with EtOAc, and washed with water (×2). The separated organic layer was dried over MgSO$_4$, filtered and concentrated in vacuo. Purification by silica gel chromatography (50-100% EtOAc in heptane) gave the title compound (325 mg, 61%). $^1$H NMR (400 MHz, CDCl$_3$) δ ppm 8.00 (t, J=1.1 Hz, 1H), 6.96-7.26 (m, 1H), 4.27-4.37 (m, 4H), 3.69-3.80 (m, 2H), 3.34 (s, 3H), 1.36 (t, J=7.2 Hz, 3H). MS (ESI): 249.1 [M+H]$^+$.

Step B: 3-(Difluoromethyl)-1-(2-methoxyethyl)-1H-pyrazole-4-carboxylic acid

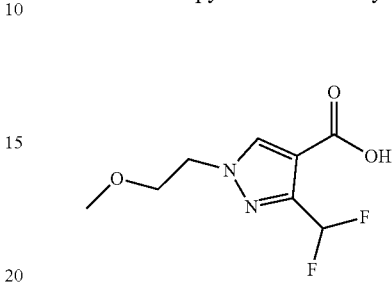

Ethyl 3-(difluoromethyl)-1-(2-methoxyethyl)pyrazole-4-carboxylate (200 mg, 0.81 mmol) was dissolved in a solution of THF (4.0 mL) and MeOH (4.0 mL). NaOH (1 M, 1 mL) was then added and the reaction was heated at 60° C. for 1 h. After this time the reaction was acidified by addition of 1N HCl and the mixture was partitioned between EtOAc and water. The separated organic phase was dried, filtered over MgSO$_4$ and concentrated in vacuo to give the title compound (170 mg, 96%). MS (ESI): 221.0 [M+H]$^+$.

Step C: (S)-3-(Difluoromethyl)-1-(2-methoxyethyl)-N-(6-(4-(1,1,1-trifluoropropan-2-yl)-4H-1,2,4-triazol-3-yl)pyridin-2-yl)-1H-pyrazole-4-carboxamide

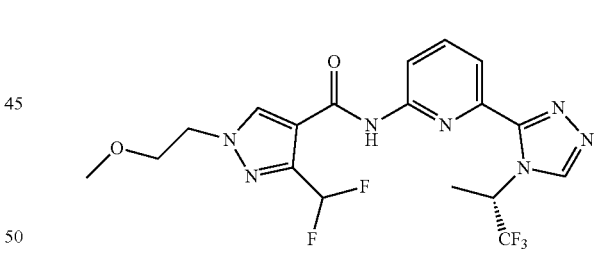

3-(Difluoromethyl)-1-(2-methoxyethyl)pyrazole-4-carboxylic acid (178 mg, 0.81 mmol) and 6-[4-[(1S)-2,2,2-trifluoro-1-methyl-ethyl]-1,2,4-triazol-3-yl]pyridin-2-amine (208 mg, 0.81 mmol) were dissolved in Et$_3$N (1.1 mL, 8.1 mmol). Propylphosphonic anhydride (≥50 wt % in EtOAc, 825 µL) was then added and the reaction was heated at 80° C. for 3 h. After this time the reaction was cooled to rt and quenched by addition of MeOH (3 mL). The resulting solid was filtered and dried under vacuum to afford the title compound (290 mg, 75%). $^1$H NMR (400 MHz, CDCl$_3$) δ ppm 8.87 (br t, J=5.1 Hz, 1H), 8.43 (d, J=1.0 Hz, 1H), 8.38 (dd, J=8.3, 0.8 Hz, 1H), 8.23 (s, 1H), 8.13 (dd, J=7.8, 0.8 Hz, 1H), 7.92 (t, J=8.0 Hz, 1H), 6.69-7.09 (m, 2H), 4.34 (t, J=4.9 Hz, 2H), 3.73-3.84 (m, 2H), 3.36 (s, 3H), 1.80 (d, J=7.3 Hz, 3H). MS (ESI): 460.1 [M+H]$^+$.

Example 52: (S)-3-Methoxy-1-(2-methoxyethyl)-N-(6-(4-(1,1,1-trifluoropropan-2-yl)-4H-1,2,4-triazol-3-yl)pyridin-2-yl)-1H-pyrazole-4-carboxamide

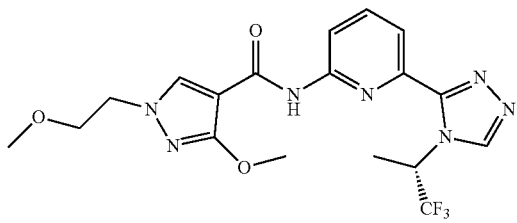 [SMILES: COCCn1cc(C(=O)Nc2cccc(-c3nncn3[C@@H](C)C(F)(F)F)n2)c(OC)n1]

The title compound was synthesized according to the general procedure described in Example 41 but using (S)-6-(4-(1,1,1-trifluoropropan-2-yl)-4H-1,2,4-triazol-3-yl)pyridin-2-amine in place of 6-(4-isopropyl-4H-1,2,4-triazol-3-yl)pyridin-2-amine in Step D to give the title compound (23 mg, 51%) as a white powder. $^1$H NMR (400 MHz, MeOD) δ ppm 9.01 (s, 1H), 8.33 (dd, J=8.16, 0.88 Hz, 1H), 8.05 (s, 1H), 7.87-8.03 (m, 2H), 6.79 (dt, J=14.49, 7.18 Hz, 1H), 4.20 (t, J=5.15 Hz, 2H), 4.11 (s, 3H), 3.74 (t, J=5.15 Hz, 2H), 3.34 (s, 3H), 1.87 (d, J=7.28 Hz, 3H). MS (ESI): 440.1 [M+H]$^+$.

Example 53: (R)-3-Methoxy-1-(2-methoxyethyl)-N-(6-(4-(1,1,1-trifluoropropan-2-yl)-4H-1,2,4-triazol-3-yl)pyridin-2-yl)-1H-pyrazole-4-carboxamide

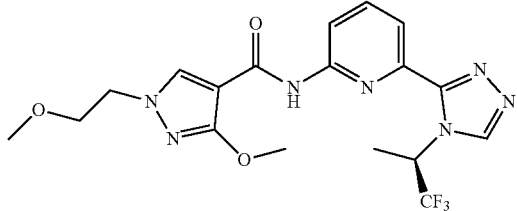 [SMILES: COCCn1cc(C(=O)Nc2cccc(-c3nncn3[C@H](C)C(F)(F)F)n2)c(OC)n1]

The title compound was synthesized according to the general procedure described in Example 41 but using (R)-6-(4-(1,1,1-trifluoropropan-2-yl)-4H-1,2,4-triazol-3-yl)pyridin-2-amine in place of 6-(4-isopropyl-4H-1,2,4-triazol-3-yl)pyridin-2-amine in Step D to give the title compound (23 mg, 52%) as a white powder. $^1$H NMR (400 MHz, MeOD) δ ppm 9.01 (s, 1H), 8.33 (d, J=8.03 Hz, 1H), 8.05 (s, 1H), 7.83-8.02 (m, 2H), 6.59-6.90 (m, 1H), 4.20 (t, J=5.02 Hz, 2H), 4.11 (s, 3H), 3.74 (t, J=5.15 Hz, 2H), 3.34 (s, 3H), 1.88 (d, J=7.28 Hz, 3H). MS (ESI): 440.1 [M+H]$^+$.

Example 54: N-(6-(4-Cyclopropyl-4H-1,2,4-triazol-3-yl)pyridin-2-yl)-3-methoxy-1-(2-methoxyethyl)-1H-pyrazole-4-carboxamide

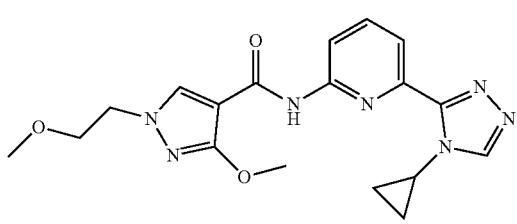 [SMILES: COCCn1cc(C(=O)Nc2cccc(-c3nncn3C3CC3)n2)c(OC)n1]

The title compound was synthesized according to the general procedure described in Example 41 but using 6-(4-cyclopropyl-4H-1,2,4-triazol-3-yl)pyridin-2-amine in place of 6-(4-isopropyl-4H-1,2,4-triazol-3-yl)pyridin-2-amine in Step D to give the title compound (19 mg, 26%) as an off-white solid. $^1$H NMR (500 MHz, MeOD) δ ppm 8.63 (s, 1H), 8.35 (d, J=8.55 Hz, 1H), 8.05 (s, 1H), 7.97 (t, J=7.94 Hz, 1H), 7.81 (d, J=7.94 Hz, 1H), 4.20 (t, J=5.19 Hz, 2H), 4.09 (s, 3H), 3.81-4.00 (m, 1H), 3.74 (t, J=4.88 Hz, 2H), 3.34 (s, 3H), 1.18 (q, J=6.92 Hz, 2H), 0.94-1.11 (m, 2H). MS (ESI): 384.2 [M+H]$^+$.

Example 55: 1-Allyl-N-(6-(4-isopropyl-4H-1,2,4-triazol-3-yl)pyridin-2-yl)-3-methoxy-1H-pyrazole-4-carboxamide

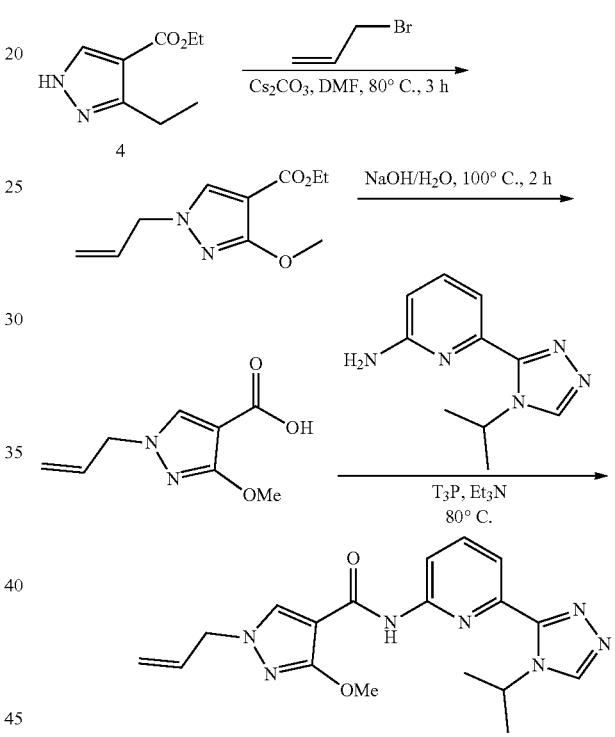

Step A: Ethyl 1-allyl-3-methoxy-1H-pyrazole-4-carboxylate

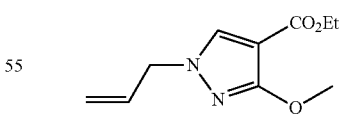

A mixture of ethyl 3-methoxy-1H-pyrazole-4-carboxylate (1.72 g, 10.1 mmol), 3-bromoprop-1-ene (1.59 g, 13.1 mmol) and Cs$_2$CO$_3$ (3.29 g, 10.1 mmol) in DMF (50 mL) was stirred at 80° C. for 3 h. After this time the reaction was quenched with water (50 mL) and extracted with EtOAc (50 mL×3) and the combined organic extracts were washed with water (50 mL), brine (50 mL), dried over MgSO$_4$, filtered and concentrated in vacuo to give the title compound (1.5 g, 68%) as a yellow oil.

Step B: 1-Allyl-3-methoxy-1H-pyrazole-4-carboxylic acid

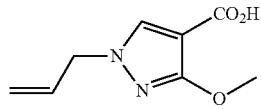

A mixture of ethyl 1-allyl-3-methoxy-1H-pyrazole-4-carboxylate (19 g, 90 mmol) and NaOH (7.23 g, 180 mmol) in H$_2$O (190 mL) was stirred at 100° C. for 3 h. After this time the reaction was cooled to rt, and then it was acidified by addition of an aqueous solution of HCl (3M). The resulting precipitate was filtered, washed with water and dried under vacuum (lyophilization) to give the title compound (13 g, 79%) as a white solid. $^1$H NMR (400 MHz, DMSO-d$_6$) δ ppm 11.96 (s, 1H), 8.03 (s, 1H), 6.16-5.83 (m, 1H), 5.45-5.01 (m, 2H), 4.61 (d, J=6.0 Hz, 2H), 3.81 (s, 3H). MS (ESI): 182.9 [M+H]$^+$.

Step C: 1-Allyl-N-(6-(4-isopropyl-4H-1,2,4-triazol-3-yl)pyridin-2-yl)-3-methoxy-1H-pyrazole-4-carboxamide

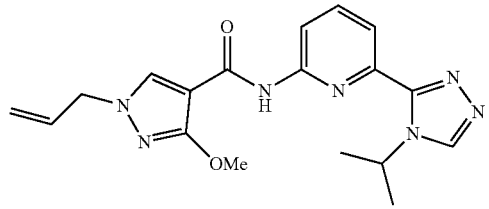 [SMILES: C=CCn1cc(C(=O)Nc2cccc(-c3nncn3C(C)C)n2)c(OC)n1]

To a mixture of 1-allyl-3-methoxy-pyrazole-4-carboxylic acid (182 mg, 1.0 mmol) and 6-(4-isopropyl-1,2,4-triazol-3-yl)pyridin-2-amine (203 mg, 1.0 mmol) was added Et$_3$N (2 mL, 14.4 mmol) and propylphosphonic anhydride (≥50 wt % in EtOAc, 2 mL) and the mixture was heated at 80° C. for 4 h. After this time the reaction was quenched with a small amount of MeOH (~2 mL) and then it was partitioned between EtOAc and water. The separated aqueous layer was extracted with EtOAc and the combined organic extracts were dried over MgSO$_4$, filtered and concentrated in vacuo. Purification by normal phase column eluting with EtOAc/EtOH (3/1) gave the title compound (200 mg, 54%). $^1$H NMR (400 MHz, MeOD) δ ppm 8.85 (s, 1H), 8.34 (d, J=8.53 Hz, 1H), 8.06 (s, 1H), 7.98 (t, J=7.91 Hz, 1H), 7.81 (d, J=7.78 Hz, 1H), 5.91-6.16 (m, 1H), 5.39-5.56 (m, 1H), 5.16-5.36 (m, 2H), 4.67 (d, J=5.77 Hz, 2H), 4.11 (s, 3H), 1.64 (d, J=6.78 Hz, 6H). MS (ESI): 368.0 [M+H]$^+$.

Example 56: 1-Allyl-3-methoxy-N-(6-(4-(1,1,1-trifluoropropan-2-yl)-4H-1,2,4-triazol-3-yl)pyridin-2-yl)-1H-pyrazole-4-carboxamide

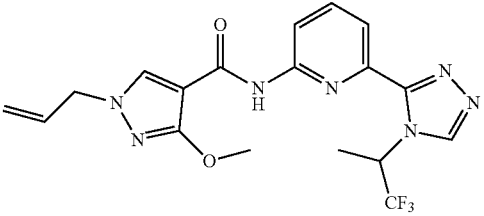 [SMILES: C=CCn1cc(C(=O)Nc2cccc(-c3nncn3C(C)C(F)(F)F)n2)c(OC)n1]

The product was synthesized according to the general procedure described in Example 55 but using 6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine to give the title compound (168 mg, 40%) as an off-white solid. $^1$H NMR (400 MHz, MeOD) δ ppm 9.01 (s, 1H), 8.33 (dd, J=8.16, 0.88 Hz, 1H), 8.06 (s, 1H), 7.75-8.04 (m, 2H), 6.79 (quin, J=7.22 Hz, 1H), 6.05 (ddt, J=16.78, 10.57, 5.90, 5.90 Hz, 1H), 5.21-5.34 (m, 2H), 4.68 (d, J=5.77 Hz, 2H), 4.11 (s, 3H), 1.87 (d, J=7.28 Hz, 3H). MS (ESI): 421.9 [M+H]$^+$.

Example 57: (S)-1-Allyl-3-methoxy-N-(6-(4-(1,1,1-trifluoropropan-2-yl)-4H-1,2,4-triazol-3-yl)pyridin-2-yl)-1H-pyrazole-4-carboxamide

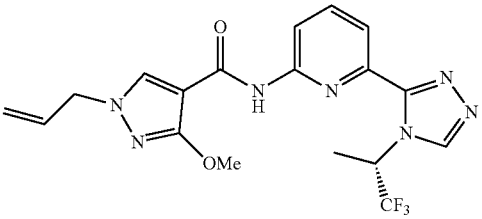 [SMILES: C=CCn1cc(C(=O)Nc2cccc(-c3nncn3[C@@H](C)C(F)(F)F)n2)c(OC)n1]

The product was synthesized according to the general procedure described in Example 55 but using (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine to give the title compound (10 mg, 19%) as an off-white solid. $^1$H NMR (400 MHz, MeOD) δ ppm 9.01 (s, 1H), 8.33 (dd, J=8.16, 0.88 Hz, 1H), 8.06 (s, 1H), 7.81-8.04 (m, 2H), 6.79 (dt, J=14.37, 7.25 Hz, 1H), 6.05 (ddt, J=16.82, 10.54, 5.90, 5.90 Hz, 1H), 5.16-5.34 (m, 2H), 4.67 (d, J=6.02 Hz, 2H), 4.10 (s, 3H), 1.87 (d, J=7.28 Hz, 3H). MS (ESI): 422.1 [M+H]$^+$.

Example 58: N-(6-(4-Isopropyl-4H-1,2,4-triazol-3-yl)pyridin-2-yl)-3-methoxy-1-propyl-1H-pyrazole-4-carboxamide

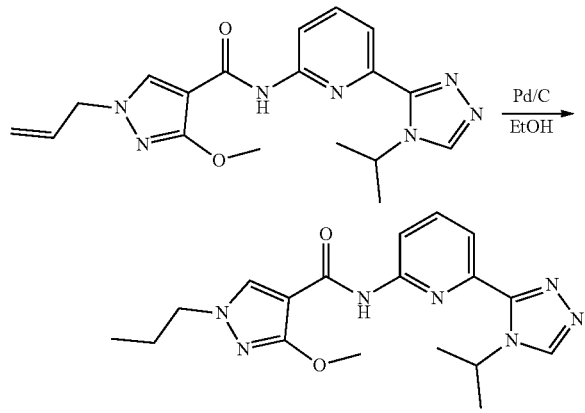

To a solution of 1-allyl-N-[6-(4-isopropyl-1,2,4-triazol-3-yl)-2-pyridyl]-3-methoxy-pyrazole-4-carboxamide (37 mg, 0.1 mmol) in EtOH (5 mL) was added 10% Pd/C (11 mg, 0.01 mmol) and the suspension was stirred under a H$_2$ atmosphere (using a balloon) for 3 h. After this time, the solid was filtered off, and the filtrate was concentrated to give the title compound (35 mg, 96%) as an off-white solid. $^1$H NMR (400 MHz, MeOD) δ ppm 8.85 (s, 1H), 8.34 (d, J=8.03 Hz, 1H), 8.05 (s, 1H), 7.98 (t, J=8.03 Hz, 1H), 7.81 (d, J=7.28 Hz, 1H), 5.44 (quin, J=6.71 Hz, 1H), 4.11 (s, 3H), 4.01 (t, J=6.90 Hz, 2H), 1.88 (sxt, J=7.18 Hz, 2H), 1.64 (d, J=6.78 Hz, 6H), 0.92 (t, J=7.40 Hz, 3H). MS (ESI): 370.2 [M+H]$^+$.

Example 59: 3-Methoxy-1-propyl-N-(6-(4-(1,1,1-trifluoropropan-2-yl)-4H-1,2,4-triazol-3-yl)pyridin-2-yl)-1H-pyrazole-4-carboxamide

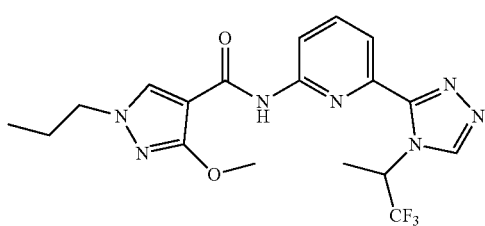 [SMILES: CCCn1cc(C(=O)Nc2cccc(-c3nncn3C(C)C(F)(F)F)n2)c(OC)n1]

The product was synthesized according to the general procedure described in Example 58 but using 1-allyl-3-methoxy-N-(6-(4-(1,1,1-trifluoropropan-2-yl)-4H-1,2,4-triazol-3-yl)pyridin-2-yl)-1H-pyrazole-4-carboxamide in place of 1-allyl-N-[6-(4-isopropyl-1,2,4-triazol-3-yl)-2-pyridyl]-3-methoxy-pyrazole-4-carboxamide to give the title compound (48 mg, 65%) as an off-white solid. $^1$H NMR (400 MHz, MeOD) δ ppm 9.01 (s, 1H), 8.33 (dd, J=8.03, 0.75 Hz, 1H), 8.05 (s, 1H), 7.84-8.03 (m, 2H), 6.79 (quin, J=7.22 Hz, 1H), 4.10 (s, 3H), 4.01 (t, J=6.90 Hz, 2H), 1.68-2.00 (m, 5H), 0.92 (t, J=7.40 Hz, 3H). MS (ESI): 423.9 [M+H]$^+$.

Example 60: N-(6-(4-Isopropyl-4H-1,2,4-triazol-3-yl)pyridin-2-yl)-3-methoxy-1-phenyl-1H-pyrazole-4-carboxamide

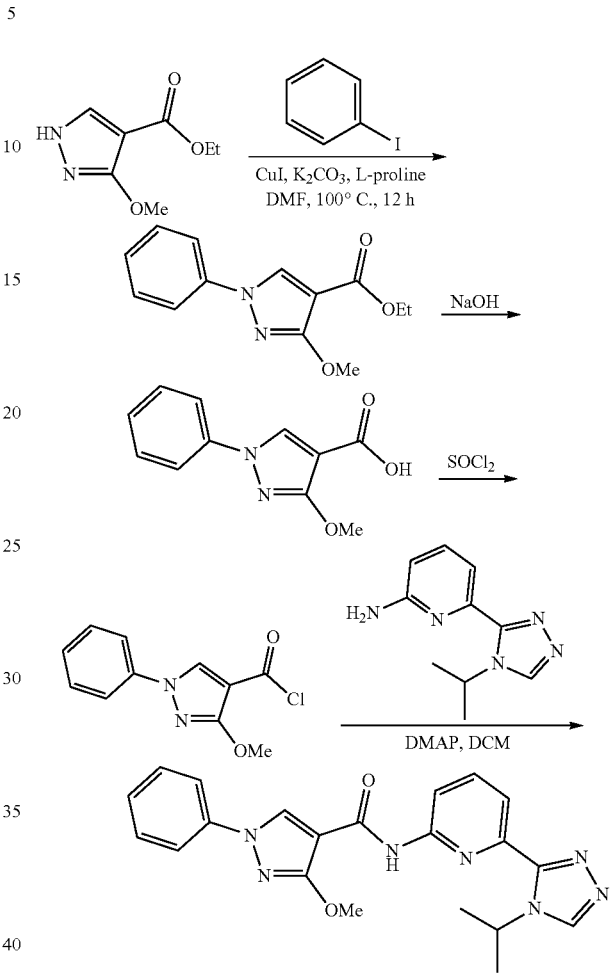

Step A: Ethyl 3-methoxy-1-phenyl-1H-pyrazole-4-carboxylate

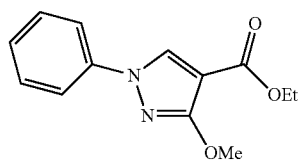 [SMILES: CCOC(=O)c1cn(-c2ccccc2)nc1OC]

A mixture of ethyl 3-methoxy-1H-pyrazole-4-carboxylate (440 mg, 2.59 mmol), iodobenzene (791 mg, 3.88 mmol), CuI (49 mg, 0.26 mmol), K$_2$CO$_3$ (714 mg, 5.17 mmol) and L-proline (59 mg, 0.52 mmol) in DMF (4 mL) was degassed with N$_2$ and the mixture was stirred at 100° C. for 12 h. After this time the mixture was cooled to rt and filtered. The filtrate was purified by column chromatography using EtOAc/Petroleum Ether (from 1/20 to 1/1) as eluent to give the title compound (390 mg, 61%) as a yellow solid. MS (ESI): 247.0 [M+H]$^+$.

Step B:
3-Methoxy-1-phenyl-1H-pyrazole-4-carboxylic acid

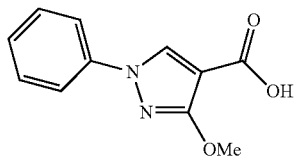 [SMILES: COc1nn(-c2ccccc2)cc1C(=O)O]

To a solution of ethyl 3-methoxy-1-phenyl-1H-pyrazole-4-carboxylate (190 mg, 0.77 mmol) in MeOH (7.5 mL) was added NaOH (93 mg, 2.3 mmol) in H$_2$O (1.5 mL) and the mixture was stirred at 50° C. for 2 h. After this time the mixture was concentrated in vacuo and acidified to pH 2-3 by addition of an aqueous solution of HCl (1M). The solid was collected by filtration and dissolved in EtOAc (15 mL), dried over Na$_2$SO$_4$, filtered and concentrated in vacuo to give the title compound (152 mg, 90%) as a white solid. MS (ESI): 219.2 [M+H]$^+$.

Step C:
3-Methoxy-1-phenyl-1H-pyrazole-4-carbonyl chloride

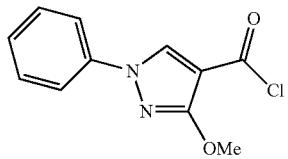 [SMILES: COc1nn(-c2ccccc2)cc1C(=O)Cl]

A mixture of 3-methoxy-1-phenyl-1H-pyrazole-4-carboxylic acid (100 mg, 0.46 mmol) and SOCl$_2$ (6 mL) was stirred at 60° C. for 1.5 h. After this time the mixture was concentrated in vacuo to give the title compound (108 mg, crude) as a yellow solid.

Step D: N-(6-(4-Isopropyl-4H-1,2,4-triazol-3-yl)pyridin-2-yl)-3-methoxy-1-phenyl-1H-pyrazole-4-carboxamide

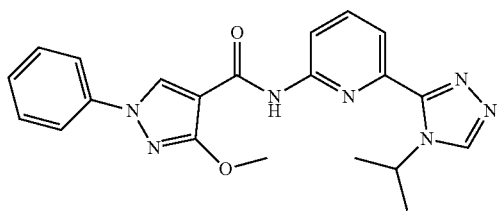 [SMILES: COc1nn(-c2ccccc2)cc1C(=O)Nc1cccc(-c2nncn2C(C)C)n1]

To a solution of 3-methoxy-1-phenyl-1H-pyrazole-4-carbonyl chloride (217 mg, 0.91 mmol) in DCM (10 mL) under N$_2$ was added 6-(4-isopropyl-4H-1,2,4-triazol-3-yl)pyridin-2-amine (370 mg, 1.82 mmol) and DMAP (222 mg, 1.82 mmol) and the mixture was stirred at 29° C. for 16 h. After this time the mixture was concentrated in vacuo and purified by prep-HPLC (using a Phenomenex Synergi C18 4 μm, 150×30 mm column and using, water (containing 0.225% HCOOH) and MeCN from 48 to 78% as the mobile phase at a flow rate of 25 mL/min) to give the title compounds (24 mg, 13%) as a white solid. $^1$HNMR (400 MHz, CDCl$_3$) δ ppm 9.25 (s, 1H), 8.46 (s, 1H), 8.38-8.45 (m, 2H), 7.99 (d, J=7.2 Hz, 1H), 7.89 (t, J=8.0 Hz, 1H), 7.69 (d, J=7.0 Hz, 2H), 7.49 (t, J=8.0 Hz, 2H), 7.30-7.37 (m, 1H), 5.47-5.58 (m, 1H), 4.22 (s, 3H), 1.65 (d, J=6.8 Hz, 6H). MS (ESI): 404.2 [M+H]$^+$.

Example 61: N-(6-(4-isopropyl-4H-1,2,4-triazol-3-yl)pyridin-2-yl)-3-methoxy-1-(pyridin-3-yl)-1H-pyrazole-4-carboxamide

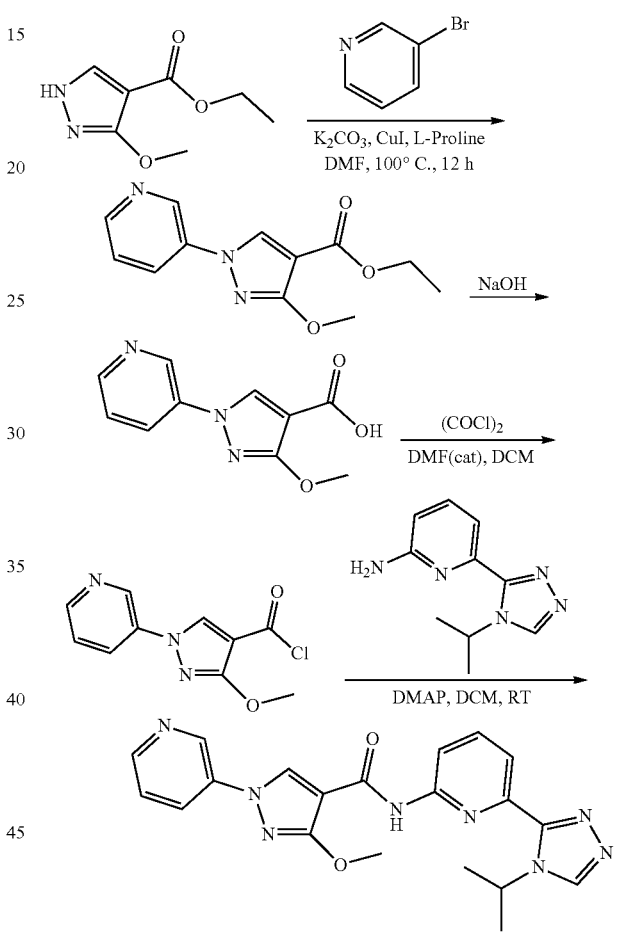

Step A: Ethyl 3-methoxy-1-(pyridin-3-yl)-1H-pyrazole-4-carboxylate

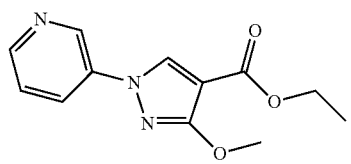 [SMILES: CCOC(=O)c1cn(-c2cccnc2)nc1OC]

A solution of ethyl 3-methoxy-1H-pyrazole-4-carboxylate (2 g, 11.8 mmol), 3-bromopyridine (2.79 g, 17.6 mmol), L-proline (270 mg, 2.36 mmol), CuI (224 mg, 1.18 mmol) and K$_2$CO$_3$ (4.06 g, 29.4 mmol) in DMF (30 mL) was stirred at 100° C. under N₂ for 17 h. After this time the mixture was diluted with H₂O (100 mL) and extracted with EtOAc (50 mL×3). The combined organic layers were dried over Na₂SO₄, filtered and concentrated in vacuo to give a crude which was purified by HPLC (using a Phenomenex Synergi C18 4 μm, 150×30 mm column and using water (containing 0.05% HCl) and MeCN from 16 to 36% as the mobile phase at a flow rate of 25 mL/min) to give the title compound (600 mg, 21%) as a white solid. MS (ESI): 248.0 [M+H]⁺.

Step B: 3-Methoxy-1-(pyridin-3-yl)-1H-pyrazole-4-carboxylic acid

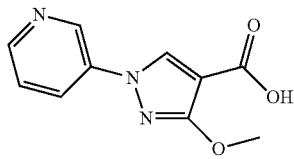 [SMILES: COc1nn(-c2cccnc2)cc1C(=O)O]

A mixture of ethyl 3-methoxy-1-(pyridin-3-yl)-1H-pyrazole-4-carboxylate (500 mg, 2.02 mmol) and NaOH (243 mg, 6.06 mmol) in MeOH/H₂O (6 mL, 5/1) was stirred at 50° C. for 3 h. After this time, the mixture was concentrated in vacuo and diluted with water (10 mL). The pH of the mixture was adjusted to 3-4 by addition of aqueous HCl (3M) and then it was extracted with EtOAc (300 mL×3). The combined organic layers were dried over Na₂SO₄, filtered and concentrated to give the title compound (300 mg, 68%) as a white solid.

Step C: 3-Methoxy-1-(pyridin-3-yl)-1H-pyrazole-4-carbonyl chloride

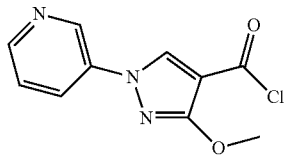 [SMILES: COc1nn(-c2cccnc2)cc1C(=O)Cl]

To a solution of 3-methoxy-1-(pyridin-3-yl)-1H-pyrazole-4-carboxylic acid (150 mg, 0.68 mmol) in DCM (10 mL) under N₂ was added (COCl)₂ (174 mg, 1.37 mmol) followed by DMF (5 drops) and the mixture was stirred at 25° C. for 2 h. After this time the mixture was concentrated under reduced pressure to give the title compound (162 mg, crude) which was used without further purification in the next step.

Step D: N-(6-(4-Isopropyl-4H-1,2,4-triazol-3-yl)pyridin-2-yl)-3-methoxy-1-(pyridin-3-yl)-1H-pyrazole-4-carboxamide

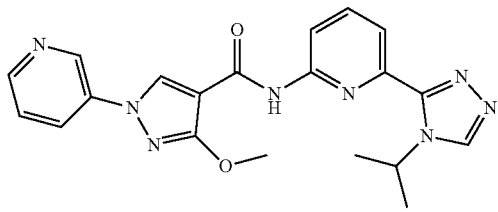 [SMILES: COc1nn(-c2cccnc2)cc1C(=O)Nc1cccc(-c2nncn2C(C)C)n1]

To a solution of 3-methoxy-1-(pyridin-3-yl)-1H-pyrazole-4-carbonyl chloride (162 mg, 0.68 mmol) and 6-(4-isopropyl-4H-1,2,4-triazol-3-yl)pyridin-2-amine (277 mg, 1.36 mmol) in DCM (10 mL) under a N₂ atmosphere was added DMAP (166 mg, 1.36 mmol) and the mixture was stirred at 25° C. for 17 h. After this time the mixture was concentrated in vacuo and purified by prep-HPLC (using a Waters Xbridge Prep OBD C18 5 μm, 150×30 mm column and using water (containing 0.05% NH₃·H₂O) and MeCN, from 20 to 50% as the mobile phase at a flow rate of 25 mL/min) to give the title compound (29 mg, 5%) as a white solid. ¹H NMR (400 MHz, DMSO-d₆) δ ppm 9.46 (s, 1H), 9.19-9.16 (m, 1H), 9.13 (d, J=2.2 Hz, 1H), 8.90 (s, 1H), 8.53 (d, J=3.9 Hz, 1H), 8.30-8.20 (m, 2H), 8.02 (t, J=7.9 Hz, 1H), 7.83 (d, J=7.5 Hz, 1H), 7.55 (dd, J=4.6, 8.1 Hz, 1H), 5.45-5.25 (m, 1H), 4.14 (s, 3H), 1.53 (d, J=6.6 Hz, 6H). MS (ESI): 405.1 [M+H]⁺.

Example 62: N-(6-(4-Isopropyl-4H-1,2,4-triazol-3-yl)pyridin-2-yl)-3-methoxy-1-(3-methylpyridin-2-yl)-1H-pyrazole-4-carboxamide

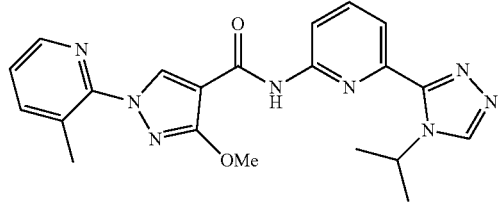 [SMILES: COc1nn(-c2ncccc2C)cc1C(=O)Nc1cccc(-c2nncn2C(C)C)n1]

The title compound was synthesized according to the general procedure described in Example 61 but using 2-fluoro-3-methylpyridine in place of 3-bromopyridine. The final product was purified by prep-HPLC (using an Xtimate C18 5 μm, 150×25 mm column and using water (containing 10 mM NH₄HCO₃) and MeCN from 30 to 60% as the mobile phase at a flow rate of 25 mL/min) to give the title compound (14 mg, 9% for the last two steps) as a white solid. ¹HNMR (400 MHz, MeOD) δ ppm 8.89 (s, 1H), 8.76 (s, 1H), 8.41 (d, J=8.0 Hz, 1H), 8.37 (d, J=4.0 Hz, 1H), 8.04 (t, J=8.0 Hz, 1H), 7.84-7.90 (m, 2H), 7.39 (dd, J=4.4, 7.2 Hz, 1H), 5.46-5.54 (m, 1H), 4.23 (s, 3H), 2.61 (s, 3H), 1.68 (d, J=6.8 Hz, 6H). MS (ESI): 419.1 [M+H]⁺.

Example 63: N-(6-(4-Isopropyl-4H-1,2,4-triazol-3-yl)pyridin-2-yl)-3-methoxy-1-(pyrimidin-5-yl)-1H-pyrazole-4-carboxamide

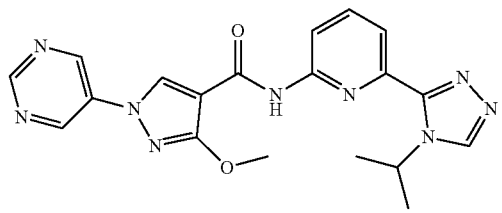

The title compound was synthesized according to the general procedure described in Example 61 but using 5-bromopyrimidine in place of 3-bromopyridine. The final product was purified by prep-HPLC (using an Xtimate C18 5 μm, 150×25 mm column and using water (containing 10 mM NH$_4$HCO$_3$) and MeCN from 23 to 53% as the mobile phase at a flow rate of 25 mL/min) to give the title compound (34 mg, 9% for the last two steps) as a white solid. $^1$HNMR (400 MHz, DMSO-d$_6$) δ ppm 9.49 (s, 1H), 9.36 (s, 2H), 9.27 (s, 1H), 9.17 (s, 1H), 8.92 (s, 1H), 8.26 (d, J=8.0 Hz, 1H), 8.05 (t, J=8.0 Hz, 1H), 7.86 (d, J=7.2 Hz, 1H), 5.31-5.48 (m, 1H), 4.18 (s, 3H), 1.56 (d, J=6.8 Hz, 6H). MS (ESI): 406.1 [M+H]$^+$.

Example 64: N-(6-(4-Isopropyl-4H-1,2,4-triazol-3-yl)pyridin-2-yl)-3-methoxy-1-(pyrazin-2-yl)-1H-pyrazole-4-carboxamide

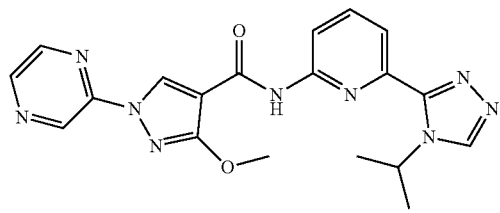

The title compound was synthesized according to the general procedure described in Example 61 but using 2-chloropyrazine in place of 3-bromopyridine. The final product was purified by prep-HPLC (using a Waters Xbridge Prep OBD C18 5 µm, 150×30 mm column and using water (containing 0.05% NH$_3$·H$_2$O) and MeCN from 24 to 54% as the mobile phase at a flow rate of 25 mL/min) to give the title compound (22 mg, 8% for the last two steps) as a white solid. $^1$H NMR (400 MHz, DMSO-d$_6$) δ ppm 9.74 (s, 1H), 9.17 (d, J=1.6 Hz, 1H), 9.10 (s, 1H), 8.91 (s, 1H), 8.67 (d, J=2.4 Hz, 1H), 8.61 (m, 1H), 8.23 (dd, J=3.6 Hz, 0.8 Hz, 1H), 8.04 (t, J=8.0 Hz, 1H), 7.85 (dd, J=7.6, 0.8 Hz, 1H), 5.49-5.39 (m, 1H), 4.17 (s, 3H), 1.53 (d, J=6.8 Hz, 6H). MS (ESI): 406.1 [M+H]$^+$.

Example 65: 1-(4-Cyanopyridin-2-yl)-N-(6-(4-isopropyl-4H-1,2,4-triazol-3-yl)pyridin-2-yl)-3-methoxy-1H-pyrazole-4-carboxamide

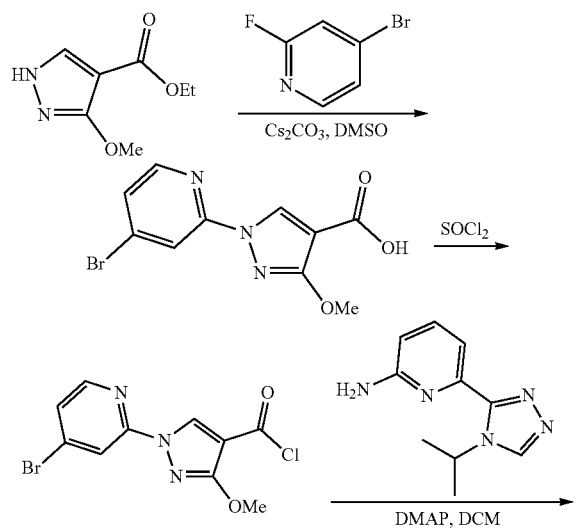

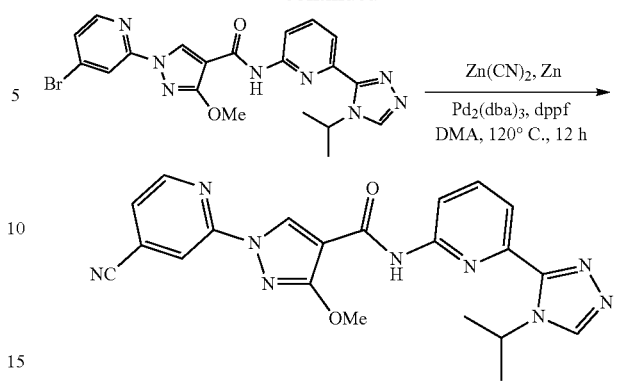

Step A: 1-(4-Bromopyridin-2-yl)-3-methoxy-1H-pyrazole-4-carboxylic acid

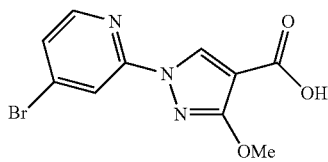 [SMILES: COc1nn(-c2cc(Br)ccn2)cc1C(=O)O]

To a solution of ethyl 3-methoxy-1H-pyrazole-4-carboxylate (1 g, 5.88 mmol) in DMSO (20 mL) was added 4-bromo-2-fluoropyridine (1.03 g, 5.88 mmol) and Cs$_2$CO$_3$ (7.66 g, 23.5 mmol) and the mixture was stirred at 120° C. for 17 h under N$_2$. After this time the mixture was poured into water (100 mL) and washed with EtOAc (100 mL). The aqueous phase was adjusted to pH~3-4 with 3 M HCl, the solid was filtered and dried under vacuum to give the title compound (320 mg, 18%) as a white solid.

Step B: 1-(4-Bromopyridin-2-yl)-N-(6-(4-isopropyl-4H-1,2,4-triazol-3-yl)pyridin-2-yl)-3-methoxy-1H-pyrazole-4-carboxamide

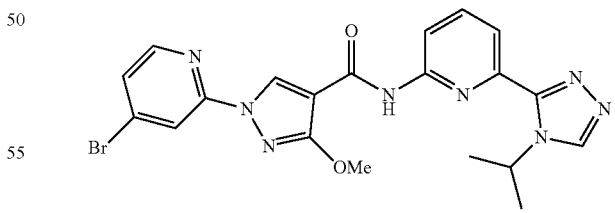

The product was synthesized according to the general procedure described in Example 60, Steps B and C but using 1-(4-bromopyridin-2-yl)-3-methoxy-1H-pyrazole-4-carboxylic acid in place of ethyl 3-methoxy-1-phenyl-1H-pyrazole-4-carboxylate. The final product was purified by column chromatography on silica gel eluting with DCM/MeOH (from 1/0 to 20/1) to give the title compound (237 mg, 49% for two steps) as a white solid.

Step C: 1-(4-Cyanopyridin-2-yl)-N-(6-(4-isopropyl-4H-1,2,4-triazol-3-yl)pyridin-2-yl)-3-methoxy-1H-pyrazole-4-carboxamide

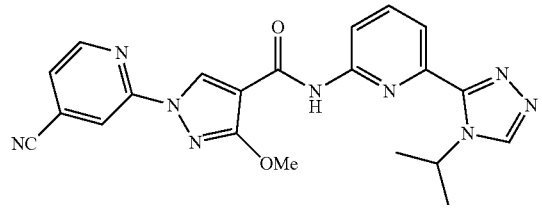 [SMILES: COc1nn(-c2cc(C#N)ccn2)cc1C(=O)Nc1cccc(-c2nncn2C(C)C)n1]

To a solution of 1-(4-bromopyridin-2-yl)-N-(6-(4-isopropyl-4H-1,2,4-triazol-3-yl)pyridin-2-yl)-3-methoxy-1H-pyrazole-4-carboxamide (200 mg, 0.41 mmol) in DMA (10 mL) under a N$_2$ atmosphere was added zinc cyanide (97 mg, 0.83 mmol) and zinc (16 mg, 0.25 mmol) followed by Pd$_2$(dba)$_3$ (38 mg, 0.041 mmol) and dppf (46 mg, 0.083 mmol) and the resulting mixture was stirred at 110° C. for 1 h. After this time the reaction was cooled to rt and filtered. The filtrate was purified by prep-HPLC (using a Waters Xbridge Prep OBD C18 5 μm, 150×30 mm column and using MeCN and H$_2$O (containing 0.05% NH$_3$·H$_2$O) from 26 to 56% as the mobile phase at a flow rate of 25 mL/min) to give the title compound (31 mg, 18%) as a white solid. $^1$H NMR (400 MHz, DMSO-d$_6$) δ ppm 9.69 (s, 1H), 9.06 (s, 1H), 8.88 (s, 1H), 8.72 (d, J=5.2 Hz, 1H), 8.22-8.20 (m, 2H), 8.00 (t, J=8.4 Hz, 1H), 7.83-7.82 (m, 2H), 5.43-5.41 (m, 1H), 4.14 (s, 3H), 1.51 (d, J=6.8 Hz, 6H). MS (ESI): 430.2 [M+H]$^+$.

Example 66: N-(6-(4-Isopropyl-4H-1,2,4-triazol-3-yl)pyridin-2-yl)-3-methoxy-1-(pyridin-4-yl)-1H-pyrazole-4-carboxamide

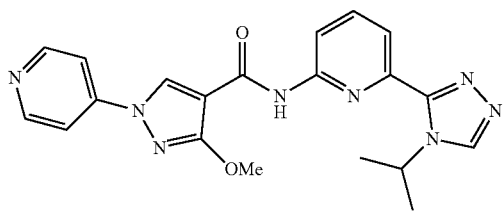 [SMILES: COc1nn(-c2ccncc2)cc1C(=O)Nc1cccc(-c2nncn2C(C)C)n1]

The product was synthesized according to the general procedure described in Example 61 but using 4-bromopyridine in place of 3-bromopyridine in Step A. The final product was purified by trituration with MeOH (20 mL) to give the title compound (120 mg, 65% for the last two steps) as a gray solid. $^1$HNMR (400 MHz, D$_2$O) δ ppm 9.72 (s, 1H), 8.78 (s, 1H), 8.62 (d, J=6.4 Hz, 2H), 7.97-8.09 (m, 3H), 7.81 (t, J=8.0 Hz, 1H), 7.57 (d, J=7.6 Hz, 1H), 5.23-5.56 (m, 1H), 4.04 (s, 3H), 1.56 (br d, J=6.8 Hz, 6H). MS (ESI): 405.2 [M+H]$^+$.

Example 67: N-(6-(4-Isopropyl-4H-1,2,4-triazol-3-yl)pyridin-2-yl)-3-methoxy-1-(5-methylpyridin-3-yl)-1H-pyrazole-4-carboxamide

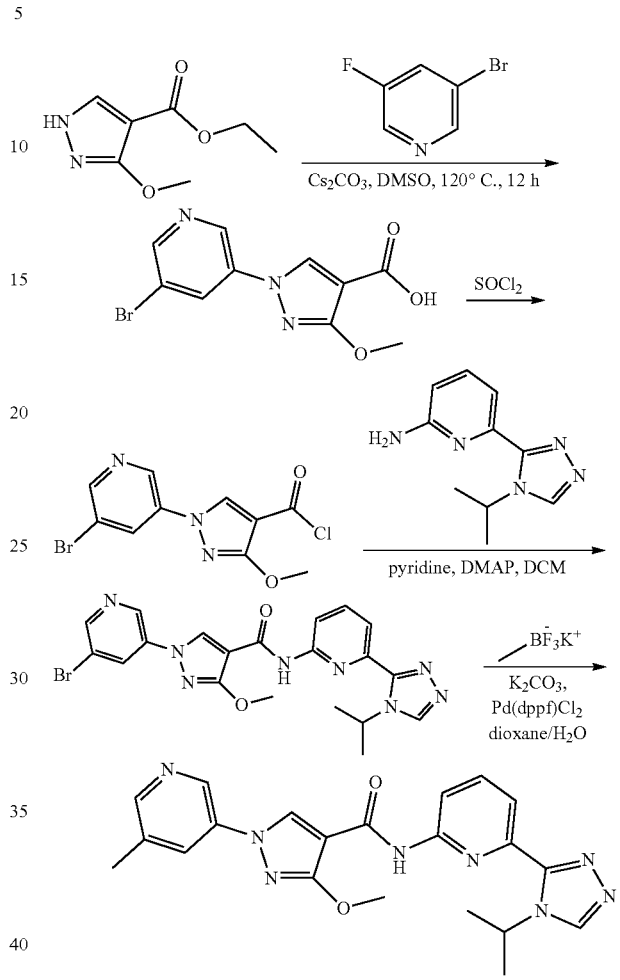

Step A: 1-(5-Bromopyridin-3-yl)-3-methoxy-1H-pyrazole-4-carboxylic acid

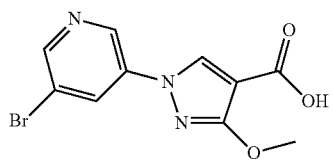 [SMILES: COc1nn(-c2cncc(Br)c2)cc1C(=O)O]

To a solution of ethyl 3-methoxy-1H-pyrazole-4-carboxylate (10 g, 59 mmol) in DMSO (100 mL) was added Cs$_2$CO$_3$ (58.6 g, 0.18 mol) and 3-bromo-5-fluoropyridine (10.3 g, 59 mmol) and the mixture was stirred at 120° C. for 18 h. After this time the mixture was poured into water (500 mL) and adjusted to pH~3 with 2N HCl. The resulting solid was filtered, collected and lyophilized to give the title compound (10 g, 57%) as a yellow solid. $^1$H NMR (400 MHz, DMSO-d$_6$) δ ppm 12.53 (br, 1H), 9.11 (s, 1H), 9.04 (s, 1H), 8.64 (s, 1H), 8.54 (d, J=1.6 Hz, 1H), 3.98 (s, 3H).

Step B: 1-(5-Bromopyridin-3-yl)-3-methoxy-1H-pyrazole-4-carbonyl chloride

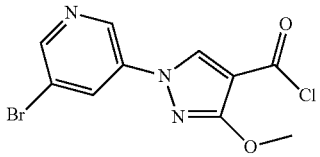 [SMILES: COc1nn(-c2cncc(Br)c2)cc1C(=O)Cl]

1-(5-bromopyridin-3-yl)-3-methoxy-1H-pyrazole-4-carboxylic acid (9.5 g, 3.1 mmol) was treated with SOCl$_2$ (90 mL) and the mixture was stirred at 60° C. for 2 h. After this time, the mixture was concentrated in vacuo to give the crude title compound (10 g, crude) as an off-white solid.

Step C: 1-(5-Bromopyridin-3-yl)-N-(6-(4-isopropyl-4H-1,2,4-triazol-3-yl)pyridin-2-yl)-3-methoxy-1H-pyrazole-4-carboxamide

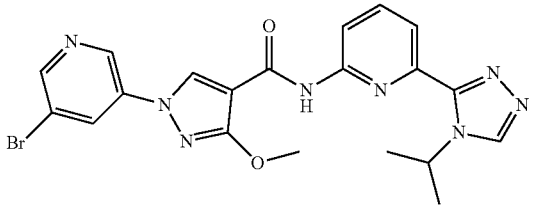 [SMILES: COc1nn(-c2cncc(Br)c2)cc1C(=O)Nc1cccc(-c2nncn2C(C)C)n1]

To a solution of 1-(5-bromopyridin-3-yl)-3-methoxy-1H-pyrazole-4-carbonyl chloride (10 g, crude, 3.1 mmol) in DCM (120 mL) was added 6-(4-isopropyl-4H-1,2,4-triazol-3-yl)pyridin-2-amine (6.3 g, 3.1 mmol). Pyridine (10 mL) and DMAP (7.6 g, 6.2 mmol) were then added and the mixture was stirred at 29° C. for 0.5 h. After this time the mixture was filtered and the solid was washed with water and MeOH and then it was lyophilized to give the crude title compound (12 g, 80%, two steps) as a white solid. $^1$H NMR (400 MHz, DMSO-d$_6$) δ ppm 9.20 (s, 1H), 8.89 (d, J=2.0 Hz, 1H), 8.62 (d, J=2.0 Hz, 1H), 8.49 (s, 1H), 8.39-8.36 (m, 2H), 8.22 (t, J=2.0 Hz, 1H), 8.01 (d, J=7.6 Hz, 1H), 7.92-7.89 (m, 1H), 5.51-5.47 (m, 1H), 4.22 (s, 3H), 1.63 (d, J=6.8 Hz, 6H).

Step D: N-(6-(4-Isopropyl-4H-1,2,4-triazol-3-yl)pyridin-2-yl)-3-methoxy-1-(5-methylpyridin-3-yl)-1H-pyrazole-4-carboxamide

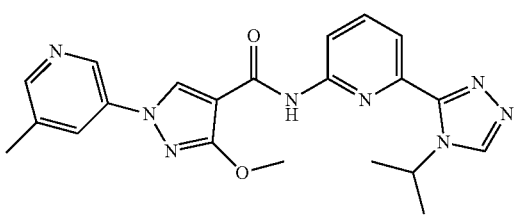 [SMILES: COc1nn(-c2cncc(C)c2)cc1C(=O)Nc1cccc(-c2nncn2C(C)C)n1]

To a solution of 1-(5-bromopyridin-3-yl)-N-(6-(4-isopropyl-4H-1,2,4-triazol-3-yl)pyridin-2-yl)-3-methoxy-1H-pyrazole-4-carboxamide (150 mg, 0.31 mmol) in dioxane/H$_2$O (5/1, 6 mL) under N$_2$ was added potassium trifluoro(methyl)borate (76 mg, 0.62 mmol), K$_2$CO$_3$ (86 mg, 0.62 mmol) and Pd(dppf)Cl$_2$ (22 mg, 0.03 mmol) and the mixture was stirred at 90° C. for 18 h. After this time the reaction was concentrated under vacuum and purified by prep-HPLC (using a Waters Xbridge Prep OBD C18 5 mm, 150×30 mm column and using MeCN and H$_2$O (containing 0.05% NH$_3$·H$_2$O) from 23 to 53% as the mobile phase at a flow rate of 25 m/min) to give the title compound (37 mg, 28%) as an off-white solid. $^1$H NMR (400 MHz, DMSO-d$_6$) δ ppm 9.45 (s, 1H), 9.13 (s, 1H), 8.92 (d, J=2.4 Hz, 1H), 8.90 (s, 1H), 8.37 (s, 1H), 8.23 (d, J=7.2 Hz, 1H), 8.11 (s, 1H), 8.02 (t, J=8.0 Hz, 1H), 7.82 (d, J=7.2 Hz, 1H), 5.39-5.31 (m, 1H), 4.13 (s, 3H), 2.37 (s, 3H), 1.53 (d, J=6.4 Hz, 6H). MS (ESI): 419.2 [M+H]$^+$.

Example 68: N-(6-(4-Isopropyl-4H-1,2,4-triazol-3-yl)pyridin-2-yl)-3-methoxy-1-(pyridin-4-yl)-1H-pyrazole-4-carboxamide

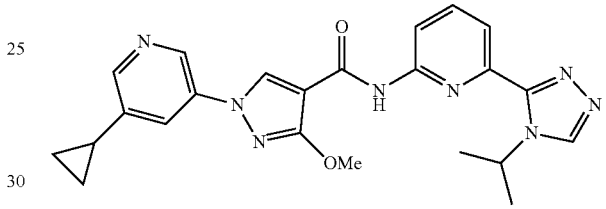

To a solution of 1-(5-bromopyridin-3-yl)-N-(6-(4-isopropyl-4H-1,2,4-triazol-3-yl)pyridin-2-yl)-3-methoxy-1H-pyrazole-4-carboxamide (100 mg, 0.2 mmol) in toluene/water (10 mL, 10:1) under N$_2$ was added cyclopropylboronic acid (107 mg, 1.24 mmol), PCy$_3$ (58 mg, 0.2 mmol) and Cs$_2$CO$_3$ (404 mg, 1.24 mmol) followed by Pd(OAc)$_2$ (23 mg, 0.1 mmol) and the mixture was stirred at 110° C. for 2 h. After this time the mixture was concentrated in vacuo and purified by prep-HPLC (using a Waters Xbridge Prep OBD C18 5 μm, 150×30 mm column and using water (containing 0.05% NH$_3$·H$_2$O) and MeCN from 30 to 60% as the mobile phase at a flow rate of 25 mL/min) to give the title compound (46 mg, 50%). $^1$H NMR (400 MHz, DMSO-d$_6$) δ ppm 9.42 (s, 1H), 9.18 (s, 1H), 8.94-8.84 (m, 2H), 8.37 (s, 1H), 8.24 (d, J=8.4 Hz, 1H), 8.02 (t, J=8 Hz, 1H), 7.88-7.80 (m, 2H), 5.36 (m, 1H), 4.14 (s, 3H), 2.10-1.97 (m, 1H), 1.55 (d, J=6.6 Hz, 6H), 1.12-0.97 (m, 2H), 0.89 (d, J=3.6 Hz, 2H). MS (ESI): 445.2 [M+H]$^+$.

Example 69: 1-(5-Cyanopyridin-3-yl)-N-(6-(4-isopropyl-4H-1,2,4-triazol-3-yl)pyridin-2-yl)-3-methoxy-1H-pyrazole-4-carboxamide

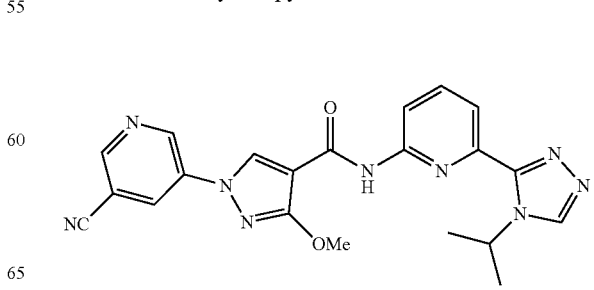

To a solution of 1-(5-bromopyridin-3-yl)-N-(6-(4-isopropyl-4H-1,2,4-triazol-3-yl)pyridin-2-yl)-3-methoxy-1H-pyrazole-4-carboxamide (150 mg, 0.31 mmol) and Zn(CN)$_2$ (44 mg, 0.37 mmol) in DMA (3.5 mL) was added Zn (14 mg, 0.21 mmol), Pd$_2$(dba)$_3$ (32 mg, 0.035 mmol) and dppf (17 mg, 0.070 mmol) and the mixture was stirred at 120° C. under a N$_2$ atmosphere for 20 h. After this time the mixture was concentrated in vacuo and purified by prep-HPLC (using a Phenomenex Synergi C18 4 μm, 150×30 mm column and using water (containing 0.225% HCOOH) and MeCN from 33 to 53% as the mobile phase at a flow rate of 25 mL/min) to give the title compound (50 mg, 37%) as a white solid. $^1$HNMR (400 MHz, DMSO-d$_6$) δ ppm 9.48 (s, 1H), 9.41 (d, J=2.4 Hz, 1H), 9.25 (s, 1H), 8.92 (s, 1H), 8.97 (s, 1H), 8.82 (s, 1H), 8.26 (d, J=8.2 Hz, 1H), 8.05 (t, J=8.2 Hz, 1H), 7.86 (d, J=7.6 Hz, 1H), 5.34-5.44 (m, 1H), 4.18 (s, 3H), 1.56 (d, J=6.4 Hz, 6H). MS (ESI): 430.2 [M+H]$^+$.

Example 70: 1-(5-Hydroxypyridin-3-yl)-N-(6-(4-isopropyl-4H-1,2,4-triazol-3-yl)pyridin-2-yl)-3-methoxy-1H-pyrazole-4-carboxamide Step A: N-(6-(4-Isopropyl-4H-1,2,4-triazol-3-yl)pyridin-2-yl)-3-methoxy-1-(5-(4,4,5,5-tetramethyl-1,3,2-dioxaborolan-2-yl)pyridin-3-yl)-1H-pyrazole-4-carboxamide

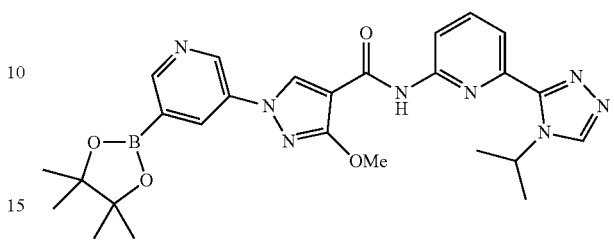

A mixture of 1-(5-bromopyridin-3-yl)-N-(6-(4-isopropyl-4H-1,2,4-triazol-3-yl)pyridin-2-yl)-3-methoxy-1H-pyrazole-4-carboxamide (1 g, 2.07 mmol), 4,4,4',4',5,5,5',5'-octamethyl-2,2'-bi(1,3,2-dioxaborolane) (1.58 g, 6.21 mmol), KOAc (406 mg, 4.14 mmol) and Pd(dppf)Cl$_2$ (454 mg, 0.62 mmol) in dioxane (20 mL) was degassed with N$_2$ and stirred at 100° C. for 17 h. After this time the solvent was evaporated in vacuo and the residue was dissolved in DCM (100 mL) and washed with H$_2$O (100 mL×2). The separated organic layer was dried over Na$_2$SO$_4$, filtered and concen-

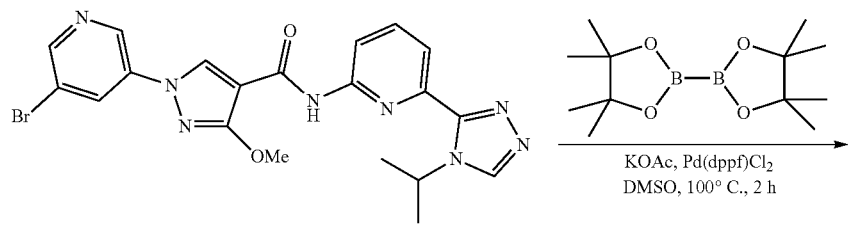

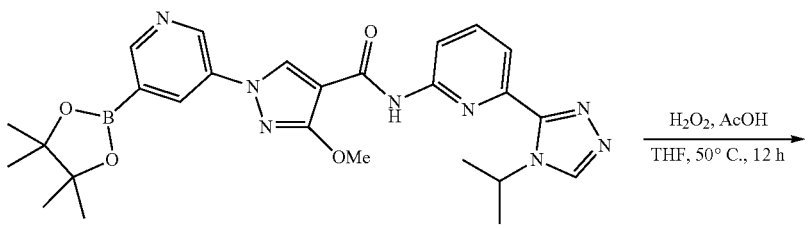

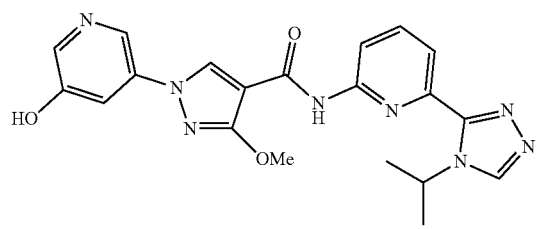

trated in vacuo to give the title compound (2.5 g, crude) which was used without further purification in the next step.

Step B: 1-(5-Hydroxypyridin-3-yl)-N-(6-(4-isopropyl-4H-1,2,4-triazol-3-yl)pyridin-2-yl)-3-methoxy-1H-pyrazole-4-carboxamide

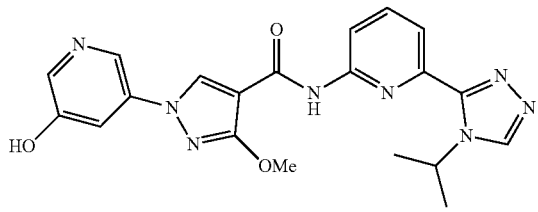 [SMILES: COc1nn(-c2cncc(C#N)c2)cc1C(=O)Nc1cccc(-c2nncn2C(C)C)n1]

A mixture of N-(6-(4-isopropyl-4H-1,2,4-triazol-3-yl)pyridin-2-yl)-3-methoxy-1-(5-(4,4,5,5-tetramethyl-1,3,2-dioxaborolan-2-yl)pyridin-3-yl)-1H-pyrazole-4-carboxamide (2.3 g, 5.13 mmol) in THF (50 mL) was treated with AcOH (2.5 mL) and H₂O₂ (2.5 mL, 30%) and the reaction was stirred at 50° C. for 2 h. After this time the mixture was filtered and the filter cake was concentrated in vacuo to give the title compound (450 mg, 21%) as a brown solid. MS (ESI): 443.2 [M+Na]⁺.

Example 71: N-(6-(4-Isopropyl-4H-1,2,4-triazol-3-yl)pyridin-2-yl)-3-methoxy-1-(5-methoxypyridin-3-yl)-1H-pyrazole-4-carboxamide

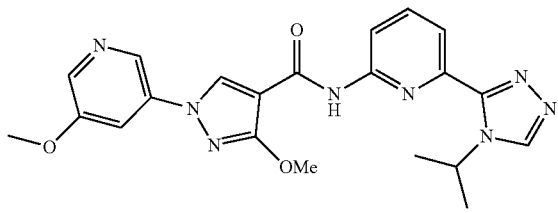 [SMILES: COc1cncc(-n2cc(C(=O)Nc3cccc(-c4nncn4C(C)C)n3)c(OC)n2)c1]

A mixture of 1-(5-hydroxypyridin-3-yl)-N-(6-(4-isopropyl-4H-1,2,4-triazol-3-yl)pyridin-2-yl)-3-methoxy-1H-pyrazole-4-carboxamide (100 mg, 0.24 mmol), MeI (41 mg, 0.29 mmol), K₂CO₃ (66 mg, 0.48 mmol) and KI (40 mg, 0.24 mmol) in DMF (4 mL) was stirred at 25° C. for 2 h. After this time the mixture was filtered, the filtrate was concentrated in vacuo and purified by prep-HPLC (using a Waters Xbridge Prep OBD C18 5 µm, 150×30 mm column and using water (containing 0.04% NH₃H₂O and 10 mM NH₄HCO₃) and MeCN, from 27 to 54% as the mobile phase at a flow rate of 25 mL/min) to give the title compound (3.5 mg, 3.4%) as a white solid. ¹H NMR (400 MHz, DMSO-d₆) δ ppm 9.44 (s, 1H), 9.22 (s, 1H), 8.90 (s, 1H), 8.72 (s, 1H), 8.27-8.20 (m, 2H), 8.02 (t, J=7.2 Hz, 1H), 7.89-7.79 (m, 2H), 5.41-5.30 (m, 1H), 4.14 (s, 3H), 3.91 (s, 3H), 1.53 (d, J=6.8 Hz, 6H). MS (ESI): 435.1 [M+H]⁺.

Example 72: 1-(5-Isopropoxypyridin-3-yl)-N-(6-(4-isopropyl-4H-1,2,4-triazol-3-yl)pyridin-2-yl)-3-methoxy-1H-pyrazole-4-carboxamide

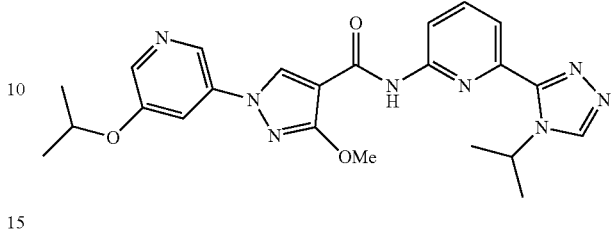

A mixture of 1-(5-hydroxypyridin-3-yl)-N-(6-(4-isopropyl-4H-1,2,4-triazol-3-yl)pyridin-2-yl)-3-methoxy-1H-pyrazole-4-carboxamide (100 mg, 0.24 mmol), 2-iodopropane (81 mg, 0.46 mmol), K₂CO₃ (66 mg, 0.48 mmol) and KI (40 mg, 0.24 mmol) in DMF (2 mL) was stirred at 80° C. for 2 h. After this time DMF (3 mL) was added and the mixture was purified by prep-HPLC (using a Waters Xbridge Prep OBD C18 5 µm, 150×30 mm column and using water (containing 0.04% NH₃H₂O and 10 mM NH₄HCO₃) and MeCN, from 32 to 62% as the mobile phase at a flow rate of 25 mL/min) to give the title compound (37 mg, 34%) as a white solid. ¹H NMR (400 MHz, DMSO-d₆) δ ppm 9.44 (s, 1H), 9.22 (s, 1H), 8.90 (s, 1H), 8.69 (d, J=2.2 Hz, 1H), 8.34-8.13 (m, 2H), 8.02 (t, J=8.1 Hz, 1H), 7.89-7.80 (m, 2H), 5.40-5.31 (m, 1H), 4.88-4.79 (m, 1H), 4.14 (s, 3H), 1.53 (d, J=6.6 Hz, 6H), 1.31 (d, J=5.7 Hz, 6H). MS (ESI): 463.2 [M+H]⁺.

Example 73: 1-(5-(Dimethylamino)pyridin-3-yl)-N-(6-(4-isopropyl-4H-1,2,4-triazol-3-yl)pyridin-2-yl)-3-methoxy-1H-pyrazole-4-carboxamide

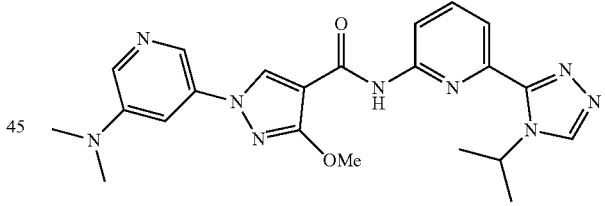

A solution of 1-(5-bromopyridin-3-yl)-N-(6-(4-isopropyl-4H-1,2,4-triazol-3-yl)pyridin-2-yl)-3-methoxy-1H-pyrazole-4-carboxamide (100 mg, 0.21 mmol), dimethylamine hydrochloride (20 mg, 0.25 mmol), RuPhos (19 mg, 0.041 mmol), NaOtBu (79 mg, 0.83 mmol) and Pd₂(dba)₃ (19 mg, 0.021 mmol) in toluene (8 mL) under a N₂ atmosphere was stirred at 100° C. for 12 h. After this time the mixture was concentrated and purified by prep-HPLC (using a Waters Xbridge Prep OBD C18 5 mm, 150×30 mm column and using water (containing 0.04% NH₃H₂O and 10 mM NH₄HCO₃) and MeCN, from 29 to 43% as the mobile phase at a flow rate of 25 mL/min) to give the title compound (15 mg, 16%) as a white solid. ¹H NMR (400 MHz, DMSO-d₆) δ ppm 9.47 (s, 1H), 9.21 (s, 1H), 8.92 (s, 1H), 8.42 (d, J=2.0 Hz, 1H), 8.27 (d, J=8.4 Hz, 1H), 8.10-8.01 (m, 2H), 7.85 (d, J=7.6 Hz, 1H), 7.48 (t, J=2.4 Hz, 1H), 5.38 (quin, J=6.4 Hz, 1H), 4.16 (s, 3H), 3.03 (s, 6H), 1.56 (d, J=6.8 Hz, 6H). MS (ESI): 448.1 [M+H]⁺.

Example 74: 1-(5-Bromopyridin-3-yl)-3-(difluoromethyl)-N-(6-(4-isopropyl-4H-1,2,4-triazol-3-yl)pyridin-2-yl)-1H-pyrazole-4-carboxamide

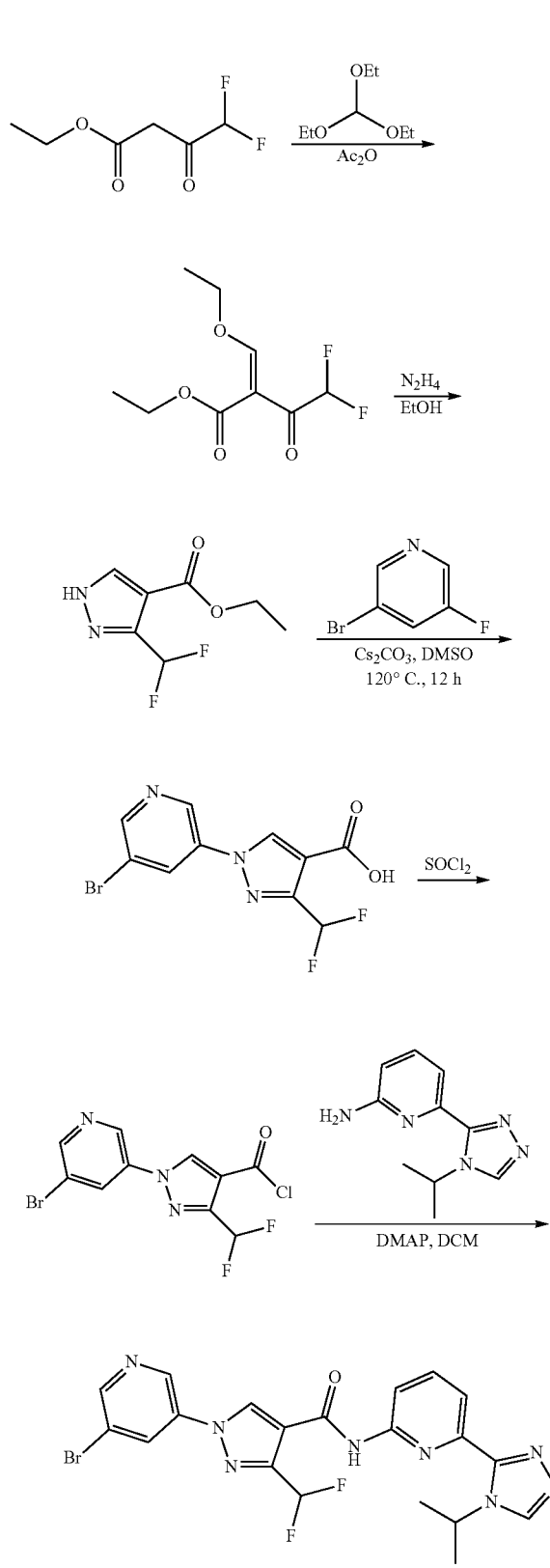

Step A: Ethyl (Z)-2-(ethoxymethylene)-4,4-difluoro-3-oxobutanoate

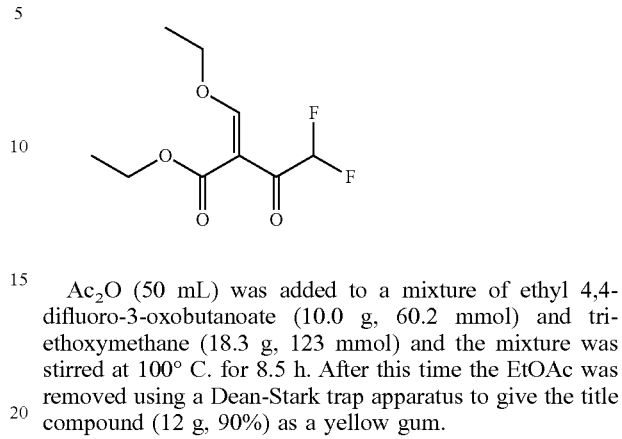

Ac₂O (50 mL) was added to a mixture of ethyl 4,4-difluoro-3-oxobutanoate (10.0 g, 60.2 mmol) and triethoxymethane (18.3 g, 123 mmol) and the mixture was stirred at 100° C. for 8.5 h. After this time the EtOAc was removed using a Dean-Stark trap apparatus to give the title compound (12 g, 90%) as a yellow gum.

Step B: Ethyl 3-(difluoromethyl)-1H-pyrazole-4-carboxylate

To a solution of ethyl (Z)-2-(ethoxymethylene)-4,4-difluoro-3-oxobutanoate (11 g, 49.5 mmol) in MeOH (100 mL) at 0° C. was added N₂H₄·H₂O (7.6 g, 149 mmol) dropwise and the mixture was stirred at 70° C. for 3 h. After this time the mixture was concentrated in vacuo to give the title compound (10 g, crude) as yellow gum. MS (ESI): 190.9 [M+H]⁺.

Step C: 1-(5-Bromopyridin-3-yl)-3-(difluoromethyl)-1H-pyrazole-4-carboxylic acid A mixture of ethyl 3-(difluoromethyl)-1H-pyrazole-4-carboxylate (5.00 g, 26.3 mmol) and 3-bromo-5-fluoropyridine (4.63 g, 26.3 mmol) and Cs₂CO₃ (34.27 g, 105 mmol) in DMSO (100 mL) was stirred at 120° C. for 12 h. After this time the mixture was poured into water (100 mL) and washed with EtOAc (100 mL). The aqueous phase was adjusted to pH 3~4 with 3M HCl. The solid was filtered and dried under vacuum to give the title compound (4.4 g, 81%) as a white solid. MS (ESI): 317.9 [(M+H) (⁷⁹Br)]⁺.

Step D: 1-(5-Bromopyridin-3-yl)-3-(difluoromethyl)-1H-pyrazole-4-carbonyl chloride

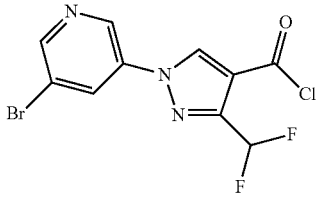 [SMILES: O=C(Cl)c1cn(-c2cncc(Br)c2)nc1C(F)F]

A solution of 1-(5-bromopyridin-3-yl)-3-(difluoromethyl)-1H-pyrazole-4-carboxylic acid (3.80 g, 11.95 mmol) in SOCl$_2$ (100 mL) was stirred at 60° C. for 12 h. After this time the mixture was concentrated in vacuo to give the title compound (4.00 g, crude) as a yellow solid.

Step E: 1-(5-Bromopyridin-3-yl)-3-(difluoromethyl)-N-(6-(4-isopropyl-4H-1,2,4-triazol-3-yl)pyridin-2-yl)-1H-pyrazole-4-carboxamide

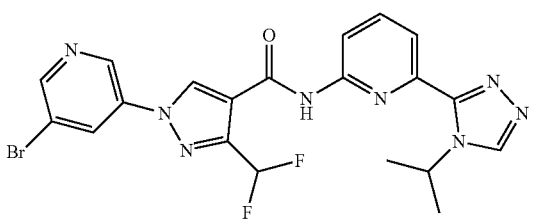

A solution of 1-(5-bromopyridin-3-yl)-3-(difluoromethyl)-1H-pyrazole-4-carbonyl chloride (4.00 g, 11.9 mmol) and 6-(4-isopropyl-4H-1,2,4-triazol-3-yl)pyridin-2-amine (4.83 g, 23.8 mmol) in DCM (110 mL) was adjusted pH to 7~8 with pyridine and then DMAP (2.90 g, 23.8 mmol) was added. The mixture was stirred at 28° C. for 3 h. After this time, the mixture was diluted with sat. NH$_4$Cl (100 mL), and the aqueous layer was extracted with DCM (100 mL×2). The combined organic extracts were dried, filtered and concentrated in vacuo. The mixture was purified by column chromatography on silica gel eluting with DCM/MeOH (from 100/1 to 10/1) to give the title compound (5.00 g, 83.6%) as a white solid. MS (ESI): 503.0 [(M+H) ($^{79}$Br)]$^+$.

Example 75: 3-(Difluoromethyl)-N-(6-(4-isopropyl-4H-1,2,4-triazol-3-yl)pyridin-2-yl)-1-(5-methylpyridin-3-yl)-1H-pyrazole-4-carboxamide

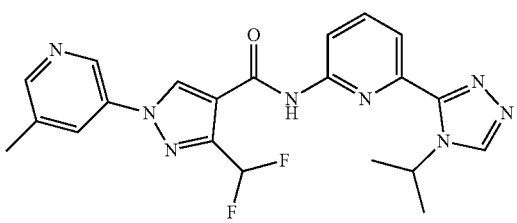 [SMILES: Cc1cncc(-n2cc(C(=O)Nc3cccc(-c4nncn4C(C)C)n3)c(C(F)F)n2)c1]

To a solution of 1-(5-bromopyridin-3-yl)-3-(difluoromethyl)-N-(6-(4-isopropyl-4H-1,2,4-triazol-3-yl)pyridin-2-yl)-1H-pyrazole-4-carboxamide (150 mg, 0.30 mmol) in dioxane/H$_2$O (5/1, 3 mL) under a N$_2$ atmosphere was added potassium trifluoro(methyl)borate (73 mg, 0.60 mmol) and K$_2$CO$_3$ (82 mg, 0.60 mmol) followed by Pd(dppf)Cl$_2$ (21.8 mg, 0.03 mmol) and the mixture was heated at 100° C. for 48 h. After this time the mixture was poured into water (10 mL) and extracted with DCM/MeOH (10/1, 10 mL×3). The combined organic layers were washed with brine (15 mL), dried over Na$_2$SO$_4$, filtered and concentrated in vacuo. The mixture was purified by prep-HPLC (using a Waters Xbridge Prep OBD C18 5 μm, 150×30 mm column and using MeCN and H$_2$O (containing 0.05% NH$_3$·H$_2$O) from 20 to 50% as the mobile phase at a flow rate of 25 mL/min) to give the title compound (28 mg, 22%) as a gray solid. $^1$H NMR (400 MHz, DMSO-d$_6$) δ ppm 10.69 (s, 1H), 9.44 (s, 1H), 8.91 (s, 1H), 8.90 (s, 1H), 8.86 (s, 1H), 8.50-8.49 (m, 1H), 8.19-8.16 (m, 1H), 8.12-8.01 (m, 1H), 7.82-7.79 (m, 1H), 7.41 (t, J=53.6 Hz, 1H), 5.56-5.48 (m, 1H), 2.41 (s, 3H), 1.41 (d, J=6.8 Hz, 6H). MS (ESI): 439.0 [M+H]$^+$.

Example 76: 1-(5-Cyanopyridin-3-yl)-3-(difluoromethyl)-N-(6-(4-isopropyl-4H-1,2,4-triazol-3-yl)pyridin-2-yl)-1H-pyrazole-4-carboxamide

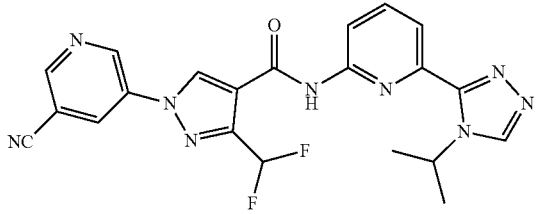 [SMILES: CC(C)n1cnnc1-c1cccc(NC(=O)c2cn(-c3cncc(C#N)c3)nc2C(F)F)n1]

To a solution of 1-(5-bromopyridin-3-yl)-3-(difluoromethyl)-N-(6-(4-isopropyl-4H-1,2,4-triazol-3-yl)pyridin-2-yl)-1H-pyrazole-4-carboxamide (150 mg, 0.30 mmol) in DMA (4 mL) was added, Zn(CN)$_2$ (43 mg, 0.36 mmol), Zn (12 mg, 0.18 mmol), dppf (34 mg, 0.06 mmol) and Pd$_2$(dba)$_3$ (28 mg, 0.03 mmol) at 30° C. The mixture was degassed with N$_2$ and stirred at 120° C. for 20 h. After this time the mixture was concentrated in vacuo and purified by prep-HPLC (using a Waters Xbridge Prep OBD C18 5 μm, 150×30 mm column and using water (containing 0.04% NH$_3$H$_2$O and 10 mM NH$_4$HCO$_3$) and MeCN, from 33 to 53% as the mobile phase at a flow rate of 25 mL/min) to give the title compound (80 mg, 60%) as a white solid. $^1$HNMR (400 MHz, DMSO-d$_6$) δ ppm 10.73 (s, 1H), 9.51 (s, 1H), 9.40 (d, J=2.4 Hz, 1H), 9.13 (d, J=1.6 Hz, 1H), 8.89 (s, 1H), 8.84 (t, J=2.0 Hz, 1H), 8.21 (d, J=8.2 Hz, 1H), 8.06 (t, J=8.0 Hz, 1H), 7.85 (d, J=7.6 Hz, 1H), 7.30-7.61 (m, 1H), 5.490-5.59 (m, 1H), 1.45 (d, J=6.8 Hz, 6H). MS (ESI): 450.1 [M+H]$^+$.

Example 77: 1-(5-Cyclopropylpyridin-3-yl)-3-(difluoromethyl)-N-(6-(4-isopropyl-4H-1,2,4-triazol-3-yl)pyridin-2-yl)-1H-pyrazole-4-carboxamide

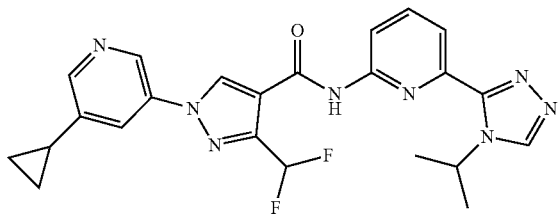 [SMILES: CC(C)n1cnnc1-c1cccc(NC(=O)c2cn(-c3cncc(C4CC4)c3)nc2C(F)F)n1]

A mixture of 1-(5-bromopyridin-3-yl)-3-(difluoromethyl)-N-(6-(4-isopropyl-4H-1,2,4-triazol-3-yl)-1H-pyrazole-4-carboxamide (100 mg, 0.20 mmol), cyclopropylboronic acid (51 mg, 0.60 mmol), Pd(OAc)$_2$ (18 mg, 0.060 mmol), PCy$_3$ (45 mg, 0.16 mmol) and Cs$_2$CO$_3$ (129 mg, 0.40 mmol) in toluene/H$_2$O (11 mL, 10/1) was stirred at 110° C. for 12 h. After this time the solvent was removed in vacuo and the mixture was purified by column chromatography on silica gel eluting with DCM/MeOH (from 100/1 to 30/1) to give the title compound (21 mg, 23%) as a white solid. $^1$H NMR (400 MHz, DMSO-d$_6$) δ ppm 10.66 (s, 1H), 9.41 (s, 1H), 8.85 (s, 2H), 8.49 (s, 1H), 8.16 (d, J=8.2 Hz, 1H), 8.02 (t, J=7.9 Hz, 1H), 7.89-7.74 (m, 2H), 7.60-7.22 (m, 1H), 5.57-5.43 (m, 1H), 2.18-2.01 (m, 1H), 1.41 (d, J=6.6 Hz, 6H), 1.13-1.01 (m, 2H), 0.91-0.82 (m, 2H). MS (ESI): 465.2 [M+H]$^+$.

Example 78: 3-(Difluoromethyl)-N-(6-(4-isopropyl-4H-1,2,4-triazol-3-yl)pyridin-2-yl)-1-(5-methoxypyridin-3-yl)-1H-pyrazole-4-carboxamide

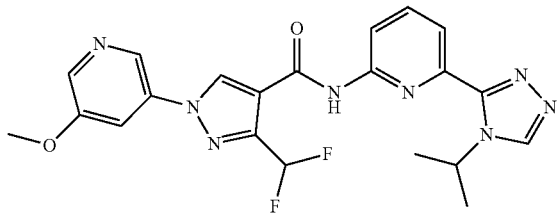 [SMILES: COc1cncc(-n2cc(C(=O)Nc3cccc(-c4nncn4C(C)C)n3)c(C(F)F)n2)c1]

To a solution of 1-(5-bromopyridin-3-yl)-3-(difluoromethyl)-N-(6-(4-isopropyl-4H-1,2,4-triazol-3-yl)pyridin-2-yl)-1H-pyrazole-4-carboxamide (300 mg, 0.59 mmol) in NMP (6 mL) was added NaOMe (0.5 mL, 30% MeOH) and the mixture was stirred at 90° C. for 30 min. After this time the mixture was poured into water (10 mL) and extracted with MeOH/DCM (1/10, 20 mL×3). The combined organic extracts were washed with brine (50 mL), dried over Na$_2$SO$_4$, filtered and concentrated in vacuo. The residue was purified by prep-HPLC (using a Waters Xbridge Prep OBD C18 5 μm, 150×30 mm column and using water (containing 0.04% NH$_3$H$_2$O and 10 mM NH$_4$HCO$_3$) and MeCN, from 27 to 57% as the mobile phase at a flow rate of 25 mL/min) to give the title compound (67 mg, 24%) as a white solid. $^1$H NMR (400 MHz, DMSO-d$_6$) δ ppm 10.98-10.49 (br s, 1H), 9.56 (s, 1H), 8.87 (s, 1H), 8.73 (d, J=1.8 Hz, 1H), 8.39 (d, J=2.4 Hz, 1H), 8.18 (d, J=8.4 Hz, 1H), 8.03 (t, J=8.0 Hz, 1H), 7.92-7.74 (m, 2H), 7.59-7.23 (m, 1H), 5.59 (td, J=6.8, 13.3 Hz, 1H), 3.95 (s, 3H), 1.43 (d, J=6.8 Hz, 6H). MS (ESI): 455.1 [M+H]$^+$.

Example 79: 3-(Difluoromethyl)-1-(5-(dimethylamino)pyridin-3-yl)-N-(6-(4-isopropyl-4H-1,2,4-triazol-3-yl)pyridin-2-yl)-1H-pyrazole-4-carboxamide

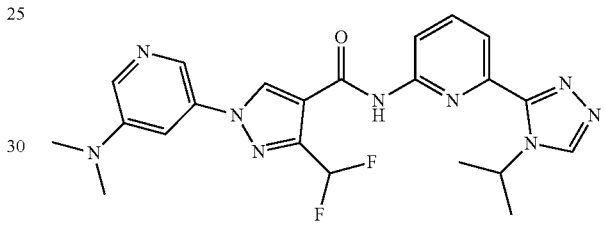

A mixture of 1-(5-bromopyridin-3-yl)-3-(difluoromethyl)-N-(6-(4-isopropyl-4H-1,2,4-triazol-3-yl)pyridin-2-yl)-1H-pyrazole-4-carboxamide (100 mg, 0.20 mmol), dimethylamine hydrochloride (24 mg, 0.30 mmol), RuPhos (18 mg, 0.04 mmol), NaOtBu (95 mg, 0.99 mmol) and Pd$_2$(dba)$_3$ (18 mg, 0.02 mmol) in DMF (5 mL) was stirred at 100° C. for 12 h. After this time the mixture was filtered and purified by prep-HPLC (using a Waters Xbridge Prep OBD C18 5 μm, 150×30 mm column and using water (containing 0.04% NH$_3$H$_2$O and 10 mM NH$_4$HCO$_3$) and MeCN, from 23-53% as the mobile phase at a flow rate of 25 mL/min) to give the title compound (8.0 mg, 8.6%) as yellow solid. $^1$H NMR (400 MHz, DMSO-d$_6$) δ ppm 10.67 (s, 1H), 9.38 (s, 1H), 8.87 (s, 1H), 8.35 (d, J=1.6 Hz, 1H), 8.20-8.13 (m, 2H), 8.03 (t, J=7.6 Hz, 1H), 7.81 (dd, J=0.8, 8.0 Hz, 1H), 7.57-7.24 (m, 2H), 5.52 (quin, J=6.6 Hz, 1H), 3.04 (s, 6H), 1.43 (d, J=6.8 Hz, 6H). MS (ESI): 468.2 [M+H]$^+$.

Example 80: 3-(Difluoromethyl)-1-(5-hydroxypyridin-3-yl)-N-(6-(4-isopropyl-4H-1,2,4-triazol-3-yl)pyridin-2-yl)-1H-pyrazole-4-carboxamide

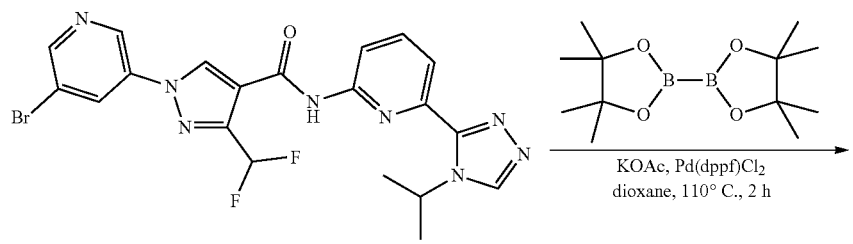

KOAc, Pd(dppf)Cl$_2$
dioxane, 110° C., 2 h

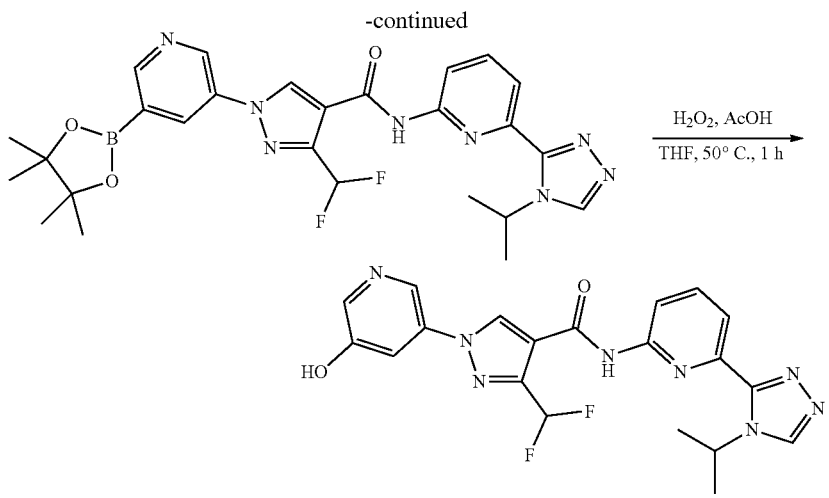

Step A: 3-(Difluoromethyl)-N-(6-(4-isopropyl-4H-1,2,4-triazol-3-yl)pyridin-2-yl)-1-(5-(4,4,5,5-tetramethyl-1,3,2-dioxaborolan-2-yl)pyridin-3-yl)-1H-pyrazole-4-carboxamide

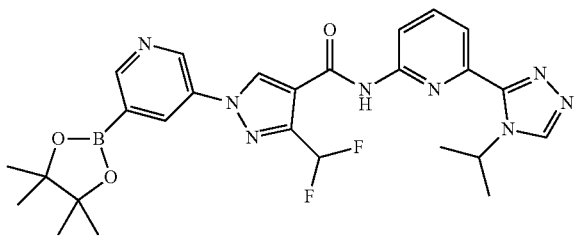 [SMILES: CC(C)n1cnnc1-c1cccc(NC(=O)c2cn(-c3cncc(B4OC(C)(C)C(C)(C)O4)c3)nc2C(F)F)n1]

To a solution of 1-(5-bromopyridin-3-yl)-3-(difluoromethyl)-N-(6-(4-isopropyl-4H-1,2,4-triazol-3-yl)pyridin-2-yl)-1H-pyrazole-4-carboxamide (300 mg, 0.59 mmol) in dioxane (5 mL) was added 4,4,4',4',5,5,5',5'-octamethyl-2,2'-bi(1,3,2-dioxaborolane) (454 mg, 1.79 mmol), KOAc (117 mg, 1.19 mmol) and Pd(dppf)Cl$_2$ (43.6 mg, 0.059 mmol) under N$_2$ and the mixture was stirred at 110° C. for 2 h. After this time the mixture was concentrated in vacuo, dissolved in DCM (20 mL) and washed with water (20 mL×2). The organic layer was dried over Na$_2$SO$_4$ and concentrated to give the title compound (600 mg, crude) as a black solid.

Step B: 3-(Difluoromethyl)-1-(5-hydroxypyridin-3-yl)-N-(6-(4-isopropyl-4H-1,2,4-triazol-3-yl)pyridin-2-yl)-1H-pyrazole-4-carboxamide

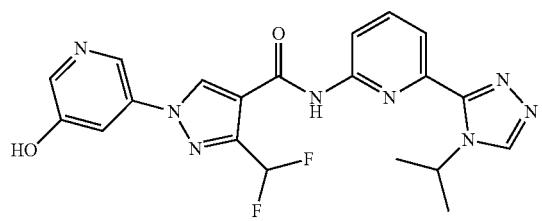

To a solution of 3-(difluoromethyl)-N-(6-(4-isopropyl-4H-1,2,4-triazol-3-yl)pyridin-2-yl)-1-(5-(4,4,5,5-tetramethyl-1,3,2-dioxaborolan-2-yl)pyridin-3-yl)-1H-pyrazole-4-carboxamide (500 mg, 1.07 mmol) in THF (10 mL) was added H$_2$O$_2$/AcOH (1 mL, 1:1) and the mixture was stirred at 50° C. for 1 h under N$_2$. After this time the mixture was diluted with water (20 mL) and extracted with DCM/MeOH (10:1, 60 mL×3). The combined organic layers were washed with brine (50 mL), dried over Na$_2$SO$_4$, filtered and concentrated in vacuo. The crude product was purified by column chromatography on silica gel eluting with DCM/MeOH (20/1) to give the title compound (110 mg, 23%) as a white solid. MS (ESI): 441.2 [M+H]$^+$.

Example 81: 3-(Difluoromethyl)-1-(5-isopropoxypyridin-3-yl)-N-(6-(4-isopropyl-4H-1,2,4-triazol-3-yl)pyridin-2-yl)-1H-pyrazole-4-carboxamide

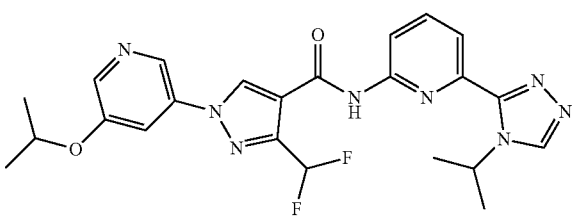 [SMILES: CC(C)Oc1cncc(-n2cc(C(=O)Nc3cccc(-c4nncn4C(C)C)n3)c(C(F)F)n2)c1]

To a solution of 3-(difluoromethyl)-1-(5-hydroxypyridin-3-yl)-N-(6-(4-isopropyl-4H-1,2,4-triazol-3-yl)pyridin-2-yl)-1H-pyrazole-4-carboxamide (90 mg, 0.21 mmol) in DMF (3 mL) was added 2-iodopropane (69.5 mg, 0.42 mmol), K$_2$CO$_3$ (54 mg, 0.42 mmol) and KI (34 mg, 0.21 mmol) and the mixture was stirred at 80° C. for 2 h under N$_2$. After this time the mixture was filtered and the filtrate was purified by prep-HPLC (using an Xtimate C18 5 μm, 150×25 mm column and using water (containing 10 mM NH$_4$HCO$_3$) and MeCN from 35 to 54% as the mobile phase at a flow rate of 25 mL/min) to give the title compound (42 mg, 43%) as a white solid. $^1$H NMR (400 MHz, DMSO-d$_6$) δ ppm 10.66 (s, 1H), 9.41 (s, 1H), 8.86 (s, 1H), 8.67 (d, J=2.0 Hz, 1H), 8.34 (d, J=2.4 Hz, 1H), 8.17-8.15 (m, 1H), 8.04-7.99 (t, J=8.0 Hz, 1H), 7.82-7.79 (m, 2H), 7.53-7.28 (m, 1H), 5.54-5.37 (m, 1H), 4.84 (m, 1H), 1.42-1.40 (d, J=6.6 Hz, 6H), 1.32-1.31 (d, J=6.0 Hz, 6H). MS (ESI): 483.1 [M+H]$^+$.

Example 82: 3-(Difluoromethyl)-N-(6-(4-isopropyl-4H-1,2,4-triazol-3-yl)pyridin-2-yl)-1-(pyridin-3-yl)-1H-pyrazole-4-carboxamide

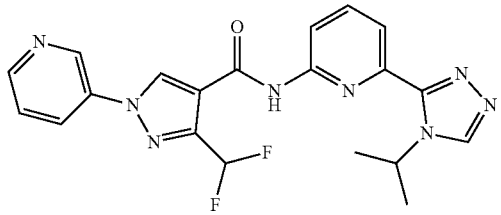 [SMILES: CC(C)n1cnnc1-c1cccc(NC(=O)c2cn(-c3cccnc3)nc2C(F)F)n1]

To a solution of 1-(5-bromopyridin-3-yl)-3-(difluoromethyl)-N-(6-(4-isopropyl-4H-1,2,4-triazol-3-yl)pyridin-2-yl)-1H-pyrazole-4-carboxamide (100 mg, 0.21 mmol) in MeOH (25 mL) was added Pd/C (98 mg) and the mixture was stirred at 28° C. under H$_2$ (15 psi) for 4 h. After this time the mixture was filtered and concentrated in vacuo. The resulting solid was dried under reduced pressure to give the title compound (40 mg, 46%) as a white solid. $^1$H NMR (400 MHz, DMSO-d$_6$) δ ppm 10.74 (s, 1H), 9.57 (s, 1H), 9.14 (d, J=2.4 Hz, 1H), 8.88 (s, 1H), 8.68 (d, J=3.6 Hz, 1H), 8.33-8.27 (m, 1H), 8.22-8.16 (m, 1H), 8.04 (t, J=7.6 Hz, 1H), 7.84 (dd, J=0.8, 7.6 Hz, 1H), 7.67 (dd, J=4.8, 8.4 Hz, 1H), 7.58-7.31 (s, 1H), 5.59 (td, J=6.8, 13.6 Hz, 1H), 1.44 (d, J=6.8 Hz, 6H). MS (ESI): 425.1 [M+H]$^+$.

Example 83: N-(6-(4-Isopropyl-4H-1,2,4-triazol-3-yl)pyridin-2-yl)-3-methoxy-1-(pyridin-2-yl)-1H-pyrazole-4-carboxamide

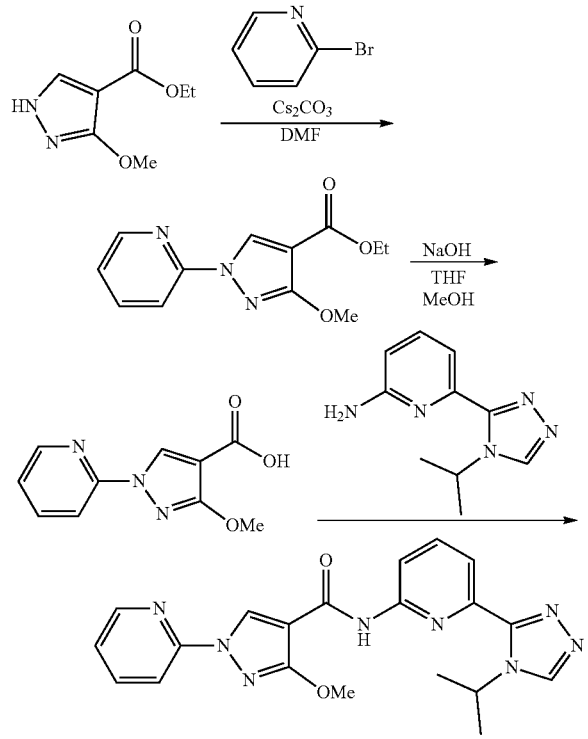

Step A: Ethyl 3-methoxy-1-(pyridin-2-yl)-1H-pyrazole-4-carboxylate

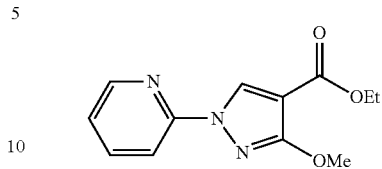

The mixture ethyl 3-methoxy-1H-pyrazole-4-carboxylate (170 mg, 1.0 mmol), 2-bromopyridine (174 mg, 1.1 mmol) and Cs$_2$CO$_3$ (326 mg, 1.0 mmol) in DMF (1 mL) was heated in a sealed tube at 120° C. overnight. After this time the mixture was partitioned between EtOAc and water, the aqueous layer was extracted with EtOAc and the combined organic extracts were dried over MgSO$_4$, filtered and concentrated in vacuo. The resulting crude mixture was purified by normal phase column eluting with 10-20% EtOAc in heptane to give the title compound (36 mg, 15%) as a white solid. MS (ESI): 248.1 [M+H]$^+$.

Step B: 3-Methoxy-1-(pyridin-2-yl)-1H-pyrazole-4-carboxylic acid

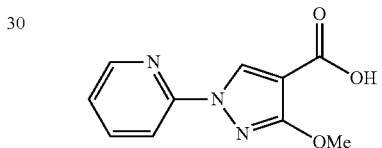

A stirred solution of ethyl 3-methoxy-1-(2-pyridyl)pyrazole-4-carboxylate (36 mg, 0.145 mmol) in THF (0.5 mL) and MeOH (0.5 mL) in a reaction vial was added 1N sodium hydroxide (0.3 mL). The reaction mixture was heated at 60° C. for 1.5 h. After this time the mixture was acidified by addition of a 1N aqueous solution of HCl and concentrated in vacuo to give the title compound as a solid which was used without further purification in the next step.

Step C: N-(6-(4-Isopropyl-4H-1,2,4-triazol-3-yl)pyridin-2-yl)-3-methoxy-1-(pyridin-2-yl)-1H-pyrazole-4-carboxamide

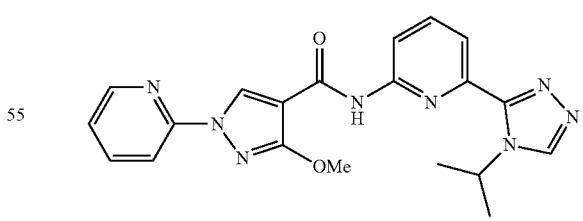

To a stirred mixture of 6-(4-isopropyl-1,2,4-triazol-3-yl)pyridin-2-amine (30 mg, 0.15 mmol) and 3-methoxy-1-(2-pyridyl)pyrazole-4-carboxylic acid (32 mg, 0.15 mmol) in a reaction vial was added Et$_3$N (0.5 mL, 3.61 mmol) and propylphosphonic anhydride (≥50 wt % in EtOAc, 0.5 mL) and the mixture was heated at 80° C. for 1.5 h. After this time the reaction mixture was cooled to rt and quenched with MeOH and water. The resulting suspension was filtered and washed with water, EtOAc and MeOH to give the title compound (9 mg, 15%) as a white solid. ¹H NMR (400 MHz, MeOD) δ ppm 10.47 (s, 1H), 9.87 (s, 1H), 9.72 (s, 1H), 9.34 (d, J=3.76 Hz, 1H), 9.06 (d, J=8.03 Hz, 1H), 8.77-8.94 (m, 2H), 8.67 (t, J=8.78 Hz, 2H), 8.23 (dd, J=6.78, 5.02 Hz, 1H), 5.94-6.46 (m, 1H), 4.96 (s, 3H), 2.35 (d, J=6.53 Hz, 6H). MS (ESI): 405.2 [M+H]⁺.

Example 84: N-(6-(4-Isopropyl-4H-1,2,4-triazol-3-yl)pyridin-2-yl)-3-methoxy-1-(pyridazin-3-yl)-1H-pyrazole-4-carboxamide

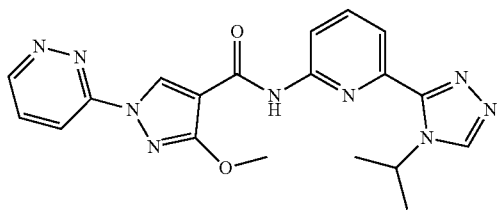 [SMILES: COc1nn(-c2cccnn2)cc1C(=O)Nc1cccc(-c2nncn2C(C)C)n1]

The title compound was synthesized according to the general procedure described in Example 83 but using 3-chloropyridazine in place of 2-bromopyridine in Step A to give the title compound (43 mg, 63% for the last step) as an off-white solid. ¹H NMR (400 MHz, DMSO-d₆) δ ppm 9.76 (s, 1H), 9.27-9.35 (m, 1H), 9.25 (dd, J=4.77, 1.25 Hz, 1H), 8.90 (s, 1H), 8.11-8.34 (m, 2H), 8.04 (t, J=7.91 Hz, 1H), 7.95 (dd, J=9.04, 4.77 Hz, 1H), 7.85 (d, J=7.53 Hz, 1H), 5.46 (quin, J=6.65 Hz, 1H), 4.15 (s, 3H), 1.53 (d, J=6.53 Hz, 6H). MS (ESI): 406.2 [M+H]⁺.

Example 85: (S)-3-Methoxy-1-(pyridazin-3-yl)-N-(6-(4-(1,1,1-trifluoropropan-2-yl)-4H-1,2,4-triazol-3-yl)pyridin-2-yl)-1H-pyrazole-4-carboxamide

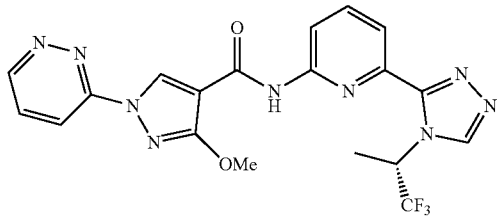 [SMILES: COc1nn(-c2cccnn2)cc1C(=O)Nc1cccc(-c2nncn2[C@@H](C)C(F)(F)F)n1]

The title compound was synthesized according to the general procedure described in Example 83 but using 3-chloropyridazine in place of 2-bromopyridine in Step A and (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine in Step C to give the title compound (12 mg, 46% for the last step) as an off-white solid. ¹H NMR (400 MHz, DMSO-d₆) δ ppm 9.95 (s, 1H), 9.19-9.42 (m, 2H), 9.15 (s, 1H), 8.10-8.33 (m, 2H), 8.06 (t, J=7.91 Hz, 1H), 7.83-8.01 (m, 2H), 6.77-6.99 (m, 1H), 4.13 (s, 3H), 1.85 (d, J=7.28 Hz, 3H). MS (ESI): 460.1 [M+H]⁺.

Example 86: (R)-3-Methoxy-1-(pyridazin-3-yl)-N-(6-(4-(1,1,1-trifluoropropan-2-yl)-4H-1,2,4-triazol-3-yl)pyridin-2-yl)-1H-pyrazole-4-carboxamide

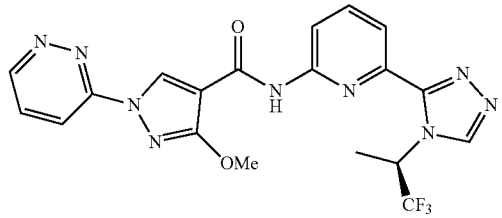 [SMILES: COc1nn(-c2cccnn2)cc1C(=O)Nc1cccc(-c2nncn2[C@H](C)C(F)(F)F)n1]

The title compound was synthesized according to the general procedure described in Example 83 but using 3-chloropyridazine in place of 2-bromopyridine in Step A and (R)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine in Step C to give the title compound (11 mg, 43% for the last step) as an off-white solid. ¹H NMR (400 MHz, MeOD) δ ppm 9.23 (s, 1H), 9.11-9.17 (m, 1H), 9.02 (s, 1H), 8.37 (d, J=8.28 Hz, 1H), 8.25 (dd, J=8.91, 1.13 Hz, 1H), 7.94-8.11 (m, 2H), 7.89 (dd, J=8.78, 4.77 Hz, 1H), 6.85 (quin, J=7.15 Hz, 1H), 4.25 (s, 3H), 1.90 (d, J=7.03 Hz, 3H). MS (ESI): 460.1 [M+H]⁺.

Example 87: (S)-3-Methoxy-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide

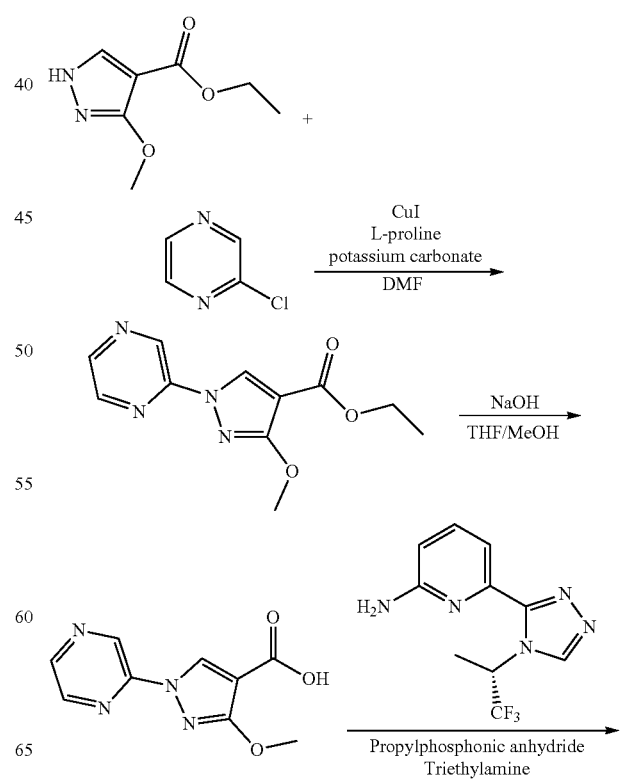

-continued

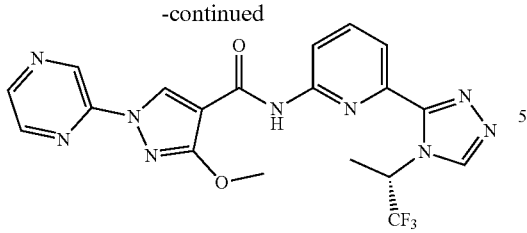

Step A: Ethyl 3-methoxy-1-(pyrazin-2-yl)-1H-pyrazole-4-carboxylate

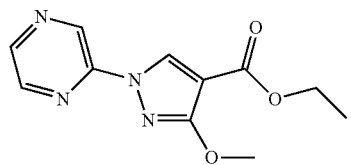 [SMILES: CCOC(=O)c1cn(-c2cnccn2)nc1OC]

A mixture of ethyl 3-methoxy-1H-pyrazole-4-carboxylate (250 mg, 1.5 mmol), 2-chloropyrazine (202 mg, 1.8 mmol), CuI (28 mg, 0.15 mmol), L-proline (34 mg, 0.29 mmol) and potassium carbonate (447 mg, 3.2 mmol) were dissolved in DMF (6 mL) and the reaction was heated at 100° C. overnight under $N_2$. After this time the reaction was filtered and the filtrate was evaporated in vacuo and purified by column chromatography using $CH_2Cl_2$ as eluent to give the title compound (275 mg, 75%). MS (ESI): 249.0 [M+H]$^+$.

Step B: 3-Methoxy-1-(pyrazin-2-yl)-1H-pyrazole-4-carboxylic acid

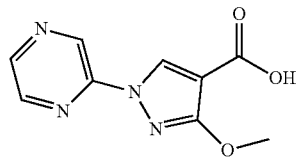 [SMILES: COc1nn(-c2cnccn2)cc1C(=O)O]

Ethyl 3-methoxy-1-pyrazin-2-yl-pyrazole-4-carboxylate (220 mg, 0.89 mmol) was dissolved in a solution of THF (2 mL) and MeOH (2 mL). NaOH (1 M, 1.1 mL) was added and the reaction was heated at 60° C. for 1 h. After this time the reaction was cooled to rt, and acidified by addition of a 1N aqueous solution of HCl. The resulting mixture was partitioned between EtOAc and water, and the separated organic layer was dried over $MgSO_4$, filtered and concentrated in vacuo to give the title compound (165 mg, 85%) as a white solid. $^1$H NMR (400 MHz, MeOD) δ ppm 9.17 (d, J=1.5 Hz, 1H), 8.89 (s, 1H), 8.55 (d, J=2.5 Hz, 1H), 8.49 (dd, J=2.6, 1.4 Hz, 1H), 4.11 (s, 3H). MS (ESI): 221.0 [M+H]$^+$.

Step C: (S)-3-Methoxy-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide

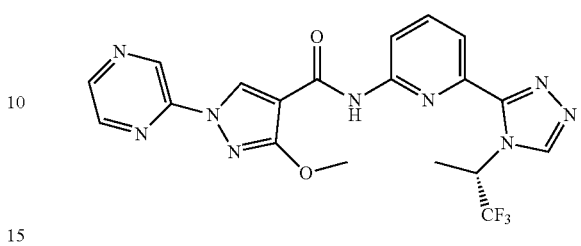

3-Methoxy-1-pyrazin-2-yl-pyrazole-4-carboxylic acid (80 mg, 0.36 mmol) and 6-[4-[(1S)-2,2,2-trifluoro-1-methyl-ethyl]-1,2,4-triazol-3-yl]pyridin-2-amine (93 mg, 0.36 mmol) were dissolved in $Et_3N$ (503 μL, 3.6 mmol). Propylphosphonic anhydride (346 mg, 0.4 mL, 1.1 mmol) was then added and the reaction mixture was heated at 80° C. for 3 h. After this time the reaction was cooled to rt and quenched by addition of MeOH (2 mL). The resulting solid was filtered and dried under vacuum to give the title compound (95 mg, 57%). $^1$H NMR (400 MHz, CDCl$_3$) δ ppm 9.23 (d, J=1.5 Hz, 2H), 9.03 (s, 1H), 8.54 (d, J=2.5 Hz, 1H), 8.41-8.47 (m, 2H), 8.40 (dd, J=2.5, 1.5 Hz, 1H), 8.08-8.14 (m, 1H), 7.92 (t, J=8.0 Hz, 1H), 6.73 (quin, J=7.2 Hz, 1H), 4.25 (s, 3H), 1.83 (d, J=7.3 Hz, 3H). MS (ESI): 460.1 [M+H]$^+$.

Example 88: (R)-3-Methoxy-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide

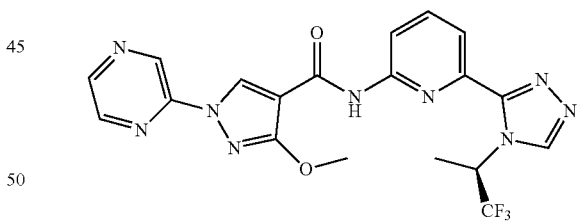

3-Methoxy-1-pyrazin-2-yl-pyrazole-4-carboxylic acid (147 mg, 0.67 mmol) and (R)-6-(4-(1,1,1-trifluoropropan-2-yl)-4H-1,2,4-triazol-3-yl)pyridin-2-amine (110 mg, 0.43 mmol) were dissolved in $Et_3N$ (593 μL, 4.3 mmol). Propylphosphonic anhydride (≥50 wt % in EtOAc, 0.4 mL) was added and the reaction was heated at 80° C. for 3 h. After this time the reaction was cooled to rt and quenched by addition of MeOH (2 mL). The resulting solid was filtered and dried under vacuum to give the title compound (114 mg, 58%). $^1$H NMR (400 MHz, MeOD) δ ppm 9.19 (s, 1H), 9.06 (d, J=6.8 Hz, 2H), 8.58 (d, J=2.8 Hz, 1H), 8.52 (s, 1H), 8.38 (d, J=8.0 Hz, 1H), 7.92-8.10 (m, 2H), 6.86 (dt, J=14.4, 7.3 Hz, 1H), 4.28 (s, 3H), 1.92 (d, J=7.3 Hz, 3H). MS (ESI): 460.1 [M+H]$^+$.

Example 89: (S)-3-(Difluoromethyl)-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide

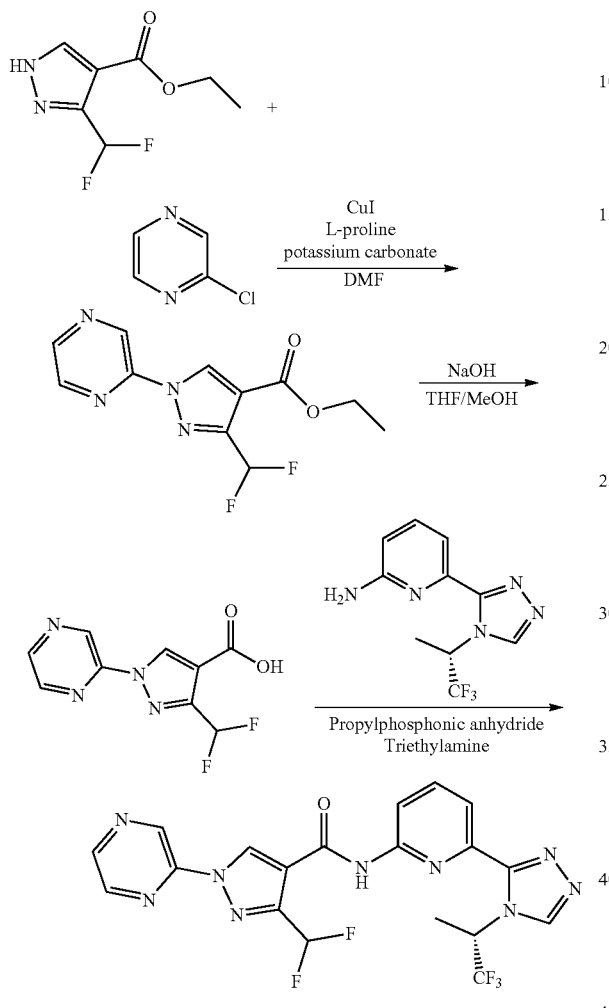

Step A: Ethyl 3-(difluoromethyl)-1-(pyrazin-2-yl)-1H-pyrazole-4-carboxylate

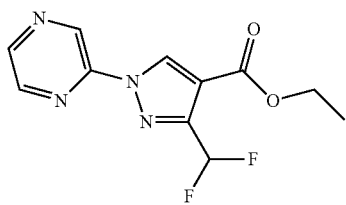 [SMILES: CCOC(=O)c1cn(-c2cnccn2)nc1C(F)F]

A mixture of ethyl 3-(difluoromethyl)-1H-pyrazole-4-carboxylate (350 mg, 1.8 mmol), 2-chloropyrazine (253 mg, 2.2 mmol), CuI (35 mg, 0.18 mmol), L-proline (42 mg, 0.37 mmol) and potassium carbonate (559 mg, 4 mmol) were dissolved in DMF (12 mL) and heated to 100° C. overnight under a $N_2$ atmosphere. After this time, the reaction was cooled to rt, filtered and the solvent was evaporated in vacuo. The crude material was purified by column chromatography using $CH_2Cl_2$ as eluent to give the title compound (350 mg, 71%). $^1$H NMR (400 MHz, CDCl$_3$) δ ppm 9.42 (d, J=1.3 Hz, 1H), 9.03 (s, 1H), 8.64 (d, J=2.5 Hz, 1H), 8.44 (dd, J=2.3, 1.5 Hz, 1H), 7.16-7.28 (m, 1H), 4.38 (q, J=7.0 Hz, 2H), 1.40 (t, J=7.2 Hz, 3H). MS (ESI): 269.0 [M+H]$^+$.

Step B: 3-(Difluoromethyl)-1-(pyrazin-2-yl)-1H-pyrazole-4-carboxylic acid

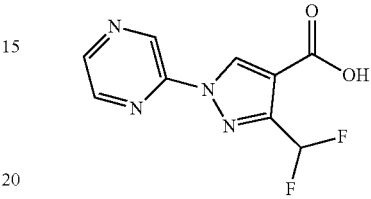

Ethyl 3-(difluoromethyl)-1-pyrazin-2-yl-pyrazole-4-carboxylate (345 mg, 1.3 mmol) was dissolved in a solution of THF (4 mL) and MeOH (4 mL). NaOH (1 M, 1.6 mL) was added and the reaction was heated at 60° C. for 1 h. After this time the solution was acidified by addition of 1N HCl and the mixture was partitioned between EtOAc and water. The organic phase was dried over MgSO$_4$, filtered and evaporated in vacuo to give the title compound (296 mg, 96%) as a white solid. MS (ESI): 240.9 [M+H]$^+$.

Step C: (S)-3-(Difluoromethyl)-1-(pyrazin-2-yl)-N-(6-(4-(1,1,1-trifluoropropan-2-yl)-4H-1,2,4-triazol-3-yl)pyridin-2-yl)-1H-pyrazole-4-carboxamide

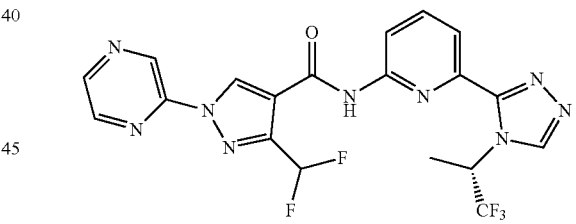

3-(Difluoromethyl)-1-pyrazin-2-yl-pyrazole-4-carboxylic acid (95 mg, 0.40 mmol) and 6-[4-[(1S)-2,2,2-trifluoro-1-methyl-ethyl]-1,2,4-triazol-3-yl]pyridin-2-amine (102 mg, 0.40 mmol) were dissolved in Et$_3$N (543 μL, 4 mmol). Propylphosphonic anhydride (≥50 wt % in EtOAc, 404 μL) was added and the reaction mixture was heated at 80° C. for 3 h. After this time the reaction was cooled to rt and quenched by addition of MeOH (2 mL). The resulting solid was filtered and dried under vacuum to give the title compound (80 mg, 42%). $^1$H NMR (400 MHz, MeOD) δ ppm 9.41 (t, J=1.3 Hz, 1H), 9.36 (d, J=1.5 Hz, 1H), 9.00 (s, 1H), 8.67 (d, J=3.0 Hz, 1H), 8.57 (dd, J=2.5, 1.5 Hz, 1H), 8.23 (dd, J=7.9, 1.4 Hz, 1H), 7.90-8.06 (m, 2H), 7.21-7.51 (m, 1H), 7.15 (quin, J=7.3 Hz, 1H), 1.90 (d, J=7.0 Hz, 3H). MS (ESI): 480.0 [M+H]$^+$.

Example 90: N-(6-(1-Isopropyl-1H-imidazol-5-yl)pyridin-2-yl)-3-methoxy-1-methyl-1H-pyrazole-4-carboxamide

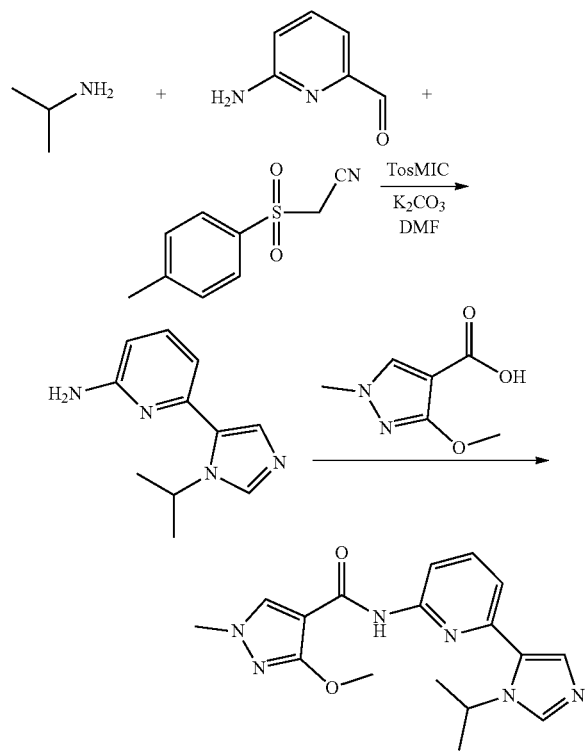

Step A:
6-(1-Isopropyl-1H-imidazol-5-yl)pyridin-2-amine

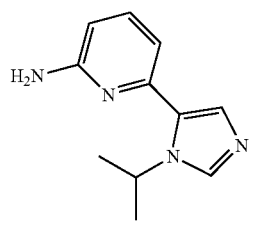

A mixture of propan-2-amine (1.4 mL, 16 mmol), 6-aminopyridine-2-carbaldehyde (997 mg, 8.16 mmol) in DMF (8 mL) was heated to 100° C. for 30 min resulting in a dark solution. After this time the mixture was cooled to rt and $K_2CO_3$ (2.26 g, 16.3 mmol) and TosMIC (1.59 g, 8.16 mmol) was added. The resulting mixture was stirred at 100° C. overnight. After this time the reaction mixture was partitioned between EtOAc and satd. $NaHCO_3$ and the organic extracts were dried over $MgSO_4$, filtered and concentrated in vacuo. The mixture was purified by normal phase column eluting with EtOAc/EtOH (3/1) to give the product as a dark brown solid. This solid was triturated with MeCN (5 mL) to give the title compound (402 mg, 24%) as a grey crystalline solid. $^1$H NMR (400 MHz, MeOD) δ ppm 7.89 (s, 1H), 7.50 (dd, J=8.16, 7.66 Hz, 1H), 7.19 (d, J=1.00 Hz, 1H), 6.83 (d, J=7.28 Hz, 1H), 6.52 (d, J=8.28 Hz, 1H), 5.32 (dt, J=13.36, 6.75 Hz, 1H), 1.49 (d, J=6.78 Hz, 6H). MS (ESI): 203.0 [M+H]+

Step B: N-(6-(1-Isopropyl-1H-imidazol-5-yl)pyridin-2-yl)-3-methoxy-1-methyl-1H-pyrazole-4-carboxamide

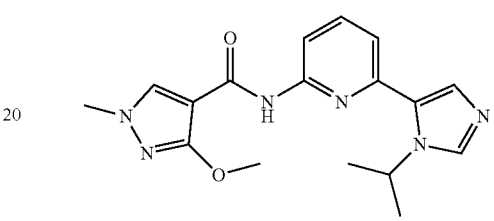

The title compound was synthesized according to the general procedure described in Example 2 but using 6-(1-isopropyl-1H-imidazol-5-yl)pyridin-2-amine in place of 6-(4-isopropyl-1,2,4-triazol-3-yl)pyridin-2-amine to give the title compound (80 mg, 29%) as an off-white solid. $^1$H NMR (400 MHz, MeOD) δ ppm 8.13 (d, J=8.28 Hz, 1H), 7.95-8.06 (m, 2H), 7.84 (t, J=8.03 Hz, 1H), 7.35-7.54 (m, 2H), 5.31-5.49 (m, 1H), 4.12 (s, 3H), 3.83 (s, 3H), 1.62 (d, J=6.78 Hz, 6H). MS (ESI): 341.0 [M+H]$^+$.

Example 91: 1-(Cyclopropylmethyl)-N-(6-(1-isopropyl-1H-imidazol-5-yl)pyridin-2-yl)-3-methoxy-1H-pyrazole-4-carboxamide

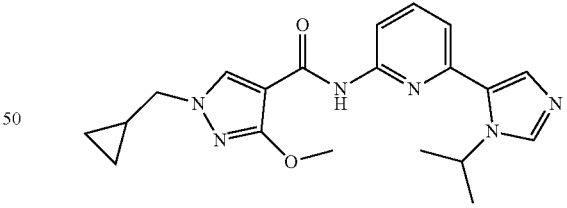

The title compound was synthesized according to the general procedure described in Example 2 but using 1-(cyclopropylmethyl)-3-methoxy-1H-pyrazole-4-carboxylic acid in place of 1-methyl-1H-pyrazole-4-carboxylic acid and 6-(1-isopropyl-1H-imidazol-5-yl)pyridin-2-amine in place of 6-(4-isopropyl-1,2,4-triazol-3-yl)pyridin-2-amine to give the title compound (4 mg, 14%) as an off-white solid. $^1$H NMR (400 MHz, MeOD) δ ppm 8.06-8.20 (m, 2H), 7.98 (s, 1H), 7.82 (t, J=7.91 Hz, 1H), 7.25-7.47 (m, 2H), 5.39 (quin, J=6.71 Hz, 1H), 4.11 (s, 3H), 3.90 (d, J=7.03 Hz, 2H), 1.54-1.65 (m, 6H), 1.25-1.41 (m, 1H), 0.57-0.74 (m, 2H), 0.26-0.48 (m, 2H). MS (ESI): 381.0 [M+H]$^+$.

Example 92: N-(6-(1-Isopropyl-1H-imidazol-5-yl)pyridin-2-yl)-3-methoxy-1-(2-methoxyethyl)-1H-pyrazole-4-carboxamide

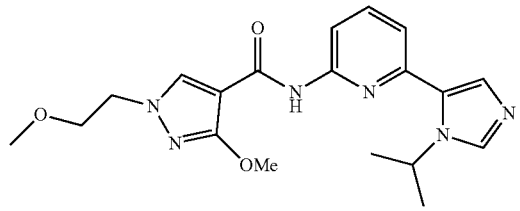 [SMILES: COCCn1cc(C(=O)Nc2cccc(-c3cncn3C(C)C)n2)c(OC)n1]

The title compound was synthesized according to the general procedure described in Example 4 but using 3-methoxy-1-(2-methoxyethyl)-1H-pyrazole-4-carboxylic acid in place of 3-(methoxymethyl)-1-methyl-pyrazole-4-carboxylic acid and 6-(1-isopropyl-1H-imidazol-5-yl)pyridin-2-amine in place of 6-(4-isopropyl-1,2,4-triazol-3-yl)pyridin-2-amine to give the title compound (23 mg, 42%) as an off-white solid. $^1$H NMR (400 MHz, MeOD) δ ppm 8.12 (d, J=8.28 Hz, 1H), 8.05 (s, 1H), 8.00 (s, 1H), 7.83 (t, J=8.03 Hz, 1H), 7.27-7.47 (m, 2H), 5.31-5.46 (m, 1H), 4.20-4.29 (m, 2H), 4.12 (s, 3H), 3.76 (t, J=5.15 Hz, 2H), 3.36 (s, 3H), 1.61 (d, J=6.78 Hz, 6H). MS (ESI): 385.0 [M+H]$^+$.

Example 93: 3-(Difluoromethyl)-N-(6-(1-isopropyl-1H-imidazol-5-yl)pyridin-2-yl)-1-(5-methylpyridin-3-yl)-1H-pyrazole-4-carboxamide

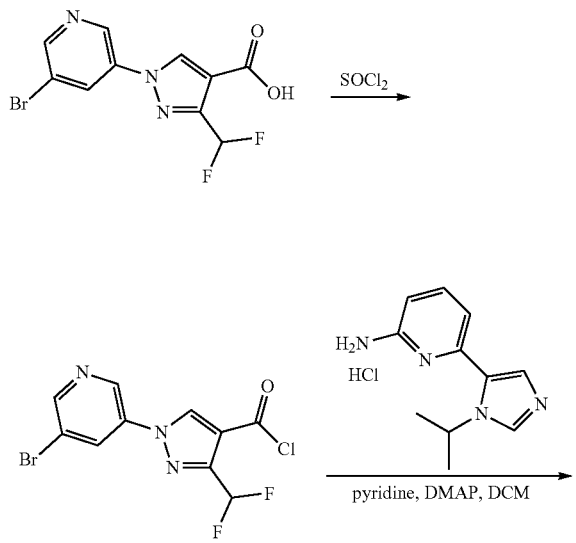

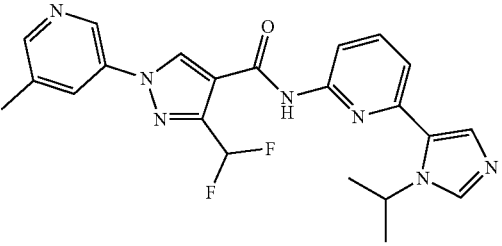

Step A: 1-(5-Bromopyridin-3-yl)-3-(difluoromethyl)-1H-pyrazole-4-carbonyl chloride

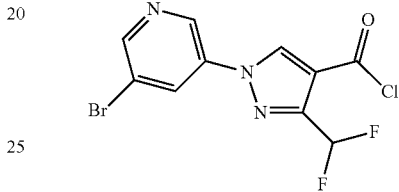

A solution of 1-(5-bromopyridin-3-yl)-3-(difluoromethyl)-1H-pyrazole-4-carboxylic acid (3.8 g, 12 mmol) in SOCl$_2$ (50 mL) was heated at 50° C. for 1 h. After this time the mixture was concentrated in vacuo to give the title compound (4 g, crude) as a yellow gum.

Step B: 1-(5-Bromopyridin-3-yl)-3-(difluoromethyl)-N-(6-(1-isopropyl-1H-imidazol-5-yl)pyridin-2-yl)-1H-pyrazole-4-carboxamide

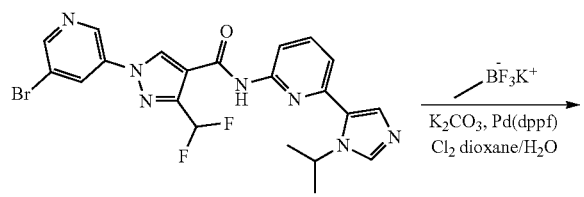

To a solution of 1-(5-bromopyridin-3-yl)-3-(difluoromethyl)-1H-pyrazole-4-carbonyl chloride (4 g, crude, 12.5 mmol) in DCM (100 mL) was added 6-(1-isopropyl-1H-imidazol-5-yl)pyridin-2-amine hydrogen chloride (4 g, 15 mmol) and pyridine (6 mL) followed by DMAP (3 g, 25 mmol) and the mixture was stirred at 24° C. for 1 h. After this time the mixture was concentrated in vacuo and purified by flash column using DCM/MeOH (from 1/0 to 20/1) as eluent to give the title compound (2.6 g, 41%, two steps) as a brown solid. MS (ESI): 504.1 [(M+H) ($^{80}$Br)]$^+$.

Step C: 3-(Difluoromethyl)-N-(6-(1-isopropyl-1H-imidazol-5-yl)pyridin-2-yl)-1-(5-methylpyridin-3-yl)-1H-pyrazole-4-carboxamide

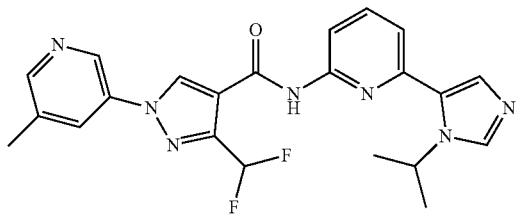

A mixture of 1-(5-bromopyridin-3-yl)-3-(difluoromethyl)-N-(6-(1-isopropyl-1H-imidazol-5-yl)pyridin-2-yl)-1H-pyrazole-4-carboxamide (80 mg, 159 mmol), potassium; trifluoro(methyl)boranuide (39 mg, 0.32 mmol), $K_2CO_3$ (44 mg, 0.32 mmol) and Pd(dppf)Cl$_2$ (23 mg, 0.032 mmol) in dioxane/H$_2$O (2 mL, 5/1) was stirred at 90° C. for 17 h. After this time the mixture was concentrated in vacuo and the mixture was purified by prep-HPLC (using an Xtimate C18 5 μm, 150×25 mm column and using water and MeCN, from 37-67% as the mobile phase at a flow rate of 25 mL/min) to give the title compound (7 mg, 8%) as a green solid. $^1$H NMR (400 MHz, DMSO-d$_6$) δ ppm 10.52 (s, 1H), 9.44 (s, 1H), 8.90 (d, J=2.2 Hz, 1H), 8.50 (s, 1H), 8.11 (s, 1H), 8.00 (d, J=7.5 Hz, 1H), 7.95 (s, 1H), 7.88 (t, J=7.9 Hz, 1H), 7.57-7.27 (t, J=53.6 Hz, 1H), 7.44-7.41 (m, 1H), 7.38 (d, J=0.9 Hz, 1H), 5.42 (m, 1H), 2.42 (s, 3H), 1.38 (d, J=6.6 Hz, 6H). MS (ESI): 438.2 [M+H]$^+$.

Example 94: 3-(Difluoromethyl)-N-(6-(1-isopropyl-1H-imidazol-5-yl)pyridin-2-yl)-1-(pyridin-3-yl)-1H-pyrazole-4-carboxamide

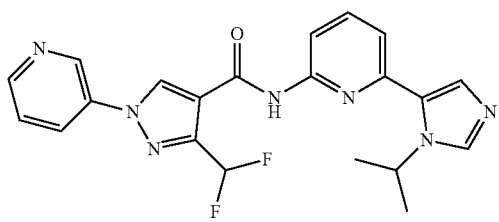

To a mixture of 1-(5-bromopyridin-3-yl)-3-(difluoromethyl)-N-(6-(1-isopropyl-1H-imidazol-5-yl)pyridin-2-yl)-1H-pyrazole-4-carboxamide (80 mg, 0.16 mmol) in MeOH (6 mL) was added Pd/C (50 mg, 0.47 mmol) and the mixture was stirred at 20° C. for 3 h under H$_2$ (15 psi). After this time, the mixture was filtered and the filtrate was purified by prep-HPLC (using a Waters Xbridge Prep OBD C18 5 μm, 150×30 mm column and using water (containing 0.04% NH$_3$H$_2$O and 10 mM NH$_4$HCO$_3$) and MeCN, from 32 to 62% as the mobile phase at a flow rate of 25 mL/min) to give the title compound (12 mg, 14%) as a white solid. $^1$H NMR (400 MHz, DMSO-d$_6$) δ ppm 10.54 (s, 1H), 9.46 (s, 1H), 9.10 (d, J=2.4 Hz, 1H), 8.70-8.62 (m, 1H), 8.26 (d, J=9.6 Hz, 1H), 8.01 (d, J=8.4 Hz, 1H), 7.95 (s, 1H), 7.88 (t, J=8.0 Hz, 1H), 7.65 (dd, J=4.8, 8.0 Hz, 1H), 7.44-7.38 (m, 3H), 5.48-5.38 (m, 1H), 1.38 (d, J=6.8 Hz, 6H). MS (ESI): 424.1 [M+H]$^+$.

Example 95: 1-(5-Cyanopyridin-3-yl)-3-(difluoromethyl)-N-(6-(1-isopropyl-1H-imidazol-5-yl)pyridin-2-yl)-1H-pyrazole-4-carboxamide

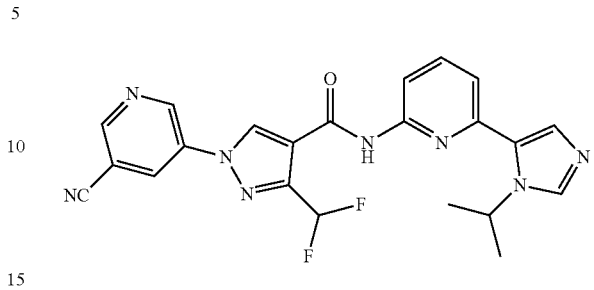

To a solution of 1-(5-bromopyridin-3-yl)-3-(difluoromethyl)-N-(6-(1-isopropyl-1H-imidazol-5-yl)pyridin-2-yl)-1H-pyrazole-4-carboxamide (40 mg, 0.079 mmol) in DMA (2.0 mL) was added Pd$_2$(dba)$_3$ (7.3 mg, 0.0079 mmol), dppf (8.8 mg, 0.015 mmol), Zn(CN)$_2$ (5.6 mg, 0.047 mmol) and Zn (6.3 mg, 0.095 mmol) at 30° C. The mixture was degassed with N$_2$ and stirred at 120° C. for 20 h. After this time the mixture was concentrated in vacuo and the mixture was purified by prep-HPLC (using an Xtimate C18 5 μm, 150×25 mm column and using water (containing 10 mM NH$_4$HCO$_3$) and MeCN, from 40 to 70% as the mobile phase at a flow rate of 25 m/min) to give the title compound (5 mg, 14%) as a yellow solid. $^1$HNMR (400 MHz, DMSO-d$_6$) δ ppm 10.58 (s, 1H), 9.53 (s, 1H), 9.40 (d, J=2.6 Hz, 1H), 9.12 (s, 1H), 8.82 (s, 1H), 8.03 (d, J=7.8 Hz, 1H), 7.98 (s, 1H), 7.91 (t, J=8.0 Hz, 1H), 7.59 (s, 1H), 7.31-7.48 (m, 3H), 5.41-5.51 (m, 1H), 1.41 (d, J=6.8 Hz, 6H). MS (ESI): 449.1 [M+H]$^+$.

Example 96: 1-(5-Cyclopropylpyridin-3-yl)-3-(difluoromethyl)-N-(6-(1-isopropyl-1H-imidazol-5-yl)pyridin-2-yl)-1H-pyrazole-4-carboxamide

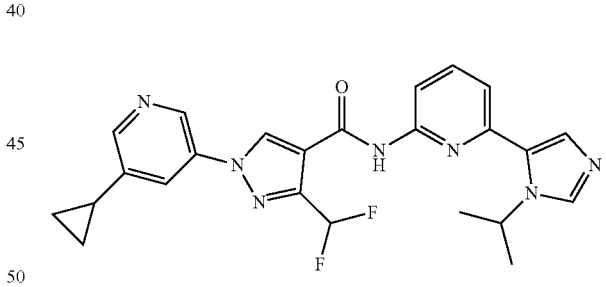

To a solution of 1-(5-bromopyridin-3-yl)-3-(difluoromethyl)-N-(6-(1-isopropyl-1H-imidazol-5-yl)pyridin-2-yl)-1H-pyrazole-4-carboxamide (200 mg, 0.39 mmol) in toluene/water (5.5 mL, 10:1) was added cyclopropylboronic acid (68 mg, 0.79 mmol), Cs$_2$CO$_3$ (259 mg, 0.79 mmol). Then PCy$_3$ (56 mg, 0.2 mmol), Pd(OAc)$_2$ (22 mg, 0.09 mmol) was added under N$_2$ and the mixture was stirred at 110° C. for 2 h. After this time, the solvent was removed under reduced pressure and the mixture was purified by prep-HPLC (using an Xtimate C18 5 μm, 150×25 mm column and using water and MeCN, from 39-69% as the mobile phase at a flow rate of 25 m/min) to give the title compound (71 mg, 38%) as a white solid. $^1$H NMR (400 MHz, DMSO-d$_6$) δ ppm 10.55 (s, 1H), 9.44 (s, 1H), 8.87 (s, 1H), 8.51 (s, 1H), 8.02 (d, J=8.0 Hz, 1H), 7.93-7.88 (m, 1H), 7.88-7.85 (m, 1H), 7.47-7.41 (m, 2H), 5.46-5.43 (m, 1H), 2.16-2.07 (m, 1H), 1.75 (s, 1H), 1.40 (d, J=6.6 Hz, 7H), 1.13-1.04 (m, 2H), 0.93-0.85 (m, 2H). MS (ESI): 464.2 [M+H]⁺.

Example 97: 3-(Difluoromethyl)-N-(6-(1-isopropyl-1H-imidazol-5-yl)pyridin-2-yl)-1-(5-methoxypyridin-3-yl)-1H-pyrazole-4-carboxamide

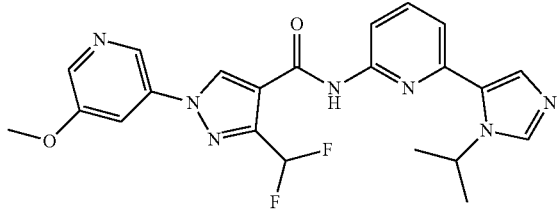 [SMILES: COc1cncc(-n2cc(C(=O)Nc3cccc(-c4cncn4C(C)C)n3)c(C(F)F)n2)c1]

A mixture of 1-(5-bromopyridin-3-yl)-3-(difluoromethyl)-N-(6-(1-isopropyl-1H-imidazol-5-yl)pyridin-2-yl)-1H-pyrazole-4-carboxamide (200 mg, 0.40 mmol) and NaOMe (500 uL, 25% purity in MeOH) in NMP (2 mL) was stirred at 90° C. for 30 min. After this time, the mixture was diluted with DMF (5.0 mL) and the solid was filtered. The filtrate was purified by prep-HPLC (using a Waters Xbridge Prep OBD C18 5 μm, 150×30 mm column and using water (containing 0.04% NH₃H₂O and 10 mM NH₄HCO₃) and MeCN from 32 to 62% as the mobile phase at a flow rate of 25 mL/min) to give the title compound (21 mg, 11%) as a white solid. ¹H NMR (400 MHz, DMSO-d₆) δ ppm 10.55 (s, 1H), 9.47 (s, 1H), 8.73 (d, J=1.6 Hz, 1H), 8.41 (d, J=2.8 Hz, 1H), 8.01-8.04 (m, 1H), 7.97 (s, 1H), 7.90 (t, J=7.6 Hz, 1H), 7.85 (t, J=2.4 Hz, 1H), 7.30-7.58 (m, 3H), 5.42-5.48 (m, 1H), 3.96 (s, 3H), 1.41 (d, J=6.4 Hz, 6H). MS (ESI): 454.2 [M+H]⁺.

Example 98: 3-(Difluoromethyl)-1-(5-(dimethylamino)pyridin-3-yl)-N-(6-(1-isopropyl-1H-imidazol-5-yl)pyridin-2-yl)-1H-pyrazole-4-carboxamide

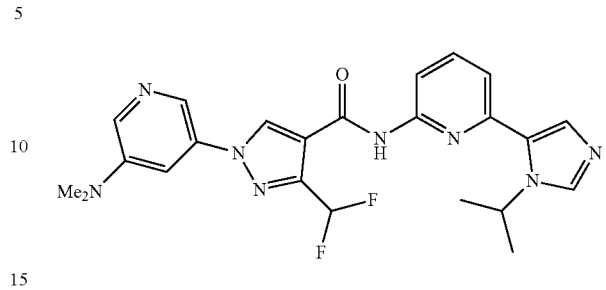

A mixture of 1-(5-bromopyridin-3-yl)-3-(difluoromethyl)-N-(6-(1-isopropyl-1H-imidazol-5-yl)pyridin-2-yl)-1H-pyrazole-4-carboxamide (100 mg, 0.20 mmol), dimethylamine hydrochloride (32.5 mg, 0.40 mmol), RuPhos (18.6 mg, 0.04 mmol), Pd₂(dba)₃ (18.2 mg, 0.02 mmol), tBuONa (76.5 mg, 0.80 mmol) in DMF (5 mL) was stirred at 100° C. under N₂ for 3 h. After this time the mixture was filtered and the filtrate was purified by prep-HPLC (using a Waters Xbridge Prep OBD 5 m C18, 150×30 mm column and using water (containing 0.04% NH₃H₂O and 10 mM NH₄HCO₃) and MeCN from 38-61% as the mobile phase at a flow rate of 25 mL/min) to give the title compound (21 mg, 22%) as a white solid. ¹H NMR (400 MHz, DMSO-d₆) δ ppm 10.55 (s, 1H), 9.42 (s, 1H), 8.36 (d, J=2.0 Hz, 1H), 8.18 (d, J=2.8 Hz, 1H), 8.05-8.02 (m, 2H), 7.92-7.90 (m, 1H), 7.46-7.42 (m, 4H), 5.49-5.42 (m, 1H), 3.05 (s, 6H), 1.40 (d, J=6.8 Hz, 6H). MS (ESI): 467.1 [M+H]⁺.

Example 99: 3-(Difluoromethyl)-1-(5-hydroxypyridin-3-yl)-N-(6-(1-isopropyl-1H-imidazol-5-yl)pyridin-2-yl)-1H-pyrazole-4-carboxamide

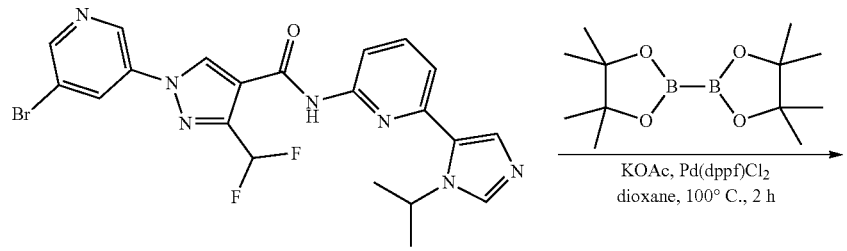

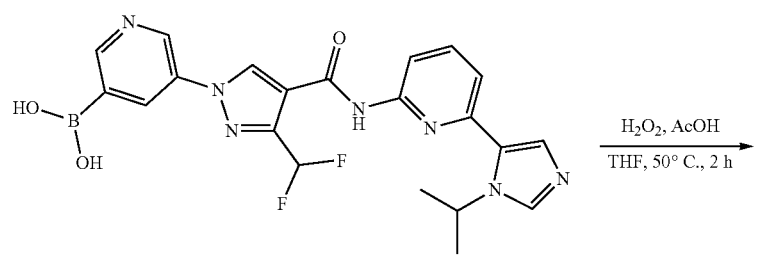

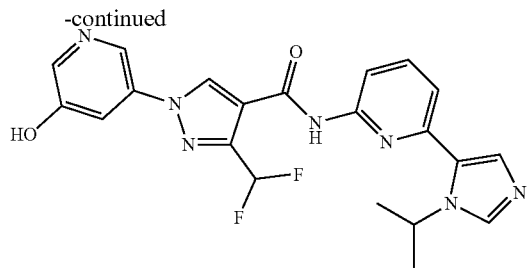

Step A: (5-(3-(Difluoromethyl)-4-((6-(1-isopropyl-1H-imidazol-5-yl)pyridin-2-yl)carbamoyl)-1H-pyrazol-1-yl)pyridin-3-yl)boronic acid

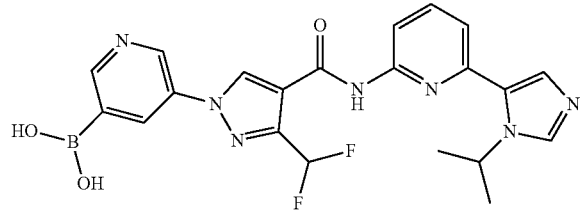 [SMILES: CC(C)n1cncc1-c1cccc(NC(=O)c2cn(-c3cncc(B(O)O)c3)nc2C(F)F)n1]

A mixture of 1-(5-bromopyridin-3-yl)-3-(difluoromethyl)-N-(6-(1-isopropyl-1H-imidazol-5-yl)pyridin-2-yl)-1H-pyrazole-4-carboxamide (400 mg, 0.80 mmol), 4,4,4',4',5,5,5',5'-octamethyl-2,2'-bi(1,3,2-dioxaborolane) (607 mg, 2.4 mmol), KOAc (156 mg, 1.6 mmol) and Pd(dppf)Cl₂ (175 mg, 0.24 mmol) in dioxane (10 mL) was stirred at 100° C. for 17 h under a N₂ atmosphere. After this time, the mixture was concentrated in vacuo and dissolved in DCM (20 mL). The resulting mixture was washed with H₂O (20 mL×2), the organic layer was dried over Na₂SO₄, filtered and concentrated in vacuo to give the title compound (1.20 g, crude), which was used without further purification in the next step. MS (ESI): 468.2 [M+H]⁺.

Step B: 3-(Difluoromethyl)-1-(5-hydroxypyridin-3-yl)-N-(6-(1-isopropyl-1H-imidazol-5-yl)pyridin-2-yl)-1H-pyrazole-4-carboxamide

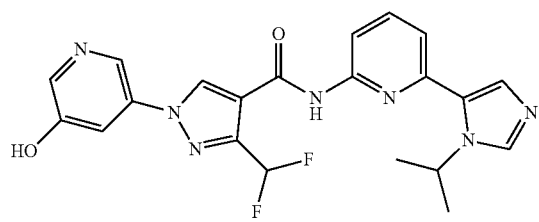

A mixture of (5-(3-(difluoromethyl)-4-((6-(1-isopropyl-1H-imidazol-5-yl)pyridin-2-yl)carbamoyl)-1H-pyrazol-1-yl)pyridin-3-yl)boronic acid (1.2 g, 2.57 mmol) in THF (20 mL) was added AcOH (1 mL) and H₂O₂ (1 mL, 30%) and the mixture was stirred at 50° C. for 2 h. After this time, the mixture was filtered and the filter cake was concentrated in vacuo to give the title compound (200 mg, 18%). ¹H NMR (400 MHz, DMSO-d₆) δ ppm 10.52 (s, 1H), 9.40 (s, 1H), 8.55 (d, J=1.6 Hz, 1H), 8.20 (d, J=2.0 Hz, 1H), 8.00 (d, J=7.6 Hz, 1H), 7.95 (s, 1H), 7.87 (t, J=8.0 Hz, 1H), 7.61 (t, J=2.4 Hz, 1H), 7.43-7.38 (m, 3H), 5.47-5.40 (m, 1H), 1.38 (d, J=6.4 Hz, 6H). MS (ESI): 440.2 [M+H]⁺.

Example 100: 3-(Difluoromethyl)-1-(5-isopropoxypyridin-3-yl)-N-(6-(1-isopropyl-1H-imidazol-5-yl)pyridin-2-yl)-1H-pyrazole-4-carboxamide

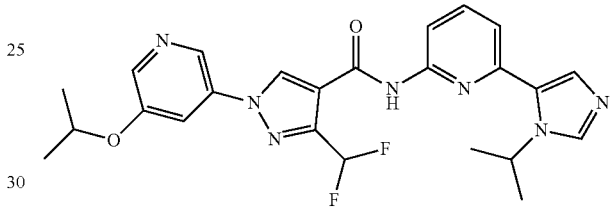

A mixture of 3-(difluoromethyl)-1-(5-hydroxypyridin-3-yl)-N-(6-(1-isopropyl-1H-imidazol-5-yl)pyridin-2-yl)-1H-pyrazole-4-carboxamide (80 mg, 0.18 mmol), 2-iodopropane (62 mg, 0.36 mmol), K₂CO₃ (50 mg, 0.36 mmol) and KI (30 mg, 0.18 mmol) in DMF (2 mL) was stirred at 80° C. for 2 h. After this time, the mixture was filtered and the filtrate was purified by prep-HPLC (using a Waters Xbridge Prep OBD C18 5 μm, 150×30 mm column and using water (containing 0.04% NH₃H₂O and 10 mM NH₄HCO₃) and MeCN; from 35-65% as the mobile phase at a flow rate of 25 mL/min) to give the title compound (6.3 mg, 6%) as a white solid. ¹H NMR (400 MHz, DMSO-d₆) δ ppm 10.50 (br s, 1H), 9.42 (s, 1H), 8.66 (d, J=2.0 Hz, 1H), 8.33 (d, J=2.4 Hz, 1H), 8.02-7.92 (m, 2H), 7.87 (t, J=8.0 Hz, 1H), 7.81 (t, J=2.0 Hz, 1H), 7.56-7.25 (m, 3H), 5.46-5.39 (m, 1H), 4.87-4.80 (m, 1H), 1.38 (d, J=6.8 Hz, 6H), 1.32 (d, J=6.0 Hz, 6H). MS (ESI): 482.2 [M+H]⁺.

Example 101: N-(3-(1-cyclopropyl-1H-imidazol-5-yl)phenyl)-3-methoxy-1-methyl-1H-pyrazole-4-carboxamide

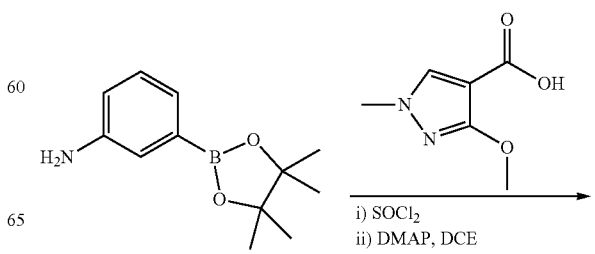

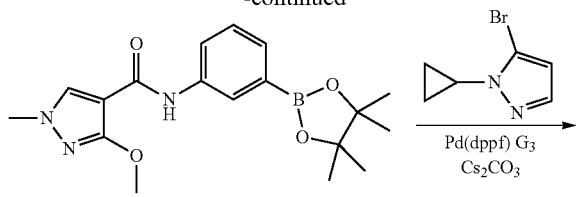

Step A: 3-Methoxy-1-methyl-N-(3-(4,4,5,5-tetramethyl-1,3,2-dioxaborolan-2-yl)phenyl)-1H-pyrazole-4-carboxamide

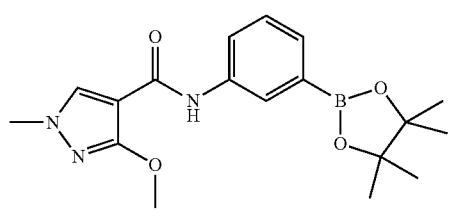

A mixture of 3-methoxy-1-methyl-pyrazole-4-carboxylic acid (2.00 g, 12.8 mmol) in thionyl chloride (7.0 mL, 96.1 mmol) was heated at reflux for 15 min. After this time the volatiles were removed under reduced pressure yielding the corresponding acid chloride as a beige solid. The solid was dissolved in DCM (7 mL) and added dropwise to a solution of 3-(4,4,5,5-tetramethyl-1,3,2-dioxaborolan-2-yl)aniline (3.1 g, 14.1 mmol), DMAP (78 mg, 0.64 mmol) and Et$_3$N (3.55 mL, 25.6 mmol) in DCM (7 mL) at 0° C. The reaction was kept stirring at rt overnight. After this time the volatiles were removed and the residue was dissolved in DCM (25 mL) and washed with sat. NaHCO$_3$ (10 mL). The organic layer was dried over Na$_2$SO$_4$, filtered and concentrated to give the title compound (4.50 g, 98%) which was used without further purification in the next step.

Step B: N-(3-(1-cyclopropyl-1H-imidazol-5-yl)phenyl)-3-methoxy-1-methyl-1H-pyrazole-4-carboxamide

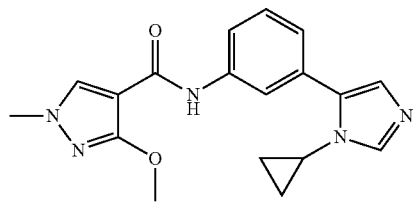 [SMILES: COc1nn(C)cc1C(=O)Nc1cccc(-c2cncn2C2CC2)c1]

A microwave vial was charged with 5-bromo-1-cyclopropyl-1H-imidazole (40 mg, 0.21 mmol), 3-methoxy-1-methyl-N-(3-(4,4,5,5-tetramethyl-1,3,2-dioxaborolan-2-yl) phenyl)-1H-pyrazole-4-carboxamide (75 mg, 0.21 mmol), cesium carbonate (137 mg, 0.42 mmol) and Pd(dppf) G3 (20 mg, 0.02 mmol). Dioxane (1.5 mL) and water (75 μL) were added. The vial was purged with N$_2$, sealed and irradiated in a biotage microwave at 120° C. for 1 h. After this time the volatiles were removed under reduced pressure and the resulting black residue was taken up in DMSO and subjected to prep-HPLC (using a Sunfire Prep C18 OBD, 5 μm 30×50 mm column and using 95% water/5% MeCN (initial conditions) to 50% water/50% MeCN over 20 minutes in 0.1% TFA as the mobile phase at a flow rate of 50 m/min). The fractions containing product were combined, evaporated to dryness and the resulting residue was dissolved in DCM (20 mL) and washed with satd. NaHCO$_3$ (10 mL). The organic layer was separated, dried over Na$_2$SO$_4$, filtered and concentrated to give the title compound (28 mg, 40%) as a white solid. $^1$H NMR (400 MHz, CDCl$_3$) δ ppm 8.53 (s, 1H), 8.01 (t, J=1.8 Hz, 1H), 7.79 (s, 1H), 7.57 (d, J=0.8 Hz, 1H), 7.46-7.41 (m, 1H), 7.36 (t, J=7.8 Hz, 1H), 7.25 (td, J=1.4, 7.8 Hz, 1H), 7.11 (d, J=1.3 Hz, 1H), 4.09 (s, 3H), 3.78 (s, 3H), 3.42 (tt, J=3.7, 7.2 Hz, 1H), 1.06-0.98 (m, 2H), 0.90-0.82 (m, 2H). MS (ESI): 338.1 [M+H]$^+$.

Example 102: N-(6-(4-Isopropyl-4H-1,2,4-triazol-3-yl)pyridin-2-yl)-3-methoxy-1-(2,2,2-trifluoroethyl)-1H-pyrazole-4-carboxamide

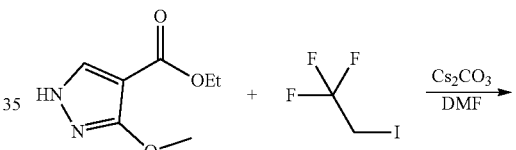

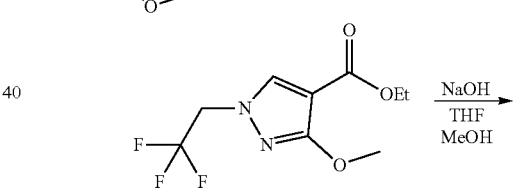

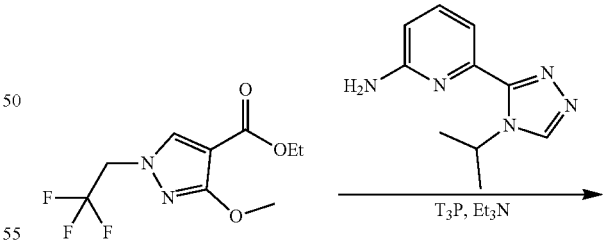

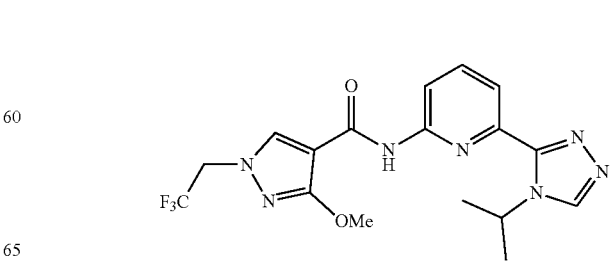

Step A: Ethyl 3-methoxy-1-(2,2,2-trifluoroethyl)-1H-pyrazole-4-carboxylate

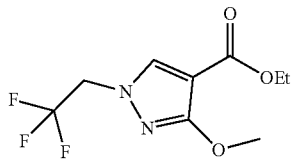 [SMILES: CCOC(=O)c1cn(CC(F)(F)F)nc1OC]

A mixture of ethyl 3-methoxy-1H-pyrazole-4-carboxylate (170 mg, 1.0 mmol), 1,1,1-trifluoro-2-iodoethane (108 µL, 1.1 mmol) and Cs₂CO₃ (284 mg, 0.087 mmol) in DMF (2 mL) was heated with microwave irritation at 100° C. for 30 min. The reaction was carried out twice under the same conditions and the combined crude mixture was partitioned between EtOAc and water. The aqueous layer was extracted with EtOAc and the combined organic extracts were dried over MgSO₄, filtered and concentrated in vacuo. The residue was purified by normal phase column eluting with 30% EtOAc in heptane to give the title compound (220 mg, 44%) as a white solid. ¹H NMR (400 MHz, MeOD) δ ppm 8.08 (s, 1H), 4.71-4.82 (m, 2H), 4.25 (q, J=7.11 Hz, 2H), 3.93 (s, 3H), 1.31 (t, J=7.15 Hz, 3H). MS (ESI): 252.9 [M+H]+.

Step B: 3-Methoxy-1-(2,2,2-trifluoroethyl)-1H-pyrazole-4-carboxylic acid

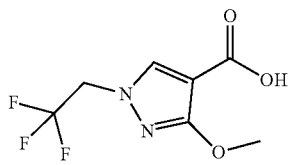

To a solution of ethyl 3-methoxy-1-(2,2,2-trifluoroethyl)-1H-pyrazole-4-carboxylate (203 mg, 0.8 mmol) in THF (0.5 mL) and MeOH (0.5 mL) was added 1N NaOH (1 mL). The reaction mixture was stirred at rt overnight. After this time the mixture was acidified by addition of an aqueous solution of 1N HCl and the mixture was partitioned between EtOAc and water. The organic layer was dried over MgSO₄, filtered and concentrated in vacuo to give title compound (170 mg, 95%) as a white solid. ¹H NMR (400 MHz, MeOD) δ ppm 8.05 (s, 1H), 4.72-4.80 (m, 2H), 3.93 (s, 3H).

Step C: N-(6-(4-Isopropyl-4H-1,2,4-triazol-3-yl)pyridin-2-yl)-3-methoxy-1-(2,2,2-trifluoroethyl)-1H-pyrazole-4-carboxamide

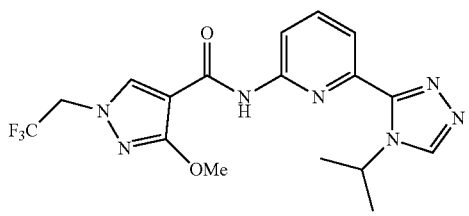 [SMILES: COc1nn(CC(F)(F)F)cc1C(=O)Nc1cccc(-c2nncn2C(C)C)n1]

To a mixture of 6-(4-isopropyl-1,2,4-triazol-3-yl)pyridin-2-amine (41 mg, 0.20 mmol) and 3-methoxy-1-(2,2,2-trifluoroethyl)-1H-pyrazole-4-carboxylic acid (45 mg, 0.21 mmol) was added Et₃N (0.4 mL, 2.9 mmol) and propylphosphonic anhydride (≥50 wt % in EtOAc, 0.4 mL). The mixture was heated with microwave irritation at 110° C. for 90 min. After this time the mixture was quenched with a small amount of MeOH (~1 mL) and then it was partitioned between EtOAc and water. The aqueous layer was extracted with EtOAc and the combined organic extracts were dried over MgSO₄, filtered and concentrated in vacuo. The crude product was purified by normal phase column eluting with EtOAc/EtOH (7/1) to give the title compound as an off-white solid (39 mg, 48%). ¹H NMR (400 MHz, MeOD) δ ppm 8.85 (s, 1H), 8.35 (d, J=7.78 Hz, 1H), 8.22 (s, 1H), 7.99 (t, J=8.03 Hz, 1H), 7.83 (d, J=7.28 Hz, 1H), 5.45 (quin, J=6.71 Hz, 1H), 4.87-4.96 (m, 2H), 4.13 (s, 3H), 1.64 (d, J=6.78 Hz, 6H). MS (ESI): 409.9 [M+H]+.

Example 103: (S)-3-Methoxy-1-(2,2,2-trifluoroethyl)-N-(6-(4-(1,1,1-trifluoropropan-2-yl)-4H-1,2,4-triazol-3-yl)pyridin-2-yl)-1H-pyrazole-4-carboxamide

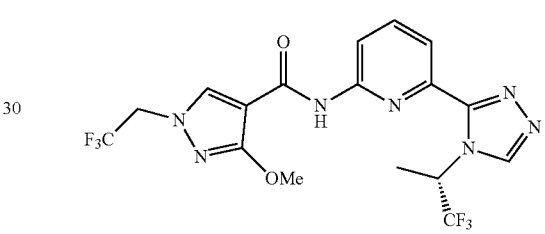

The product was synthesized according to the general procedure described in Example 102 but using (S)-6-(4-(1,1,1-trifluoropropan-2-yl)-4H-1,2,4-triazol-3-yl)pyridin-2-amine in place of 6-(4-isopropyl-1,2,4-triazol-3-yl)pyridin-2-amine in Step C to give the title compound (48 mg, 57%) as an off-white solid. ¹H NMR (400 MHz, MeOD) δ ppm 9.01 (s, 1H), 8.31-8.42 (m, 1H), 8.22 (s, 1H), 7.85-8.08 (m, 2H), 6.79 (quin, J=7.22 Hz, 1H), 4.87-4.95 (m, 2H), 4.12 (s, 3H), 1.87 (d, J=7.28 Hz, 3H). MS (ESI): 463.9 [M+H]+.

Example 104: (S)-3-Methoxy-N-(6-(4-(3-methylbutan-2-yl)-4H-1,2,4-triazol-3-yl)pyridin-2-yl)-1-(2,2,2-trifluoroethyl)-1H-pyrazole-4-carboxamide

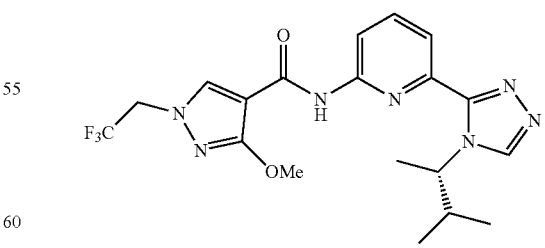

The product was synthesized according to the general procedure described in Example 102 but using (S)-6-(4-(3-methylbutan-2-yl)-4H-1,2,4-triazol-3-yl)pyridin-2-amine in place of 6-(4-isopropyl-1,2,4-triazol-3-yl)pyridin-2-amine in Step C to give the title compound (50 mg, 67%) as an off-white solid. ¹H NMR (400 MHz, MeOD) δ ppm 8.84 (s, 1H), 8.36 (d, J=7.78 Hz, 1H), 8.22 (s, 1H), 7.99 (t, J=8.03 Hz, 1H), 7.83 (d, J=7.28 Hz, 1H), 5.16-5.34 (m, 1H), 4.88-4.97 (m, 2H), 4.14 (s, 3H), 2.08-2.27 (m, 1H), 1.60 (d, J=7.03 Hz, 3H), 1.04 (d, J=6.78 Hz, 3H), 0.86 (d, J=6.78 Hz, 3H). MS (ESI): 438.0 [M+H]⁺.

Example 105: N-(6-(4-Cyclopropyl-4H-1,2,4-triazol-3-yl)pyridin-2-yl)-3-methoxy-1-(2,2,2-trifluoroethyl)-1H-pyrazole-4-carboxamide

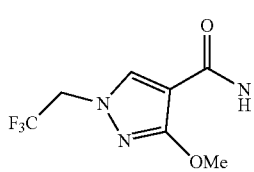

The product was synthesized according to the general procedure described in Example 102 but using 6-(4-cyclopropyl-4H-1,2,4-triazol-3-yl)pyridin-2-amine in place of 6-(4-isopropyl-1,2,4-triazol-3-yl)pyridin-2-amine in Step C to give the title compound (18 mg, 43%) as an off-white solid. ¹H NMR (400 MHz, MeOD) δ ppm 8.64 (s, 1H), 8.36 (d, J=7.78 Hz, 1H), 8.22 (s, 1H), 7.99 (t, J=7.91 Hz, 1H), 7.83 (d, J=7.28 Hz, 1H), 4.87-4.94 (m, 2H), 4.11 (s, 3H), 3.91 (dt, J=7.53, 3.51 Hz, 1H), 1.12 (s, 2H), 0.95-1.09 (m, 2H). MS (ESI): 407.9 [M+H]⁺.

Example 106: N-(6-(1-Isopropyl-1H-imidazol-5-yl)pyridin-2-yl)-3-methoxy-1-(2,2,2-trifluoroethyl)-1H-pyrazole-4-carboxamide

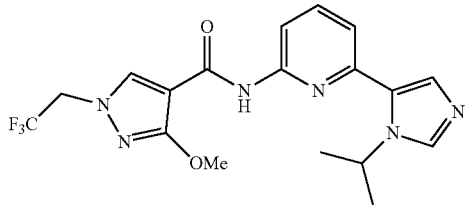 [SMILES: COc1nn(CC(F)(F)F)cc1C(=O)Nc1cccc(-c2cncn2C(C)C)n1]

The product was synthesized according to the general procedure described in Example 102 but using 6-(1-isopropyl-1H-imidazol-5-yl)pyridin-2-amine in place of 6-(4-isopropyl-1,2,4-triazol-3-yl)pyridin-2-amine in Step C to give the title compound (11 mg, 46%) as an off-white solid. ¹H NMR (400 MHz, MeOD) δ ppm 8.21 (s, 1H), 8.13 (d, J=8.03 Hz, 1H), 8.00 (s, 1H), 7.84 (t, J=7.91 Hz, 1H), 7.28-7.48 (m, 2H), 5.40 (dt, J=13.55, 6.78 Hz, 1H), 4.88-4.96 (m, 2H), 4.14 (s, 3H), 1.61 (d, J=6.78 Hz, 6H). MS (ESI): 408.9 [M+H]⁺.

Example 107: 3-Methoxy-1-methyl-N-(6-(4-(oxetan-3-yl)-4H-1,2,4-triazol-3-yl)pyridin-2-yl)-1H-pyrazole-4-carboxamide

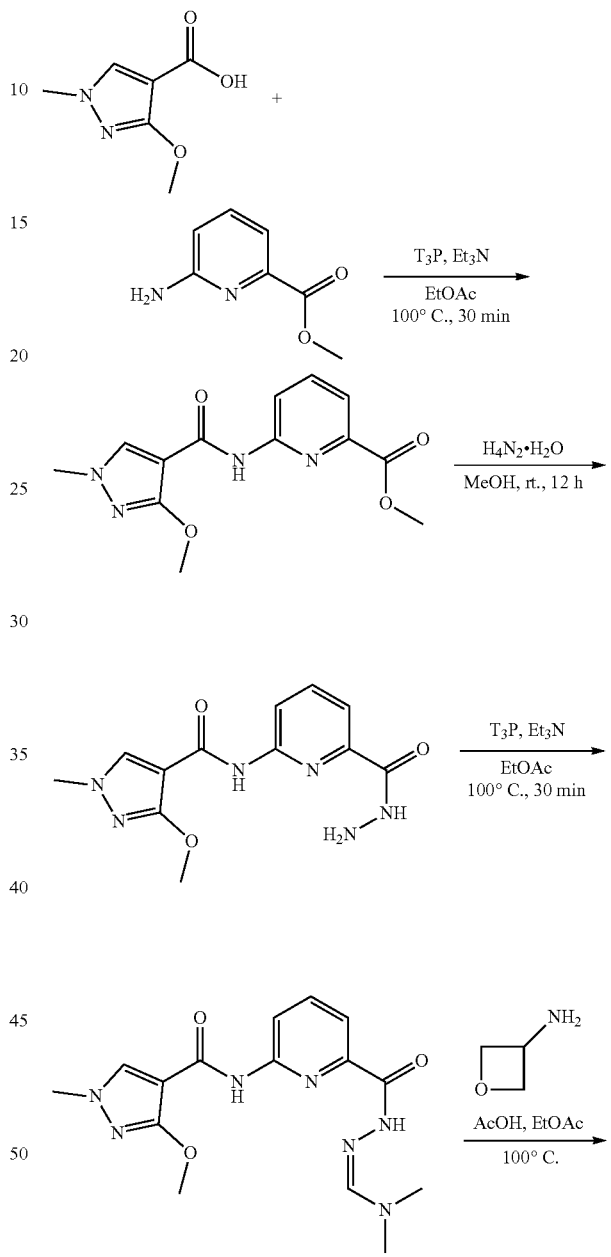

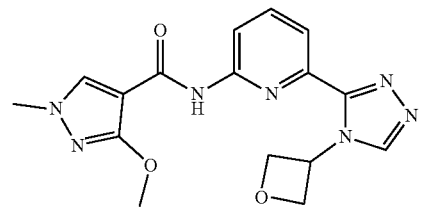

Step A: Methyl 6-(3-methoxy-1-methyl-1H-pyrazole-4-carboxamido)picolinate

A mixture of 3-methoxy-1-methyl-1H-pyrazole-4-carboxylic acid (1.23 g, 7.9 mmol), methyl 6-aminopicolinate (1.0 g, 6.7 mmol), propylphosphonic anhydride (4.38 mL, 3M in EtOAc) and Et₃N (5.5 mL, 40 mmol) in EtOAc (2 mL) was heated to 110° C. for 30 min. After this time, the reaction mixture was cooled to rt and the title compound was obtained by filtration as a beige solid which was used without further purification in the next step.

Step B: N-(6-(hydrazinecarbonyl)pyridin-2-yl)-3-methoxy-1-methyl-1H-pyrazole-4-carboxamide

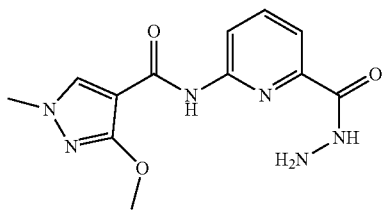 [SMILES: COc1nn(C)cc1C(=O)Nc1cccc(C(=O)NN)n1]

A solution of crude methyl 6-(3-methoxy-1-methyl-1H-pyrazole-4-carboxamido)picolinate (2 g, 6.89 mmol) and hydrazine hydrate (1.8 mL, 55 wt % in water) in MeOH (2 mL) was stirred at rt for 12 h. The desired product was obtained by filtration as a 2:1 mixture with unreacted starting material. The crude mixture was subjected to the next step without further purification.

Step C: N-(6-(2-((Dimethylamino)methylene)hydrazine-1-carbonyl)pyridin-2-yl)-3-methoxy-1-methyl-1H-pyrazole-4-carboxamide

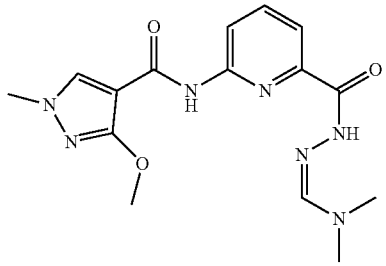

The crude mixture (1.5 g) from step B was dissolved in N,N-dimethylformamide dimethyl acetal (3.8 mL, 29 mmol) and stirred at rt overnight. The volatiles were removed and the residue was dissolved in MeOH and evaporated on silica gel (4 g) and purified by column chromatography (12 g, SiO₂, using 0-15% MeOH (containing 5% NH₄OH) in DCM as eluent) to give the title compound as a white solid (550 mg, 46%). ¹H NMR (500 MHz, CDCl₃) δ ppm 9.78 (s, 1H), 9.01 (br s, 1H), 8.45 (d, J=1.2 Hz, 1H), 8.44-8.39 (m, 1H), 7.93-7.90 (m, 1H), 7.86 (d, J=7.9 Hz, 1H), 7.83 (s, 1H), 4.15 (s, 3H), 3.81 (s, 3H), 2.99 (s, 6H). MS (ESI): 346.2 [M+H]⁺.

Step D: 3-Methoxy-1-methyl-N-(6-(4-(oxetan-3-yl)-4H-1,2,4-triazol-3-yl)pyridin-2-yl)-1H-pyrazole-4-carboxamide

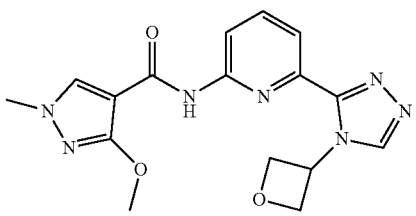 [SMILES: COc1nn(C)cc1C(=O)Nc1cccc(-c2nncn2C2COC2)n1]

A reaction vial was charged with a mixture of N-(6-(2-((dimethylamino)methylene)hydrazine-1-carbonyl)pyridin-2-yl)-3-methoxy-1-methyl-1H-pyrazole-4-carboxamide (138 mg, 0.4 mmol), oxetan-3-amine (44 mg, 0.6 mmol), MeCN (3 mL) and acetic acid (1 mL). The resulting mixture was heated at reflux for 12 h. After this time the volatiles were removed under reduced pressure and the resulting residue was subjected to mass-directed HPLC (using 5-65% MeCN in H₂O (containing 4% NH₄OH) as eluent) to give the title compound (12 mg, 8%). ¹H NMR (500 MHz, CDCl₃) δ ppm 8.51-8.44 (m, 1H), 8.48 (s, 1H), 8.02 (d, J=9.2 Hz, 1H), 7.77-7.64 (m, 1H), 7.41 (t, J=8.0 Hz, 1H), 7.25 (dd, J=1.2, 6.7 Hz, 1H), 5.24-5.13 (m, 1H), 4.74-4.66 (m, 1H), 4.52 (br d, J=14.7 Hz, 1H), 4.02 (br dd, J=4.9, 12.2 Hz, 1H), 3.95 (s, 3H), 3.91 (br dd, J=6.7, 11.6 Hz, 1H), 3.75 (s, 3H). MS (ESI): 356.2 [M+H]⁺.

Example 108: 3-Methoxy-1-methyl-N-(6-(4-(tetrahydro-2H-pyran-4-yl)-4H-1,2,4-triazol-3-yl)pyridin-2-yl)-1H-pyrazole-4-carboxamide

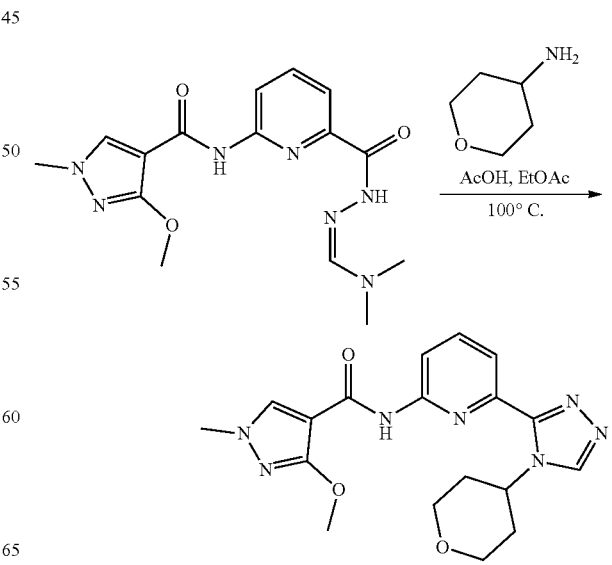

A reaction vial was charged with a mixture of N-(6-(2-((dimethylamino)methylene)hydrazine-1-carbonyl)pyridin-2-yl)-3-methoxy-1-methyl-1H-pyrazole-4-carboxamide (50 mg, 0.15 mmol), tetrahydro-2H-pyran-4-amine (30 mg, 0.29 mmol), MeCN (2 mL) and acetic acid (0.7 mL). The resulting mixture was heated at reflux for 1 h. The crude title compound was isolated by filtration from the reaction mixture and was further purified by mass directed HPLC (5-65% MeCN in H$_2$O (4% NH$_4$OH)) to give the title compound (7 mg, 13%). $^1$H NMR (500 MHz, CDCl$_3$) δ ppm 8.95 (br s, 1H), 8.46-8.30 (m, 2H), 8.05 (br d, J=7.3 Hz, 1H), 7.92-7.76 (m, 2H), 5.50 (br t, J=11.6 Hz, 1H), 4.27-4.16 (m, 2H), 4.11 (s, 3H), 3.82 (s, 3H), 3.61 (br t, J=11.9 Hz, 2H), 2.23 (br d, J=11.0 Hz, 2H), 2.16-1.95 (m, 2H). MS (ESI): 384.2 [M+H]$^+$.

Example 109 and Example 110: (R)-3-Methoxy-1-methyl-N-(6-(4-(tetrahydrofuran-3-yl)-4H-1,2,4-triazol-3-yl)pyridin-2-yl)-1H-pyrazole-4-carboxamide and (S)-3-Methoxy-1-methyl-N-(6-(4-(tetrahydrofuran-3-yl)-4H-1,2,4-triazol-3-yl)pyridin-2-yl)-1H-pyrazole-4-carboxamide

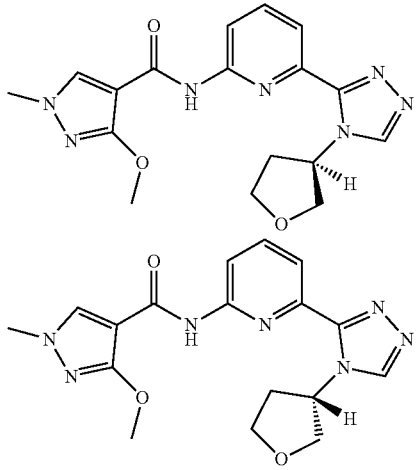

Step A: rac-3-Methoxy-1-methyl-N-(6-(4-(tetrahydrofuran-3-yl)-4H-1,2,4-triazol-3-yl)pyridin-2-yl)-1H-pyrazole-4-carboxamide

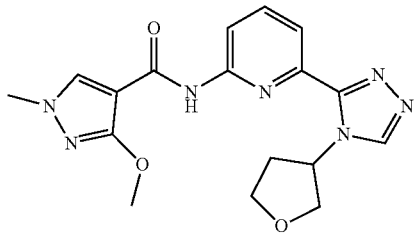 [SMILES: COc1nn(C)cc1C(=O)Nc1cccc(-c2nncn2C2CCOC2)n1]

A reaction vial was charged with a mixture of N-(6-(2-((dimethylamino)methylene)hydrazine-1-carbonyl)pyridin-2-yl)-3-methoxy-1-methyl-1H-pyrazole-4-carboxamide (50 mg, 0.15 mmol), tetrahydrofuran-3-amine (25 mg, 0.29 mmol), MeCN (2 mL) and acetic acid (0.7 mL). The resulting mixture was heated at reflux for 1 h. The crude compound was isolated by filtration from the reaction mixture and was further purified by mass directed HPLC (using 5-65% MeCN in H$_2$O (containing 4% NH$_4$OH) as eluent) to give the title compound (24 mg, 24%). $^1$H NMR (500 MHz, CDCl$_3$) δ ppm 8.74 (s, 1H), 8.35-8.30 (m, 1H), 8.00 (s, 1H), 8.00-7.95 (m, 1H), 7.87-7.84 (m, 1H), 5.81 (tdd, J=2.6, 5.3, 7.8 Hz, 1H), 4.27-4.19 (m, 1H), 4.17-4.11 (m, 2H), 4.10 (s, 3H), 4.00 (dt, J=5.8, 9.0 Hz, 1H), 3.81 (s, 3H), 2.68 (dddd, J=6.7, 7.8, 9.2, 14.2 Hz, 1H), 2.42-2.34 (m, 1H). MS (ESI): 370.2 [M+H]$^+$.

Step B: (R)-3-Methoxy-1-methyl-N-(6-(4-(tetrahydrofuran-3-yl)-4H-1,2,4-triazol-3-yl)pyridin-2-yl)-1H-pyrazole-4-carboxamide and (S)-3-Methoxy-1-methyl-N-(6-(4-(tetrahydrofuran-3-yl)-4H-1,2,4-triazol-3-yl)pyridin-2-yl)-1H-pyrazole-4-carboxamide

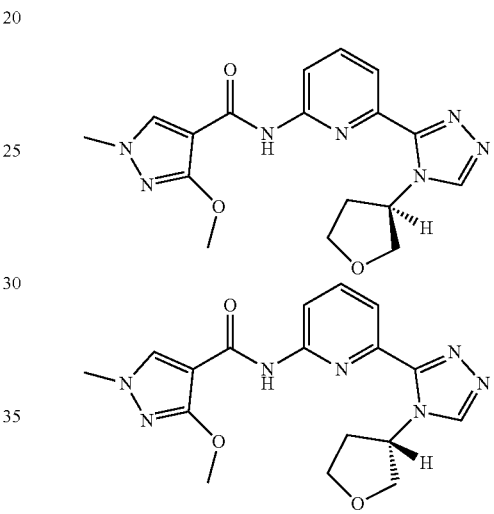

rac-3-Methoxy-1-methyl-N-(6-(4-(tetrahydrofuran-3-yl)-4H-1,2,4-triazol-3-yl)pyridin-2-yl)-1H-pyrazole-4-carboxamide (24 mg, 0.06 mmol) was purified by SFC (using a Chiralpak AD-H 5 μm, 30×250 mm column and using 30% MeOH in 0.1% Et$_2$NH in CO$_2$ as the mobile phase at a flow rate of 100 mL/min) to give in order of elution: (R)-3-methoxy-1-methyl-N-(6-(4-(tetrahydrofuran-3-yl)-4H-1,2,4-triazol-3-yl)pyridin-2-yl)-1H-pyrazole-4-carboxamide (12 mg, stereochemistry arbitrarily assigned) and (S)-3-methoxy-1-methyl-N-(6-(4-(tetrahydrofuran-3-yl)-4H-1,2,4-triazol-3-yl)pyridin-2-yl)-1H-pyrazole-4-carboxamide (10 mg, stereochemistry arbitrarily assigned). $^1$H NMR (500 MHz, CDCl$_3$) δ ppm 8.74 (s, 1H), 8.35-8.30 (m, 1H), 8.00 (s, 1H), 8.00-7.95 (m, 1H), 7.87-7.84 (m, 1H), 5.81 (tdd, J=2.6, 5.3, 7.8 Hz, 1H), 4.27-4.19 (m, 1H), 4.17-4.11 (m, 2H), 4.10 (s, 3H), 4.00 (dt, J=5.8, 9.0 Hz, 1H), 3.81 (s, 3H), 2.68 (dddd, J=6.7, 7.8, 9.2, 14.2 Hz, 1H), 2.42-2.34 (m, 1H). MS (ESI): 370.2 [M+H]$^+$.

Example 111: Brief Description of ASK1 TR-FRET Assay

The protein kinase inhibitory activity of the compounds described herein were tested using the ASK1/MAP3K5 assay by Reaction Biology Corp. (Malvern, PA). The assay procedure follows (and is also available on the Reaction Biology Corp. website).

Base Reaction Buffer: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO;

Substrate: 20 µM of myelin basic protein (MBP) and 10 µM ATP;

Protein kinase: ASK1/MAP3K5.

Reaction Procedure:
1. Prepare indicated substrate in freshly prepared Base Reaction Buffer.
2. Deliver any required cofactors to the substrate solution.
3. Deliver indicated kinase into the substrate solution and gently mix.
4. Deliver compounds in DMSO into the kinase reaction mixture by Acoustic; technology (Echo550; nanoliter range), incubate for 20 minutes at room temperature.
5. Deliver $^{33}$P-ATP (specific activity 10 µCi/µL) into the reaction mixture to initiate the reaction.
6. Incubate kinase reaction for 2 hours at room temperature.
7. Reactions are spotted onto P81 ion exchange paper.
8. Detect kinase activity by filter-binding method.

The results are provided below, wherein the compound number corresponds to the numbers set forth in the examples above, "+" represents an IC$_{50}$ of less than 10 µM, but greater than 1 µM, "++" represents an IC$_{50}$ of less than or equal to 1 µM but greater than 0.1 µM, and "+++" represents an IC$_{50}$ of less than or equal to 0.1 µM.

TABLE 1

| IC$_{50}$ | Compounds |
| --- | --- |
| +++ | 1, 3, 7, 8, 12, 13, 15, 16, 17, 18, 19, 20, 21, 23, 24, 25, 26, 27, 28, 29, 30, 31, 33, 35, 36, 37, 41, 42, 43, 44, 45, 46, 47, 48, 50, 51, 52, 54, 55, 56, 57, 59, 61, 62, 63, 64, 65, 67, 68, 69, 70, 71, 72, 73, 74, 75, 76, 77, 78, 79, 80, 81, 82, 83, 84, 85, 87, 89, 90, 92, 93, 94, 95, 97, 99, 100, 102, 103, 104, 105, 106, 109, 110 |
| ++ | 2, 4, 5, 6, 9, 11, 14, 32, 34, 38, 40, 53, 86, 88, 96, 98, 108 |
| + | 22, 39, 101 |
| Greater than or equal to 10 µM | 49, 107 |

Example 112: Brief Description of ASK1(AUTO PHOS T838) Assay

ASK1 T838 auto phosphorylation was measured in HEK-293T cells using MSD assay format. HEK 293T cells were seeded in 15 cm plates at a density of 18 million cells and 20 mL DMEM with 10% FBS, Pen/Strep media. The plates were incubated at 37° C. overnight. Media on plates was changed to OPTI-MEM, serum free media and cells were transfected with 9 µg of ASK1-V5 tagged full length plasmid using Lipofectamine 2000 (Invitrogen) and the plates were incubated at 37° C. overnight. Cells were trypsinized, counted on Nexcellometer and plated into 96 well tissue culture plates with 100,000 cells/well and 200 µL media. Cells were incubated for 4 hr at 37° C. then ASK1 compounds were added using a HP 300e. Compounds were tested at 20 µM with 3 fold, 10 point dilution points then incubated for 1 hr at 37° C. A lysis buffer (Cell Signaling) was prepared with protease and phosphatase inhibitor and maintained at 4° C. until use. Media from cells was discarded and 120 µL of cold lysis buffer was added to the cells, the plate was shaken 4° C. for 1 hr. Lysate was mixed using Apricot liquid handler; aspirating up and down 16 times at high speed using 50 µL volume. 50 µL of cell lysates were transferred to a pre-coated MSD plates containing mouse anti-V5 antibody (1:500 dilution) and washed 3× with MSD wash buffer (TBST) and blocked with a 3% BSA solution. Plates were then incubated on a plate shaker overnight at 4° C. Plates were washed 3× with MSD wash buffer and 50 µL of rabbit anti-pASK1 T838 antibody was added to the wells and incubated for 2 hr at room temperature on a plate shaker. Plates were then washed and 50 µL of goat anti-rabbit sulfa-tag (1:500 dilution) was added to wells, and incubated for 1 hr at room temperature on a plate shaker. Plates were washed 3× and 150 µL of 2×MSD Read buffer was added to wells. Plates were immediately read on a MSD Instrument Reader where chemoluminescence signal was measured. Data was analyzed using Graph Pad or Genedata, the data was normalized and plotted, % activity versus log of compound concentration. The IC$_{50}$ values were obtained from a 4 parameter fit.

The compounds described herein were tested for in the above cell-based assay. The results are provided below, wherein the compound number corresponds to the numbers set forth in the examples above, "†" represents an IC$_{50}$ of greater than 10 µM, "††" represents an IC$_{50}$ of equal to or less than 10 µM but greater than 1 µM, and "†††" represents an IC$_{50}$ of equal to or less than 1 µM.

TABLE 2

| IC$_{50}$ | Compounds |
| --- | --- |
| ††† | 1, 3, 6, 7, 8, 9, 10, 11, 12, 13, 14, 15, 16, 17, 18, 19, 20, 21, 23, 24, 25, 26, 27, 28, 29, 30, 31, 32, 33, 34, 36, 38, 41, 42, 43, 44, 45, 46, 47, 48, 50, 51, 52, 53, 54, 55, 56, 57, 58, 59, 60, 61, 62, 63, 64, 65, 67, 68, 69, 71, 72, 73, 74, 75, 76, 77, 78, 79, 80, 81, 82, 83, 84, 85, 87, 89, 90, 91, 92, 93, 94, 95, 96, 97, 98, 99, 100, 102, 103, 104, 105, 106, 109, 110 |
| †† | 2, 4, 5, 22, 35, 37, 39, 40, 66, 70, 86, 88, 108, |
| † | 49, 101, 107, |

Example 113: In Vivo Brain Penetration

To evaluate the CNS penetration of the compounds described herein, several compounds were selected for in vivo rat K$_{puu}$ studies. In these experiments the compounds are administered via an IV infusion (using N,N-dimethyl-acetamide:ethanol:1,2-propylene glycol:water in a 1:1:3:5 ratio as the vehicle) in the carotid artery for a period of four hours (1 mg/kg, 0.1 mg/mL) to reach steady state. After this time the plasma and brain concentration levels are quantified, and the values are adjusted by the measured protein binding in plasma and brain homogenate to calculate the K$_{puu}$ (see Di, L.; Kerns, E. H. *Blood-Brain Barrier in Drug Discovery* (Wiley)) according to the equation below.

$$K_{puu} = C_{u,b}/C_{u,p}$$

Wherein:
C$_{u,b}$=Unbound concentration in brain (C×f$_{u,b}$). (C=concentration at steady state; f$_{u,b}$=fraction unbound in brain)

And in which: C$_{u,p}$=Unbound concentration in plasma (C×f$_{u,p}$). (C=concentration at steady state; f$_{u,p}$=fraction unbound in plasma)

Plasma and brain protein binding values were generated via the Rapid Equilibrium Dialysis method. The compound of interest was incubated in K$_2$EDTA plasma and brain homogenate (homogenized 1:7 (w:v) in 1×PBS) purchased from BioIVT (Westbury, NY), opposite a buffered compartment of 100 mM Potassium phosphate/150 mM Sodium chloride, pH 7.4, at 1 µM for 4 hr and 6 hr respectively. At the conclusion of incubation samples were taken from both matrix and buffered compartments, matrix-matched using blank buffer and matrix, extracted with acetonitrile, diluted with water, and analyzed utilizing an Agilent RapidFire 365 high-throughput LC coupled with MS/MS detection via an AB Sciex 5500. Free fractions ($f_u$) were then calculated by comparing internal standard/analyte peak-area ratios of matrix and buffered compartments. Cross-species brain protein binding was considered to be equivalent for the purposes of calculating free fraction (see Di, L., et al., (2011a) *Species Independence in Brain Tissue Binding Using Brain Homogenates*, Drug Metab Dispos 39:1270-1277).

Total drug concentration in plasma and brain tissue was measured via well-established bioanalytical extraction (protein precipitation) and detection methods (LC-MS/MS). Brain tissues were homogenized 1:4 (w:v) with 1×PBS in MP Biomedicals Lysing Matrix D tubes via an MP Biomedicals FastPrep-24™ homogenizer and were then extracted alongside plasma samples by matrix-matching with blank $K_2$EDTA plasma (purchased from BioIVT), followed by protein crash/extraction with acetonitrile, supernatant dry down under nitrogen, and reconstitution with an acidified aqueous/organic mixture before being measured against a calibration curve of the compound of interest prepared in plasma, matrix-matched with blank brain homogenate (generated with brains purchased from BioIVT), and similarly extracted. Reconstituted extracts were then analyzed via LC-MS/MS (AB Sciex 5500) utilizing a binary HPLC setup (Shimadzu LC-20ADvp) and reverse-phase chromatography gradient (ACE 3 C18-AR). Peak area ratios and a $1/x^2$ regression fit were used to generate sample concentration values that, combined with plasma and brain protein binding values, were used to generate free drug concentration values and partitioning coefficient ($K_{puu}$).

This experiment is conducted with various compounds described in the foregoing examples, and the $K_{puu}$ values are provided below.

TABLE 3

| Example | Rat $K_{puu}$ |
|---|---|
| 12 | 0.26 |
| 23 | 0.14 |
| 41 | 0.047 |
| 56 | 0.33 |
| 62 | 0.16 |
| 64 | 0.38 |
| 87 | 0.32 |
| 90 | 0.61 |

Aspects of the present invention are additionally set forth in the enumerated embodiments below.

1. A compound of Formula (I):

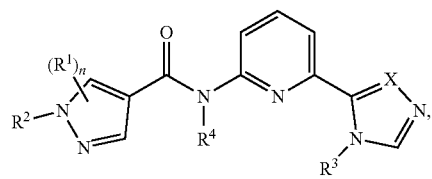

(I)

or a pharmaceutically acceptable salt thereof, wherein:
X is CH or N;
n is 1 or 2;

$R^1$ in each occurrence is independently selected from H, $C_{1-6}$alkyl, $C_{2-6}$alkenyl, $C_{2-6}$alkynyl, carbocyclyl, heterocyclyl, halo, —CN, —C(O)$R^{1a}$, —C(O)O$R^{1a}$, —C(O)N($R^{1a}$)$_2$, —N($R^{1a}$)$_2$, —N($R^{1a}$)C(O)$R^{1a}$, —N($R^{1a}$)C(O)O$R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, carbocyclyl, and heterocyclyl, are optionally substituted with one or more $R^{10}$.

$R^{1a}$ in each occurrence is independently selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$^2$;

$R^{10a}$ in each occurrence is independently selected from H, $C_{1-6}$alkyl, $C_{2-6}$alkenyl, $C_{2-6}$alkynyl, carbocyclyl, and heterocyclyl;

$R^2$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally and independently substituted with one or more $R^{20}$;

$R^{20}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{20a}$, —C(O)O$R^{20a}$, —C(O)N($R^{20a}$)$_2$, —N($R^{20a}$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{20a}$, —C(O)O$R^{20a}$, —C(O)N($R^{20a}$)$_2$, —N($R^2$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2R^2$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$;

$R^{20a}$ in each occurrence is independently selected from H, $C_{1-6}$alkyl, $C_{2-6}$alkenyl, $C_{2-6}$alkynyl, carbocyclyl, and heterocyclyl;

$R^3$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally substituted with one or more $R^{30}$.

$R^{30}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, carbocyclyl, and heterocyclyl, wherein said carbocyclyl, and heterocyclyl are each optionally substituted with $C_{1-4}$alkyl or halo; and $R^4$ is H or $C_{1-6}$alkyl.

2. The compound of embodiment 1, wherein the compound is represented by Formula (II):

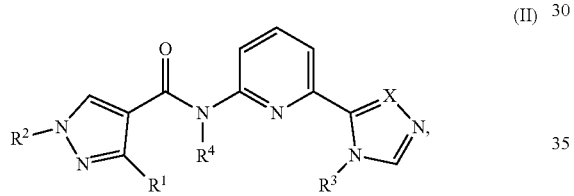

(II)

or a pharmaceutically acceptable salt thereof.

3. The compound of embodiment 1 or 2, wherein the compound is represented by Formula (III):

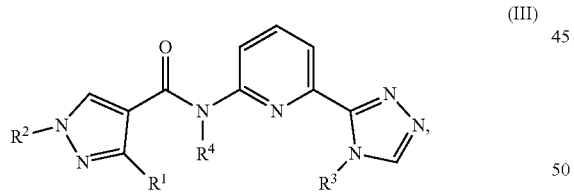

(III)

or a pharmaceutically acceptable salt thereof.

4. The compound of embodiment 1 or 2, wherein the compound is represented by Formula (IV):

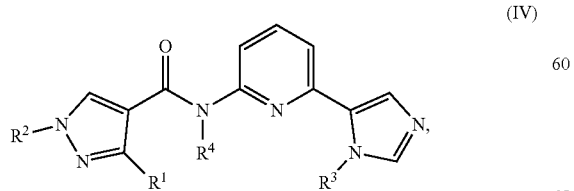

(IV)

or a pharmaceutically acceptable salt thereof.

5. The compound of any one of embodiments 1-4, wherein:
   $R^1$ is H, $C_{1-6}$alkyl or —O$R^{1a}$, wherein said $C_{1-6}$alkyl is optionally substituted with one to three $R^{10}$;
   $R^{1a}$ in each occurrence is independently H or $C_{1-6}$alkyl;
   $R^{10}$ in each occurrence is independently halo or —O$R^{1a}$.

6. The compound of embodiment 5, wherein $R^1$ is H, —OCH$_3$, —OCH$_2$CH$_3$, —CH$_2$OCH$_3$, —CF$_3$, or —CHF$_2$.

7. The compound of any one of embodiments 1-6, wherein:
   $R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$;
   $R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —C(O)$R^{20a}$, —C(O)O$R^{20a}$, —C(O)N($R^{20a}$)$_2$, —N($R^{20a}$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2$$R^{20a}$, —O$R^{20a}$, —OC(O)$R^{20a}$, —OC(O)N($R^{20a}$)$_2$, —S$R^{20a}$, —S(O)$R^{20a}$, —S(O)$_2$$R^{20a}$, —S(O)N($R^{20a}$)$_2$, and —S(O)$_2$N($R^{20a}$)$_2$, wherein said $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl in each occurrence are optionally and independently substituted with one or more substituents independently selected from halo, —CN, —C(O)$R^{20a}$, —C(O)O$R^{20a}$, —C(O)N($R^{20a}$)$_2$, —N($R^{20a}$)$_2$, —N($R^{20a}$)C(O)$R^{20a}$, —N($R^{20a}$)C(O)O$R^{20a}$, —N($R^{20a}$)C(O)N($R^{20a}$)$_2$, —N($R^{20a}$)S(O)$_2$$R^{20a}$, —O$R^{20a}$, —OC(O)$R^{20a}$, —OC(O)N($R^{20a}$)$_2$, —S$R^{20a}$, —S(O)$R^{20a}$, —S(O)$_2$$R^{20a}$, —S(O)N($R^{20a}$)$_2$, and —S(O)$_2$N($R^{20a}$)$_2$;
   $R^{20a}$ in each occurrence is independently H or $C_{1-4}$alkyl.

8. The compound of embodiment 7, wherein:
   $R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$;
   $R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —N($R^{20a}$)$_2$, and —O$R^{20a}$;
   $R^{20a}$ in each occurrence is independently H or $C_{1-4}$alkyl.

9. The compound of embodiment 7 or 8, wherein the 5- or 6-membered heteroaryl is selected from pyridinyl, pyrimidinyl, pyrazinyl, and pyridazinyl.

10. The compound of embodiment 8 or 9, wherein the 4- to 7-membered monocyclic saturated heterocyclyl is selected from azetidinyl, piperidinyl, oxetanyl, piperazinyl and morpholinyl.

11. The compound of embodiment 7, wherein $R^2$ is —CH$_3$, —CH$_2$CH$_3$, —CH$_2$CF$_3$, —C(CH$_3$)$_3$, —CH$_2$CH$_2$OCH$_3$, —CH$_2$CH(CH$_3$)$_2$, —CH$_2$CH$_2$N(CH$_3$)$_2$, —CH$_2$CH=CH$_2$, —CH$_2$CH$_2$CH$_3$,

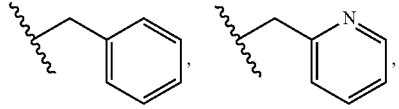

-continued

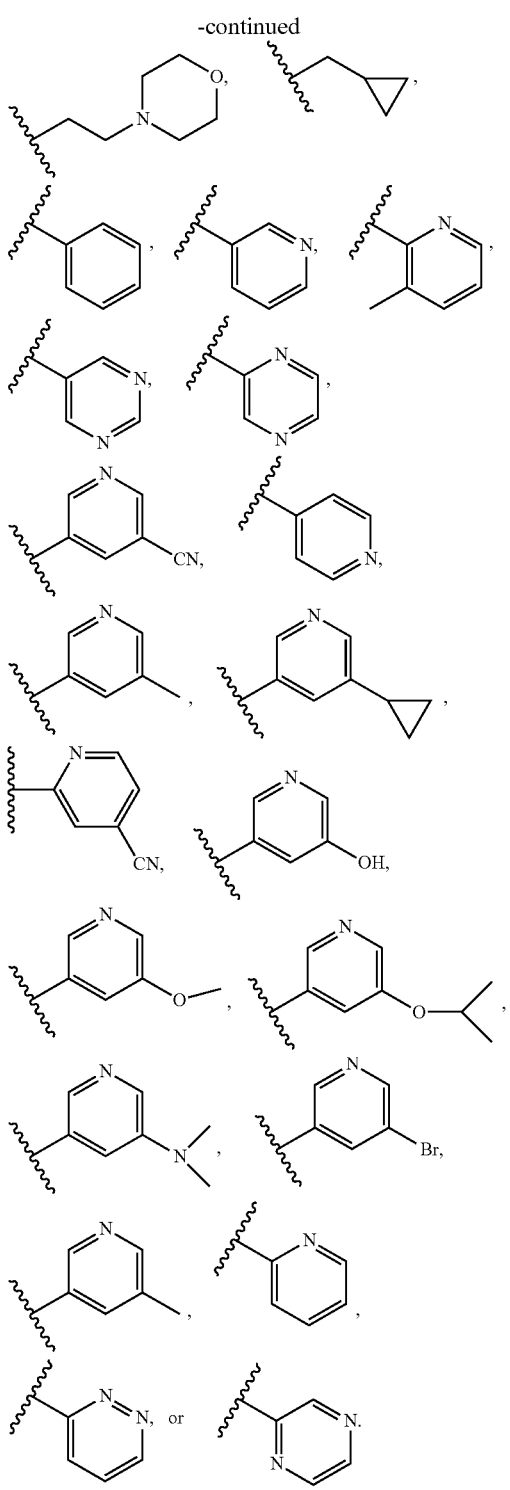

12. The compound of any one of embodiments 1-11, wherein:
   $R^3$ is selected from H, $C_{1-6}$alkyl, $C_{3-6}$cycloalkyl, and 4 to 7-membered monocyclic saturated heterocyclyl, wherein said $C_{1-6}$alkyl, $C_{3-6}$cycloalkyl, and 4 to 7-membered monocyclic saturated heterocyclyl are optionally substituted with one to three $R^{30}$;
   $R^{30}$ in each occurrence is independently selected from $C_{1-6}$alkyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$, wherein said $C_{1-6}$alkyl in each occurrence are optionally and independently substituted with one to three substituents independently selected from $C_{1-4}$alkyl and halo;
   $R^{30a}$ in each occurrence is independently selected from H and $C_{1-6}$alkyl, wherein $C_{1-6}$alkyl is optionally substituted with one to three substituents independently selected from $C_{1-4}$alkyl and halo.

13. The compound of embodiment 12, wherein:
   $R^3$ is $C_{1-6}$alkyl, $C_{3-6}$cycloalkyl, or 4 to 7-membered monocyclic saturated heterocyclyl, wherein said $C_{1-6}$alkyl, $C_{3-6}$cycloalkyl, and 4 to 7-membered monocyclic saturated heterocyclyl are each optionally substituted with one to three $R^{30}$;
   $R^{30}$ in each occurrence is independently $C_{1-3}$alkyl, halo, —C(O)O$R^{30a}$, or —O$R^{30a}$, wherein said $C_{1-3}$alkyl is optionally substituted with one to three halo; and
   $R^{30a}$ in each occurrence is independently H or $C_{1-4}$alkyl.

14. The compound of embodiment 13, wherein:
   $R^3$ is —CH(CH$_3$)$_2$, —CH(CH$_3$)CF$_3$, —C(CH$_3$)$_3$, —CH(CH$_3$)CHF$_2$, —CH(CH$_3$)CH(CH$_3$)$_2$, —CH(CH$_3$)CH$_2$OCH$_3$, —CH(CH$_3$)CH$_2$OH,

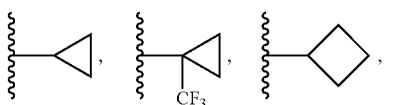

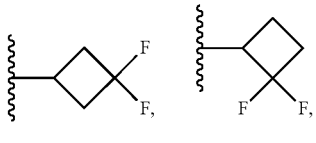

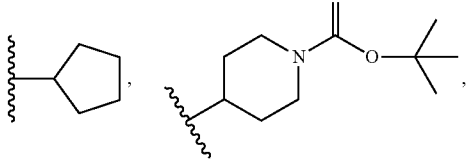

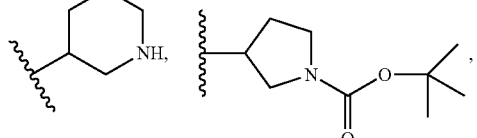

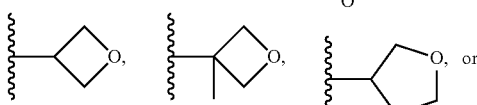

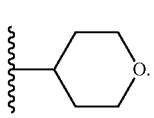

15. The compound of any one of embodiments 1-14, wherein $R^4$ is H or —CH$_3$.

16. The compound of embodiment 15, wherein $R^4$ is H.

17. The compound of embodiment 1, wherein the compound is represented by Formula (V) or (VI):

(V)

[Structure V: pyrazole-carboxamide-pyridine-triazole with R², R¹, R³ substituents]

(VI)

[Structure VI: pyrazole-carboxamide-pyridine-imidazole with R², R¹, R³ substituents]

or a pharmaceutically acceptable salt thereof, wherein:
R¹ is $C_{1-4}$alkyl or —OR$^{1a}$, wherein said $C_{1-4}$alkyl is optionally substituted with one to three halo;
R$^{1a}$ in each occurrence is independently H or $C_{1-4}$alkyl;
R² is $C_{1-4}$alkyl, $C_{2-4}$alkenyl or 5- or 6-membered heteroaryl, wherein said $C_{1-4}$alkyl, $C_{2-4}$alkenyl and 5- or 6-membered heteroaryl are optionally and independently substituted with one to three R²⁰;
R²⁰ in each occurrence is independently selected from $C_{3-6}$cycloalkyl, halo and —OR$^{20a}$;
R$^{20a}$ in each occurrence is independently H or $C_{1-4}$alkyl;
R³ is $C_{1-4}$alkyl or $C_{3-6}$cycloalkyl, wherein said $C_{1-4}$alkyl and $C_{3-6}$cycloalkyl are each optionally substituted with one to three R³⁰; and
R³⁰ in each occurrence is independently $C_{1-3}$alkyl or halo, wherein said $C_{1-3}$alkyl is optionally substituted with one to three halo.

18. The compound of embodiment 17, wherein:
R¹ is —OCH₃, —OCH₂CH₃, or —CHF₂;
R² is —CH₃, —CH₂CH₃, —CH₂CH₂OCH₃, —CH₂CF₃, —CH₂CH=CH₂,

[Structures: cyclopropylmethyl, pyridyl, pyrazinyl groups]

[Structures: pyridyl with isopropoxy, pyridazinyl groups]

R is —CH(CH₃)₂, —CH(CH₃)CF₃, —CH(CH₃)CHF₂,

[Structures: 1-(trifluoromethyl)cyclopropyl, cyclobutylmethyl, 3,3-difluorocyclobutylmethyl]

[Structure: cyclopentylmethyl]

19. A pharmaceutical composition comprising a compound of any one of embodiments 1-18 or a pharmaceutically acceptable salt thereof, and a pharmaceutically acceptable excipient.

20. A method treating a disorder responsive to inhibition of apoptosis signal-regulating kinase 1 (ASK1) in a subject comprising administering to the subject an effective amount of a compound of any one of embodiments 1-18 or a pharmaceutically acceptable salt thereof.

21. A method of treating neurodegenerative disorder, cardiovascular disease, metabolic disorder, inflammatory disease, autoimmune disorder, destructive bone disorder, polyglutamine disease, glutamate neurotoxicity, pain, traumatic brain injury, hemorrhagic stroke, ischemia, acute hypoxia, kidney fibrosis (renal fibrosis), kidney injury, diabetic kidney disease, diabetic nephropathy, non-alcoholic steatohepatitis (NASH), pulmonary arterial hypertension (PAH), optic neuritis, liver disease, respiratory disease, heart reperfusion injury, cardiac hypertrophy, cardiac fibrosis, energy metabolic disorder, cancer or an infection in a subject, comprising administering to the subject an effective amount of a compound of any one of embodiments 1-18 or a pharmaceutically acceptable salt thereof.

22. A method for treating a neurodegenerative disorder in a subject comprising administering to the subject an effective amount of a compound of any one of embodiments 1-18 or a pharmaceutically acceptable salt thereof.

23. The method of embodiment 22, wherein the neurodegenerative disorder is Alzheimer's disease (AD), Parkinson's disease, Huntington's disease, or amyotrophic lateral sclerosis (ALS).

24. A method for treating an autoimmune disease in a subject comprising administering to the subject an effective amount of a compound of any one of embodiments 1-18 or a pharmaceutically acceptable salt thereof.

25. The method of embodiment 24, wherein the autoimmune disease is multiple sclerosis.

26. A method for treating a cardiovascular disease in a subject comprising administering to the subject an effective amount of a compound of any one of embodiments 1-18 or a pharmaceutically acceptable salt thereof.

27. The method of embodiment 26, wherein the cardiovascular disease is ischemia.

What is claimed is:
1. A compound of Formula (I):

(I)

[Structure I: pyrazole with $(R^1)_n$ and R² substituents, carboxamide linker with R⁴, pyridine, and imidazole/triazole ring with X and R³]

or a pharmaceutically acceptable salt thereof, wherein:
X is CH or N;
n is 1 or 2;
R¹ in each occurrence is independently selected from H, $C_{1-6}$alkyl, $C_{2-6}$alkenyl, $C_{2-6}$alkynyl, carbocyclyl, heterocyclyl, halo, —CN, —C(O)R$^{1a}$, —C(O)OR$^{1a}$, —C(O)N(R$^{1a}$)₂, —N(R$^{1a}$)₂, —N(R$^{1a}$)C(O)R$^{1a}$, —N(R$^{1a}$)C(O)OR$^{1a}$, —N(R$^{1a}$)C(O)N(R$^{1a}$)₂, —N(R$^{1a}$)S(O)₂R$^{1a}$, —OR$^{1a}$, —OC(O)R$^{1a}$, —OC(O)N(R$^{1a}$)₂, —SR$^{1a}$, —S(O)R$^{1a}$, —S(O)₂R$^{1a}$, —S(O)N(R$^{1a}$)₂, and —S(O)₂N(R$^{1a}$)₂, wherein said $C_{1-6}$alkyl, $C_{2-6}$alkenyl, $C_{2-6}$alkynyl, carbocyclyl, and heterocyclyl are optionally substituted with one or more R¹⁰;

$R^{1a}$ in each occurrence is independently selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{10a}$, —C(O)OR$^{10a}$, —C(O)N(R$^{10a}$)$_2$, —N(R$^{10a}$)$_2$, —N(R$^{10a}$)C(O)R$^{10a}$, —N(R$^{10a}$)C(O)OR$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)R$^{10a}$, —C(O)OR$^{10a}$, —C(O)N(R$^{10a}$)$_2$, —N(R$^{10a}$)$_2$, —N(R$^{10a}$)C(O)R$^{10a}$, —N(R$^{10a}$)C(O)OR$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$;

$R^{10a}$ in each occurrence is independently selected from H, $C_{1-6}$alkyl, $C_{2-6}$alkenyl, $C_{2-6}$alkynyl, carbocyclyl, and heterocyclyl;

$R^2$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally and independently substituted with one or more $R^{20}$;

$R^{20}$ in each occurrence is independently selected from $C_{1-6}$alkyl, $C_{2-6}$alkenyl, $C_{2-6}$alkynyl, carbocyclyl, heterocyclyl, halo, —CN, —C(O)R$^{20a}$, —C(O)OR$^{20a}$, —C(O)N(R$^{20a}$)$_2$, —N(R$^{20a}$)$_2$, —N(R$^{20a}$)C(O)R$^{20a}$, —N(R$^{20a}$)C(O)OR$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$, —S(O)$_2$R$^{20a}$, —S(O)N(R$^{20a}$)$_2$, and —S(O)$_2$N(R$^{20a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)R$^{20a}$, —C(O)OR$^{20a}$, —C(O)N(R$^{20a}$)$_2$, —N(R$^2$)$_2$, —N(R$^{20a}$)C(O)R$^{20a}$, —N(R$^{20a}$)C(O)OR$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$, —S(O)$_2$R$^{20a}$, —S(O)N(R$^{20a}$)$_2$, and —S(O)$_2$N(R$^{20a}$)$_2$;

$R^{20a}$ in each occurrence is independently selected from H, $C_{1-6}$alkyl, $C_{2-6}$alkenyl, $C_{2-6}$alkynyl, carbocyclyl, and heterocyclyl;

$R^3$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally substituted with one or more $R^{30}$;

$R^{30}$ in each occurrence is independently selected from $C_{1-6}$alkyl, $C_{2-6}$alkenyl, $C_{2-6}$alkynyl, carbocyclyl, heterocyclyl, halo, —CN, —C(O)R$^{30a}$, —C(O)OR$^{30a}$, —C(O)N(R$^{30a}$)$_2$, —N(R$^{30a}$)$_2$, —N(R$^{30a}$)C(O)R$^{30a}$, —N(R$^{30a}$)C(O)OR$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)R$^{30a}$, —C(O)OR$^{30a}$, —C(O)N(R$^{30a}$)$_2$, —N(R$^{30a}$)$_2$, —N(R$^{30a}$)C(O)R$^{30a}$, —N(R$^{30a}$)C(O)OR$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$;

$R^{30a}$ in each occurrence is independently selected from H, $C_{1-6}$alkyl, $C_{2-6}$alkenyl, $C_{2-6}$alkynyl, carbocyclyl, and heterocyclyl, wherein said carbocyclyl, and heterocyclyl are each optionally substituted with $C_{1-4}$alkyl or halo; and $R^4$ is H or $C_{1-6}$alkyl.

2. The compound of claim 1, wherein the compound is represented by Formula (III):

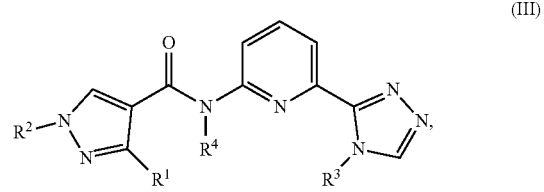

(III)

or a pharmaceutically acceptable salt thereof.

3. The compound of claim 1, wherein the compound is represented by Formula (IV):

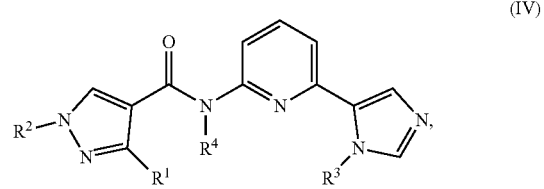

(IV)

or a pharmaceutically acceptable salt thereof.

4. The compound of claim 1, wherein:
$R^1$ is H, $C_{1-6}$alkyl or —OR$^{1a}$, wherein said $C_{1-6}$alkyl is optionally substituted with one to three $R^{10}$;
$R^{1a}$ in each occurrence is independently H or $C_{1-6}$alkyl;
$R^{10}$ in each occurrence is independently halo or —OR$^{1a}$.

5. The compound of claim 4, wherein $R^1$ is H, —OCH$_3$, —OCH$_2$CH$_3$, —CH$_2$OCH$_3$, —CF$_3$, or —CHF$_2$.

6. The compound of claim 1, wherein:
$R^2$ is selected from H, $C_{1-6}$alkyl, $C_{2-6}$alkenyl, $C_{3-6}$cycloalkyl, phenyl, and 5- or 6-membered heteroaryl, wherein said $C_{1-6}$alkyl, $C_{2-6}$alkenyl, $C_{3-6}$cycloalkyl, phenyl, and 5- or 6-membered heteroaryl are optionally and independently substituted with one to three $R^{20}$;
$R^{20}$ in each occurrence is independently selected from $C_{1-4}$alkyl, $C_{2-4}$alkenyl, $C_{3-6}$cycloalkyl, phenyl, 4- to 7-membered monocyclic saturated heterocyclyl, 5- or 6-membered heteroaryl, halo, —CN, —C(O)R$^{20a}$, —C(O)OR$^{20a}$, —C(O)N(R$^{20a}$)$_2$, —N(R$^{20a}$)$_2$, —N(R$^{20a}$)C(O)R$^{20a}$, —N(R$^{20a}$)C(O)OR$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$, —S(O)$_2$R$^{20a}$, —S(O)N(R$^{20a}$)$_2$, and —S(O)$_2$N(R$^{20a}$)$_2$, wherein said C$_{1-4}$alkyl, C$_{2-4}$alkenyl, C$_{3-6}$cycloalkyl, phenyl, 4- to 7-membered monocyclic saturated heterocyclyl, 5- or 6-membered heteroaryl in each occurrence are optionally and independently substituted with one or more substituents independently selected from halo, —CN, —C(O)R$^{20a}$, —C(O)OR$^{20a}$, —C(O)N(R$^{20a}$)$_2$, —N(R$^{20a}$)$_2$, —N(R$^{20a}$)C(O)R$^{20a}$, —N(R$^{20a}$)C(O)OR$^{20a}$, —N(R$^{20a}$)C(O)N(R$^{20a}$)$_2$, —N(R$^{20a}$)S(O)$_2$R$^{20a}$, —OR$^{20a}$, —OC(O)R$^{20a}$, —OC(O)N(R$^{20a}$)$_2$, —SR$^{20a}$, —S(O)R$^{20a}$, —S(O)$_2$R$^{20a}$, —S(O)N(R$^{20a}$)$_2$, and —S(O)$_2$N(R$^{20a}$)$_2$;

R$^{20a}$ in each occurrence is independently H or C$_{1-4}$alkyl.

7. The compound of claim 6, wherein:

R$^2$ is selected from H, C$_{1-6}$alkyl, C$_{2-6}$alkenyl, C$_{3-6}$cycloalkyl, phenyl, and 5- or 6-membered heteroaryl, wherein said C$_{1-6}$alkyl, C$_{2-6}$alkenyl, C$_{3-6}$cycloalkyl, phenyl, and 5- or 6-membered heteroaryl are optionally and independently substituted with one to three R$^{20}$;

R$^{20}$ in each occurrence is independently selected from C$_{1-4}$alkyl, C$_{2-4}$alkenyl, C$_{3-6}$cycloalkyl, phenyl, 4- to 7-membered monocyclic saturated heterocyclyl, 5- or 6-membered heteroaryl, halo, —CN, —N(R$^{20a}$)$_2$, and —OR$^{20a}$;

R$^{20a}$ in each occurrence is independently H or C$_{1-4}$alkyl.

8. The compound of claim 6, wherein the 5- or 6-membered heteroaryl is selected from pyridinyl, pyrimidinyl, pyrazinyl, and pyridazinyl.

9. The compound of claim 7, wherein the 4- to 7-membered monocyclic saturated heterocyclyl is selected from azetidinyl, piperidinyl, oxetanyl, piperazinyl and morpholinyl.

10. The compound of claim 6, wherein R$^2$ is —CH$_3$, —CH$_2$CH$_3$, —CH$_2$CF$_3$, —C(CH$_3$)$_3$, —CH$_2$CH$_2$OCH$_3$, —CH$_2$CH(CH$_3$)$_2$, —CH$_2$CH$_2$N(CH$_3$)$_2$, —CH$_2$CH=CH$_2$, —CH$_2$CH$_2$CH$_3$,

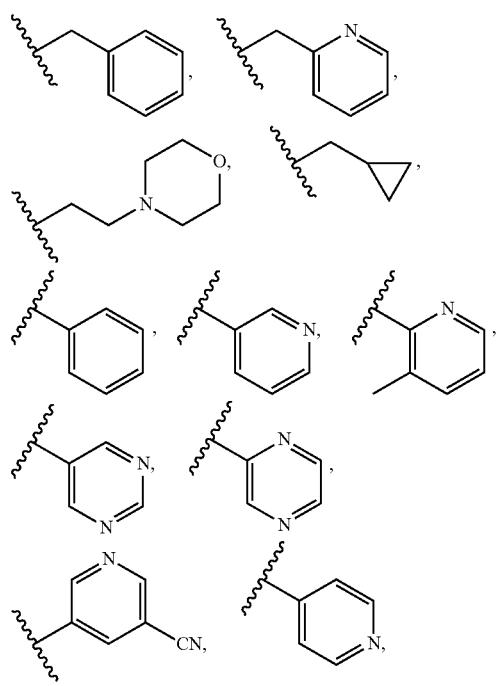

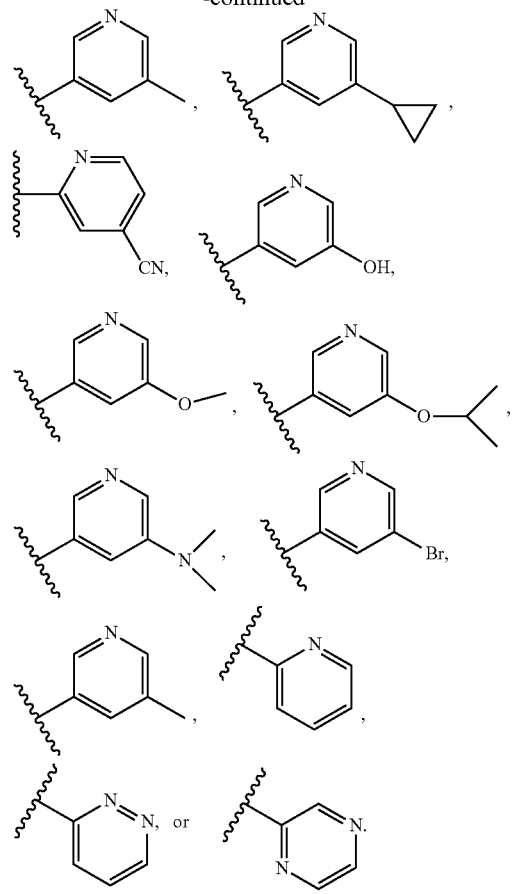

11. The compound of claim 1, wherein:

R$^3$ is selected from H, C$_{1-6}$alkyl, C$_{3-6}$cycloalkyl, and 4 to 7-membered monocyclic saturated heterocyclyl, wherein said C$_{1-6}$alkyl, C$_{3-6}$cycloalkyl, and 4 to 7-membered monocyclic saturated heterocyclyl are optionally substituted with one to three R$^{30}$;

R$^{30}$ in each occurrence is independently selected from C$_{1-6}$alkyl, halo, —CN, —C(O)R$^{30a}$, —C(O)OR$^{30a}$, —C(O)N(R$^{30a}$)$_2$, —N(R$^{30a}$)$_2$, —N(R$^{30a}$)C(O)R$^{30a}$, —N(R$^{30a}$)C(O)OR$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$, wherein said C$_{1-6}$alkyl in each occurrence are optionally and independently substituted with one to three substituents independently selected from halo;

R$^{30a}$ in each occurrence is independently selected from H and C$_{1-6}$alkyl, wherein C$_{1-6}$alkyl is optionally substituted with one to three substituents independently selected from C$_{1-4}$alkyl and halo.

12. The compound of claim 11, wherein:

R$^3$ is C$_{1-6}$alkyl, C$_{3-6}$cycloalkyl, or 4 to 7-membered monocyclic saturated heterocyclyl, wherein said C$_{1-6}$alkyl, C$_{3-6}$cycloalkyl, and 4 to 7-membered monocyclic saturated heterocyclyl are each optionally substituted with one to three R$^{30}$;

R$^{30}$ in each occurrence is independently C$_{1-3}$alkyl, halo, —C(O)OR$^{30a}$, or —OR$^{30a}$, wherein said C$_{1-3}$alkyl is optionally substituted with one to three halo; and R$^{30a}$ in each occurrence is independently H or C$_{1-4}$alkyl.

13. The compound of claim 12, wherein:
R$^3$ is —CH(CH$_3$)$_2$, —CH(CH$_3$)CF$_3$, —C(CH$_3$)$_3$, —CH(CH$_3$)CHF$_2$, —CH(CH$_3$)CH(CH$_3$)$_2$, —CH(CH$_3$)CH$_2$OCH$_3$, —CH(CH$_3$)CH$_2$OH,

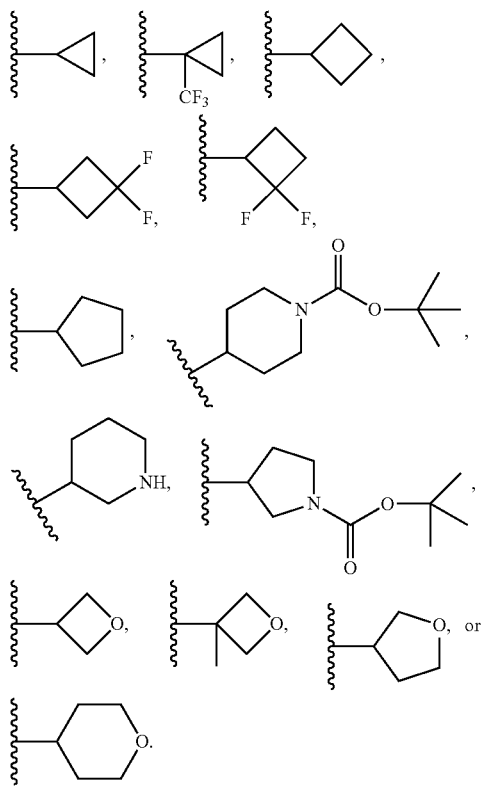

14. The compound of claim 1, wherein R$^4$ is H or —CH$_3$.
15. The compound of claim 14, wherein R$^4$ is H.
16. The compound of claim 1, wherein the compound is represented by Formula (V) or (VI):

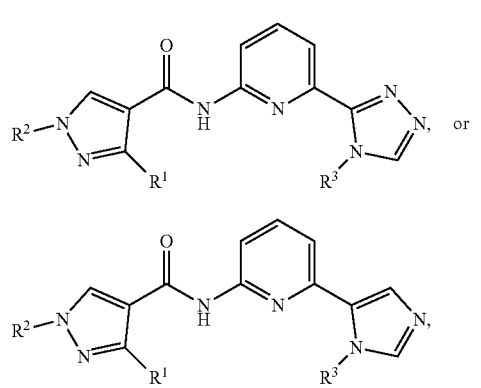

or a pharmaceutically acceptable salt thereof, wherein:
R$^1$ is C$_{1-4}$alkyl or —OR$^{1a}$, wherein said C$_{1-4}$alkyl is optionally substituted with one to three halo;
R$^{1a}$ in each occurrence is independently H or C$_{1-4}$alkyl;
R$^2$ is C$_{1-4}$alkyl, C$_{2-4}$alkenyl or 5- or 6-membered heteroaryl, wherein said C$_{1-4}$alkyl, C$_{2-4}$alkenyl and 5- or 6-membered heteroaryl are optionally and independently substituted with one to three R$^{20}$;
R$^{20}$ in each occurrence is independently selected from C$_{3-6}$cycloalkyl, halo and —OR$^{20a}$;
R$^{20a}$ in each occurrence is independently H or C$_{1-4}$alkyl;
R$^3$ is C$_{1-4}$alkyl or C$_{3-6}$cycloalkyl, wherein said C$_{1-4}$alkyl and C$_{3-6}$cycloalkyl are each optionally substituted with one to three R$^{30}$; and
R$^{30}$ in each occurrence is independently C$_{1-3}$alkyl or halo, wherein said C$_{1-3}$alkyl is optionally substituted with one to three halo.

17. The compound of claim 16, wherein:
R$^1$ is —OCH$_3$, —OCH$_2$CH$_3$, or —CHF$_2$;
R$^2$ is —CH$_3$, —CH$_2$CH$_3$, —CH$_2$CH$_2$OCH$_3$, —CH$_2$CF$_3$, —CH$_2$CH=CH$_2$,

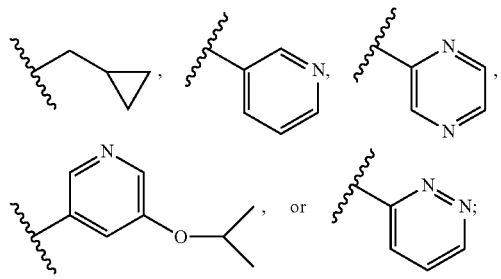

R$^3$ is —CH(CH$_3$)$_2$, —CH(CH$_3$)CF$_3$, —CH(CH$_3$)CHF$_2$,

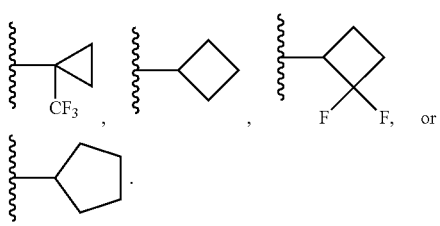

18. A pharmaceutical composition comprising a compound of claim 1 or a pharmaceutically acceptable salt thereof, and a pharmaceutically acceptable excipient.

19. A method of treating a disorder responsive to inhibition of apoptosis signal-regulating kinase 1 (ASK1) in a subject, the method comprising administering to the subject an effective amount of a compound of claim 1 or a pharmaceutically acceptable salt thereof.

20. The method of claim 19, wherein the disorder is neurodegenerative disorder, cardiovascular disease, metabolic disorder, inflammatory disease, autoimmune disorder, destructive bone disorder, polyglutamine disease, glutamate neurotoxicity, pain, traumatic brain injury, hemorrhagic stroke, ischemia, acute hypoxia, kidney fibrosis (renal fibrosis), kidney injury, diabetic kidney disease, diabetic nephropathy, non-alcoholic steatohepatitis (NASH), pulmonary arterial hypertension (PAH), optic neuritis, liver disease, respiratory disease, heart reperfusion injury, cardiac hypertrophy, cardiac fibrosis, energy metabolic disorder, or cancer.

* * * * *